United States Patent [19]
Setoi et al.

[11] Patent Number: 6,054,457
[45] Date of Patent: Apr. 25, 2000

[54] BENZAMIDE DERIVATIVES AND THEIR USE AS VASOPRESSIN ANTAGONISTS

[75] Inventors: Hiroyuki Setoi, Tsukuba; Takehiko Ohkawa, Ishigemachi; Tatsuya Zenkoh, Moriyamachi; Hitoshi Sawada; Kentaro Sato, both of Tsukuba; Hirokazu Tanaka, Takarazuka, all of Japan

[73] Assignee: Fujisawa Pharmaceutical Co., Ltd., Osaka, Japan

[21] Appl. No.: 08/973,103

[22] PCT Filed: Jun. 6, 1996

[86] PCT No.: PCT/JP96/01533

§ 371 Date: Dec. 9, 1997

§ 102(e) Date: Dec. 9, 1997

[87] PCT Pub. No.: WO96/41795

PCT Pub. Date: Dec. 27, 1996

[30] Foreign Application Priority Data

Jun. 9, 1995 [GB] United Kingdom .................... 9511694

[51] Int. Cl.[7] ................... A61K 31/165; A61K 31/33; C07C 237/42; C07C 237/44; C07C 271/16; C07D 209/48; C07D 211/46; C07D 211/58; C07D 213/80; C07D 295/18; C07D 295/20

[52] U.S. Cl. ................ 514/255; 514/218; 514/235.8; 514/237.5; 514/252; 514/253; 514/256; 514/318; 514/323; 514/327; 514/329; 514/330; 514/352; 514/356; 514/357; 514/365; 514/374; 514/381; 514/417; 514/423; 514/427; 514/447; 514/518; 514/532; 514/534; 514/535; 514/538; 514/539; 514/540; 514/543; 514/544; 514/595; 514/602; 514/603; 514/604; 514/616; 514/617; 514/618; 514/619; 514/620; 514/622; 540/575; 544/121; 544/165; 544/335; 544/357; 544/360; 544/373; 544/379; 544/382; 544/388; 544/391; 544/400; 546/194; 546/200; 546/221; 546/223; 546/226; 546/298; 546/309; 546/322; 546/336; 548/204; 548/238; 548/253; 548/479; 548/537; 548/540; 548/561; 549/69; 558/49; 558/50; 560/9; 560/11; 560/12; 560/13; 560/15; 560/16; 560/18; 560/19; 560/20; 560/21; 560/22; 560/23; 560/24; 560/25; 560/27; 560/29; 560/31; 560/32; 560/34; 560/37; 560/38; 560/39; 560/41; 560/42; 560/43; 560/45; 560/46; 560/47; 560/48; 560/49; 560/51; 560/52; 560/53; 560/55; 560/59; 560/61; 560/62; 560/64; 560/65; 560/66; 560/72; 560/73; 560/76; 560/81; 560/83; 560/85; 560/102; 560/103; 560/104; 560/105; 560/107; 560/251; 564/47; 564/84; 564/85; 564/86; 564/87; 564/88; 564/89; 564/90; 564/91; 564/92; 564/152; 564/154; 564/155; 564/157; 564/158; 564/161; 564/162; 564/163; 564/164; 564/165; 564/166; 564/167; 564/168; 564/169; 564/170; 564/171; 564/172; 564/174; 564/176; 564/177; 564/180; 564/181; 564/183; 564/184; 564/185; 564/186; 564/187

[58] Field of Search .................... 560/21, 25, 27, 560/29, 45, 46, 48, 251; 564/47, 155, 157, 158, 166, 168; 544/121, 165, 335, 357, 360, 373, 379, 382, 388, 391, 400; 540/575; 546/194, 200, 221, 223, 226, 298, 309, 322, 336; 548/204, 238, 253, 479, 537, 540, 561; 549/69; 514/218, 235.8, 237.5, 252, 253, 255, 256, 318, 323, 327, 329, 330, 352, 356, 357, 365, 374, 381, 417, 423, 427, 447, 535, 538, 539, 543, 595, 616, 619

[56] References Cited

U.S. PATENT DOCUMENTS 5,521,170  5/1996  Setoi et al. ............................ 514/183

FOREIGN PATENT DOCUMENTS 0 196 070   10/1986   European Pat. Off. .
35 23 705   1/1987    Germany .
WO 95/29152 11/1995   WIPO .

OTHER PUBLICATIONS

Plescia et al., A New Pyrazolo[4,3–c][1,5]benzodiazocine Derivative, Bollettino Chimico Farmaceutico, vol. 122, No. 4, pp. 190–195, Apr. 1983.

(List continued on next page.)

*Primary Examiner*—Mukund J. Shah
*Assistant Examiner*—Brenda Coleman
*Attorney, Agent, or Firm*—Oblon, Spivak, McClelland, Maier & Neustadt, P.C.

[57] ABSTRACT

This invention relates to new benzamide derivatives having a vasopressin antagonistic activity, etc, and represented by general formula (I):

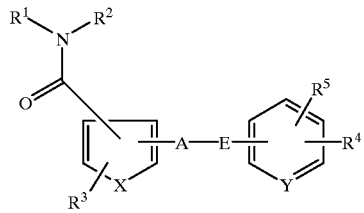

wherein $R^1$ is aryl optionally substituted with lower alkoxy, etc.,
$R^2$ is lower alkyl, etc.,
$R^3$ is hydrogen, etc.,
$R^4$ is lower alkoxy, etc.,
$R^5$ is hydrogen, etc.,
A is NH, etc.,
E is

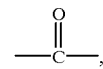

etc.,
X is —CH=CH—, —CH=N—, or S, and
Y is CH or N,
and pharmaceutically acceptable salts thereof, to processes for preparation thereof and to a pharmaceutical composition comprising the same.

6 Claims, No Drawings

OTHER PUBLICATIONS

CAS Online Printout for WO 95/29152, Nov. 1995.

Imagawa et al., Studies on Cyclic–Oligo–Amides (III) Syntheses of 1,9,17–Triaza[2.2.2]orthocyclophane–2,10,18–trione and N–Methyl Derivative, Memoirs of Osaka Kyoiku University, Series III, vol. 36, No. 2, pp. 123–128, Dec. 1987.

CAS Online Printout for DE 35 23 705, Jan. 1987.

Hoorfar et al., Conformational Behaviour of Medium–sized Rings. Part 11. Dianthranilides and Trianthranilides, Journal of the Chemical Society, Perkin Transactions I, vol. 8, pp. 1649–1699, Aug. 1982.

Elhadi et al., Conformational Behaviour of Medium–sized Rings. Part 15. 1,9,17–Triaza[2.2.2]metacyclophane–2,10, 18–trione Derivatives, Journal of the Chemical Society, Perkin Transactions I, vol. 8, pp. 1727–1732, Aug. 1982.

Hoorfar et al., Conformational Behaviour of Medium–sized Rings. Part 14. Tetraanthranilides, Journal of the Chemical Society, Perkin Transactions I, vol. 8, pp. 1721–1726, Aug. 1982.

Edge et al., Conformational Behaviour of Medium–sized Rings. Part 12. Tri–3–methyltrianthranilide, Journal of the Chemical Society, Perkin Transactions I, vol. 8, pp. 1701–1714, Aug. 1982.

Ollis et al., Synthese und Konformationsverhalten von N,N', N"–Trimethyltrianthranilid, Angewandte Chemie, vol. 87, No. 5, pp. 169–170, Mar. 1975.

BENZAMIDE DERIVATIVES AND THEIR USE AS VASOPRESSIN ANTAGONISTS

This application is a National Stage under 35 U.S.C. 371 of PCT/JP96/01533, filed Jun. 6, 1996.

TECHNICAL FIELD

This invention relates to new benzamide derivatives and pharmaceutically acceptable salts thereof which are useful as a medicament.

BACKGROUND ART

Some benzamide derivatives have been known as vasopressin antagonist, for example, in PCT International Publication Nos. WO 91/05549 and WO 95/29152, and EP Application Publication No. 0620216.

DISCLOSURE OF INVENTION

This invention relates to new benzamide derivatives and pharmaceutically acceptable salts thereof.

More particularly, it relates to new benzamide derivatives and pharmaceutically acceptable salts thereof which possess activities as vasopressin antagonistic activity, vasodilating activity, hypotensive activity, activity for inhibiting saccharide release in liver, activity for inhibiting growth of mesangium cells, water diuretic activity, platelet agglutination inhibitory activity, oxytocin antagonistic activity and the like, to a pharmaceutical composition comprising the same and to a method for the treatment and/or prevention of hypertension, heart failure, renal insufficiency, edema, ascites, vasopressin parasecretion syndrome, hepatocirrhosis, hyponatremia, hypokalemia, diabetic, circulation disorder, cerebrovascular disease (e.g. cerebral edema, cerebral infarction, etc.), Meniere's syndrome (e.g. Meniere's disease, etc.), motion sickness and the like in human beings or animals.

One object of this invention is to provide new and useful benzamide derivative which possess aforesaid activities.

Another object of this invention is to provide processes for the preparation of said benzamide derivatives and salts thereof.

A further object of this invention is to provide a pharmaceutical composition comprising, as an active ingredient, said benzamide derivatives and pharmaceutically acceptable salts thereof.

Still further object of this invention is to provide a therapeutical method for the treatment and/or prevention of aforesaid diseases in human beings or animals, using said benzamide derivatives and pharmaceutically acceptable salts thereof.

The object benzamide derivatives of this invention are new and can be represented by the following general formula (I):

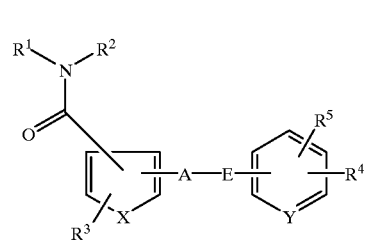

wherein:
R¹ is aryl, cyclo(lower)alkyl or a heterocyclic group, each of which may be substituted with substituent(s) selected from the group consisting of halogen; hydroxy; nitro; amino; acyl; substituted acyl; acyl(lower)alkylsulfinyl; acyl(lower)alkylsulfonyl; acyloxy; lower alkylamino(lower) alkylcarbamoyloxy; aryl; cyano; a heterocyclic group; lower alkenyl optionally substituted with acyl, substituted acyl, aryl or acyl-substituted aryl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl, acyl(lower)alkoxyimino, aryl or acyl-substituted aryl; lower alkylthio optionally substituted with acyl or substituted acyl; alkoxy optionally substituted with aryl, substituted aryl, hydroxy, acyloxy, amino, lower alkylamino, protected amino, a heterocyclic group, acyl-substituted pyridyl, substituted acyl-substituted pyridyl, halogen, acyl(lower)alkylamino, N-protected-acyl(lower)alkylamino, N-acyl(lower) alkyl-N-lower alkylamino, acyl, substituted acyl, acylamino, substituted acylamino, lower alkylhydrazinocarbonylamino, hydroxyimino, acyl(lower)alkoxyimino, substituted acyl(lower) alkoxyimino, acyl(lower)alkoxy, guanidino or N-protected guanidino; and lower alkenyloxy optionally substituted with acyl or substituted acyl;
R² is hydrogen; lower alkyl optionally substituted with hydroxy, aryl or acyl; or cyclo(lower)alkyl;
R³ is hydrogen; halogen; hydroxy; acyloxy; substituted acyloxy; lower alkyl optionally substituted with hydroxy or lower alkoxy; lower alkoxy optionally substituted with aryl, amino, protected amino, acyl, hydroxy, cyano or lower alkylthio; nitro; amino; acyl; substituted acyl; or cyclo(lower)alkyloxy;
R⁴ is hydroxy; halogen; nitro; amino; protected amino; lower alkylamino; acyloxy; amino(lower)alkylamino; N-protected amino(lower)alkylamino; lower alkoxy optionally substituted with hydroxy, aryl, substituted aryl, acyl, substituted acyl, amino, lower alkylamino, acylamino, substituted acylamino, protected amino, a heterocyclic group or guanidino; lower alkylthio optionally substituted with acyl, substituted acyl, amino, lower alkylamino, acylamino, substituted acylamino, protected amino, a heterocyclic group, hydroxy, lower alkylsulfonyloxy, arylsulfonyloxy, ar(lower)alkoxy or substituted ar(lower)alkoxy; lower alkyl substituted with acyl, substituted acyl, amino, lower alkylamino, acylamino, substituted acylamino, protected amino, a heterocyclic group, hydroxy, lower alkylsulfonyloxy or arylsulfonyloxy; lower alkenyl optionally substituted with acyl; lower alkynyl optionally substituted with hydroxy, amino, protected amino, lower alkylsulfonyloxy or arylsulfonyloxy; amino(lower)alkylsulfonyl; N-protected amino(lower)alkylsulfonyl; lower alkylaminosulfonyl; a heterocyclicsulfonyl; amino(lower)alkylsulfinyl; N-protected amino(lower)alkylsulfinyl; piperidyloxy; or N-protected piperidyloxy;

$R^5$ is hydrogen, lower alkyl, lower alkoxy or halogen;

A is a single bond, O or NH:

E is lower alkylene, lower alkenylene,

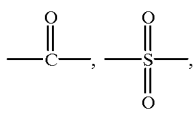

or a group of the formula:

in which G is lower alkylene and J is O or

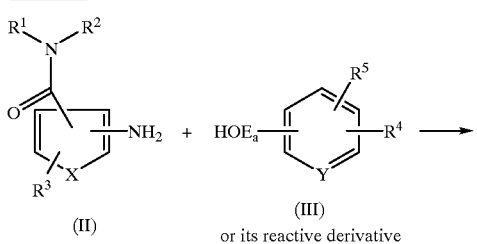

(wherein $R^6$ is hydrogen or N-protective group);

X is —CH=CH—, —C=N— or S; and

Y is CH or N;

and pharmaceutically acceptable salts thereof.

The object compound (I) for its salt can be prepared by the processes as illustrated in the following reaction schemes.

Process 1

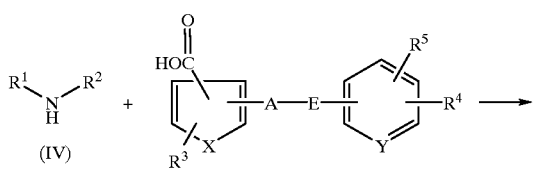

Process 2

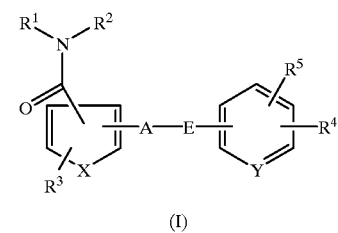

Process 3

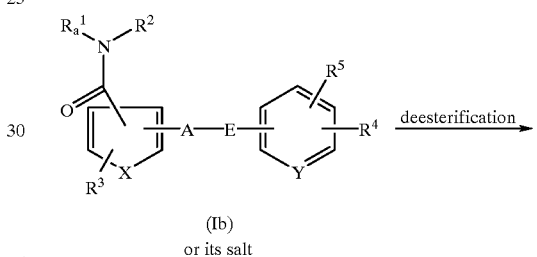

Process 4

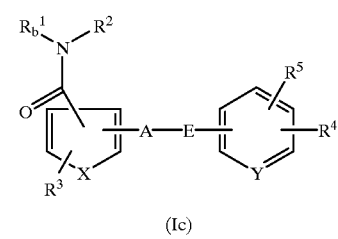

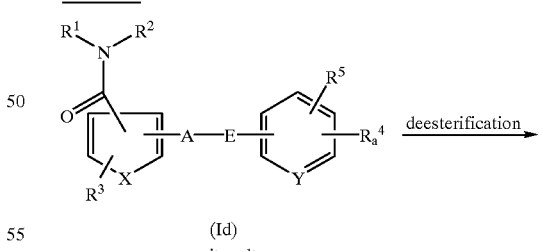

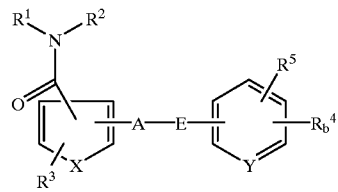

-continued
Process 5
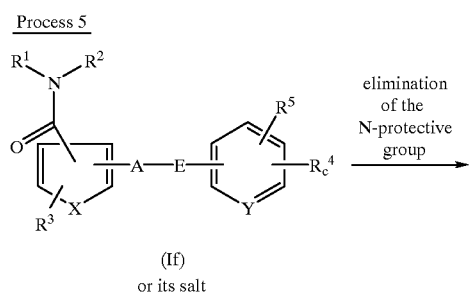
(If)
or its salt
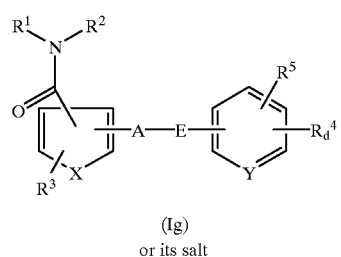
(Ig)
or its salt
Process 6
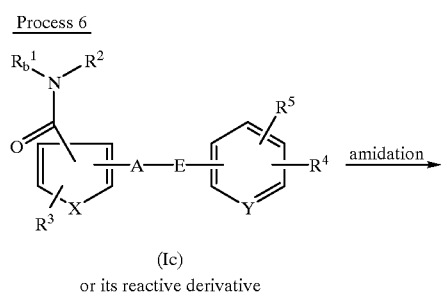
(Ic)
or its reactive derivative
at the carboxy group
or a salt thereof
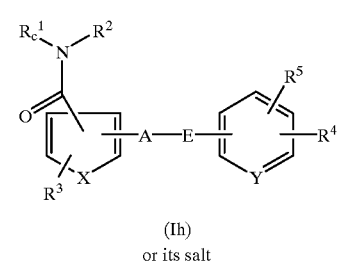
(Ih)
or its salt
Process 7
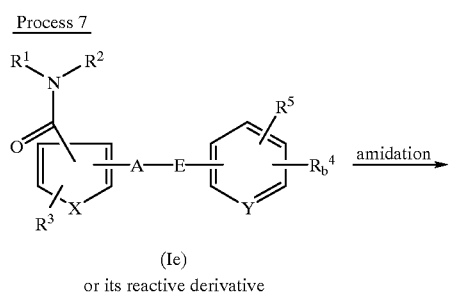
(Ie)
or its reactive derivative
at the carboxy group
or a salt thereof
-continued
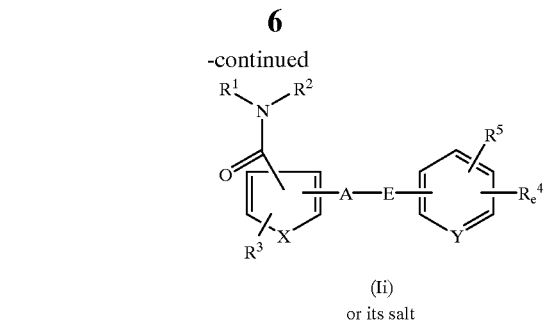
(Ii)
or its salt
Process 8
(Ij)
or its salt
(Ik)
or its salt
Process 9
(Ika)
or its salt
(Il)
or its salt
Process 10
(Iga)
or its salt

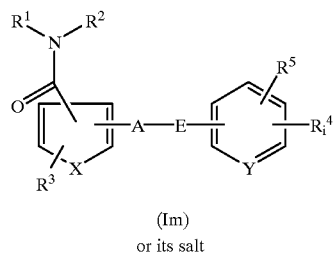
(Im) or its salt
Process 11
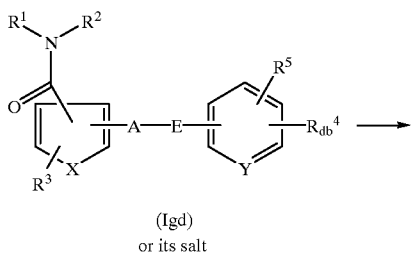
(Igd) or its salt
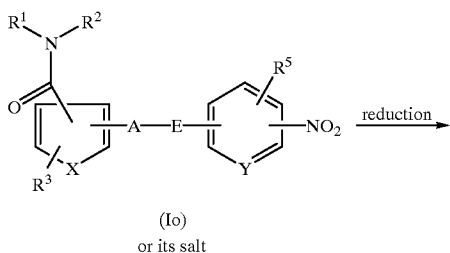
(In) or its salt
Process 12
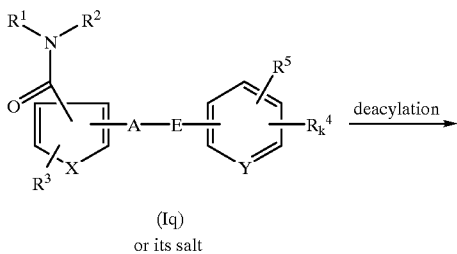
(Io) or its salt
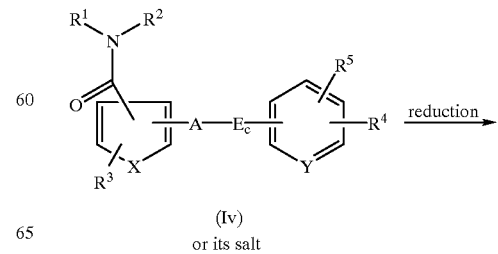
(Ip) or its salt
Process 13
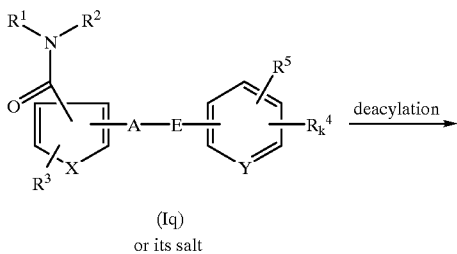
(Iq) or its salt
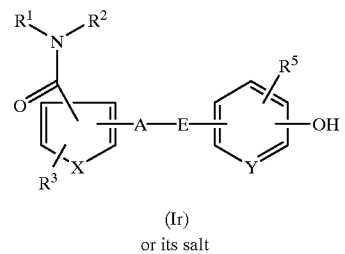
(Ir) or its salt
Process 14
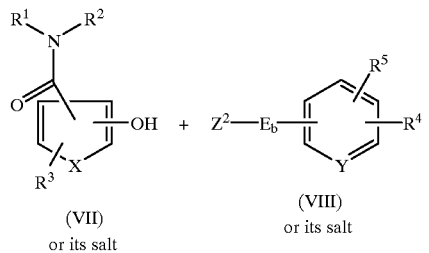
(VII) or its salt    (VIII) or its salt
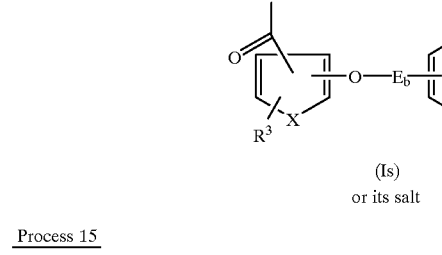
(Is) or its salt
Process 15
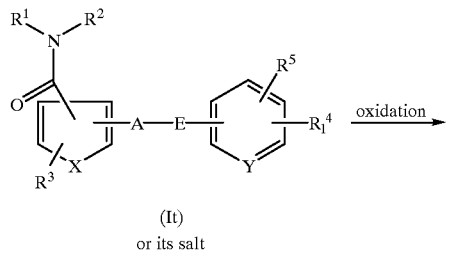
(It) or its salt
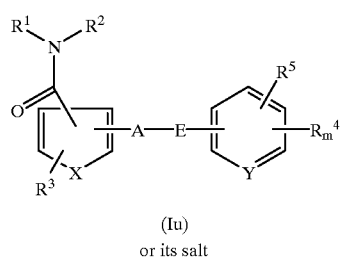
(Iu) or its salt
Process 16
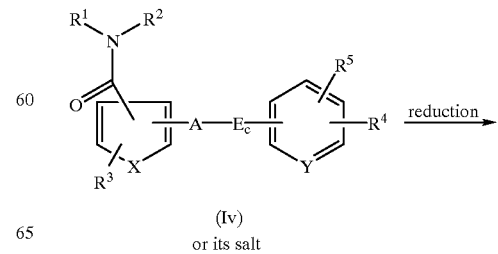
(Iv) or its salt -continued
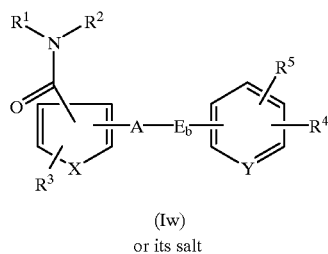
(Iw) or its salt
Process 17
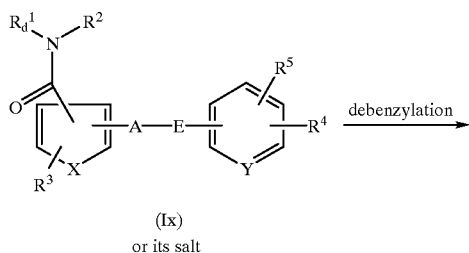
debenzylation →
(Ix) or its salt
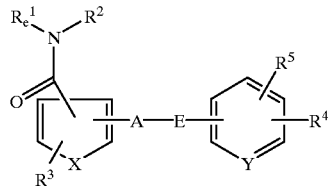
(Iy) or its salt
Process 18
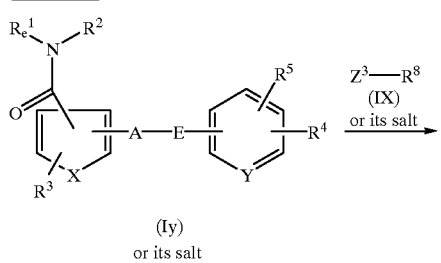
$Z^3$—$R^8$
(IX)
or its salt
(Iy) or its salt
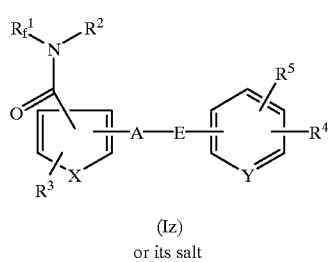
(Iz) or its salt
Process 19
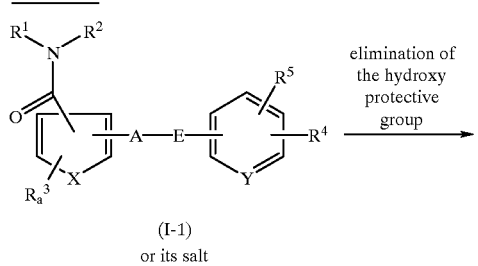
elimination of the hydroxy protective group →
(I-1) or its salt
-continued
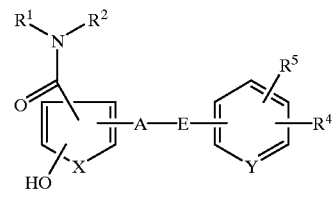
(I-2) or its salt
Process 20
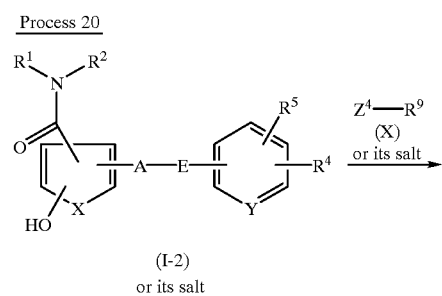
$Z^4$—$R^9$
(X)
or its salt
(I-2) or its salt
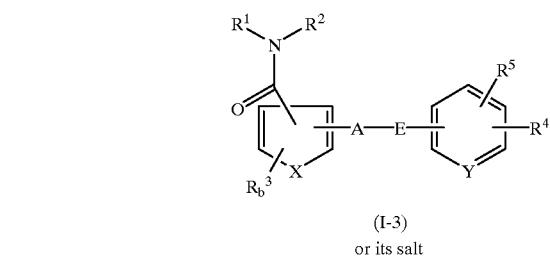
(I-3) or its salt
Process 21
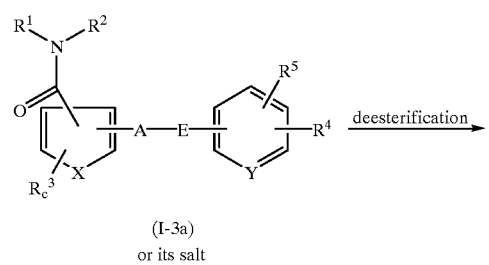
deesterification →
(I-3a) or its salt
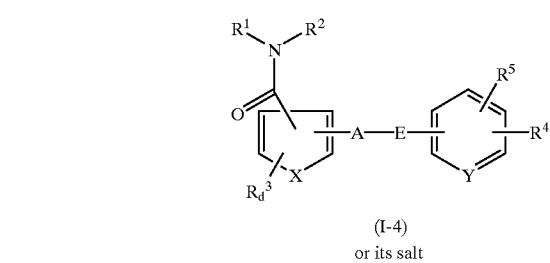
(I-4) or its salt
Process 22
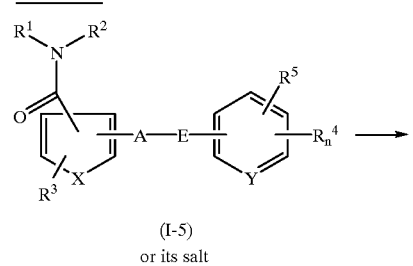
(I-5) or its salt -continued
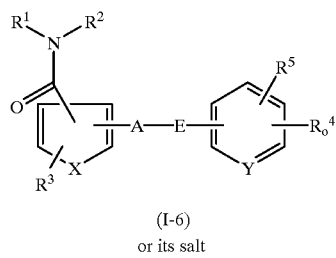
(I-6) or its salt
Process 23
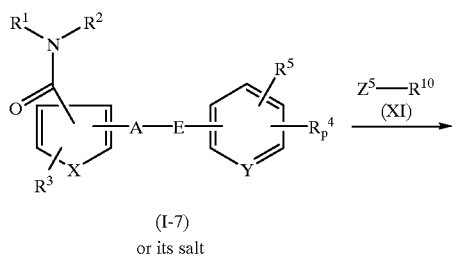
(I-7) or its salt
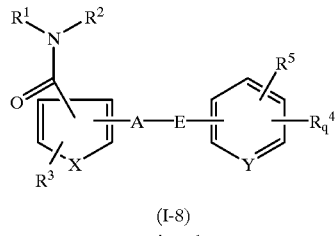
(I-8) or its salt
Process 24
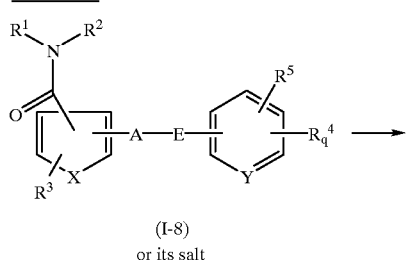
(I-8) or its salt
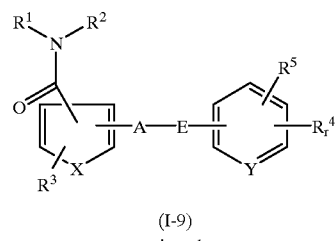
(I-9) or its salt
Process 25
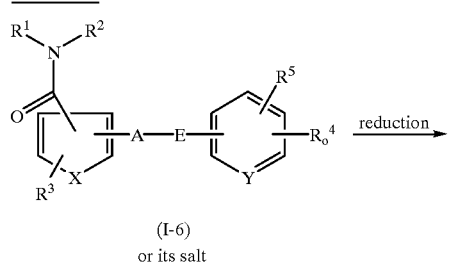
(I-6) or its salt
-continued
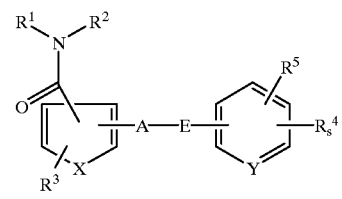
(I-10) or its salt
Process 26
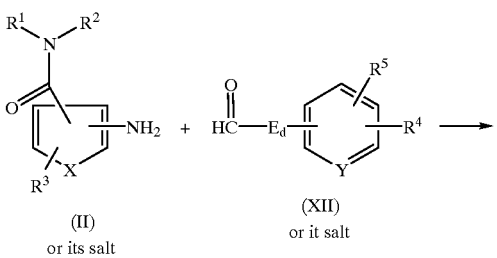
(II) or its salt  (XII) or it salt
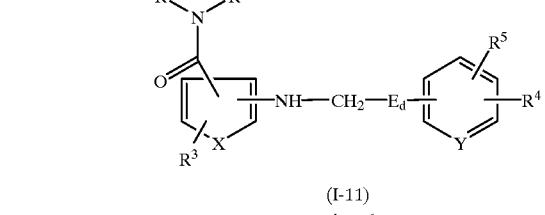
(I-11) or its salt
Process 27
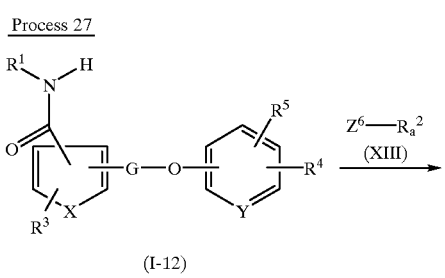
(I-12) or its salt
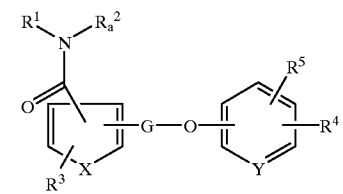
(I-13) or its salt
Process 28
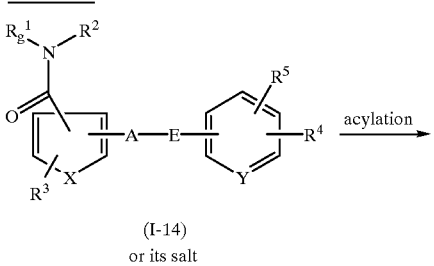
(I-14) or its salt -continued
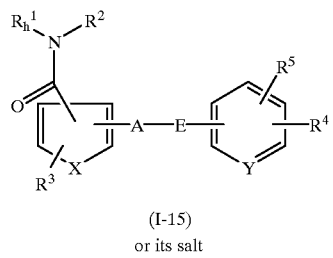
(I-15)
or its salt
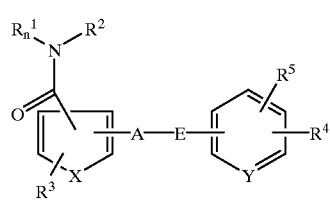
(I-20)
or its salt
Process 29
(I-16a)
or its salt
→ reduction
Process 32
(I-21)
or its salt
→ reduction
(I-17)
or its salt
(I-22)
or its salt
Process 30
(I-16)
or its salt
→
Process 33
(I-22)
or its salt
→
(I-18)
or its salt
(I-23)
or its salt
Process 31
(I-19)
or its reactive derivative
at the carboxy group
or a salt thereof
→
Process 34
(I-24)
or its salt
→

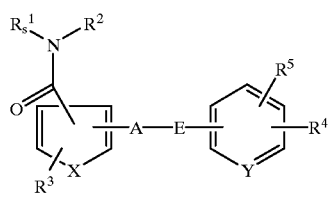

(I-25)
or its salt

Process 35

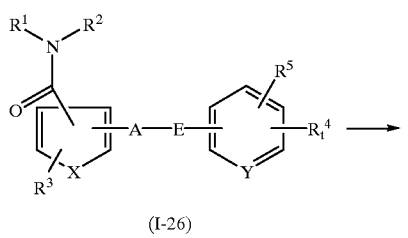

(I-26)
or its salt

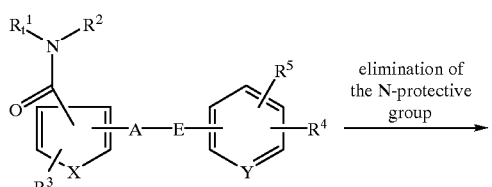

(I-27)
or its salt

Process 36

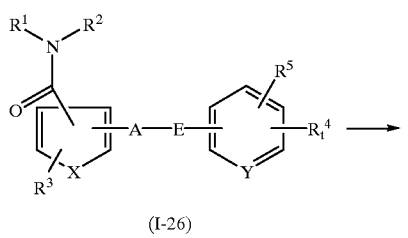

elimination of
the N-protective
group (I-28)
or its salt

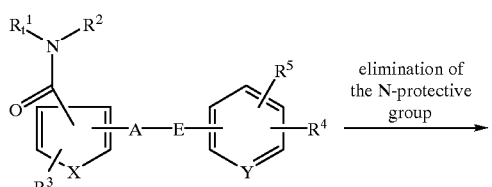

(I-29)
or its salt

Process 37

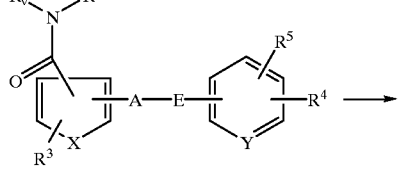

(I-30)
or its salt

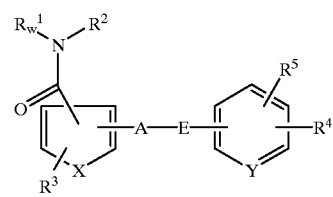

(I-31)
or its salt

Process 38

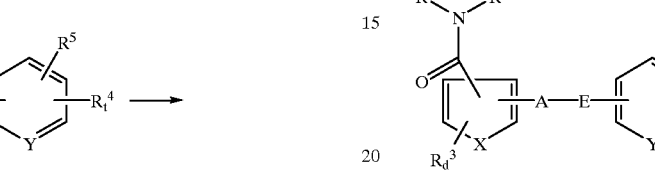

esterification (I-4)
or its reactive derivative
at the carboxy group
or a salt thereof

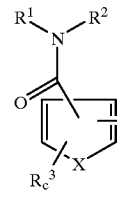

(I-3a)
or its salt

Process 39

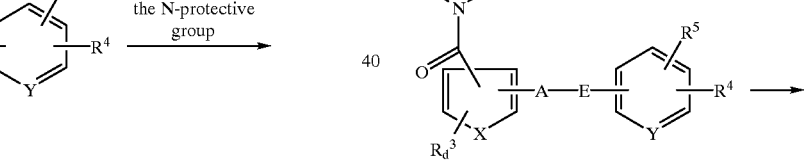

(I-4)
or its reactive derivative
at the carboxy group
or a salt thereof

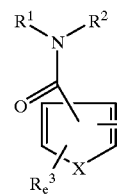

(I-32)
or its salt wherein $R^1$, $R^2$, $R^3$, $R^4$, $R^5$, A, E, X and Y are each as defined above, $E_a$ is

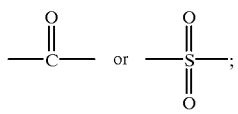

$R_a^1$ is aryl, haloaryl, cyclo(lower)alkyl or a heterocyclic group, each of which is substituted with esterified carboxy; lower alkenyl substituted with esterified carboxy or esterified carboxy-substituted aryl; lower alkyl substituted with esterified carboxy, esterified carboxy (lower)alkanoyloxy or esterified carboxy(lower) alkoxyimino; lower alkylthio substituted with esterified carboxy; alkoxy substituted with esterified carboxy-substituted aryl, esterified carboxy-substituted pyridyl, esterified carboxy(lower)alkylamino, N-protected-esterified carboxy(lower)alkylamino, N-esterified carboxy(lower)alkyl-N-lower alkylamino, esterified carboxy or esterified carboxy(lower)alkoxyimino; or lower alkenyloxy substituted with esterified carboxy;

$R_b^1$ is aryl, haloaryl, cyclo(lower)alkyl or a heterocyclic group, each of which is substituted with carboxy; lower alkenyl substituted with carboxy or carboxy-substituted aryl; lower alkyl substituted with carboxy, carboxy (lower)alkanoyloxy or carboxy(lower)alkoxyimino; lower alkylthio substituted with carboxy; alkoxy substituted with carboxy-substituted aryl, carboxy-substituted pyridyl, carboxy(lower)alkylamino, N-protected-carboxy(lower)alkylamino, N-carboxy (lower)alkyl-N-lower alkylamino, carboxy or carboxy (lower)alkoxyimino; or lower alkenyloxy substituted with carboxy;

$R_a^4$ is lower alkoxy substituted with esterified carboxy; lower alkylthio substituted with esterified carboxy; lower alkyl substituted with esterified carboxy; or lower alkenyl substituted with esterified carboxy;

$R_b^4$ is lower alkoxy substituted with carboxy; lower alkylthio substituted with carboxy; lower alkyl substituted with carboxy; or lower alkenyl substituted with carboxy;

$R_c^4$ is protected amino; N-protected piperidyloxy; N-protected amino(lower)alkylamino; lower alkoxy substituted with protected amino; lower alkylthio substituted with protected amino; lower alkyl substituted with protected amino; lower alkynyl substituted with protected amino; or N-protected amino(lower) alkylsulfonyl;

$R_d^4$ is amino; piperidyloxy; amino(lower)alkylamino; lower alkoxy substituted with amino; lower alkylthio substituted with amino; lower alkyl substituted with amino; lower alkynyl substituted with amino; or amino(lower)alkylsulfonyl;

$R_c^1$ is aryl, haloaryl, cyclo(lower)alkyl or a heterocyclic group, each of which is substituted with substituted or unsubstituted N-containing heterocycliccarbonyl; carbamoyl; substituted or unsubstituted lower alkylcarbamoyl; lower alkenyl substituted with substituted or unsubstituted N-containing heterocycliccarbonyl, carbamoyl, substituted or unsubstituted lower alkylcarbamoyl or N-containing heterocycliccarbonyl-substituted aryl; lower alkyl substituted with substituted or unsubstituted N-containing heterocycliccarbonyl, carbamoyl, substituted or unsubstituted lower alkylcarbamoyl, substituted or unsubstituted N-containing heterocycliccarbonyl(lower) alkanoyloxy, carbamoyl(lower)alkanoyloxy, substituted or unsubstituted lower alkylcarbamoyl (lower)alkanoyloxy, substituted or unsubstituted N-containing heterocycliccarbonyl(lower) alkoxyimino, carbamoyl(lower)alkoxyimino or substituted or unsubstituted lower alkylcarbamoyl(lower) alkoxyimino; lower alkylthio substituted with substituted or unsubstituted N-containing heterocycliccarbonyl, carbamoyl or substituted or unsubstituted lower alkylcarbamoyl; alkoxy substituted with substituted or unsubstituted N-containing heterocycliccarbonyl-substituted aryl, carbamoyl-substituted aryl, substituted or unsubstituted lower alkylcarbamoyl-substituted aryl, substituted or unsubstituted N-containing heterocycliccarbonyl-substituted pyridyl, carbamoyl-substituted pyridyl, substituted or unsubstituted lower alkylcarbamoyl-substituted pyridyl, substituted or unsubstituted N-containing heterocycliccarbonyl(lower)alkylamino, carbamoyl (lower)alkylamino, substituted or unsubstituted lower alkylcarbamoyl(lower)alkylamino, N-protected-(substituted or unsubstituted N-containing heterocyclic)carbonyl(lower)alkylamino, N-protected-carbamoyl(lower)alkylamino, N-protected substituted or unsubstituted lower alkylcarbamoyl(lower) alkylamino, N-(substituted or unsubstituted N-containing heterocyclic)carbonyl(lower)alkyl-N-lower alkylamino, N-carbamoyl(lower)alkyl-N-lower alkylamino, substituted or unsubstituted N-lower alkylcarbamoyl-N-lower alkylamino, substituted or unsubstituted N-containing heterocycliccarbonyl, carbamoyl, aminocarbamoyl, pyridylcarbamoyl, N-(lower alkyl)piperazinylcarbonyl, substituted or unsubstituted lower alkylcarbamoyl, substituted or unsubstituted N-containing heterocycliccarbonyl (lower)alkoxyimino, carbamoyl(lower)alkoxyimino or substituted or unsubstituted lower alkylcarbamoyl (lower)alkoxyimino; or lower alkenyloxy substituted with substituted or unsubstituted N-containing heterocycliccarbonyl, carbamoyl or substituted or unsubstituted lower alkylcarbamoyl;

$R_e^4$ is lower alkoxy, lower alkylthio, lower alkyl or lower alkenyl, each of which is substituted with substituted or unsubstituted N-containing heterocycliccarbonyl, carbamoyl, or substituted or unsubstituted lower alkylcarbamoyl;

$R_f^4$ is methoxy substituted with aryl or substituted aryl; or lower alkylthio which is substituted with methoxy substituted with aryl or substituted aryl;

$R_g^4$ is hydroxy; or lower alkylthio substituted with hydroxy;

$R_{ga}^4$ is hydroxy;

$R^7$ is lower alkyl substituted with hydroxy, aryl, substituted aryl, acyl, amino, lower alkylamino, acylamino, protected amino or a heterocyclic group; or N-protected piperidyl;

$Z^1$ is hydroxy; or acid residue;

$R_h^4$ is lower alkoxy substituted with hydroxy, aryl, substituted aryl, acyl, amino, lower alkylamino, acylamino, protected amino or a heterocyclic group; or N-protected piperidyloxy;

$R_{da}^4$ is lower alkoxy substituted with amino; lower alkylthio substituted with amino; or lower alkyl substituted with amino;

$R_i^4$ is lower alkoxy substituted with acylamino or substituted acylamino; lower alkylthio substituted with acylamino or substituted acylamino; or lower alkyl substituted with acylamino or substituted acylamino;

$R_{db}^4$ is amino; lower alkoxy substituted with amino; lower alkylthio substituted with amino; or lower alkyl substituted with amino;

$R_j^4$ is lower alkoxy substituted with lower alkylamino; lower alkylthio substituted with lower alkylamino; lower alkyl substituted with lower alkylamino; lower alkylamino; or N-protected amino(lower)alkylamino;

$R_k^4$ is acyloxy;

$Z^2$ is acid residue;

$E_b$ is lower alkylene;

$R_l^4$ is lower alkylthio substituted with amino or protected amino;

$R_m^4$ is lower alkylsulfinyl substituted with amino or protected amino, or lower alkylsulfonyl substituted with amino or protected amino;

$E_c$ is lower alkenylene;

$R_d^1$ is aryl which is substituted with methoxy substituted with aryl or substituted aryl;

$R_e^1$ is aryl which is substituted with hydroxy;

$Z^3$ is hydroxy; or acid residue;

$R^8$ is lower alkyl optionally substituted with acyl, acylamino, protected amino, aryl, substituted aryl, acyl-substituted pyridyl or N-protected guanidino;

$R_f^1$ is aryl which is substituted with lower alkoxy optionally substituted with acyl, acylamino, protected amino, aryl, substituted aryl, acyl-substituted pyridyl or N-protected guanidino;

$R_a^3$ is methoxy substituted with aryl; acyloxy; or substituted acyloxy;

$Z^4$ is acid residue;

$R^9$ is lower alkyl optionally substituted with esterified carboxy;

$R_b^3$ is lower alkoxy optionally substituted with esterified carboxy;

$R_c^3$ is lower alkoxy substituted with esterified carboxy;

$R_d^3$ is lower alkoxy substituted with carboxy;

$R_n^4$ is halogen;

$R_o^4$ is lower alkynyl optionally substituted with hydroxy, amino, protected amino, lower alkylsulfonyloxy or arylsulfonyloxy;

$R_p^4$ is lower alkylthio, lower alkyl or lower alkynyl, each of which is substituted with hydroxy;

$Z^5$ is halogen;

$R^{10}$ is lower alkylsulfonyl or arylsulfonyl;

$R_q^4$ is lower alkylthio, lower alkyl or lower alkynyl, each of which is substituted with lower alkylsulfonyloxy or arylsulfonyloxy;

$R_r^4$ is lower alkylthio, lower alkyl or lower alkynyl, each of which is substituted with phthalimido;

$R_s^4$ is lower alkyl optionally substituted with hydroxy, amino, protected amino, lower alkylsulfonyloxy or arylsulfonyloxy;

$E_d$ is a single bond or lower alkylene;

$Z^6$ is acid residue;

$R_a^2$ is lower alkyl optionally substituted with aryl or acyl;

$R_g^1$ is aryl which is substituted with lower alkoxy substituted with amino;

$R_h^1$ is aryl which is substituted with lower alkoxy substituted with acylamino or substituted acylamino;

$R_i^1$ is aryl which is substituted with lower alkoxy substituted with oxopiperidylcarbonyl;

$R_j^1$ is aryl which is substituted with lower alkoxy substituted with hydroxypiperidylcarbonyl;

$R_k^1$ is aryl which is substituted with lower alkoxy substituted with formyl or oxopiperidylcarbonyl;

$R_l^1$ is aryl which is substituted with lower alkoxy substituted with aminopiperidylcarbonyl or N-lower alkylpiperazinyl;

$R_m^1$ is aryl which is substituted with lower alkoxy substituted with carboxy;

$R_n^1$ is aryl which is substituted with lower alkoxy substituted with lower alkylamino (lower)-alkoxycarbonyl;

$R_o^1$ is aryl which is substituted with lower alkoxy substituted with esterified carboxy;

$R_p^1$ is aryl which is substituted with lower alkoxy substituted with hydroxy;

$R_q^1$ is aryl which is substituted with lower alkoxy substituted with formyl;

$R_r^1$ is aryl which is substituted with lower alkoxy substituted with cyano-substituted aryl;

$R_s^1$ is aryl which is substituted with lower alkoxy substituted with tetrazolyl-substituted aryl;

$R_t^4$ is lower alkoxy substituted with amino;

$R_u^4$ is lower alkoxy substituted with guanidino;

$R_t^1$ is aryl which is substituted with lower alkoxy substituted with protected amino, N-protected amino(lower)alkanoylamino, N-protected piperazinylcarbonyl or N-protected guanidino;

$R_u^1$ is aryl which is substituted with lower alkoxy substituted with amino, amino(lower)alkanoylamino, piperazinylcarbonyl or guanidino;

$R_v^1$ is aryl which is substituted with lower alkoxy substituted with phenoxycarbonylamino;

$R_w^1$ is aryl which is substituted with lower alkoxy substituted with N-lower alkylpiperazinylcarbonylamino, dimethylaminopiperidylcarbonylamino, carbamoylamino or dimethylcarbamoylamino; and $R_e^3$ is lower alkoxy which is substituted with carbamoyl optionally substituted with lower alkyl.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The "higher" is intended to mean 7 to 20 carbon atoms, unless otherwise provided.

The lower moiety in the terms "cyclo(lower)alkyl" and "cyclo(lower)alkyloxy" is intended to mean a group having 3 to 6 carbon atoms.

The lower moiety in the terms "lower alkenyl", "lower alkenyloxy" and "lower alkynyl" is intended to mean a group having 2 to 6 carbon atoms.

The term "alkoxy" may included lower alkoxy and higher alkoxy.

Suitable "lower alkoxy" and lower alkoxy moiety in the terms "acyl(lower)alkoxy", "acyl(lower)alkoxyimino", "esterified carboxy(lower)alkoxyimino", "carboxy(lower)alkoxyimino", "N-containing heterocycliccarbonyl(lower)alkoxyimino", "carbamoyl(lower)alkoxyimino", "lower alkylcarbamoyl-(lower) alkoxyimino", "lower alkoxycarbonyl" and "ar(lower)alkoxy" may be straight or branched $C_1$–$C_6$ alkoxy such as methoxy, ethoxy, propoxy, isopropoxy, methylpropoxy, butoxy, isobutoxy, tert-butoxy, pentyloxy, hexyloxy or the like.

Suitable "higher alkoxy" may be straight or branched $C_7$–$C_{20}$ alkoxy such as heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, methylheptyloxy, methyloctyloxy, methylnonyloxy, methyldecyloxy, ethylheptyloxy, ethyloctyloxy, ethylnonyloxy, ethyldecyloxy or the like, in which preferable one is heptyloxy.

Suitable "lower alkyl" and lower alkyl moiety in the terms "acyl(lower)alkylsulfinyl", "acyl(lower)alkyl-sulfonyl", "lower alkylamino(lower)alkylcarbamoyloxy", "acyl (lower)alkylamino", "N-protected-acyl(lower)-alkylamino", "N-acyl(lower)alkyl-N-lower alkylamino", "lower alkylhydrazinocarbonylamino", "esterified carboxy (lower)alkylamino", "N-protected-esterified carboxy(lower) alkylamino", "N-esterified carboxy(lower)alkyl-N-lower alkylamino", "carboxy(lower)alkylamino", "N-protected-carboxy(lower)-alkylamino", "N-carboxy(lower)alkyl-N-lower alkylamino", "lower alkylcarbamoyl", "lower alkylcarbamoyl(lower)alkanoyloxy", "lower alkylcarbamoyl(lower)alkoxyimino", "lower alkylthio", "N-protected-(substituted or unsubstituted N-containing heterocyclic)carbonyl(lower)alkylamino", "N-protected-carbamoyl (lower)alkylamino", "N-protected-substituted or unsubstituted lower alkylcarbamoyl(lower)alkylamino", "N-(substituted or unsubstituted N-containing heterocyclic) carbonyl(lower)alkyl-N-lower alkylamino", "N-carbamoyl (lower)alkyl-N-lower alkylamino", "N-lower alkylcarbamoyl-N-lower alkylamino", "lower alkylcarbamoyl-(lower) alkoxyimino", "1-hydroxy(lower) alkyl", "1-(lower alkyl)amino(lower)alkyl", "mono(lower) alkylamino", "acyl(lower)alkyl", "di(lower)alkylamino", "lower alkylsulfinyl", "lower alkylsulfonyl", "lower alkylamino", "amino(lower)alkylamino", "N-protected amino(lower)alkylamino", "lower alkylsulfonyloxy", "amino(lower)alkylsulfonyl", "N-protected amino(lower) alkylsulfonyl", "lower alkylaminosulfonyl", "amino(lower) alkylsulfinyl" and "N-protected amino(lower)alkylsulfinyl" may be straight or branched $C_1$–$C_6$ alkyl such as methyl, ethyl, propyl, isopropyl, butyl, isobutyl, tert-butyl, pentyl, ethylpropyl, hexyl or the like.

Suitable "cyclo(lower)alkyl" and cyclo(lower) alkyl moiety in the term "cyclo(lower)alkyloxy" may be cyclo ($C_3$–$C_6$)alkyl such as cyclopropyl, cyclobutyl, cyclopentyl or cyclohexyl, in which preferable one is cyclopentyl or cyclohexyl.

Suitable "lower alkenyl" and lower alkenyl moiety in the term "lower alkenyloxy" may be straight and branched $C_2$–$C_6$ alkenyl such as ethenyl, propenyl, pentenyl, isopropenyl, butenyl, hexenyl or the like, in which preferable one is ethenyl, propenyl, pentenyl or hexenyl.

Suitable "lower alkynyl" may be straight and branched $C_2$–$C_6$ alkynyl such as ethynyl, propargyl, butynyl or the like, in which preferable one is butynyl.

Suitable "aryl" and aryl moiety in the terms "haloaryl", "arylsulfonyl", "acyl-substituted aryl", "ar(lower)alkoxy", "substituted ar(lower)alkoxy" and "arylsulfonyloxy" may be phenyl, naphthyl, phenyl substituted with lower alkyl [e.g. tolyl, xylyl, mesityl, cumenyl, di(tert-butyl)phenyl, etc.] and the like, in which preferable one is phenyl, tolyl or xylyl.

Suitable "substituted aryl" may be aryl substituted with suitable substituent(s) such as acyl, substituted acyl, N-protected piperazinylsulfonyl, piperazinylsulfonyl, N-lower alkylpiperazinylsulfonyl, hydroxy(lower)alkyl, a heterocyclic(lower)alkyl, halogen, nitro, amino, lower alkylamino, a heterocyclic group [e.g. thiazolyl, oxazolyl, tetrazolyl, oxazolinyl, pyridyl, pyrimidinyl, pyrrolyl optionally substituted with lower alkyl and cyano, etc.], cyano, lower alkoxy or the like, in which preferable one for the substituent of alkoxy for $R^1$ is aryl substituted with N-methylpiperazinylsulfonyl, N-t-butoxycarbonyl-piperazinylsulfonyl, piperazinylsulfonyl, carboxy, esterified carboxy, N-lower alkylpiperazinylcarbonyl, lower alkanoyl, hydroxy(lower)alkyl, N-lower alkyl-piperazinyl (lower) alkyl, thiazolyl, oxazolyl, tetrazolyl, oxazolinyl, pyridyl, pyrimidinyl, pyrrolyl substituted with lower alkyl and cyano, cyano, lower alkoxy, lower alkylaminopiperidylcarbonyl, and preferable one for $R^4$ is aryl substituted with halogen, nitro, amino, lower alkylamino or lower alkoxy.

Suitable "halogen" and halo moiety in the term "haloaryl" may be fluorine, chlorine, bromine and iodine, in which preferable one is chlorine or bromine.

Suitable "lower alkylamino" and lower alkylamino moiety in the terms "lower alkylamino(lower)-alkylcarbamoyloxy", "acyl(lower)alkylamino", "esterified carboxy(lower)alkylamino", "carboxy(lower)alkylamino", "N-containing heterocycliccarbonyl(lower)alkylamino", "carbamoyl(lower)alkylamino", "lower alkylcarbamoyl-(lower) alkylamino" "amino(lower)alkylamino", "N-protected amino(lower)alkylamino", "lower alkylaminosulfonyl" and "lower alkylaminopiperidylcarbonyl" may be mono or di(lower alkyl)amino such as methylamino, ethylamino, propylamino, isopropylamino, butylamino, tert-butylamino, isobutylamino, pentylamino, hexylamino, dimethylamino, diethylamino, dipropylamino, dibutylamino, diisoprophyamino, dipentylamino, dihexylamino, N-methylethylamino or the like, in which preferable one is methylamino, dimethylamino or diethylamino.

Suitable "1-hydroxy(lower)alkyl" may be 1-hydroxy-($C_1$–$C_6$) alkyl such as hydroxymethyl, 1-hydroxyethyl, 1-hydroxypropyl, 1-hydroxybutyl, 1-hydroxy-3-methylpropyl or the like, in which preferable one is hydroxymethyl or 1-hydroxyethyl.

Suitable "1-(lower alkyl)amino(lower)alkyl" may be 1-mono or di($C_1$–$C_6$ alkyl)amino($C_1$–$C_6$)alkyl such as methylaminomethyl, dimethylaminomethyl, 1-methylaminoethyl, 1-dimethylaminoethyl, ethylaminomethyl, 1-ethylaminoethyl or the like, in which preferable one is methylaminomethyl, dimethylaminomethyl, 1-methylaminoethyl or 1-dimethylaminoethyl.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidaxolyl, pyrazolyl, pyridyl, pyrimidinyl, pyrazinyl, pyridazinyl, triazolyl, [e.g. 4H-1,2, 4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 7-membered heteromonocyclic group containing 1 to 4 nitrogen atoms [e.g. pyrrolidinyl, imidazolidinyl, piperidyl, piperazinyl, homopiperazinyl, etc.]; unsaturated condensed heterocyclic group containing 1 to 5 nitrogen atoms, for example, indolyl, isoindolyl, indolizinyl, benzimidazolyl,quinolyl, isoquinolyl, imidazopyridyl, indazolyl, benzotriazolyl, tetrazolo-pyridazinyl [e.g. tetrazolo[1,5-b]pyridazinyl, etc.], etc.; unsaturated 3 to 6-membered heteromonocyclic group containing an oxygen atom, for example, pyranyl, furyl, etc.; saturated 3 to 6-membered heteromonocyclic group containing an oxygen atom, for example, 1H-tetrahydropyranyl, tetrahydrofuranyl, etc.; unsaturated, 3 to 6-membered heteromonocyclic group containing 1 to 2 sulfur atoms, for example, theinyl, etc.; unsaturated 3 to 6-membered heteromonocyclic group containing 1 to 2 oxygen atoms and 1 to 3 nitrogen atoms, for example, oxazolyl, isoxazolyl, oxadiazolyl, [e.g. 1,2,4-oxadiazolyl, 1,3,4-oxadiazolyl, 1,2,5-oxadiazolyl, etc.], oxazolinyl [e.g. 2-oxazolinyl, etc.], etc.; saturated 3 to 6-membered heteromonocyclic group containing 1 to 2 oxygen atoms and 1 to 3 nitrogen atoms [e.g. morpholinyl, etc.]; unsaturated condensed heterocyclic group containing 1 to 2 oxygen atoms and 1 to 3 nitrogen atoms [e.g. benzofurazanyl, benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl, [e.g., 1,2,4-thiadiazolyl, 1,3,4-thiadiazolyl, 1,2,5-thiadiazolyl, etc.], etc.; saturated 3 to 6-membered heteromonocyclic group containing 1 to 2 sulfur atoms and 1 to 3 nitrogen atoms [e.g., thiazolidinyl, etc.]; unsaturated condensed heterocyclic group containing 1 to 2 sulfur atoms and 1 to 3 nitrogen atoms [e.g., benzothiazolyl, benzothiadiazolyl, etc.]; unsaturated condensed heterocyclic group containing 1 to 2 oxygen atoms [e.g. benzofuranyl, benzodioxolyl, etc.]and the like.

Said "heterocyclic group" may be substituted with lower alkyl as exemplified above or oxo, in which preferable one is N-methylpiperazinyl, tetrazolyl, morpholinyl, pyrrolidinyl, N-methylpiperidyl, N-methylhomopiperazinyl, 1H-tetrahydropyranyl, thienyl, pyridyl, piperidyl or oxopiperidyl.

Suitable acyl and acyl moiety in the terms "acyl(lower) alkylsulfinyl", "acyl(lower)alkylsulfonyl", "acyloxy", "acylamino", "acyl(lower)alkanoyloxy", "acyl(lower) alkoxyimino", "acyl(lower)alkylamino", "N-protected-acyl (lower)alkylamino", "N-acyl(lower)alkyl-N-lower alkylamino" and "acyl(lower)alkoxy" may be carboxy, esterified carboxy, carbamoyl, lower alkylcarbamoyl, lower alkanoyl, aroyl, a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, tert-butoxycarbonyl, hexyloxycarbonyl, 2-iodoethoxycarbonyl, 2,2,2-trichloroethoxycarbonyl, dimethylaminopropoxycarbonyl, dimethylaminoethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g.benzyloxycarbonyl, phenethyloxycarbonyl, benzhydryloxycarbonyl, 4-nitrobenzyloxycarbonyl, 3-methoxy-4-nitrobenzyloxy-carbonyl, etc.], N-containing heterocyclicoxycarbonyl [e.g. N-methylpiperidyloxycarbonyl, etc.]and the like, in which preferable one is lower alkoxycarbonyl, N-methylpiperidyloxycarbonyl, dimethylaminopropoxycarbonyl or dimethylaminoethoxycarbonyl.

The lower alkylcarbamoyl may be mono or di(lower alkyl) carbamoyl such as methylcarbamoyl, ethylcarbamoyl, propylcarbamoyl, dimethylcarbamoyl, diethylcarbamoyl, N-methyl-N-ethylcarbamoyl or the like.

The lower alkanoyl may be substituted or unsubstituted $C_1$–$C_6$ alkanoyl such as formyl, acetyl, propionyl, butyryl, isobutyryl, valeryl, isovaleryl, pivaloyl, hexanoyl, trifluoroacetyl or the like, in which preferable one is formyl, acetyl or butyryl.

The aroyl may be benzoyl, naphthoyl, toluoyl, di(tert-butyl)benzoyl and the like, in which preferable one is benzoyl.

The heterocyclic moiety in the terms "a heterocycliccarbonyl", "heterocyclicoxycarbonylamino" and "heterocyclicsulfonyl" may be one mentioned above as a heterocyclic group.

Preferred "a heterocycliccarbonyl" may be N-containing heterocycliccarbonyl.

The "N-containing heterocycliccarbonyl" may be one containing at least one nitrogen atom in heterocyclic group mentioned above, in which preferable one is N-(lower alkyl)piperazinylcarbonyl (e.g. N-methyl-piperazinylcarbonyl, etc.), N-(lower alkyl)-homopiperazinylcarbonyl (e.g. N-methylhomopiperazinylcarbonyl, etc.), piperazinylcarbonyl, pyrrodinylcarbonyl, piperidylcarbonyl, morpholinocarbonyl, lower alkylpiperidylcarbonyl (e.g. methylpiperidylcarbonyl, etc.) or oxopiperidylcarbonyl.

Suitable "substituted acyl" may be carbamoyl substituted with amino, a heterocyclic group [e.g. N-(lower alkyl) piperazinyl, pyridyl, etc.], lower alkylsulfonyl or arysulfonyl, substituted lower alkylcarbamoyl [e.g. N-lower alkylamino-N-lower alkylcarbamoyl, pyridyl(lower) alkylcarbamoyl, morpholino(lower)alkylcarbamoyl, bis [hydroxy(lower)alkyl]carbamoyl, hydroxy(lower) alkylcarbamoyl, carbamoyl(lower)alkylcarbamoyl, lower alkylamino(lower)alkylcarbamoyl, N-lower alkyl-N-lower alkylcarbamoyl, etc.], substituted N-containing heterocycliccarbonyl [e.g. trifluoroacetyl-piperazinylcarbonyl, pyridylpiperazinylcarbonyl, hydroxypiperidylcarbonyl, dimethylaminopiperidylcarbonyl, diethylaminopiperidylcarbonyl, carbamoylpyrrolidinylcarbonyl, dimethylaminopiperazinylcarbonyl, hydroxyethoxyethyl-piperazinylcarbonyl, pyrrolidinylcarbonylmethyl-piperazinylcarbonyl, etc.], N-protected-N-containing heterocycliccarbonyl [e.g. N-t-butoxycarbonylpiperidyl-carbonyl, N-t-butoxycarbonylpiperazinylcarbonyl, etc.], N-protected amino(lower)alkanoyl, amino(lower)alkanoyl, benzyloxybenzoyl, and the like.

"N-Protective group" in "protected amino" may be common N-protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.],substituted or unsubstituted aralkyloxycarbonyl [e.g. benzyloxycarbonyl, p-nitrobenzyloxycarbonyl, etc.], 9-fluorenylmethoxycarbonyl, substituted or unsubstituted arenesulfonyl [e.g. benzenesulfonyl, tosyl, etc.], nitrophenylsulfenyl, aralkyl [e.g. trityl, benzyl, etc.]or the like, in which preferable one is phthaloyl, tert-butoxycarbonyl or 9-fluorenylmethoxycarbonyl.

"N-protective group" in "N-protected guanidino" may be common N-protective group such as lower alkoxycarbonyl [e.g. tert-butoxycarbonyl, etc.]or the like.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Suitable "lower alkylsulfonyl" and lower alkylsulfonyl moiety in the term "lower alkylsulfonyloxy" may be ($C_1$–$C_6$)alkylsulfonyl such as methylsulfonyl, ethylsulfonyl, propylsulfonyl or the like, in which preferable one is methylsulfonyl.

Suitable "lower alkylene" may be straight or branched $C_1$–$C_6$ alkylene such as methylene, ehtylene, propylene or the like, in which preferable one is methylene or ethylene.

Suitable "lower alkenylene" may be straight or branched $C_2$–$C_6$ alkenylene such as ethenylene, propenylene or the like, in which preferable one is ethenylene.

The substitutent(s) on aryl for $R^1$ may be plural and in such case the substitutents may be the same or different.

Preferred "aryl" for $R^1$ may be phenyl or phenyl substituted with lower alkyl.

Preferred "cyclo(lower)alkyl" for $R^1$ may be cyclopentyl.

Preferred "a heterocyclic group" for $R^1$ may be pyridyl or thienyl.

Preferred compound (I) is one having aryl (more preferably phenyl or phenyl substituted with lower alkyl) which may be substituted with lower alkoxy optionally substituted with acylamino or acyl for $R^1$, lower alkyl for $R^2$, hydrogen, lower alkyl or lower alkoxy for $R^3$, hydroxy, or lower alkoxy, lower alkylthio or lower alkyl, each of which may be substituted with hydroxy, aryl, substituted aryl, acyl, amino, lower alkylamino, acylamino, protected amino or a heterocyclic group for $R^4$, hydrogen, lower alkyl, lower alkoxy or halogen for $R^5$, NH for A,

for E, —CH=CH— for X, and CH for Y.

More preferred compound (I) is one having phenyl or tolyl, each of which is substituted with lower alkoxy substituted with N-(lower alkyl)piperazinylcarbonyl for $R^1$, lower alkyl for $R^2$, hydrogen, lower alkyl or lower alkoxy for $R^3$, lower alkoxy substituted with amino for $R^4$, hydrogen for $R^5$, NH for A,

for E, —CH=CH— for X and CH for Y.

Most preferred compound (I) is one having tolyl which is substituted with lower alkoxy substituted with N-(lower alkyl)piperazinylcarbonyl for $R^1$, lower alkyl for $R^2$, lower alkoxy for $R^3$, lower alkoxy substituted with amino for $R^4$, hydrogen for $R^5$, NH for A,

for E, —CH=CH— for X and CH for Y.

Suitable pharmaceutically acceptable salts of the object compound (I) are conventional non-toxic salts and include an acid addition salt such as an inorganic acid addition salt [e.g. hydrochloride, hydrobromide, sulfate, phosphate, etc. ], an organic acid addition salt [e.g. formate, acetate, trifluoroacetate, maleate, tartrate, methanesulfonate, benzenesulfonate, toluenesulfonate, etc. ], a metal salt such as an alkali metal salt [e.g. sodium salt, potassium salt, etc. ] and an alkaline earth metal salt [e.g. calcium salt, magnesium salt, etc. ] and the like.

The processes for preparing the object compound (I) are explained in detail in the following.

Process 1

The object compound (Ia) or its salt can be prepared by reacting a compound (II) or its salt with a compound (III) or its reactive derivative at the carboxy group or the sulfo group, or a salt thereof.

Suitable salts of the compounds (Ia) and (II) may be the same as those exemplified for the compound (I).

Suitable salts of the compound (III) and its reactive derivative at the carboxy group or the sulfo group may be base salts as exemplified for the compound (I).

Suitable reactive derivative at the carboxy group or the sulfo group of the compound (III) may include an acid halide, an acid anhydride containing intramolecular, intermolecular and a mixed ones, an activated amide, an activates ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc. ], dialkylphosphorous acid, sulfurous acid, thiosulfuric acid, sulfuric acid, sulfonic acid, [e.g. methanesulfonic acid, etc. ], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc. ] or aromatic carboxylic acid [e.g. benzoic acid, etc. ]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2\overset{+}{N}$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc. ] or an ester with an N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc. ], and the like. These reactive derivatives can optionally be selected from them according to the kind of the compound (III) to be used.

The reaction is usually carried out in a conventional solvent such as water, alcohol [e.g. methanol, ethanol, etc. ], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (III) is used in a free acid form or its salt form, the reaction is preferably carried out in the presence of a conventional condensing agent such a N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'- (3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenylphosphoryl azide; diphenyl chlorophosphate; diphenylphosphinic chloride; thionyl chloride; oxalyl chloride; lower alkyl haloformate [e.g. ethyl chloroformate, isopropyl chloroformate, etc. ]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; of the like.

The reaction may also be carried out in the presence of an inorganic or organic base such as an alkali metal bicarbonate, tri(lower)alkylamine, pyridine, 4-dimethylaminopyridine, N-(lower)alkylmorpholine, N,N-di(lower)alkylbenzylamine, or the like.

The reaction temperature is not critical, and the reaction is usually carried out under cooling to heating.

Process 2

The object compound (I) or its salt can be prepared by reacting a compound (IV) or its salt with a compound (V) or its reactive derivative at the carboxy group or a salt thereof.

Suitable salts of the compounds (IV) and (V) and its reactive derivative at the carboxy group may be the same as those exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

Process 3

The object compound (Ic) or its salt can be prepared by subjecting a compound (Ib) or its salt to deesterification reaction.

Suitable salt of the compound (Ic) may be the same as those exemplified for the compound (I).

Suitable salt of the compound (Ib) may be an acid addition salt as exemplified for the compound (I).

The reaction is carried out in accordance with a conventional method such as hydrolysis, reduction or the like.

The hydrolysis is preferably carried out in the presence or a base or an acid including Lewis acid. Suitable base may include an inorganic base and an organic base such as an alkali metal [e.g. lithium, sodium, potassium, etc. ], an alkaline earth metal [e.g. magnesium, calcium, etc. ], the hydroxide or carbonate or bicarbonate thereof, trialkylamine, [e.g. trimethylamine, triethylamine, etc. ], picoline, 1,5-diazabicyclo[4.3.0]-non-5-ene, 1,4-diazabicyclo[2.2.2]octane, 1,8-diazabicyclo[5.4.0]undec-7ene, or the like. Suitable acid may include an organic acid [e.g. formic acid, acetic acid, propionic acid, trichloroacetic acid, trifluoroacetic acid, hydrobromic acid, hydroiodic acid, sulfuric acid, etc. ] and Lewis acid [e.g. boron tribromide, etc. ].

The reaction is usually carried out in a solvent such as water, an alcohol [e.g. methanol, ethanol, etc. ], xylene, diethylene glycol monoethyl ethyl, methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalitic reduction.

Suitable reducing agents to be used in chemical reduction are a combination of metal [e.g. tin, zinc, iron, etc. ] or metallic compound [e.g. chromium chloride, chromium acetate, etc. ] and an organic or inorganic acid [e.g. formic acid, acetic acid, propionic acid, trifluoroacetic acid, p-toluenesulfonic acid, hydrochloric acid, hydrobromic acid, etc. ].

Suitable catalysts to be used in catalytic reduction are conventional ones such as platinum catalysts [e.g. platinum plate, spongy platinum, platinum black, colloidal platinum, platinum oxide, platinum wire, etc. ], palladium catalyst [e.g. spongy palladium, palladium black, palladium oxide, palladium on carbon, colloidal palladium, palladium on barium sulfate, palladium on barium carbonate, etc. ], nickel catalyst [e.g. reduced nickel, nickel oxide, Raney nickel, etc. ], cobalt catalyst [e.g. reduced cobalt, Raney cobalt, etc. ], iron catalyst [e.g. reduced iron, Raney iron, etc. ], copper catalyst [e.g. reduced copper, Raney copper, Ullman copper, etc. ] or the like.

The reduction is usually carried out in a conventional solvent which does not adversely influence the reaction such as water, an alcohol [e.g. methanol, ethanol, proponal, etc. ], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional; solvent such a diethyl ether, dioxane, tetrahydrofuran, etc., or a mixture thereof.

The reaction temperature of this reduction is not critical and the reaction is usually carried out under cooling to warming.

In this reaction, in case that the compound (Ib) having lower alkyl substituted with esterified carboxy for $R^2$ and/or acyloxy, lower alkoxy substituted with esterified carboxy, lower alkylthio substituted with esterified carboxy, or lower alkyl substituted with esterified carboxy for $R^4$ is used as a starting compound, the compound (Ic) having lower alkyl substituted with carboxy for $R^2$ and/or hydroxy, lower alkoxy substituted with carboxy, lower alkylthio substituted with carboxy, or lower alkyl substituted with carboxy for $R^4$ may be obtained according to reaction condition. This case is included within the scope of this reaction.

Process 4

The object compound (Ie) or its salt can be prepared by subjecting a compound (Id) or its salt to deesterification reaction.

Suitable salt of the compound (Id) may be an acid addition salt as exemplified for the compound (I).

Suitable salt of the compound (Ie) may be the same as those exemplified for the compound (I).

This reaction can be carried out in substantially the same manner as hydrolysis in Process 3, and therefore the reaction mode and reaction condition (e.g. solvent, reaction temperature, etc. ) of this reaction are to be referred to those as explained in hydrolysis in Process 3.

In this reaction, in case that the compound (Id) having aryl, haloaryl, cyclo(lower)alkyl or a heterocyclic group, each of which is substituted with esterified carboxy, lower alkenyl substituted with esterified carboxy, lower alkyl substituted with esterified carboxy, esterified carboxy(lower)alkanoyloxy or esterified carboxy(lower)alkoxyimino; lower alkylthio substituted with esterified carboxy; alkoxy substituted with esterified carboxy-substituted aryl, esterified carboxy-substituted pyridyl, esterified carboxy(lower)alkylamino, N-protected-esterified carboxy(lower)alkylamino, N-esterified carboxy(lower)alkyl-N-lower alkylamino, esterified carboxy or esterified carboxy(lower)alkoxyimino; or lower alkenyloxy substituted with esterified carboxy for $R^1$ and/or lower alkyl substituted with esterified carboxy for $R^2$ is used as a starting compound, the compound (Ie) having aryl, haloaryl, cyclo(lower)alkyl or a heterocyclic group, each of which is substituted with carboxy; lower alkenyl substituted with carboxy; lower alkyl substituted with carboxy, carboxy(lower)alkanoyloxy or carboxy(lower)alkoxyimino; lower alkylthio substituted with carboxy; alkoxy substituted with carboxy-substituted aryl, carboxy-substituted pyridyl, carboxy(lower)-alkylamino, N-protected-carboxy(lower)alkylamino, N-carboxy(lower)alkyl-N-lower alkylamino, carboxy or carboxy(lower)alkoxyimino; or lower alkenyloxy substituted with carboxy for $R^1$ and/or lower alkyl substituted with carboxy for $R^2$ may be obtained according to reaction condition. This case is included within the scope of this reaction.

Process 5

The object compound (Ig) or its salt can be prepared by subjecting a compound (If) or its salt to elimination reaction of the N-protective group.

Suitable salts of the compounds (If) and (Ig) may be acid addition salts as exemplified for the compound (I).

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, alkylamine [e.g. methylamine, trimethylamine, triethylamine, etc.], picoline, 1,5-diazabicyclo[4.3.0]non-5-ene, 1,4-diazabicyclo[2.2.2]octane, 1,8-diazabicyclo[5.4.0] undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence or cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compounds [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the N-protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

In this reaction, in case that the compound (If) having aryl which is substituted with alkoxy substituted with protected amino, N-protected amino(lower)alkanoylamino, N-protected piperazinylcarbonyl or N-protected guanidino for $R^1$ is used as a starting compound, the compound (Ig) having aryl which is substituted with alkoxy substituted with amino, amino(lower)alkanoylamino, piperazinylcarbonyl or guanidino for $R^1$ may be obtained according to reaction condition. This case is included within the scope of this reaction.

Process 6

The object compound (Ih) or its salt can be prepared by reacting a compound (Ic) or its reactive derivative at the carboxy group or a salt thereof with an amine or its salt.

Suitable salt of amine may be an acid addition salt as exemplified for the compound (I).

Suitable salts of the compounds (Ih) and (Ic) and its reactive derivative at the carboxy group may be the same as those exemplified for the compound (I).

Suitable "amine" may be ammonia, substituted or unsubstituted lower alkylamine, substituted or unsubstituted N-containing heterocyclic compound, a heterocyclic group substituted with amino and the like.

The substituted or unsubstituted lower alkylamine may be mono or di(lower)alkylamine (e.g. methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine, etc.), pyridyl(lower)alkylamine, (e.g. pyridylmethylamine, etc.), lower alkylamino(lower)alkylamine (e.g. N-dimethylaminoethylamine, N-dimethylaminopropylamine, N-diethylaminoethyl-N-methylamine, etc.), morpholino(lower)alkylamine (e.g. morpholinoethylamine, etc.) or the like.

The substituted or unsubstituted N-containing heterocyclic compound may be a heterocyclic group substituted with amino (e.g. aminopyridine, N-methyl-N'-aminopiperazine, etc.), saturated 5 or 6-membered N-, or N- or S-, or N- and O-containing heterocyclic compound such as pyrrolidine, imidazolidine, piperidine, piperidone, piperazine, lower alkylaminopiperidine (e.g. dimethylaminopiperidine, etc.), N-(lower)alkylhomopiperazine (e.g. N-methylhomopiperazine, etc.), N-(lower)alkylpiperazine (e.g. N-methylpiperazine, N-ethylpiperazine, etc.), morpholine, thiomorpholine, N-pyridylpiperazine, N-hydroxy(lower)alkoxy(lower)-alkylpiperazine (e.g. N-hydroxyethoxyethylpiperazine, etc.), N-pyrrolidinylcarbonyl(lower)alkylpiperazine (e.g. N-pyrrodidinylcarbonylmethylpiperazine, etc.), or the like, in which preferable one is N-methylpiperazine.

This reaction can be carried out in substantially the same manner as Process 1, and therefore the reaction mode and reaction condition (e.g. solvent, reaction temperature, etc.) of this reaction are to be referred to those as explained in Process 1.

Process 7

The object compound (Ii) or its salt can be prepared by reacting a compound (Ie) or its reactive derivative at the carboxy group or a salt thereof with an amine or its salt.

Suitable salt of amine may be an acid addition salt as exemplified for the compound (I).

Suitable salts of the compounds (Ii) and (Ie) and its reactive derivative at the carboxy group may be the same as those exemplified for the compound (I).

This reaction can be carried out in substantially the same manners as Processes 1 and 6, and therefore the reaction mode and reaction condition (e.g. amine, solvent, reaction temperature, etc.) of this reaction are to be referred to those as explained in Processes 1 and 6.

Process 8

The object compound (Ik) or its salt can be prepared by subjecting a compound (Ij) or its salt to debenzylation reaction.

Suitable salts of the compounds (Ij) and (Ik) may be the same as those exemplified for the compound (I).

This reaction can be carried out in substantially the same manner as hydrolysis using an acid or catalytic reduction in Process 5, and therefore the reaction mode and reaction condition (e.g. solvent, reaction temperature, etc.) of this reaction are to be referred to those as explained in hydrolysis using an acid or catalylic reduction in Process 5.

In this catalytic reduction, in case that the compound (Ij) having nitro for $R^3$ is used as a starting compound, the compound (Ik) having amino for $R^3$ may be obtained according to reaction condition. This case is included within the scope of this reaction.

Process 9

The object compound (Il) or its salt can be prepared by reacting a compound (Ika) or its salt with a compound (VI) or its salt.

Suitable salts of the compounds (Ika), (Il) and (VI) may be the same as those exemplified for the compound (I).

When the compound (VI) having halogen for $Z^1$ is used in this reaction, the reaction is preferably carried out in the presence of a base such as an alkali metal (e.g. sodium, potassium, etc.), an alkaline earth metal (e.g. magnesium, calcium, etc.), the hydride or hydroxide or carbonate or bicarbonate thereof.

When the compound (VI) having hydroxy for $Z^1$ is used in this reaction, the reaction is preferably carried out in the presence of diethyl azodicarboxylate and triphenylphosphine.

The reaction is usually carried out in a conventional solvent which does not adversely influence the reaction such as water, dioxane, alcohol (e.g. methanol, ethanol, etc.), acetonitrile, tetrahydrofuran, acetic acid, N,N-dimethylformamide, or a mixture thereof.

The reaction temperature is not critical and the reaction can be carried out under cooling to heating.

Process 10

The object compound (Im) or its salt can be prepared by reacting a compound (Iga) or its salt with an acylating agent.

Suitable salts of the compounds (Iga) and (Im) may be the same as those exemplified for the compound (I).

The acylating agent may include an organic acid represented by the formula: $R^{11}$-OH, in which $R^{11}$ is acyl or substituted acyl as illustrated above, or its reactive derivative.

The suitable reactive derivative of organic acid may be a conventional one such as an acid halide [e.g. acid chloride, acid bromide, etc.], an acid azide, an acid anhydride containing intramolecular and intermolecular ones, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, pyridine, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, sodium hydroxide or the like.

The reaction temperature is not critical, and the reaction can be carried out under cooling to heating.

Process 11

The object compound (In) or its salt can be prepared by reacting a compound (Igb) or its salt with lower alkanal or N-protected amino(lower)alkanal in the presence of a reducing agent.

Suitable salts of the compounds (Igb) and (In) may be the same as those exemplified for the compound (I).

Suitable lower alkanal may be $C_1$–$C_6$ alkanal such as formaldehyde, ethanal, propanal or the like, in which preferable one is formaldehyde.

Suitable N-protected amino(lower)alkanal may be N-protected amino($C_1$–$C_6$)alkanal such as phthalimidopropanal or the like.

Suitable reducing agent may be diborane, borane-organic amine complex [e.g. borane-pyridine complex, etc.], alkali metal cyanoborohydride [e.g. sodium cyanoborohydride, lithium cyanoborohydride, etc.], sodium borohydride and the like.

The reaction is preferably carried out in the presence of molecular sieves.

The reaction is usually carried out in a conventional solvent such as water, an alcohol [e.g. methanol, ethanol, etc.], dioxane, tetrahydrofuran, a mixture thereof or any other organic solvent which does not adversely influence the reaction.

The reaction may also be carried out in an acidic condition [e.g. presence of acetic acid, sulfuric acid, etc.] and the reaction temperature is not critical, and the reaction is usually carried out under cooling to warming.

Process 12

The object compound (Ip) or its salt can be prepared by subjecting a compound (Io) or its salt to reduction.

Suitable salts of the compounds (Io) and (Ip) may be the same as those exemplified for the compound (I).

The reduction may include chemical reduction and catalytic reduction, which are carried out in a conventional manner.

Suitable reducing agents to be used in chemical reduction are a metal [e.g. thin, zinc, iron, nickel, etc.], a combination of such metal and/or metallic compound [e.g. nickel chloride, chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, and alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under cooling to heating.

Process 13

The object compound (Ir) or its salt can be prepared by subjecting a compound (Iq) or its salt to deacylation reaction.

Suitable salts of the compounds (Iq) and (Ir) may be the same as those exemplified for the compound (I).

This reaction can be carried out in substantially the same manner as Process 3, and therefore the reaction mode and reaction condition (e.g. solvent, reaction temperature, etc.) of this reaction are to be referred to those as explained in Process 3.

Process 14

The object compound (Is) or its salt can be prepared by reacting a compound (VII) or its salt with a compound (VIII) or its salt.

Suitable salts of the compounds (Is), (VII) and (VIII) may be the same as those exemplified for the compound (I).

This reaction can be carried out in substantially the same manner as Process 9, and therefore the reaction mode and reaction condition (e.g. solvent, reaction temperature, etc.) of this reaction are to be referred to those as explained in Process 9.

Process 15

The object compound (Iu) or its salt can be prepared by reacting a compound (It) or its salt with an oxidizing agent.

Suitable salts of the compounds (It) or (Iu) may be the same as those exemplified for the compound (I).

The suitable oxidizing agent may be hydrogen peroxide, Jones reagent, peracid [e.g. peracetic acid, perbenzoic acid, m-chloroperbenzoic acid, etc.], chromic acid, potassium permanganate, alkali metal periodate [e.g. sodium periodate, etc.] and the like.

This reaction is usually carried out in a solvent which does not adversely influence the reaction such as acetic acid, dichloromethane, acetone, ethyl acetate, chloroform, water, an alcohol [e.g. methanol, ethanol, etc.], a mixture thereof or the like.

The reaction temperature is not critical, and the reaction is usually carried out under cooling to warming.

Process 16

The object compound (Iw) or its salt can be prepared by subjecting a compound (Iv) or its salt to catalytic reduction.

Suitable salts of the compounds (Iv) and (Iw) may be the same as those exemplified for the compound (I).

This reaction can be carried out in substantially the same manner as catalytic reduction in Process 5, and threfore the reaction mode and reaction condition (e.g. solvent, reaction temperature, etc.) of this reaction are to be referred to those as explained in catalytic reduction in Process 5.

Process 17

The object compound (Iy) or its salt can be prepared by subjecting a compound (Ix) or its salt to debenzylation reaction.

Suitable salts of the compounds (Ix) and (Iy) may be the same as those exemplified for the compound (I).

This reaction can be carried out in substantially the same manner as Process 8, and therefore the reaction mode and reaction condition (e.g. solvent, reaction temperature, etc.) of this reaction are to be referred to those as explained in Process 8.

Process 18

The object compound (Iz) or its salt can be prepared by reacting a compound (Iy) or its salt with a compound (IX) or its salt.

Suitable salts of the compounds (Iy), (Iz) and (IX) may be the same as those exemplified for the compound (I).

This reaction can be carried out in substantially the same manner as Process 9, and therefore the reaction mode and reaction condition (e.g. solvent, reaction temperature, etc.) of this reaction are to be referred to those as explained in Process 9.

Process 19

The object compound (I-2) or its salt can be prepared by subjecting a compound (I-1) or its salt to elimination reaction of the hydroxy protective group.

Suitable salts of the compounds (I-1) and (I-2) may be the same as those exemplified for the compound (I).

Suitable hydroxy protective group may be benzyloxy, acyloxy, substituted acyloxy or the like.

This reaction can be carried out in substantially the same manner as Processes 8 and 13, and therefore the reaction mode and reaction condition (e.g. solvent, reaction temperature, etc.) of this reaction are to be referred to those as explained in Processes 8 and 13.

Process 20

The object compound (I-3) or its salt can be prepared by reacting a compound (I-2) or its salt with a compound (X) or its salt.

Suitable salts of the compounds (I-2), (I-3) and (X) may be the same as those exemplified for the compound (I).

This reaction can be carried out in substantially the same manner as Process 9, and therefore the reaction mode and reaction condition (e.g. solvent, reaction temperature, etc.) of this reaction are to be referred to those as explained in Process 9.

Process 21

The object compound (I-4) or its salt can be prepared by subjecting a compound (I-3a) or its salt to deesterification reaction.

Suitable salts of the compounds (I-3a) and (I-4) may be the same as those exemplified for the compound (I).

This reaction can be carried out in substantially the same manner as Process 3, and therefore the reaction mode and reaction condition (e.g. solvent, reaction temperature, etc.) of this reaction are to be referred to those as explained in Process 3.

Process 22

The object compound (I-6) or its salt can be prepared by reacting a compound (I-5) or its salt with an alkyne compound in the presence of a palladium compound and a copper compound.

Suitable salts of the compounds (I-5) and (I-6) may be the same as those exemplified for the compound (I).

Suitable alkyne compound may be lower alkyne optionally substituted with hydroxy, amino, protected amino, lower alkylsulfonyl, arylsulfonyl or the like, in which preferable one is 3-butyn-1-ol.

Suitable palladium compound may be bis(triphenylphosphine)palladium(II) chloride, or the like.

Suitable copper compound may be copper(I) iodide, or the like.

The reaction is usually carried out in a conventional solvent which does not adversely influence the reaction such as tetrahydrofuran, dioxane, ethylamine, or a mixture thereof.

The reaction temperature is not critical and the reaction is usually carried out under warming or heating.

Process 23

The object compound (I-8a) or its salt can be prepared by reacting a compound (I-7) or its salt with a compound (XI).

Suitable salts of the compounds (I-7) and (I-8a) may be the same as those exemplified for the compound (I).

The reaction is preferably carried out in the presence of a base such as trialkylamine (e.g. trimethylamine, triethylamine, etc.) or the like.

The reaction is usually carried out in a conventional solvent which does not adversely influence the reaction such as tetrahydrofuran, methylene chloride or the like.

The reaction temperature is not critical and the reaction is usually carried out under cooling to heating.

Process 24

The object compound (I-9) or its salt can be prepared by reacting a compound (I-8) or its salt with alkali metal phthalimide.

Suitable salts of the compounds (I-8) and (I-9) may be the same as those exemplified for the compound (I).

The reaction is carried out in a conventional solvent which does not adversely influence the reaction such as dimethyl sulfoxide, N,N-dimethylformamide, or the like.

The reaction temperature is not critical and the reaction is usually carried out under cooling to heating.

Process 25

The object compound (I-10) or its salt can be prepared by reacting a compound (I-6) or its salt with a reducing agent.

Suitable salts of the compounds (I-6) and (I-10) may be the same as those exemplified for the compound (I).

Suitable reducing agent may be a combination of nickel chloride and sodium borohydride, and the like.

The reaction is carried out in a conventional solvent which does not adversely influence the reaction such as an alcohol (e.g. methanol, ethanol, etc.), tetrahydrofuran, or a mixture thereof.

The reaction temperature is not critical and the reaction is usually carried out under cooling to warming.

Process 26

The object compound (I-11) or its salt can be prepared by reacting a compound (II) or its salt with a compound (XII) or its salt.

Suitable salts of the compounds (I-11), (II) and (XII) may be the same as those exemplified for the compound (I).

This reaction can be carried out in substantially the same manner as Process 11, and therefore the reaction mode and reaction condition (e.g. solvent, reaction temperature, etc.) of this reaction are to be referred to those as explained in Process 11.

Process 27

The object compound (I-13) or its salt can be prepared by reacting a compound (I-12) or its salt with a compound (XIII) in the presence of a base.

Suitable salts of the compounds (I-12) and (I-13) may be the same as those exemplified for the compound (I).

Suitable base may be an alkali metal (e.g. sodium, potassium, etc.), an alkali metal hydride (e.g. sodium hydride), and the like.

The reaction is carried out in a solvent such as N,N-dimethylformamide, tetrahydrofuran, dioxane, a mixture thereof or any other solvent which does not adversely influence the reaction.

The reaction temperature is not critical and the reaction is usually carried out under cooling to warming.

Process 28

The object compound (I-15) or its salt can be prepared by reacting a compound (I-14) or its salt with an acylating agent.

Suitable salts of the compounds (I-14) and (I-15) may be the same as those exemplified for the compound (I).

This reaction can be carried out in substantially the same manner as Process 10, and therefore the reaction mode and reaction condition (e.g. solvent, reaction temperature, etc.) of this reaction are to be referred to those as explained in Process 10.

Process 29

The object compound (I-17) or its salt can be prepared by reacting a compound (I-16a) or its salt with a reducing agent.

Suitable salts of the compounds (I-16a) and (I-17) may be the same as those exemplified for the compound (I).

Suitable reducing agent may be alkali metal borohydride (e.g. sodium borohydride, etc.), and the like.

The reaction is carried out in a solvent such as an alcohol (e.g. methanol, ethanol, etc.), tetrahydrofuran, or the like.

The reaction temperature is not critical and the reaction is usually carried out under cooling to warming.

Process 30

The object compound (I-18) or its salt can be prepared by reacting a compound (I-16) or its salt with an amine compound or its salt in the presence of a reducing agent.

Suitable salts of the compounds (I-16) and (I-18) may be the same as those exemplified for the compound (I).

Suitable amine compound may be ammonia, N-lower alkylpiperazine, and the like.

Suitable salt of amine compound may be an acid addition salt (e.g. acetate, hydrochloride, etc.), and the like.

This reaction can be carried out in substantially the same manner as Process 11, and therefore the reaction mode and reaction condition (e.g. solvent, reaction temperature, etc.) of this reaction are to be referred to those as explained in Process 11.

Process 31

The object compound (I-20) or its salt can be prepared by reacting a compound (I-19) or its reactive derivative at the carboxy group or a salt thereof with lower alkylamino(lower)alkanol.

Suitable salts of the compounds (I-20) and (I-19) and its reactive derivative at the carboxy group may be the same as those exemplified for the compound (I).

Suitable lower alkylamino(lower)alkanol may be dimethylaminoethanol, and the like.

This reaction can be carried out in substantially the same manner as Process 1, and therefore the reaction mode and reaction condition (e.g. solvent, reaction temperature, etc.) of this reaction are to be referred to those as explained in Process 1.

Process 32

The object compound (I-22) or its salt can be prepared by reacting a compound (I-21) or its salt with a reducing agent.

Suitable salts of the compounds (I-21) and (I-22) may be the same as those exemplified for the compound (I).

Suitable reducing agent may be diborane, lithium aluminum hydride and the like.

The reaction is usually carried out in a solvent which does not adversely influence the reaction such as diethyl ether, tetrahydrofuran or the like.

The reaction temperature is not critical and the reaction can be carried out under cooling to heating.

Process 33

The object compound (I-23) or its salt can be prepared by subjecting a compound (I-22) or its salt to oxidation reaction.

Suitable salts of the compounds (I-22) and (I-23) may be the same as those exemplified for the compound (I).

Suitable oxidizing agent used in this reaction may be manganese dioxide, dimethyl sulfoxide, a mixture of dimethyl sulfoxide and oxalyl chloride and the like.

The reaction is usually carried out in a conventional solvent such as pentane, hexane, benzene, diethyl ether, dimethoxyethane, acetone, chloroform, dichloromethane or any other solvent which does not adversely influence the reaction.

Additionally in case that the above-mentioned oxidizing agent is liquid, it can be used as a solvent.

In this reaction, in case that dimethyl sulfoxide or a mixture of dimethyl sulfoxide and oxalyl chloride is used as an oxidizing agent, the reaction is preferably carried out in the presence of alkali metal iodide (e.g. sodium iodide, etc.) and alkali metal carbonate (e.g. sodium carbonate) or tri(lower)alkylamine (e.g. triethylamine, etc.).

The reaction temperature is not critical, and the reaction is usually carried out under cooling to heating.

Process 34

The object compound (I-25) or its salt can be prepared by reacting a compound (I-24) or its salt with an azide compound.

Suitable salts of the compounds (I-24) and (I-25) may be the same as those exemplified for the compound (I).

Suitable azide compound may be sodium azide, trimethyltin azide and the like.

The reaction is usually carried out in a solvent which does not adversely influence the reaction such as dioxane, an aromatic hydrocarbon (e.g. benzene, toluene, xylene) or the like.

The reaction temperature is not critical and the reaction is usually carried out under warming to heating.

Process 35

The object compound (I-27) or its salt can be prepared by reacting a compound (I-26) or its salt with an isourea compound.

Suitable salts of the compounds (I-26) and (I-27) may be the same as those exemplified for the compound (I).

Suitable isourea compound may be O-alkylisourea (e.g. O-methylisourea, etc.) and the like.

The reaction is usually carried out in a solvent which does not adversely influence the reaction such as an alcohol (e.g. methanol, ethanol, etc.) or the like.

The reaction temperature is not critical and the reaction is usually carried out under warming to heating.

Process 36

The object compound (I-29) or its salt can be prepared by subjecting a compound (I-28) or its salt to elimination reaction of the N-protective group.

Suitable salts of the compounds (I-28) and (I-29) may be the same as those exemplified for the compound (I).

This reaction can be carried out in substantially the same manner as Process 5, and therefore the reaction mode and reaction condition (e.g. solvent, reaction temperature, etc.) of this reaction are to be referred to those as explained in Process 5.

Process 37

The object compound (I-31) or its salt can be prepared by reacting a compound (I-30) or its salt with N-lower alkylpiperazine, dimethylaminopiperidine, ammonia or N,N-dimethylformamide.

Suitable salts of the compounds (I-30) and (I-31) may be the same as those exemplified for the compound (I).

The reaction is usually carried out in a solvent which does not adversely influence the reaction such as N,N-dimethylformamide, dioxane or the like.

The reaction temperature is not critical and the reaction is usually carried out under warming to heating.

Process 38

The object compound (I-3a) or its salt can be prepared by reacting a compound (I-4) or its reactive derivative at the carboxy group or a salt thereof with a hydroxy compound or a diazo compound.

Suitable salts of the compounds (I-3a) and (I-4) and its reactive derivative at the carboxy group may be the same as those exemplified for the compound (I).

Suitable reactive derivative at the carboxy group (I-4) may be acid halide (e.g. acid chloride, acid bromide, etc.) and the like.

Suitable hydroxy compound may be an alcohol (e.g. methanol, ethanol, etc.), phenol, naphthol and the like.

Suitable diazo compound may be methyldiazomethane, trimethylsilyldiazomethane and the like.

The reaction is usually carried out in a conventional solvent such as diethyl ether, tetrahydrofuran, dioxane, methylene chloride, or any other organic solvent which does not adversely influence the reaction.

Additionally, in case that the above-mentioned hydroxy compound is in liquid, it can also be used as a solvent.

The reaction temperature is not critical and the reaction is usually carried out under cooling to heating.

Process 39

The object compound (I-32) or its salt can be prepared by reacting a compound (I-4) or its reactive derivative at the carboxy group or a salt thereof with an amine.

Suitable salts of the compounds (I-32) and (I-4) and its reactive derivative at the carboxy group may be the same as those exemplified for the compound (I).

Suitable amine may be ammonia, lower alkylamine (e.g. methylamine, dimethylamine, etc.) and the like.

This reaction can be carried out in substantially the same manner as Process 6, and therefore the reaction mode and reaction condition (e.g. solvent, reaction temperature, etc.) of this reaction are to be referred to those as explained in Process 6.

The compounds obtained by the above processes can be isolated and purified by a conventional method such as pulverization, recrystallization, column chromatography, reprecipitation, or the like.

It is to be noted that the compound (I) and the other compounds may include one or more stereoisomer(s) such as optical isomer(s) or geometrical isomer(s) due to asymmetric carbon atom(s) and double bond(s), and all of such isomers and mixture thereof are included within the scope of this invention.

Additionally, it is to be noted that any hydrate of the compound (I) is also included within the scope of this invention.

The object compound (I) and pharmaceutically acceptable salts thereof possess activities as vasopressin antagonistic activity, vasodilating activity, hypotensive activity, activity for inhibiting saccharide release in liver, activity for inhibiting growth of mesangium cells, water diuretic activity, platelet agglutination inhibitory activity, oxytocin antagonistic activity and the like, and are useful for the treatment and/or prevention of hypertension, heart failure, renal insufficiency, edema, ascites, vasopressin parasecretion syndrome, hepatocirrhosis, hyponatremia, hypokalemia, diabetic, circulation disorder, cerebrovascular disease (e.g. cerebral edema, cerebral infarction, etc.), Meniere's syndrome (e.g. Meniere's disease, et.), motion sickness and the like in human beings and animals.

In order to illustrate the usefulness of the object compound (I), the pharmacological data of the compound (I) are shown in the following.

Test 1
Vasopressin 1 (V1) Receptor Binding
(i) Test Method

Blood was obtained by venipuncture from normal subjects. Platelet-rich plasma (PRP) was prepared by centrifugation of whole blood at 200×g for 10 minutes. PRP was centrifuged at 45,000×g for 30 minutes. The remaining pellet was resuspended in 10 volume of ice cold 100 mM Tris-HCl (pH 7.4) buffer (containing 5 mM $MgCl_2$, 0.1% bovine serum albumin and 1 mM EGTA), and centrifuged at 45,000×g for 30 minutes again. The final pellet was resuspended in 100 mM Tris-HCl buffer. The resulting membrane preparation was used immediately for the binding assay.

Competition assays were conducted at equilibrium (15 minutes at 30° C.) by using 1.5 nM $^3$H-vasopressin (40–87 Ci/mmol; New England Nuclear) in 100 mM Tris-HCl (pH 7.4) buffer. Nonspecific binding was determined by using 1 µM vasopressin. After incubation, reaction was terminated by adding 5 ml of ice-cold 100 mM Tris-HCl (pH 7.4) buffer, and then filtered rapidly through Whatman glass filter (GF/C). The filter was washed twice with the same buffer. The glass filter was mixed with liquid scintillation cocktail, and radioactivity was counted in a liquid scintillation counter. Competition activity of the test compound was represented by $IC_{50}$ values.
(ii) Test Result

| Test Compound (Example No.) | $IC_{50}$ (nM) |
|---|---|
| 5-2) | 51 |
| 16 | 14 |
| 17-20) | 31 |

Test 2
Vasopressin 2 (V2) Receptor Binding
(i) Test Method

For binding assays, the receptor cDNA was permanently expressed in Chinese hamster ovary (CHO) cells. CHO cells were transfected with a vector directing expression of the cDNA for the human V2 receptor and the clonal cell lines expressing human V2 receptor was established essentially as described previously (Nakajima, Y., et. al. J. Biol. Chem., 1992, 267, 2437).

DNA-transfected cells were harvested and homogenized in ice cold 250 mM sucrose buffer containing 25 mM Tris-HCl (pH 7.4), 10 mM $MgCl_2$, 1 mM EDTA and 5 µg/ml p-amidinophenylmethylsulfonyl fluoride (A-PMSF). The homogenate was centrifuged at 500×g for 10 minutes. The supernatant was centrifuged at 100,000×g for 1 hour. The final pellet was suspended in 25 mM Tris-HCl (pH 7.4) buffer (containing 10 mM $MgCl_2$, 1 mM EDTA and 5 µg/ml A-PMSF), and stored in small aliquots at −80° C.

Competition assays were conducted at equilibrium (2 hours at 22° C.) by using 0.5 nM $^3$H-vasopressin (40–87 Ci/mmol, New England Nuclear) in 100 mM Tris-HCl (pH 7.4) buffer (containing 5 mM $MgCl_2$, 5 µg/ml A-PMSF, 4 µg/ml leupeptin, 40 µg/ml bacitracin, 20 µg/ml chymostatin and 0.1% bovine serum albumin). Nonspecific binding was determined by using 1 µM vasopressin. After incubation, reaction mixture was rapidly filtered through Whatman glass filter (GF/C). The filter was washed twice with the same buffer. The radioactivity was counted in a liquid scintillation counter. Competition activity of the test compound was represented by $IC_{50}$ values.
(ii) Test Result

| Test Compound (Example No.) | $IC_{50}$ (nM) |
|---|---|
| 5-2) | 1300 |
| 16 | 1400 |
| 17-20) | 1300 |

For therapeutic purpose, the compound (I) of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solution, lotion, suspension, emulsion, ointment, gel, or the like. If desires, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.
Preparation 1

To a solution of [N-methyl-N-(4-nitrobenzoyl]-2-hydroxyaniline (1.2 g) in N,N-dimethylformamide (30 ml) was added potassium carbonate (1.22 g), ethyl 6-bromohexanoate (1.03 g) and sodium iodide (catalytic amount) at 60° C. The reaction mixture was stirred at same temperature for 8 hours. The reaction mixture was cooled in an ice bath and quenched with 1 N hydrochloric acid (10 ml) and water (30 ml). The mixture was extracted with ethyl acetate. The organic phase was washed with water and brine. The organic solution was dried over magnesium sulfate. The solvent was removed by evaporation to give 2-(5-ethoxycarbonylpent-1-yloxy)-[N-methyl-N-(4-nitrobenzoyl)]aniline (1.7 g).

NMR ($CDCl_3$, δ): 1.26 (3H, t, J=7.5 Hz), 1.45–1.58 (2H, m), 1.67–1.76 (2H, m), 1.79–1.88 (2H, m), 2.34 (2H, t, J=7.5 Hz), 3.38 (3H, s), 3.84–4.00 (2H, m), 4.13 (2H, t), 6.72–6.82 (2H, m), 7.01 (1H, d, J=7 Hz), 7.17 (1H, t, J=7 Hz), 7.45 (2H, d, J=8.5 Hz), 7.98 (2H, d, J=8.5 Hz)
Preparation 2

A solution of 3-methoxy-4-nitro-N-[2-(5-ethoxycarbonylpent-1-yloxy)-4-methylphenyl]-N-methylbenzamide (7.6 g) in ethanol (76 ml) was treated with 1 N sodium hydroxide solution (33 ml) at ambient temperature and the mixture was stirred at the same temperature for 6 hours. The reaction was quenched by the dropwise addition of 1 N hydrochloric acid (35 ml). The mixture was concentrated and the residue was dissolved in a mixture of ethyl acetate and 1 N hydrochloric acid. The extracted organic layer was washed with brine and dried over magnesium sulfate. The suspension was filtered and the solvent was removed by evaporation to give 3-methoxy-4-nitro-N-[2-(5-carboxypent-1-yloxy)-4-methylphenyl]-N-methylbenzamide (7.1 g) as an oil.

NMR (CDCl$_3$, δ): 1.48–1.63 (2H, m), 1.66–1.91 (4H, m), 2.28 (3H, s), 2.41 (2H, t, J=7 Hz), 3.34 (3H, s), 3.78 (3H, s), 3.81–3.98 (2H, m), 6.58–6.67 (2H, m), 6.89 (1H, d, J=8 Hz), 6.94 (1H, d, J=8 Hz), 7.09 (1H, s), 7.61 (1H, d, J=8 Hz)

Preparation 3

3-Methoxy-4-nitro-N-[2-(5-carboxypent-1-yloxy)-4-methylphenyl]-N-methylbenzamide (5.2 g), 1-methylpiperazine (1.45 g) and 1-hydroxybenzotriazole (1.96 g) were dissolved in N,N-dimethylformamide (50 ml) and the solution was cooled in an ice bath. To the mixture was added N-ethyl-N'-(3-dimethylaminopropyl)-carbodiimide hydrochloride (2.78 g) and the solution was stirred at the same temperature for 30 minutes. The reaction mixture was allowed to warm to ambient temperature and stirring was continued for additional 20 hours. The reaction mixture was diluted with ethyl acetate and the solution was washed successively with saturated sodium hydrogen carbonate and brine, and dried over sodium sulfate. The sodium sulfate was removed and the solvent was removed by evaporation to give oil. The crude material was subjected to a silica gel column chromatography (SiO$_2$; 120 g, 2% methanol in chloroform) to give 3-methoxy-4-nitro-N-methyl-N-[4-methyl-2-[5-(4-methylpiperazin-1-ylcarbonyl)pent-1-yloxy]phenyl]benzamide (6.2 g).

NMR (CDCl$_3$, δ): 1.43–1.60 (2H, m), 1.60–1.92 (4H, m), 2.28 (3H, s), 2.30 (3H, s), 2.25–2.47 (6H, m), 3.34 (3H, s), 3.44–3.54 (2H, m) 3.58–3.70 (2H, m), 3.78 (3H, s), 3.82–4.03 (2H, m), 6.56–6.66 (2H, m), 6.86 (1H, d, J=8 Hz), 6.94 (1H, d, J=8 Hz), 7.07 (1H, s), 7.61 (1H, d, J=8 Hz)

Preparation 4

A mixture of 3-methoxy-4-nitro-N-methyl-N-[4-methyl-2-[5-(4methylpiperazin-1-ylcarbonyl)pent-1-yloxy]phenyl] benzamide (6.2 g) and iron powder (3.43 g) in a mixture of ethanol (65 ml) and ethyl acetate (6 ml) was refluxed for 2 hours. After being cooled to ambient temperature, the solution was filtered through a bed of Celite and the filtrate was evaporated in vacuo. The residue was diluted with ethyl acetate and the solution was washed with saturated sodium hydrogen carbonate and brine, and dried over magnesium sulfate. The solvent was evaporated in vacuo to give 4-amino-3-methoxy-N-methyl-N-[4-methyl-2-[5-(4-methylpiperazin-1-ylcarbonyl)pent-1-yloxy]phenyl] benzamide (4.7 g ).

NMR (CDCl$_3$, δ): 1.43—1.58 (2H, m), 1.61–1.91 (4H, m) 2.26 (3H, s), 2.30 (3H, s), 2.23–2.44 (6H, m), 3.29 (3H, s), 3.41–3.53 (2H, m) 3.61 (3H, s), 3.57–3.68 (2H, m), 3.75–4.03 (4H, m), 6.36–6.46 (1H, m), 6.53–6.67 (2H, m), 6.76–6.89 (3H, m)

Preparation 5

The following compounds were obtained according to a similar manner to that of Preparation 4.

1) 4-Amino-N-methyl-N-[2-(5-ethoxycarbonylpent-1-yloxy) phenylbenzamide

NMR (CDCl$_3$, δ): 1.26 (3H, t, J=7.5 Hz), 1.41–1.54 (2H, m), 1.62–1.73 (2H, m), 1.75–1.84 (2H, m), 2.32 (2H, t, J=7.5 Hz), 3.30 (3H, s), 3.84 (2H, br), 3.90 (2H, br), 4.13 (2H, t), 6.38 (2H, d, J=8.5 Hz), 6.79 (2H, d, J=8.5 Hz), 6.99 (2H, s), 7.09–7.18 (3H, m)

2) 4-Amino-3-methoxy-N-methyl-N-[2-[5-(4-dimethylaminopiperidin-1-yl) carbonylpent-1-yl) carbonylpent-1-yloxy]-4-methylphenyl]benzamide NMR (CDCl$_3$, δ): 1.29–1.95 (10H, m), 2.23–2.43 (12H, m), 2.57 (1H, m), 3.01 (1H, m) 3.31 (3H, s), 3.62 (3H, s), 3.73–4.03 (5H, m), 4.63 (1H, m), 6.42 (1H, d, J=9 Hz), 6.54–6.67 (2H, m), 6.77–6.89 (3H, m)

3) 4-Amino-N-[2-(5-ethoxycarbonylpent-1-yl)oxy-4-methyl]phenyl-N-methylbenzamide MASS (m/z): 399 (M+1)

4) 4-Amino-N-methyl-N-[4methyl-2-[4-(4-methylpiperazin-1-yl) carbonyl]phenylmethoxy] phenylbenzamide (CDCl$_3$, δ): 2.28 (3H, s), 2.33 (3H, s), 2.37–2.53 (4H, m), 3.36 (3H, s), 3.41–3.54 (2H, m), 3.57 (3H, s), 3.65–3.90 (4H, m), 4.90 (1H, d, J=14 Hz), 5.06 (1H, d, J=14 Hz), 6.38 (1H, d, J=7 Hz), 6.62–6.70 (2H, m), 6.78 (1H, d, J=7 Hz), 6.84 (1H, s), 6.98 (1H, d, J=7 Hz), 7.33 (2H, d, J=8 Hz), 7.41 (2H, d, J=8 Hz)

7) Methyl 4-[(E and Z)-2-(2-aminophenyl)ethen-1-yl] benzoate

NMR (CDCl$_3$, δ): 3.72 (2H, br), 3.86 (3Hx2/3, s), 3.90 (3Hx1/3, s), 6.57–7.43 (7H, m), 7.55 (1H, d, J=7 Hz), 7.86 (1H, d, J=7 Hz), 8.01 (7H, d)

8) 4-Amino-3-methoxy-N-[(E and Z)-2-(4-methoxycarbonyl-phenyl) ethen-1-yl)phenyl-N-methylbenzamide NMR (CDCl$_3$, δ): 3.39 (3Hx2/3, s), 3.40 (3Hx1/3, s), 3.50 (3Hx2/3, s), 3.51 (3Hx1/3, s), 3.81–3.96 (2H, m), 3.84 (3Hx2/3, s), 3.41 (3Hx1/3, s), 6.30–8.05 (13H, m)

9) 4-Amino-3-methoxy-N-[2-(4-methyl]phenyl-N-methylbenzamide

NMR (CDCl$_3$, δ): 2.21 (3H, s), 3.34 (3H, s), 3.50 (3H, s), 3.83 (2H, s), 3.90 (3H, s), 4.79–5.14 (2H, m), 6.37 (1H, d, J=7 Hz), 6.60 (1H, s), 6.70 (1H, d, J=7 Hz), 6.77 (1H, d, J=7 Hz), 6.81 (1H, s), 6.99 (1H, d, J=7 Hz), 7.34 (2H, d, J=8 Hz), 8.01 (2H, d, J=8 Hz)

10) 2-[3-(Ethoxycarbonylmethyl) oxyprop-1-yl]oxaniline

NMR (CDCl$_3$, δ): 1.27 (3H, t, J=7 Hz), 2.08–2.28 (2H, m), 3.73 (2H, t, J=7.5 Hz), 3.79 (2H, s), 4.09 (2H, s), 4.14 (2H, t, J=7.5 Hz), 4.21 (2H, q, J=7.5 Hz), 6.65–6.82 (4H, m)

11) 4-Amino-3-methoxy-N-[2-(3-(ethoxycarbonylmethyl)-oxyprop-1-yl]oxy]phenyl-N-methylbenzamide NMR (CDCl$_3$, δ): 1.26 (3H, t, J=7.5 Hz), 2.03–2.15 (2H, m), 3.31 (3H, s), 3.61 (3H, s), 3.69–3.77 (4H, m), 4.02 (2H, s), 4.20 (2H, q, J=7.5 Hz), 6.41 (1H, d, J=7.5 Hz), 6.64–6.89 (4H, m), 7.00 (1H, d, J=7.5 Hz), 7.13 (1H, t, J=7 Hz)

12) 2-[(E)-5-Ethoxycarbonyl-4-penten-1-yl]oxy-4-methylaniline

NMR (CDCl$_3$, δ): 1.29 (3H, t, J=7.5 Hz), 1.90–2.05 (2H, m), 2.23 (3H, s), 2.35–2.50 (2H, m) 3.65 (2H, br), 4.00 (2H, t, J=7.5 Hz), 4.18 (2H, q, J=7.5 Hz), 5.98 (1H, d, J=7.5 Hz), 6.53–6.67 (2H, m), 6.81 (1H, s), 7.00 (1H, dt, J=15, 7.5 Hz)

13) 4-Amino-3-methoxy-N-[2-[(E)-5-ethoxycarbonyl-4-penten-1-yl]oxy-4methyl]phenyl-N-methylbenzamide NMR (CDCl$_3$, δ): 1.27 (3H, t, J=7.5 Hz), 1.84–1.98 (2H, m), 2.36 (3H, s), 2.31–2.41 (2H, m), 3.29 (3H, s), 3.62 (3H, s), 3.75–3.96 (4H, m), 4.18 (2H, q, J=7.5 Hz), 5.84 (1H, d, J=15 Hz), 6.40 (1H, d, J=7 Hz), 6.58–6.63 (2H, m), 6.78–7.01 (4H, m)

14) 2-(5-Ethoxycarbonylpent-1-yloxy)-4-methylaniline

NMR (CDCl$_3$, δ): 1.26 (3H, t, J=7 Hz), 1.45–1.60 (2H, m), 1.63–1.89 (4H, m) 2.25 (3H, s), 2.33 (2H, t, J=7 Hz), 3.98 (2H, t, J=7 Hz), 4.13 (2H, q, J=7 Hz), 6.54–6.68 (3H, m)

15) 3-Methoxy-4-amino-N-(2-benzyloxy-4-methylphenyl)-N-methylbenzamide

NMR (CDCl$_3$, δ): 2.28 (3H, s), 3.32 (3H, s), 3.49 (3H, s), 3.83 (2H, br), 4.80–5.11 (2H, br), 6.34 (1H, d, J=8 Hz), 6.62–6.84 (5H, m), 6.92 (1H, d, J=8 Hz), 7.25–7.39 (4H, m)

16) 4-Amino-3-methyl-N-methyl-N-[2-[5-(4-methylpiperazin-1-yl) carbonylpent-1-yloxy]-4-methylphenyl]benzamide NMR (CDCl$_3$, δ): 1.48–1.59 (2H, m), 1.63–1.88 (4H, m), 2.00 (3H, s), 2.28 (3H, s), 2.30 (3H, s), 2.32–2.40 (6H, m), 3.29 (3H, s), 3.43–3.48 (2H, m), 3.62 (4H, br), 3.90 (2H, br), 6.32 (1H, d, J=7 Hz), 6.56–6.61 (2H, m), 6.83 (1H, d, J=7 Hz), 6.90 (1H, d, J=7 Hz), 7.17 (1H, s)

17) 4-Amino-3-hydroxy-N-methyl-N-[2-[5-(4-methylpiperazin-1-yl) carbonylpent-1-yloxy]-4-methylphenyl]benzamide NMR (CDCl$_3$, δ): 1.62 (6H, br), 2.28 (3H, s), 2.31 (3H, s), 2.38–2.49 (6H, m), 3.28 (3H, s), 3.52 (2H, br), 3.67 (2H, br), 3.78 (2H, br), 3.91 (2H, br), 6.32–6.38 (1H, m), 6.57–6.67 (3H, m), 7.00–7.03 (2H, m)

Preparation 6

The following compounds were obtained by reacting the compounds, which were prepared according to a similar manner to that of Preparation 4, with hydrogen chloride.

1) Benzyl 4-amino-3-benzyloxybenzoate hydrochloride

NMR (DMSO-d$_6$, δ): 5.18 (2H, s), 5.25 (2H, s), 5.98 (2H, br), 6.78 (1H, d, J=7 Hz), 7.29–7.52 (12H, m)

2) Methyl 2-amino-5-thiophenecarboxylate hydrochloride

NMR (DMSO-d$_6$, δ): 3.68 (3H, s), 5.90 (1H, d, J=5 Hz), 7.32–7.37 (2H, m)

Preparation 7

The following compounds were obtained according to a similar manner to that of Preparation 1.

1) 2-(3-Hydroxyprop-1-yl)oxynitrobenzene

NMR (CDCl$_3$, δ): 2.07–2.14 (2H, m), 2.22 (1H, t, J=7.5 Hz), 3.90 (2H, dd, J=7.5, 7.5 Hz), 4.29 (2H, t, J=7 Hz), 7.01 (1H, t, J=7 Hz), 7.12 (1H, t, J=7 Hz), 7.54 (1H, t, J=7 Hz), 7.89 (1H, d, J=7 Hz)

2) 3-(3-Ethoxycarbonylprop-1-yl)oxy-4-nitrotoluene

NMR (CDCl$_3$, δ): 1.24 (3H, t, J=7.5 Hz), 2.09–2.19 (2H, m), 2.56 (2H, t, J=7.5 Hz), 4.08–4.20 (4H, m), 6.81 (1H, d, J=7 Hz), 6.97 (1H, s), 7.77 (7H, d)

3) Benzyl 2-(3-phthalimidopropoxy)benzoate

NMR (CDCl$_3$, δ): 2.08–2.23 (2H, m), 3.85 (2H, t, J=7 Hz), 4.07 (2H, t, J=7 Hz), 5.32 (2H, s), 6.86–7.02 (2H, m), 7.20–7.50 (6H, m), 7.61–7.74 (2H, m), 7.75–7.90 (3H, m)

4) 2-(5-Ethoxycarbonylpent-1-yloxy)-4-methylnitrobenzene

NMR (CDCl$_3$, δ): 1.25 (3H, t, J=7 Hz), 1.46–1.63 (2H, m), 1.63–1.78 (2H, m), 1.79–1.94 (2H, m), 2.34 (2H, t, J=7 Hz), 2.40 (3H, s), 4.00–4.19 (4H, m), 6.80 (1H, d, J=9 Hz), 6.84 (1H, s), 7.76 (1H, d, J=9 Hz 5) 2-Benzyloxy-N-tert-butoxycarbonylaniline NMR (CDCl$_3$, δ): 1.49 (9H, s), 5.10 (2H, s), 6.88–6.98 (3H, m), 7.09 (1H, s), 7.32–7.43 (5H, m), 8.10 (1H, br)

6) Methyl 4-[N-[2-[(3-tert-butoxycarbonylaminoprop-1-yl) oxy]phenyl]-tert-butoxycarbonylamino]methyl-3-methoxybenzoate NMR (CDCl$_3$δ): 1.33 and 1.42 (total 18H, s), 1.92–2.00 (2H, m), 3.26–3.32 (2H, m), 3.70 and 3.77 (total 3H, s), 3.90 (3H, s), 4.03 (2H, br), 4.72 (2H, br), 6.72–6.97 (3H, m), 7.10–7.23 (2H, m), 7.40–7.53 (2H, m), 7.62 (1H, br)

7) 1-Benzyloxy-2-(3-tert-butoxycarbonylaminoprop-1-yl) oxybenzene

NMR

NMR (CDCl$_3$δ): 1.40 and 1.47 (9H, s), 1.98–2.06 (2H, m), 3.23–3.47 (2H, m), 4.10 (2H, t, J=6 Hz), 5.18 (2H, s), 5.42 (1H, br), 6.82–6.90 (4H, m), 7.28–7.47 (5H, m)

8) Methyl 4-[2-[(3-tert-butoxycarbonylaminoprop-1-yl) oxymethyl-3-methoxybenzoate

NMR

NMR (CDCl$_3$δ): 1.38 (9H, s), 2.02 (2H, br), 3.38 (2H, br), 3.90–3.92 (6H, m), 4.10–4.16 (2H, m), 5.23 (1H, s), 5.25 (1H, s), 5.44 (1H, br) 6.83–6.92 (4H, m), 7.53–7.57 (2H, m), 7.65–7.69 (1H, m)

9) Benzyl 3-benzyloxy-4-nitrobenzoate

NMR

NMR (CDCl$_3$δ): 5.28 (2H, s), 5.89 (2H, s), 7.30–7.48 (9H, m), 7.70–7.73 (1H, m), 7.81–7.85 (2H, m)

10) Benzyl 3-benzyloxy-4-[2-[(3-tert-butoxycarbonylamino-prop-1-yl) oxy]benzoyl] aminobenzoate

NMR

NMR (CDCl$_3$δ): 1.38 (9H, s), 1.60–1.70 (2H, m), 2.95–3.02 (2H, m), 3.80 (2H, t, J=6 Hz), 4.42 (1H, br), 5.22 (2H, s), 5.38 (2H, s), 6.93 (1H, d, J=8 Hz), 7.10 (1H, t, J=7 Hz), 7.32–7.50 (12H, m), 7.71–7.72 (1H, m), 7.80–7.83 (1H, m), 8.23–8.28 (1H, m), 8.78 (1H, d, J=7 Hz)

11) Methyl 2-[2-[(3-tert-butoxycarbonylaminoprop-1-yl) oxy]benzoyl]amino-5-thiophenecarboxylate This compound was used for further reaction without purification.

Prepartion 8

The following compounds were obtained according to a similar manner to that of Preparation 2.

1) 4-[N-Methyl-2-[(3-tert-butoxycarbonylaminoprop-1-yl) oxy]benzoyl]amino-3-methoxybenzoic acid

NMR

NMR (CDCl$_3$δ): 1.45 (9H, s), 1.97–2.06 (2H, m), 3.33–3.42 (5H, m), 3.87 (3H, s), 3.98–4.07 (2H, m), 5.27–5.35 (1H, br), 6.67–6.76 (2H, m), 7.03–7.19 (3H, m), 7.44–7.50 (2H, m)

ESI-MASS (m/z): 459 (M+H)

2) 4-Nitro-N-[2-(4-carboxyphenyl)methoxy-4-methyl] phenyl-N-methylbenzamide

NMR

NMR (CDCl$_3$δ): 2.27 (3H, s), 3.40 (3H, s), 4.97 (1H, d, J=14 Hz), 5.10 (1H, d, J=14 Hz), 6.65 (1H, s), 6.69 (1H, d, J=7 Hz), 7.00 (1H, d, J=7 Hz), 7.33–7.49 (4H, m), 7.97 (2H, d, J=8 Hz), 8.10 (2H, d, J=8 Hz)

3) 3-Methoxy-4-nitro-N--[2-(4-carboxy)phenylmethoxy-4-methyl]phenyl-N-methylbenzamide

NMR

NMR (CDCl$_3$δ): 2.30 (3H, s), 3.42 (3H, s), 3.61 (3H, s), 4.92 (1H, d, j=14 Hz), 5.11 (1H, d, J=14 Hz), 6.65 (1H, s), 6.73 (1H, d, J=7 Hz), 6.86 (1H, d, J=7 Hz), 7.02–7.08 (2H, m), 7.48 (2H, d, J=8 Hz), 7.54 (1H, d, J=7 Hz), 8.16 (2H, d, J=8 Hz)

4) 2-(4-Carboxyphenylmethyl)oxy-4-methyl-N,N-dimethylaniline

NMR (CDCl$_3$δ): 2.31 (3H, s), 2.89 (6H, s), 5.08 (2H, s), 6.76–7.82 (2H, m), 7.03 (1H, d, J=7 Hz), 7.40 (2H, d, J=8 Hz), 7.77 (2H, d, J=8 Hz)

5) 2-[3-(4-Methoxyphenyl)methoxypropyl-1-yl]thiobenzoic acid

NMR

NMR (CDCl$_3$δ): 1.95–2.06 (2H, m), 3.03 (2H, t, J=7.5 Hz), 3.59 (2H, t, J=7.5 Hz), 3.77 (3H, s), 4.46 (2H, s), 6.89 (2H, d, J=8 Hz), 7.19 (1H, t, J=7 Hz), 7.16 (2H, d, J=8 Hz), 7.36 (1H, d, J=7 Hz), 7.45 (1H, t, J=7 Hz), 8.10 (1H, d, J=7 Hz)

6) 4-Amino-3-methoxy-N-[2-(4-carboxyl)phenylmethoxy-4-methyl]phenyl-N-methylbenzamide NMR (DMSO-d$_6$, δ): 2.21 (3H, s), 3.15 (3H, s), 3.41 (3H, s), 4.95–5.23 (2H, m), 6.33 (1H, d, J=7 Hz), 6.63–6.72 (3H, m), 6.87 (1H, s), 7.04 (1H, d, J=7 Hz), 7.44 (2H, d, J=8 Hz), 7.95 (2H, J=8 Hz)

7) 4-Amino-3-methoxy-N-[2-[3-(carboxymethyl)oxyprop-1-yl]oxyphenyl-N-methylbenzamide NMR (CDCl$_3$δ): 2.00–2.12 (2H, m), 3.32 (3H, s), 3.60 (3H, s), 3.63–3.74 (2H, m), 3.89–4.14 (2H, m), 4.05 (2H, s), 4.50 (2H, br), 6.40 (1H, d, J=7 Hz), 6.80–6.95 (4H, m), 6.95 (1H, d, J=7 Hz), 7.16 (1H, t, J=7 Hz)

8) 4-Amino-3-methoxy-N-[2-[(E)-5-ethoxycarbonyl-4-penten-1-yl]oxy-4-methyl]phenyl-N-methylbenzamide NMR (CDCl$_3$δ): 1.87–1.99 (2H, m), 2.28 (3H, s), 2.34–2.45 (2H, m), 3.31 (3H, s), 3.61 (3H, s), 3.71–4.00 (2H, m), 5.87 (1H, d, J=15 Hz), 6.41 (1H, d, J=7 Hz), 6.57–6.68 (2H, m), 6.80–7.12 (4H, m)

9) 3-(5-Carboxypent-1-yloxy)-4-(tert-butoxycarbonylamino)toluene

NMR (CDCl$_3$δ): 1.45–1.63 (11H, m), 1.64–1.95 (4H, m), 2.28 (3H, s), 2.42 (2H, t, J=7 Hz), 3.99 (2H, t, J=7 Hz), 6.65 (1H, s), 6.72 (1H, d, J=8 Hz) 6.98 (1H, s), 7.87 (1H, m)

10) [(2-Benzyloxy)benzoyl]amino-3-chlorobenzoic acid

NMR (CDCl$_3$δ): 5.49 (2H, s), 7.18 (1H, t, J=6 Hz), 7.32–7.42 (4H, m), 7.50–7.62 (3H, m), 7.89–7.93 (2H, m), 8.10 (1H, d, J=7 Hz), 8.58–8.62 (1H, m)

11) 4-[2-(Benzyloxy)benzoyl]amino-2-nitrobenzoic acid

NMR (CDCl$_3$δ): 5.22 (2H, s), 7.10 (1H, t, J=7 Hz), 7.28–7.38 (4H, m), 7.50–7.58 (3H, m), 7.65–7.69 (1H, m), 7.86 (2H, s), 8.16 (1H, s)

12) 2-[2-(Benzyloxy)benzoyl]amino-5-pyridinecarboxylic acid

NMR (CDCl$_3$δ): 5.18 (1H, s), 5.32 (2H, s), 6.98–7.20 (2H, m), 7.29–7.67 (6H, m), 7.84–7.88 (1H, m), 8.28–8.37 (2H, m), 8.80 (1H, s)

13) 4-[N-[(3-tert-Butoxycarbonylaminoprop-1-yl) oxy phenyl]-tert-butoxycarbonylamino]methyl-3-methoxybenzoic acid NMR (CDCl$_3$δ): 1.35 and 1.43 (total 18H, s), 1.92–2.00 (2H, m), 3.28 and 3.32 (total 2H, m), 3.20 and 3.28 (total 3H, s), 4.02 (2H, br), 4.77 (2H, br), 6.77–7.99 (3H, m), 7.10–7.20 (2H, m), 7.44–7.56 (2H, m), 7.69 (1H, br)

14) 4-[2-[(3-tert-Butoxycarbonylaminoprop-1-yl) oxymethyl-3-methoxybenzoic acid

NMR (CDCl$_3$δ): 1.37 (9H, s), 2.05 (2H, br), 3.40 (2H, br), 3.93 (3H, s), 4.10–4.17 (2H, m), 5.27 (2H, s), 5.50 (1H, br), 6.87–6.93 (4H, m), 7.59 (2H, s), 7.72–7.77 (1H, m)

15) 3-Benzyloxy-4-[2-[(3-tert-butoxycarbonylaminoprop-1-yl) oxy]benzoyl]aminobenzoic acid NMR (CDCl$_3$δ): 1.30 (9H, s), 1.62–1.72 (2H, m), 2.88–2.92 (2H, m), 3.95 (2H, t, J=6 Hz), 5.37 (2H, s), 6.80 (1H, br), 7.13 (1H, t, J=7 Hz), 7.21 (1H, d, J=7 Hz), 7.30–7.67 (9H, m), 8.08 (1H, d, J=7 Hz), 8.60 (1H, d, J=7 Hz)

16) 2-[2-[(3-tert-Butoxycarbonylaminoprop-1-yl) oxy] benzoyl]amino-5-thiophenecarboxylic acid NMR (DMSO-d$_6$, δ): 1.32 (9H, s), 1.82–1.90 (2H, m), 3.08–3.14 (2H, m), 4.10 (2H, t, J=6 Hz), 6.81 (1H, d, J=5 Hz), 6.93–7.00 (1H, m), 7.07 (1H, t, J=7 Hz), 7.19 (1H, d, J=7 Hz), 7.50–7.58 (2H, m), 7.67 (1H, d, J=7 Hz)

Preparation 9

The following compounds were obtained according to a similar manner to that of Preparation 3.

1) 3-Methoxy-4-nitro-N-methyl-N-[2-[5-(4-dimethylaminopiperidin-1-yl) carbonylpent-1-yloxy]-4-methylphenyl]benzamide NMR (CDCl$_3$δ): 1.30–1.96 (10H, m), 2.28 (9H, s), 2.30–2.41 (3H, m), 2.58 (1H, m), 3.02 (1H, m), 3.33 (3H, s), 3.77 (3H, s), 3.82–4.00 (3H, m), 4.63 (1H, m), 6.56–6.66 (2H, m), 6.84 (1H, d, J=9 Hz), 6.93 (1H, d, J=9 Hz), 7.06 (1H, s), 7.61 (1H, d, J=9 Hz)

2) 4-Nitro-N-methyl-N-[4-methyl-2-[4-methylpiperazin-1yl) carbonyl]phenylmethoxy]phenylbenzamide NMR (CDCl$_3$δ): 2.26 (3H, s), 2.32 (3H, s), 2.36–2.57 (4H, m), 3.37 (3H, s), 3.42–3.59 (2H, m), 3.71–3.89 (2H, m), 4.94 (1H, d, J=14 Hz), 5.07 (1H, d, J=14 Hz), 6.60–6.69 (2H, m), 6.94 (1H, d, J=9 Hz), 7.36–7.50 (5H, m), 7.95 (2H, d, J=8 Hz)

3) 4-Amino-3-methoxy-N-[4-methyl-2-[4-(4-methylpiperazin-1-yl) carbonyl]phenylmethoxy]-phenylbenzamide NMR (CDCl$_3$δ): 2.28 (3H, s), 2.33 (3H, s), 2.37–2.53 (4H, m), 3.36 (3H, s), 3.41–3.54 (2H, m), 3.57 (3H, s), 3.65–3.90 (4H, m), 4.90 (1H, d, J=14 Hz), 5.06 (1H, d, J=14 Hz), 6.38 (1H, d, J=7 Hz), 6.62–6.70 (2H, m), 6.78 (1H, d, J=7 Hz), 6.84 (1H, s), 6.98 (1H, d, J=7 Hz), 7.33 (2H, d, J=8 Hz), 7.41 (2H, d, J=8 Hz)

4) 4-Amino-3-methoxy-N-[2-[4-(4-dimethylaminopiperidin-1-yl) carbonyl]phenylmethoxy-4-methyl]phenyl-N-methylbenzamide NMR (CDCl$_3$δ): 1.14–1.58 (2H, m), 1.75–2.00 (2H, m), 2.26 (3H, s), 2.30 (3H, s), 2.40 (1H, m), 2.73–3.10 (4H, m), 3.36 (3H, s), 3.57 (3H, s), 3.87 (3H, s), 4.83–5.12 (2H, m), 6.39 (1H, d, J=7 Hz), 6.61–6.71 (2H, m), 6.28 (1H, d, J=7 Hz), 6.33 (1H, s), 6.97 (1H, d, J=7 Hz), 7.33 (2H, d, J=8 Hz), 7.40 (2H, d, J=8 Hz)

5) 4-Amino-3-methoxy-N-methyl-N-[2-[3-(4-methylpiperazin-1-yl) carbonylmethoxyprop-1-yl]oxy] phenylbenzamide NMR (CDCl$_3$δ): 1.98–2.13 (2H, m), 2.27 (3H, s), 2.29–2.38 (4H, m), 3.30 (3H, s), 3.36–3.47 (2H, m), 3.52–3.74 (4H, m), 3.60 (3H, s), 3.94–4.17 (2H, m), 4.11 (2H, s), 6.42 (1H, d, J=7 Hz), 6.78–6.92 (4H, m), 7.00 (1H, d, J=7 Hz), 7.14 (1H, t, J=7 Hz)

6) 4-Amino-3-methoxy-N-[2-[(E)-5-(4-dimethylaminopiperidin-1-yl) carbonyl-4-penten-1-yl]oxy-4-methyl]phenyl-N-methylbenzamide NMR (CDCl$_3$δ): 1.30–1.47 (2H, m), 1.80–1.98 (2H, m), 2.21 (3H, s), 2.26 (6H, s), 2.26–2.43 (2H, s), 2.45–3.67 (6H, m), 3.30 (3H, s), 3.61 (3H, s), 3.85 (2H, br), 3.85–4.04 (2H, m), 4.62 (1H, m), 6.29 (1H, d, J=15 Hz), 6.41 (1H, d, J=7 Hz), 6.57–6.63 (2H, m), 6.77–6.90 (4H, m)

7) 3-[5-(4-Dimethylaminopiperidin-1yl)carbonylpent-1-yloxy]-4-(tert-butoxycarbonylamino)toluene NMR (CDCl$_3$δ): 1.27–2.00 (19H, m), 2.21–2.44 (12H, m), 2.58 (1H, m) 3.01 (1H, m), 3.89 (1H, m), 4.00 (2H, t, J=7 Hz), 4.64 (1H, m), 6.64 (1H, s), 6.72 (1H, d, J=8 Hz), 6.94 (1H, s), 7.89 (1H, m)

Prepartion 10

The following compounds were obtained according to a similar manner to that of Example 1.

1) Methyl 4-(2-benzyloxybenzoyl)amino-3-methoxybenzoate

NMR (CDCl$_3$δ): 3.50 (3H, s), 3.90 (3H, s), 5.36 (2H, s), 7.08 (1H, d, J=9 Hz), 7.15 (1H, t, J=9 Hz), 7.33–7.49 (8H, m), 7.73 (1H, dd, J=1, 8 Hz), 8.30 (1H, d, J=8 Hz), 8.72 (1H, d, J=8 Hz),

ESI-MASS (m/z): 392 (M+H)

2) Methyl 4-(2-acetoxybenzoyl)amino-3-methoxybenzoate

NMR (CDCl$_3$δ): 2.38 (3H, s), 3.92 (3H, s), 3.99 (3H, s), 7.19 (1H, d, J=8 Hz), 7.38 (1H, t, J=8 Hz), 7.55 (1H, t, J=8 Hz), 7.60 (1H, s), 7.75 (1H, dd, J=2, 9 Hz), 7.99 (1H, dd, J=1, 9 Hz), 8.66 (1H, d, J=8 Hz), 9.03–9.07 (1H, br s)

ESI-MASS (m/z): 392 (M+H)

3) 3-Methoxy-4-nitro-N-[2-(4-methoxycarbonyl)-phenylmethoxy-4-methyl]phenylbenzamide NMR (DMSO-d$_6$, δ): 2.31 (3H, s), 3.84 (3H, s), 3.98 (3H, s), 5.27 (2H, s), 6.81 (1H, d, J=7 Hz), 7.00 (1H, s), 7.49 (1H, d, J=7 Hz), 7.62 (2H, d, J=8 Hz), 7.79 (1H, s), 7.92 (2H, d, J=8 Hz), 8.00 (1H, d, J=7 Hz, 9.85 (1H, s)

4) 4-Nitro-3-methoxy-N-[(E and Z)-2-(4-methoxycarbonylphenyl)ethen-1-yl]phenylbenzamide NMR (CDCl$_3$δ): 3.87 (3H×⅔, s), 3.91 (3H×⅓, s), 3.95 (3H×⅔, s), 4.00 (3H×⅓, s), 6.71–8.20 (13H, m)

5) 3-Methoxy-4-nitro-N-[2-[3-(ethoxycarbonylmethyl)-oxyprop-1-yl]oxy]phenylbenzamide NMR (CDCl₃δ): 1.22 (3H, t, J=7.5 Hz), 2.10–2.23 (2H, m), 3.78 (2H, t, J=7.5 Hz), 4.01 (2H, s), 4.06 (3H, s), 4.14 (2H, q, J=7.5 Hz), 4.26 (2H, t, J=7.5 Hz), 6.91–7.06 (3H, m), 7.42 (1H, d, J=7 Hz), 7.74 (1H, s), 7.93 (1H, d, J=7 Hz), 8.49 (1H, d, J=7 Hz), 7.78 (1H, s)

6) 3-Methoxy-4-nitro-N-[2-[(E)-5-ethoxycarbonyl-4-penten-1-yl]oxy-4-methyl]phenylbenzamide NMR (CDCl₃δ): 1.27 (3H, t, J=7.5 Hz), 1.93–2.08 (2H, m), 2.27–2.50 (2H, m), 2.32 (3H, s), 4.02 (3H, s), 4.01–4.11 (2H, m), 4.18 (2H, q, J=7.5 Hz), 5.88 (1H, d, J=15 Hz), 6.72 (1H, s), 6.83 (1H, t, J=7 Hz), 6.99 (1H, dt, J=15, 7.5 Hz), 7.35 (1H, d, J=7 Hz), 7.81 (1H, s), 7.92 (1H, d, J=7 Hz), 8.28 (1H, d, J=7 Hz), 8.45 (1H, s)

7) 4-Benzyloxy-3-methoxy-N-methyl-N-[2-[5-(4-dimethylaminopiperidin-1-yl) carbonylpent-1-yloxy]-4-methylphenyl]benzamide NMR (DMSO-d₆, δ): 1.35–1.49 (2H, m_, 1.49–1.63 (2H, m), 1.64–1.79 (2H, m), 2.23 (3H, s), 2.37 (2H, t, J=7 Hz), 2.72 (3H, m), 2.78–3.11 (2H, m), 3.16 (3H, s), 3.28–3.60 (5H, m), 3.71–4.13 (5H, m), 4.43 (1H, m), 4.99 (2H, s), 6.63 (1H, d, J=8 Hz), 6.80 (2H, d, J=2 Hz), 6.86 (2H, s), 6.98 (1H, d, J=8 Hz), 7.26–7.44 (5H, m)

8) 3-Methoxy-4-nitro-N-(2-benzyloxy-4-methylphenyl)-benzamide

NMR (CDCl₃δ): 2.38 (3H, s), 3.90 (3H, s), 5.12 (2H, s), 6.88 (1H, s), 7.30 (1H, s), 7.51 (4H, s), 7.59 (1H, s), 7.82 (1H, d, J=8 Hz), 8.37 (1H, d, J=8 Hz), 8.53 (1H, br)

9) 3-Methyl-4-nitro-N-methyl-N-[2-[5-(4-methylpiperazin-1yl) carbonylpent-1-yloxy]-4-methylphenyl]benzamide NMR (CDCl₃δ): 1.48–1.60 (2H, m), 1.69–1.77 (2H, m), 1.79–1.90 (2H, m), 2.25 (3H, s), 2.29 (3H, s), 2.33–2.42 (6H, m), 2.47 (3H, s), 3.32 (3H, s), 3.45–3.50 (2H, m), 3.58–3.63 (2H, m), 3.82–3.95 (2H, m), 6.55–6.59 (2H, m), 6.83 (1H, d, J=7 Hz), 7.14 (1H, d, J=7 Hz), 7.37 (1H, s), 7.70 (1H, d, J=7 Hz)

10) Ethyl 4-[(2-benzyloxy)benzoyl]amino-3-chlorobenzene

NMR (CDCl₃δ): 1.38 (3H, t, J=7 Hz), 4.34 (2H, q, J=7 Hz), 5.38 (1H, s), 5.39 (1H, s), 7.03–7.16 (2H, m), 7.33–7.50 (6H, m), 7.92–7.99 (2H, m), 8.24–8.32 (1H, m), 8.73–8.29 (1H, m)

11) 3-Hydroxy-4-nitro-N-methyl-N-[2-[5-(4-methylpiperazin-1-yl) carbonylpent-1-yloxy]-4-methylphenyl]benzamide NMR (CDCl₃, δ): 1.48–1.60 (2H, m), 1.68–1.80 (2H, m), 1.82 –1.91 (2H, m), 2.28 (3H, s), 2.30 (3H, s), 2.37–2.42 (6H, m), 3.32 (3H, s), 3.48–3.50 (2H, m), 3.62–3.68 (2H, m), 3.90–3.97 (2H, m), 6.57–6.58 (2H, m), 6.80–6.87 (2H, m), 7.08–7.10 (1H, m), 7,85 (1H, d, J=7 Hz)

12) Ethyl 4-[2-benzyloxy)benzoyl]amino-2-nitrobenzoate

NMR (CDCl₃, δ): 1.32 (3H, t, J=7 Hz), 4.32 (2H, q, J=7 Hz), 5.22–5.30 (2H, m), 7.12–7.27 (2H, m), 7.37–7.69 (9H, m), 8.20–8.34 (1H, m)

13) Methyl 2-[2-(benzyloxy)benzoyl]amino-5-pyridinecarboxylate

NMR (CDCl₃, δ): 3.92 (3H, s), 5.12 (1H, s), 5.36 (2H, s), 6.90–7.01 (1H, m), 7.10–7.18 (2H, m), 7.32–7.55 (5H, m), 8.27–8.34 (2H, m), 8.46 (1H, d, J=6 Hz), 8.87–8.88 (1H, m)

14) Benzyl 4-(2-acetoxybenzoyl)amino-3-benzyloxybenzoate

NMR (CDCl₃, δ): 2.05 (3H, s), 5.20 (2H, s), 5.87 (2H, s), 7.13 (1H, d, J=8 Hz), 7.32–7.47 (10H, m), 7.50–7.57 (1H, m), 7.73 (1H, s), 7.80 (1H, d, J=8 Hz), 7.96 (1H, d, J=8 Hz), 8.68 (1H, d, J=7 Hz), 9.13 (1H, s)

15) Methyl 2-(2-acetoxybenzoyl)amino-5-thiophenecarboxylate

NMR (CDCl₃, δ): 2.39 (3H, s), 3.88 (3H, s), 6.69 (1H, d, J=5 Hz), 7.19–7.21 (1H, m), 7.35–7.30 (1H, m), 7.52–7.59 (1H, m), 7.63–7.66 (1H, m), 7.92–7.95 (1H, m), 9.18 (1H, s)

Preparation 11

The following compound was obtained by reacting the compound, which was prepared according to a similar manner to that of Example 1, with hydrogen chloride.

4-Benzyloxy-3-methoxy-N-mehtyl-N-[4-methyl-2-[5-(4-methylpiperazin-1-yl) carbonylpent-1-yloxy]pheyl] benzamide hydrochloride NMR (DMSO-d₆, δ): 1.35–1.49 (2H, m), 1.49–1.63 (2H, m), 1.64–1.79 (2H, m), 2.23 (3H, s), 2.37 (2H, t, J=7 Hz), 2.72 (3H, m), 2.78–3.11 (2H, m), 3.16 (3H, s), 3.28–3.60 (5H, m), 3.71–4.13 (5H, m), 4.43 (1H, m), 4.99 (2H, s), 6.63 (1H, d, J=8 Hz), 6.80 (2H, d, J=2 Hz), 6.86 (2H, s), 6.98 (1H, d, J=8 Hz), 7.26–7.44 (5H, m)

Preparation 12

The following compound was obtained according to a similar manner to that of Example 4.

4-[2-[(3-tert-Butoxycarbonylaminoprop-1-yl)oxy] benzyol]amino-3-methoxybenzoic acid NMR (DMSO-d₆, δ): 1.35 (9H, s), 2.04 (2H, quintet, J=7 Hz), 3.13 (2H, q, J=7 Hz), 3.98 (3H, s), 4.29 (2H, t, J=7 Hz), 6.95–7.00 (1H, m), 7.16 (1H, t, J=8 Hz), 7.28 (1H, d, J=8 Hz), 7.57–7.65 (3H, m), 8.11 (1H, dd, J−1, 8 Hz), 8.63 (1H, d, J=8 Hz)

ESI-MAS (m/z): 445 (M+H)

Preparation 13

The following compounds were obtained according to a similar manner to that of Example 10.

1) 4-Hydroxy-3-methoxy-N-methyl-N-[4-methyl-2-[5-(4-methylpiperazin-1-yl)carbonylpent-1-yloxy]phenyl]-benzamide NMR (CDCl₃, δ): 1.44–1.59 (2H, m), 1.62–1.92 (4H, m), 2.22–2.45 (12H, m), 3.31 (3H, s), 3.42–3.53 (2H, m), 3.58–3.74 (5H, m), 3.77–4.02 (2H, m), 6.53–6.70 (3H, m), 6.80–6.96 (3H, m)

2) Methyl 4-(N-methyl-2-hydroxybenzoylamino)-3-methoxybenzoate

NMR (CDCl₃, δ): 3.37 (3H, s), 3.69 (3H, s), 3.91 (3H, s), 6.38 (1H, t, J=8 Hz), 6.72 (1H, d, J=8 Hz), 6.91 (1H, d, J=8 Hz), 7.15 (1H, t, J=8 Hz), 7.21 (1H, d, J=9 Hz), 7.49 (1H, d, J=1 Hz), 7.62 (1H, dd, J=1, 9 Hz)

ESI-MAS (m/z): 316 (M+H)

3) 4-Hydroxy-3-methoxy-N-methyl-N-[2-[5-(4-dimethylaminopiperidin-1-yl)carbonylpent-1-yloxy]-4-methylphenyl]benzamide NMR (CDCl₃, δ): 1.25–2.00 (10H, m), 2.06–2.40 (6H, m), 2.52 (1H, m) 2.73 (6H, br s), 3.02 (1H, m), 3.30 (3H, s), 3.67 (3H, s), 3.76–4.07 (3H, m), 4.82 (1H, m), 6.56–6.72 (3H, m), 6.78–6.96 (3H, m)

4) Methyl 4-[N-(2-hydroxyphenyl)-tert-butoxycarbonylamino]methyl-3-methoxybenzoate NMR (CDCl₃, δ): 1.38 (9H, s), 3.82 and 3.83 (total 3H, s), 3.90 and 3.91 (total 3H, s), 4.88 (2H, s), 6.80–6.87 (1H, m), 6.95 (1H, br), 7.03–7.12 (2H, m), 7.25–7.30 (2H, m), 7.48–7.50 (1H, m), 7.58–7.60 (1H, m)

5) 2-(3-tert-Butoxycarbonylaminoprop-1-yl)oxyphenol

NMR (CDCl₃, δ): 1.45 (9H, s), 1.95–2.07 (2H, m), 3.25–3.45 (2H, m), 4.10 (2H, t, J=6 Hz), 4.68 (1H, br), 6.22 (1H, br), 6.78–6.97 (4H, m)

Preparation 14

The following compounds were obtained according to a similar manner to that of Example 12.

1) Methyl 4-[N-methyl-2-[(3-tert-butoxycarbonylamino-prop-1-yl)oxy]benzoyl]amino-3-methyoxybenzoate NMR (CDCl₃, δ): 1.43 (9H, s), 1.95–2.05 (2H, m), 3.30–3.40 (5H, m), 3.83 (3H, s), 3.85 (3H, s), 3.96–4.04 (2H, m), 5.23–5.32 (1H, br), 6.65–6.73 (2H, m), 7.00–7.16 (3H, m), 7.38–7.45 (2H, m)

ESI-MASS (m/z): 473 (M+H)

2) Methyl 4-[2-[(3-tert-butoxycarbonylaminoprop-1-yl)oxy]benzoyl]amino-3-methoxybenzoate NMR (CDCl$_3$, δ): 1.40 (9H, s), 2.13–2.21 (2H, m), 3.33 (2H, q, J=7 Hz), 3.92 (3H, s), 4.00 (3H, s), 4.29 (2H, t, J=7 Hz), 4.72–4.78 (1H, br), 7.03 (1H, d, J=8 Hz), 7.23 (1H, t, J=8 Hz), 7.49 (1H, t, J=8 Hz), 7.60 (1H, s), 7.75 (1H, d, J=8 Hz), 8.27 (1H, d, J=8 Hz), 8.77 (1H, d, J=8 Hz)

ESI-MASS (m/z): 459 (M+H)

3) 4-Nitro-N-[2-(4-methoxycarbonylphenyl)methoxy-4-methyl]phenyl-N-methylbenzamide NMR (CDCl$_3$, δ): 2.27 (3H, s), 3.40 (3H, s), 3.94 (3H, s), 4.95 (1H, d, J=14 Hz), 5.09 (1H, d, J=14 Hz), 6.62 (1H, s), 6.69 (1H, d, J=7 Hz), 6.97 (1H, d, J=7 Hz), 7.31–7.49 (4H, m), 7.95 (2H, d, J=8 Hz), 8.10 (2H, d, J=8 Hz)

Preparation 15

The following compound was obtained according to a similar manner to that of Example 16.

4-Amino-3-methoxy-N-methyl-N-[4-methyl-2-[5-(4-methylpiperazin-1-yl)carbonylpent-1-yloxy]phenyl]benzamide dihydrochloride p NMR (DMSO-d$_6$, δ): 1.33–1.64 (4H, m), 1.64–1.81 (2H, m), 2.20 (3H, s), 2.29–2.43 (2H, m), 2.73 (3H, s), 2.79–3.10 (4H, m), 3.14 (3H, s), 3.22–3.56 (4H, m), 3.62 (3H, s), 3.72–4.18 (3H, m), 4.42 (1H, m), 6.62 (1H, d, J=8 Hz), 6.74–6.92 (3H, m), 6.92–7.10 (2H, m)

Preparation 16

The following compounds were obtained according to a similar manner to that of Example 43.

1) Methyl 4-(2-hydroxybenzoyl)amino-3-methoxybenzoate

NMR (CDCl$_3$, δ): 3.93 (3H, s), 4.03 (3H, s), 6.96 (1H, t, J=8 Hz), 7.04 (1H, d, J=8 Hz), 7.47 (1H, t, J=8 Hz), 7.54 (1H, dd, J=1, 8 Hz), 7.62 (1H, s), 7.76 (1H, d, J=8 Hz), 8.51 (1H, d, J=8 Hz), 8.85–8.89 (1H, br s)

ESI-MASS (m/z): 302 (M+H)

2) Benzyl 3-benzyloxy-4-(2-hydroxybenzoyl)aminobenzoate

NMR (CDCl$_3$, δ): 5.23 (2H, s), 5.38 (2H, s), 6.82 (1H, t, J=7 Hz), 7.01 (1H, d J=7 Hz), 7.30–7.49 (12H, m), 7.70–7.73 (1H, m), 7.80–7.83 (1H, m), 7.52 (1H, d, J=7 Hz), 8.95 (1H, s)

3) Methyl 2-(2-hydroxybenzoyl)amino-5-thiophenecarboxylate

NMR (DMSO-d$_6$, δ): 3.79 (3H, s), 6.95–7.03 (3H, m), 7.42–7.48 (1H, m), 7.62–7.64 (1H, m), 7.88 (1H, d, J=7 Hz)

Preparation 17

The following compound was obtained according to a similar manner to that of Example 30.

3-Methoxy-4-nitro-N-methyl-N-[4-methyl-2-[4-(4-methylpiperazin-1-yl)carbonyl]phenylmethoxy]-phenylbenzamide NMR (CDCl$_3$, δ): 2.29 (3H, s), 2.35 (3H, s), 2.38–2.54 (4H, m), 3.39 (3H, s), 3.43–3.53 (2H, m), 3.66 (3H, s), 3.71–3.88 (2H, m), 4.92 (1H, d, J=14 Hz), 5.07 (1H, d, J=14 Hz), 6.65–6.72 (2H, m), 6.87 (1H, d, J=7 Hz), 6.98 (1H, d, J=7 Hz), 7.03 (1H, s), 7.37 (2H, d, J=8 Hz), 7.45 (2H, d, J=8 Hz), 7.56 (1H, d, J=7 Hz)

Preparation 18

To a mixture of 2-(4-methoxycarbonylphenyl)methoxy-4-methylaniline (420 mg) and 37% formaldeyde solution (69.7 mg) in a mixture of methanol (10 ml) and actic acid (0.1 ml) was added soduim cyanoborohydride (146 mg) and the mixture was stirred at amibient temperature for 3 hours. The solution was diluted with ethyl acetate (30 ml) and washed successively with saturated aqueous sodium hydrogen carbonate, water and brine. The organic solution was dried over magnesium sulfate and the solvent was evaporated in vacuo. The residue was purified by silica gel column (chloroform) to give 2-(4-methoxycarbonylphenyl)methoxy-4-methyl-N-methylaniline (356 mg).

NMR (CDCl$_3$, δ): 2.22 (3H, s), 2.80 (3H, s), 3.91 (3H, s), 5.11 (2H, s), 6.53 (1H, d, J=7 Hz), 6.63 (1H, s), 6.72 (1H, d, J=7 Hz), 7.49 (2H, d, J=8 Hz), 8.04 (2H, d, J=8 Hz)

Preparation 19

A solution of 2-benzyloxy-N-tert-butoxycarbonylaniline (1 g) in N, N-dimethylformamide (40 ml) was treated with sodium hydride (147 mg, 60% w/w in mineral oil) at 0°C. The reaction mixture was stirred at 0° C. for 30 minutes and then at ambient temperature for 1 hour. Methyl 4-bromomethyl-3-methoxybenzoate (909 mg) was added, and the mixture was stirred at ambient temperature for 30 minutes. The reaction was quenched with water and the mixture diluted with etyl acetate. The organic phase was washed with 0.5N hydrochloric acid, saturated aqueous sodium hydrogen carbonate, and brine. The solution was concentrated in vacuo and the residue was purified by slilica gel column chromatography (hexane:ethyl acetate=9:1) to give methyl 4-[N-[2-(benzyloxy)phenyl-tert-butoxycarbonylamino]methy-3-methoxybenzoate (1.38 g).

NMR (CDCl$_3$, δ): 1.32 and 1.40 (total 9H, s), 3.65 and 3.71 (total 3,s) 3.90 (3H, s), 4.77 (2H, s), 5.07 (2H, s), 6.78–7.00 (3H, m), 7.09–7.20 (1H, m), 7.27–7.55 (8H, m)

Preparation 20

The following compounds were obtained according to a similar manner to that of Preparation 19.

1) 4-Nitro-3-methoxy-N-[(E and Z)-2-(4-methoxycarbonyl-pheny)ethen-1-yl]phenyl-N-methylbenzamide NMR (CDCl$_3$, δ): 3.40 (3Hx⅔, s), 3.49 (3Hx⅓, s), 3.54 (3Hx⅓, s), 3.60 (3Hx⅔, s), 3.86 (3Hx⅔, s), 3.95 (3Hx⅓, s), 6.41–8.07 (7H, m)

2) 3-Methoxy-4-nitro-N-[2-[3-(ethoxycarbonylmethyl)-oxyprop-1-yl]oxy]phenyl-N-methylbenzamide NMR (CDCl$_3$, δ): 1.27 (3H, t, J=7.5 Hz), 2.04–2.17 (2H, m), 3.37 (3H, s), 3.71 (2H, t, J=7.5 Hz), 3.76 (3H, s), 4.06 (3H, s), 4.20 (2H, q, J=7.5 Hz), 6.78–7.01 (4H, m), 7.04 (1H, s), 7.19 (1H, t, J=7 Hz), 7.60 (1H, d, J=7 Hz)

3) 3-Methoxy-4-nitro-N-(2-benzyloxy-4-methylphenyl)-N-methylbenzamide

NMR (CDCl$_3$, δ): 2.28 (3H, s), 3.39 (3H, s), 3.58 (3H, s), 4.85 (1H, d, J=12 Hz), 5.07 (1H, d, J=12 Hz), 6.68 (2H, s), 6.83 (1H, d, J=9 Hz), 6.96 (1H, d, J=9 Hz), 7.00 (1H, s), 7.30–7.44 (5H, m), 7.52 (1H, d, J=9 Hz)

Preparation 21

To an ice bath cooled solution of methyl 2-(3-hydroxyprop-1-yl)thiobenzoate (3.7 g) in N,N-dimethylformamide (30 ml) was added sodium hydride (60% in oil, 719 mg) and the solution was stirred at the same temperature for 30 minutes. 4-Methoxybenzyl chloride (2.56 g) was added to the solution and the mixture was stirred at ambient temperature for 5 hours. The mixture was diluted with ethyl acetate (100 ml) and the solution was washed with water and brine. The organic phase was dried over magnesium sulfate and the solvent was evaporated in vacuo to give a crude oil. The crude product was purified by silica gel column chromatography (hexane: ethyl acetate= 10:1) to give methyl 2-[3-(4-methoxyphenyl)methoxyprop-1-yl]thiobenzoate (2.13 g).

NMR (CDCl$_3$, δ): 1.94–2.07 (2H, m), 3.03 (2H, t, J=7.5 Hz), 3.58 (2H, t, J=7.5 Hz), 3.80 (3H, s), 3.90 (3H, s), 4.39 (2H, q, J=7.5 Hz), 4.45 (2H, s), 6.87 (2H, d, J=8 Hz), 7.13 (1H, t, J=7 Hz), 7.21–7.46 (4H, m), 7.96 (1H, d, J=7 Hz)

Preparation 22

The following compound was obtained according to a similar manner to that of Preparation 21.

2-[3-(Ethoxycarbonylmethyl)oxyprop-1-yl] oxynitrobenzene

NMR (CDCl$_3$, δ): 1.25 (3H, t, J=7.5 Hz), 2.08–2.20 (2H, m), 3.73 (2H, t, J=7.5 Hz), 4.06 (2H, s), 4.13–4.32 (4H, m), 7.01 (1H, m), 7.10 (1H, d, J=7 Hz), 7.50 (1H, t, J=7 Hz), 7.82 (1H, d, J=7 Hz)

Preparation 23

To an ice bath cooled solution of 3-methoxy-4-nitro-N-[2-(4-methoxycarbonyl)phenylmethoxy-4-methyl]-phenylbenzamide (7.67 g) in N, N-dimethylformamide (50 ml) was added sodium hydride (60% in oil, 817 mg) and the solution was stirred at the same temperature for 30 minutes. Iodomethane (1.27 ml) was added to the solution and the mixture was stirred at ambient temperature for 2 hours. The mixture was diluted with ethyl acetate (100 ml) and the solution was washed with water and brine. The organic phase was dried over magnesium sulfate and the solvent was evaporated in vacuo to give an oil. The oil was solidified with diethyl ether to give 3-methoxy-4-nitro-N-[2-(4-methoxycarbonyl)phenylmethoxy-4-methyl]pheny-N-methylbenzamide (6.65 g).

NMR (CDCl$_3$, δ): 2.28 (3H, s), 3.40 (3H, s), 3.60 (3H, s), 3.94 (3H, s), 4.91 (1H, d, J=14 Hz), 5.09 (1H, d, J=14 Hz), 6.64 (1H, s), 6.71 (1H, d, J=7 Hz), 6.84 (1H, d, J=7Hz), 7.00–7.04 (2H, m), 7.42 (2H, d, J=8 Hz), 7.52 (1H, d, j=7 Hz), 8.08 (2H, d, J=8 Hz)

Preparation 24

The following compound was obtained according to a similar manner to that of Preparation 23.

3-Methoxy-4-nitro-N-[2-[(E)-5-ethoxycarbonyl-4-penten-1-yl]oxy-4-methyl]phenyl-N-methylbenzamide NMR (CDCl$_3$, δ): 1.28 (3H, t, J=7.5 Hz), 1.90–2.00 (2H, m), 2.00 (3H, s), 2.34–2.45 (2H, m), 3.35 (3H, s), 3.77 (3H, s), 3.84–3.97 (2H, m), 4.19 (2H, q, J=7.5 Hz), 5.88 (1H, d, J=15 Hz), 6.58–6.64 (2H, m), 6.84–7.02 (3H, m), 7.07 (1H, s), 7.06 (1H, d, J=7 Hz)

Preparation 25

The following compound was obtained according to a similar manner to that of Example 45.

2-[5-(4-Dimethylaminopiperidin-1-yl)carbonylpeny-1-yloxy]-4-methylaniline

NMR (CDCl$_3$, δ): 1.18–2.00 (10H, m), 2.14–2.69 (13H, m), 2.99 (1H, m), 3.44–4.07 (5H, m), 4.64 (1H, m), 6.46–6.70 (3H, m)

Preparation 26

The following compound was obtained according to a similar manner to that of Example 38.

2-Hydroxy-N-tert-butoxycarbonylaniline

NMR (CDCl$_3$, δ): 1.55 (9H, s), 6.63 (1H, s), 6.82–6.89 (1H, m), 6.97–6.99 (1H, m), 7.02–7.08 (2H, m), 8.13 (1H, br)

Preparation 27

The following compound was obtained according to a similar manner to that of Example 87.

Methyl 2-nitro-5-thiophenecarboxylate

NMR (CDCl$_3$, δ): 3.95 (3H, s), 7.70 (1H, d, J=5 Hz), 7.86–7.88 (1H, m)

Preparation 28

To a suspension of phosphonium bromide (1.9 g) in tetrahydrofuran (35 ml) at 0° C. was added 1.0 M lithium bis(trimethylsilyl)amide in tetrahydrofuran (7.88 ml) over 5 minutes period. After 40 minutes, the cooling bath was removed and the red suspension was stirred for 15 minutes at ambient temperature. The suspension was recooled to −78° C., and a solution of 2-[3-(phthalimido)prop-1-yl] oxybenzaldehyde (1.16 g) in 10 ml of tetrahydrofuran (plus a 5 ml rinse) was added via cannula. The red reaction mixture was stirred at 0° C. to ambient temperature. After 20 hours, the solution was quenched by 0.5 N hydrochloric acid at 0° C. The resulting mixture was concentrated and extracted with chloroform. The organic extract was washed with brine and dried over magnesium sulfate, filtered, and concentrated to give 4-[2-[2-[3-(phthalimido)prop-1-yl]oxy] phenyl]vinyl-3-methoxybenzoic acid (2.4 g).

NMR (DMSO-d$_6$, δ): 1.99–2.22 (2H, m), 3.72–3.94 (5H, M), 3.98–4.17 (2H, m), 6.38–7.88 (11H, m)

Preparation 29

To a suspension of sodium hydride (60% oil suspension, 88.3 mg) in N,N-dimethylformamide (6 ml) was added a solution of methyl 4-(2-benzyloxybenzoyl)amino-3-methoxybenzoate (600 mg) in N,N-dimethylformamide (4 ml) and the mixture was stirred at 0° C. for 1 hour. Methyl iodide (0.14 ml) was added dropwise to the above solution and the mixture was stirred at 0° C. for 30 minutes. The reaction temperature was raised to ambient temperature over 30 minutes and the reaction was quenched with 1 N hydrochloric acid, and then the resulting solution was extracted with ethyl acetate. Drying, filtering and removal of solvents afforded a crude product. The crude product was purified by column chromatography (eluent; hexane:ethyl acetate=3:1) to give methyl 4-(N-methyl-2-benzyloxybenzoylamino)-3-methoxybenzoate (650 mg).

NMR (CDCl$_3$, δ): 3.35 (3H, s), 3.72 (3H, s), 3.87 (3H, s), 4.93–5.00 (2H, m), 6.65 (1H, d, J=8 Hz), 6.76 (1H, t, J=8 Hz), 7.00–7.12 (2H, m), 7.18–7.23 (1H, m), 7.30–7.43 (6H, m), 8.02 (1H, s)

ESI-MASS (m/z): 4.06 (M+H)

Preparation 30

To a solution of (S)-1,3-butanediol (1.0 g) and triethylamine (1.12 g) in dichloromethane (30 ml) was added portionwise p-toluenesulfonyl chloride (2.12 g) at 0° C., and then the mixture was stirred at ambient temperature for 3hours and stand overnight. The resulting solution was dilueted with dichloromethane (30 ml) and the organic layer was washed successively with 1 N hydrochloric acid, saturated sodium bicarbonate aqueous solution and brine. Drying, filtering and removal of solvents afforded (S)-3-hyrdoxybutyl p-toluenesulfonate (2.26 g).

NMR (CDCl$_3$, δ): 1.20 (3H, d, J=8 Hz), 1.63–1.77 (1H, m), 1.78–1.93 (1H, m), 2.47 (3H, s), 3.89–4.00 (1H, m), 4.08–4.16 (1H, m), 4.20–4.29 (1H, m), 7.37 (2H, d, J=9 Hz), 7.80 (2H, d, J=9 Hz)

Preparation 31

A mixture of (S)-3-hydroxybutyl p-toluenesulfonate (2.25 g) and phthalimide potassium salt (3.41 g) in N,N-dimethylformamide (40 ml) was stirred at 60° C. for 3.5 hours. The resulting mixture was diluted with water (50 ml) and the aqueous layer was extracted with ethyl acetate. Drying, filtering and removal of solvents afforded a crude product. The crude product was chromatographed on silica gel (eluent; hexane-ethyl acetate=2:1) to give (S)-4-(phthalimido-1-yl)-2-butanol (910 mg).

NMR (CDCl$_3$, δ): 1.22 (3H, d, J=7 Hz), 1.64–1.88 (2H, m), 2.73 (1H, d, J=4 Hz), 3.68–3.78 (1H, m), 3.82–3.89 (2H, m), 7.70–7.77 (2H, m), 7.83–7.89 (2H, m)

Preparation 32

To an ice-bath cooled solution of 4-methyoxycarbonyl-phenylmethyl-tri-phenylphosphonium bromide (9.75 g) in N,N-dimethylacetamide (50 ml) was added potassium tert-butoxide (2.23 g). After being stirred in an ice-bath for 30 minutes, 2-nitrobenzaldehyde (3.0 g) was added to the solution and the mixture was stirred at the same temperature for 1 hour. The mixture was diluted with ethyl acetate and the solution was washed with water and brine. The organic solution was dried over magnesium sulfate and the solvent was evaporated in vacuo to give an oil. The crude oil was subjected to silica gel column (10% ethyl acetatein n-hexane). Trans isomer was eluted first (1.4 g) and next cis and trans mixture (3.7 g).

Methyl 4-[(E)-2-(2-nitrophenyl)ethen-1-yl]benzoate

NMR (CDCl$_3$, δ): 3.92 (3H, s), 7.10 (1H, d, J=15 Hz), 7.41 –7.50 (2H, m), 7.55–7.79 (4H, m), 8.00 (1H, d, J=7 Hz), 8.07 (2H, d, J=8 Hz)

Methyl 4-[E and Z)-2-(2-nitrophenyl)ethen-1-yl]benzoate

NMR (CDCl$_3$, δ): 3.83 (3H×⅔ (Z), s), 3.91 (3H×⅓ (E), s), 6.79 (1H×⅔, d, J=12 Hz), 6.98–8.14 (9H+⅓H, m)

Preparation 33

To a solution of 3-(3-ethoxycarbonylprop-1-yl)oxy-4-nitrotoluent (2.67 g) in dichlormethane (30 ml) was added diisobutylaluminum hydride (1.5 M solution in toluene, 7 ml) at –78° C. and the solution was stirred at the same temperature for 2 hours. The reaction was quenched with addition of small amount of water and a mixture of chloroform (30 ml) and 1 N hydrochloric acid (20 ml) was added. The organic phase was separated and washed with water and brine. The organic solution was dried over magnesium sulfate and the solvent was evaporated in vacuo to give an oil. A mixture of the crude aldehyde and carbethoxymethylene triphenylphosphorane (3.49 g) in tetrahydrofuran (20 ml) was stirred at ambient temperature overnight and the solvent was evaporated in vacuo. The residue was subjected to silica gel column and the column was eluted with 10% ethyl acetate in n-hexane to give 3-[(E)-5-ethoxycarbonyl-4-penten-1-yl]oxy-4-nitrotoleuene (2.29 g).

NMR (CDCl$_3$, δ): 1.27 (2H, t, J=7.5 Hz), 1.93–2.04 (2H, m), 2.37 (3H, s), 2.40–2.50 (2H, m), 4.09 (2H, t, J=7.5 Hz), 4.18 (2H, q, J=7.5 Hz), 5.89 (1H, d, J=15 Hz), 6.80 (1H, d, J=7 Hz), 6.82 (1H, s), 7.00 (1H, dt, J=15, 7.5 Hz), 7.78 (1 H, d, J=7 Hz)

Preparation 34

A 300 ml of hydrogenation bottle was flushed with nitrogen, and 10% palladium on carbon (1.5 g) was added into the bottle. A solution of benzyl 2-(3-phthalimidopropyloxy)benzoate (1.50 g) in methanol (50 ml) and 1,4-dioxane (50 ml) was added to the bottle, along with one drop of acetic acid. The mixture was shaken in a Parr apparatus at 3 atm of hydrogen at 35° C. for 8 hours. The catalyst was removed by filtration through a bed of Celite, and wash with 1,4-dioxane (20 ml×2). The combined solution was concentrated with a rotary evaporator to give crude solid. The crude solid in methanol (57 ml) and 1,4-dioxane (10 ml) was heated and the product was recrystallized on cooling. The crystal was collected by filtration, washed with cold methanol (5 ml) and air-dried to give 2-(3-phthalimidopropyloxy)-benzoic acid (4.18 g).

mp: 155–157° C.

NMR (DMSO-d$_6$, δ): 1.98–2.14 (2H, m), 3.79 (2H, t, J=7 Hz), 4.08 (2H, t, J=7 Hz), 6.99 (1H, dd, J=8, 8 Hz), 7.08 (1H, d, J=8 Hz), 7.47 (1H, m), 7.62 (1H, d, J=8 Hz), 7.77–7.92 (4H, m)

Preparation 35

A mixture of 4-amino-3-methoxy-N-[2-(-(4-carboxyphenylmethyl)oxy-4-methylphenyl]-N-methylbenzamide (500 mg), ethanolamine (109 mg), triphenylphosphine (936 mg) and carbon tetrachloride (0.57 ml) in a mixture of pyridine and acetonitrile (1:1, 15 ml) was stirred at ambient temperature for 18 hours. The solvent was evaporated and the residue was purified on silica gel column chromatography (SiO$_2$ 0–10% methanol in chloroform) to give 4-amino-3-methoxy-N-[2-[4-[N-(2-hydroxyethyl)-carbamoyl]phenylmethyl]oxy-4-methylphenyl]-N-methylbenzamide (392 mg).

NMR (CDCl$_3$, δ): 2.27 (3H, s), 3.33 (3H, s), 3.48 (3H, s), 3.60 (2H, q, J=5 Hz), 3.78–3.84 (2H, m), 4.97 (2H, br), 6.35 (1H, d, J=8 Hz), 6.61 (1H, s), 6.68–6.79 (3H, m), 7.04 (1H, d, J=8 Hz), 7.11 (1H, br), 7.26 (2H, d, J=8 Hz), 7.76 (2H, d, J=8 Hz)

Preparation 36

To an ice-cooled 4-amino-3-methyoxy-N-[2-[4-[N-(2-hydroxyethyl)carbamoyl]phenylmethyl]oxy-4-methylphenyl]-N-methylbenzamide (387 mg) was added dropwise thionyl chloride (129 mg), and the mixture was stirred at ambient temperature for 1 hour. The resulting mixture was added aqueous sodium hydrogen carbonate solution (15 ml). The solution was extracted with ethyl acetate (10 ml×3). The organic layer was washed with brine and dried over magnesium sulfate. The solvent was removed under reduced pressure to give 4-amino-3-methoxy-N-[2-[4-(2-oxazolin-2-yl)phenylmethyl]-4-methylphenyl]-N-methylbenzamide (315 mg).

NMR (CDCl$_3$, δ): 2.26 (3H, s), 3.35 (3H, s), 3.52 (3H, s), 4.08 (2H, t, J=10 Hz), 4.25 (2H, t, J=10 Hz), 4.94 (1H, br), 5.07 (1H, br), 6.40 (1H, d, J=8 Hz), 6.40–6.88 (4H, m), 7.00 (1H, d, J=8 Hz), 7.36 (2H, d, J=8 Hz), 7.96 (2H, d, J=8 Hz)

Preparation 37

To a solution of 3-bromopropylamine hydrobromide (5.0 g) and diisopropylethylamine (5.90 g) in dichloromethane (80 ml) was added portionwise 9-fluorenylmethoxycarbonyl chloride (5.91 g) and the mixture was stirred at ambient temperature for 3 hours and stand overnight. The resulting mixture was diluted with dichloromethane (50 ml) and the organic layer was washed successively with 1N hydrochloric acid and brine. Drying, filtering and removal of solvents afforded a crude product. The crude product was triturated with diethyl ether-hexane (1:5) to give 3-(9-fluorenylmethoxycarbonylamino)propyl bromide (7.82 g).

NMR (CDCl$_3$, δ): 2.02–2.12 (2H, m), 3.30–3.45 (4H, m), 4.21 (1H, t, J=8 Hz), 4.44 (2H, d, J=8 Hz), 4.82–4.90 (1H, br), 7.32 (2H, t, J=8 Hz), 7.40 (2H, t, J=8 Hz), 7.58 (2H, d, J=8 Hz), 7.78 (2H, d, J=8 Hz)

ESI-MASS (m/z): 360 (M+H)

Preparation 38

To a solution of thiosalicylic acid (500 mg) in ethanol (15 ml) and 2N sodium hydroxide aqueous solution (3.2 ml) was added 3-(9-fluorenylmethoxycarbonylamino)-propyl bromide at ambient temperature and the suspension was stirred for 2 hours. The resulting clear solution was diluted with water (20 ml) and acidified with 1N hydrochloric acid (6.5 ml). White crystals were collected by filtration and the solid was washed with ethanol-water (1:3, 15 ml) and then with n-hexane - diethyl and either (2:1, 15 ml) to give 2-[3-(9-fluorenylmethoxycarbonylamino)-propylthio]benzoic acid (1.07 g).

NMR (DMSO-d$_6$, δ): 1.69–1.79 (2H, m), 2.90 (2H, t, J=8 Hz), 3.08–3.18 (2H, m), 4.21 (1H, t, J=6 Hz), 4.32 (2H, d, j=6 Hz), 7.20 (1H, t, J=8 Hz), 7.28–7.45 (6H, m), 7.50 (1H, t, J=8 Hz), 7.68 (2H, d, J=8 Hz), 7.85–7.91 (3H, m)

ESI-MASS (m/z): 434 (M+H)

EXAMPLE 1

To mixture of 2-benzyloxybenzoic acid (1.17 g) and oxalyl chloride (0.536 ml) in dichloromethane (30 ml) was added 2 drops of N,N-dimethylformamide and the mixture was stirred at ambient temperature for 1 hour. After removing a solvent by evaporation, a solution of residual acid chloride in dichloromethane (5 ml) was added to a mixture of 4-amino-N-methyl-N-[2-(5-ethoxycarbonylpent-1-yloxy) phenyl]benzamide (1.97 g) and triethylamine (1.07 ml) in dichloromethane (5 ml) and the resulting solution was stirred at ambient temperature for 3 hours. The reaction mixture was washed successively with 1N hydrochloric acid, water (20 ml) and brine (20 ml), and dried over magnesium sulfate. The solvent was evaporated to give an oil and the crude product was purified by silica gel column (chloroform) to give 4-(2-benzyloxybenzoyl)amino-N-methyl-N-[2-(5-ethoxycarbonylpent-1-yloxy)phenyl] benzamide (2.89 g) as a colorless oil.

NMR (CDCl$_3$, δ): 1:23 (3H, t, J=7.5 Hz), 1.41–1.54 (2H, m), 1.63–1.75 (2H, m), 1.75–1.85 (2H, m), 2.32 (2H, t, J=7.5 Hz), 3.32 (3H, s), 3.80–3.95 (2H, br), 4.12 (2H, q, J=7.5 Hz), 5.18 (2H, s), 6.82–6.90 (2H, m), 6.92–7.00 (3H, m), 7.07–7.19 (5H, m), 7.38–7.52 (6H, m), 8.27 (1H, d, J=7 Hz)

EXAMPLE 2

The following compounds were obtained according to a similar manner to that of Example 1.

1) 4-(2-Benzyloxybenzoyl)amino-N-methyl-N-[2-[3-(4-methylpiperazin-1-yl)carbonylaminoprop-1-yloxy]-phenyl]benzamide NMR (CDCl$_3$, δ): 2.00 (2H, m), 2.26 (3H, s), 2.32–2.39 (4H, m), 3.32 (3H, s), 3.34–3.41 (6H, m), 3.81–4.02 (2H, m), 5.20 (2H, s), 6.78–7.26 (9H, m), 7.38–7.53 (7H, m), 8.27 (1H, d, J=7 Hz)

2) 3-Methoxy-4-(2-nitrobenzoyl)amino-N-methyl-N-[4-methyl-2-[5-(4-methylpiperazin-1-yl)carbonylpent-1-yloxy]phenyl]benzamide NMR (CDCl$_3$, δ): 1.43–1.60 (2H, m), 1.61–1.90 (4H, m), 2.30 (6H, s), 2.31–2.44 (6H, m), 3.33 (3H, s), 3.44–3.53 (2H, m), 3.57–3.67 (2H, m), 3.71 (3H, s), 3.81–4.03 (2H, m), 6.56–6.69 (2H, m), 6.82–6.99 (2H, m), 7.03 (1H, s), 7.57–7.66 (2H, m), 7.67–7.76 (1H, m), 8.02–8.13 (2H, m), 8.21 (1H, d, J=8 Hz)

3) 4-(2-Methoxybenzoyl)amino-N-methyl-N-[2-(5-ethoxycarbonylpent-1-yloxy)-4-methylphenyl]benzamide NMR (CDCl$_3$, δ): 1.25 (3H, t, J=7 Hz), 1.43–1.59 (2H, m), 1.63–1.90 (4H, m), 2.26 (3H, s), 2.34 (2H, t, J=7 Hz), 3.32 (3H, s), 3.79–3.99 (2H, m), 4.02 (3H, s), 4.11 (2H, q, J=7 Hz), 6.53–6.66 (2H, m), 6.87 (1H, d, J=8 Hz), 7.01 (1H, d, J=8 Hz), 7.12 (1H, dd, J=8, 8 Hz), 7.29–7.40 (2H, m), 7.42–7.56 (3H, m), 8.18–8.28 (1H, m), 9.81 (1H, br s)

4) 4-(2-Benzyloxybenzoyl)amino-3-methoxy-N-methyl-N-[2-(5-ethoxycarbonylpent-1-yloxy)phenyl]benzamide NMR (CDCl$_3$, δ): 1.25 (3H, t, J=7 Hz), 1.42–1.58 (2H, m), 1.62–1.90 (4H, m), 2.32 (2H, t, J=7 Hz), 3.28 (3H, s), 3.33 (3H, s), 3.78–4.03 (2H, m), 4.12 (2H, q, J=7 Hz), 5.30 (2H, s), 6.72–7.22 (8H, m), 7.82–7.55 (6H, m), 8.20–8.29 (1H, m), 8.38 (1H, d, J=8 Hz)

5) 4-[2-(Acetyloxy)benzoyl]amino-3-methoxy-N-methyl-N-[2-[5-(4-dimethylaminopiperidin-1-yl) carbonylpent-1-yloxy]-4-methylphenyl]benzamide NMR (CDCl$_3$, δ): 1.32–2.01 (10H, m), 2.21–2.46 (15H, m), 1.57 (1H, m), 3.02 (1H, m), 3.32 (3H, s), 3.79 (3H, s), 3.83–4.03 (3H, m), 4.69 (1H, m), 6.54–6.67 (2H, m), 6.80–8.33 (8H, m)

6) 4-[2-(Acetyloxy)benzoyl]amino-3-methoxy-N-methyl-N-[4-methyl-2-(5-ethoxycarbonylpent-1-yloxy) phenyl]-benzamide NMR (CDCl$_3$, δ): 1.26 (3H, t, J=7 Hz), 1.44–1.91 (6H, m), 2.21–2.41 (8H, m), 3.32 (3H, s), 3.80 (3H, s), 3.82–4.03 (2H, m), 6.54–6.67 (2H, m), 6.80–6.95 (2H, m), 7.07 (1H, s), 7.15 (1H, d, J=8 Hz), 7.35 (1H, m), 7.51 (1H, m), 7.94 (1H, m), 8.28 (1H, d, J=8 Hz), 8.87 (1H, s)

7) 4-(2-Benzyloxybenzoyl)amino-2-chloro-N-methyl-N-[2-(5-ethoxycarbonylpent-1-yloxy)phenyl]benzamide NMR (CDCl$_3$, δ): 1.26 (3H, t, J=7 Hz), 1.47–1.98 (6H, m, 2.36 (2H, t, J=7 Hz), 3.34 (3H, s), 3.96 (2H, t, J=7 Hz), 4.14 (2H, q, J=7 Hz), 5.17 (2H, s), 6.64–6.82 (3H, m), 6.96 (1H, d, J=8 Hz), 7.02–7.21 (5H, m), 7.41–7.62 (6H, m), 8.26 (1H, m)

8) 4-(2-Acetoxybenzoyl)amino-3-methoxy-N-methyl-N-(2-methylphenyl)benzamide

NMR (CDCl$_3$, δ): 2.21 (3H, s), 2.31 (3H, s), 3.38 (3H, s), 3.73 (3H, s), 6.87 (1H, d, J=8 Hz), 7.00 (1H, s), 7.03–7.24 (5H, m), 7.29–7.43 (1H, m), 7.51 (1H, dd, J=8, 8 Hz), 7.92 (1H, d, J=8 Hz), 8.30 (1H, d, J=8 Hz), 8.87 (1H, br s)

9) 4-(3-Benzyloxybenzoyl)amino-3-methoxy-N-methyl-N-[4-methyl-2-[5-(4-dimethylaminopiperidin-1-yl) carbonylpent-1-yloxy]phenyl]benzamide NMR (CDCl$_3$, δ): 1.32–1.42 (2H, m), 1.50–1.58 (2H, m), 1.67–1.90 (6H, m), 2.28 (3H, s), 2.29 (6H, s), 2.37 (2H, t, J=8 Hz), 2.52–2.62 (1H, m), 2.98–3.07 (1H, m), 3.34 (3H, s), 3.78 (3H, s), 3.85–3.98 (3H, m), 4.59–4.67 (1H, m), 5.12 (2H, s), 6.58 (1H, d, J=8 Hz), 6.63 (1H, d, J=8 Hz), 6.84 (1H, d, J=8 Hz), 6.92 (1H, d, J=8 Hz), 7.02 (1H, s), 7.12–7.17 (1H, m), 7.33–7.50 (8H, m), 8.28 (1H, d, J=8 Hz), 8.48 (1H, s)

ESI-MASS (m/z): 721 (M+H)

10) 4-(2-Benzyloxybenzoyl)amino-N-[2-(5-ethoxycarbonylpent-1-yl)oxy-4-methyl]phenyl-N-methylbenzamide NMR (CDCl$_3$, δ): 1.25 (3H, t, J=7.5 Hz), 1.43–1.56 (2H, m), 1.65–1.84 (4H, m), 2.25 (3H, s), 2.32 (2H, t, J=7.5 Hz), 3.29 (3H, s), 3.77–3.93 (2H, m), 4.12 (2H, q, J=7.5 Hz), 5.19 (2H, s), 6.51 (2H, m), 6.81 (1H, d, J=7 Hz), 6.98 (2H, d, J=8 Hz), 7.07–7.19 (4H, m), 7.39–7.53 (6H, m), 8.27 (1H, d, J=7 Hz)

11) 4-(2-Iodobenzoyl)amino-N-[2-(4-methoxyphenyl)-methoxy]phenyl-N-methylbenzamide NMR (CDCl$_3$, δ): 3.35 (3H, s), 3.82 (3H, s), 4.90–5.05 (2H, m), 6.83 (1H, t, J=7 Hz), 6.89–6.96 (3H, m), 7.04 (1H, d, J=7 Hz), 7.10–7.19 (2H, m), 7.22–7.32 (4H, m), 7.37–7.48 (3H, m), 7.53 (1H, s), 7.88 (1H, d, J=7 Hz)

12) 3-Methoxy-4-[2-(4-methoxyphenylmethyl) oxybenzoyl]-amino-N-methyl-N-[4-methyl-2-[4-(4-methylpiperazin-1-yl)carbonyl]phenylmethoxy] phenylbenzamide NMR (CDCl$_3$, δ): 2.27 (3H, s), 2.31 (3H, s), 2.35–2.52 (2H, m), 3.24 (3H, s), 3.37 (3H, s), 3.40–3.53 (2H, m), 3.62–3.81 (2H, m), 3.39 (3H, s), 4.89 (1H, d, J=14 Hz), 5.06 (1H, d, J=14 Hz), 5.21 (2H, s), 6.61–6.70 (2H, m), 6.80–7.18 (7H, m), 7.30–7.45 (7H, m), 8.22 (1H, d, J=7 Hz), 8.31 (1H, m, J=7 Hz)

13) 4-[2-(E)-(2-Ethoxycarbonylethen-1-yl)benzoyl] amino-3-methoxy-N-methyl-N-[4-methyl-2-[5-(4-methylpiperazin-1-yl)carbonylpent-1-yl]oxy] phenylbenzamide NMR (CDCl$_3$, δ): 1.30 (3H, t, J=7.5 Hz), 1.49–1.60 (2H, m), 1.67–1.77 (2H, m), 1.79–1.90 (2H, m), 2.29 (6H, sx2), 2.33–2.43 (6H, m), 3.33 (3H, s), 3.45–3.53 (2H, m), 3.60–3.67 (2H, m), 3.71 (3H, s), 3.85–4.01 (2H, m), 4.23 (2H, q, J=7.5 Hz), 6.40 (1H, d, J=15 Hz), 6.58–6.67 (2H, m), 6.86 (1H, d, J=7 Hz), 6.92 (1H, d J=7 Hz), 7.02 (1H, s), 7.40–7.52 (2H, m), 7.58 (1H, d, J=7 Hz), 7.68 (1H, d J=7 Hz), 8.02–8.15 (2H, m), 8.27 (1H, d, J=7 Hz)

14) 4-(2-Dimethylamino-4-methyl)phenoxymethyl-N-[2-(5-ethoxycarbonylpent-1-yl)oxy-4-methyl]phenylbenzamide NMR (CDCl$_3$, δ): 1.20 (3H, t, J=7.5 Hz), 1.45–1.58 (2H, m), 1.66–1.77 (2H, m), 1.80–1.95 (2H, m), 2.25 (3H, s), 2.29–2.34 (2H, m), 2.31 (3H, s), 2.80 (6H, s), 4.00–4.16 (4H, m), 5.20 (2H, s), 6.68–6.89 (5H, m), 7.58 (2H, d, J=8 Hz), 7.88 (2H, d, J=8 Hz), 8.37 (1H, d, J=7 Hz), 8.50 (1H, s)

15) 4-(2-Benzyloxy)benzoylamino-3-methoxy-N-[(E and Z)-2-(4-methoxycarbonylphenyl)ethen-1-yl]phenyl-N-methylbenzamide NMR (CDCl$_3$, δ): 3.06 (3Hx⅔, s), 3.10 (3Hx⅓, s), 3.40 (3Hx⅔, s), 3.43 (3Hx⅓, s), 3.46 (3Hx⅔, s), 3.91 (3Hx⅓, s), 5.20 (2Hx⅔, s), 5.27 (2Hx⅓, s), 6.38–8.37 (22H, m)

16) 3-Methoxy-4-[2-[3-(4-methoxyphenyl)methoxyprop-1-yl]thiobenzoyl]amino-N-methyl-N-[4-methyl-2-[5-(4-methylpiperazin-1-yl)carbonylpent-1-yl]oxy]-phenylbenzamide NMR (CDCl$_3$, δ): 1.44–1.58 (2H, m), 1.61–1.73 (2H, m), 1.68–1.92 (4H, m), 2.25 (3H, s), 2.27 (3H, s), 2.30–2.41 (6H, m), 2.99 (2H, t, J=7.5 Hz), 3.30 (3H, s), 3.43–3.52 (4H, m), 3.57–3.66 (2H, m), 3.70 (3H, s), 3.78 (3H, s), 3.82–3.90 (2H, m), 4.38 (2H, s), 6.53 . 6.65 (2H, m), 6.79–6.93 (3H, m), 7.02 (1H, s), 7.17–7.29 (4H, m), 7.33–7.45 (2H, m), 7.65 (1H, d, J=7 Hz), 8.29 (1H, d, J=7 Hz), 8.80 (1H, s)

17) 4-(2,4-Dimethoxybenzoyl)amino-3-methoxy-N-methyl-N-[4-methyl-2-[5-(4-methylpiperazin-1-yl)carbonylpent-1-yl]oxy]phenylbenzamide NMR (CDCl$_3$, δ): 1.43–1.57 (2H, m), 1.64–1.72 (2H, m), 1.72–1.91 (2H, m), 2.24 (3H, s), 2.27 (3H, s), 2.30–2.40 (6H, m), 3.31 (3H, s), 3.42–3.50 (2H, m), 3.59–3.65 (2H, m), 3.77 (3H, s), 3.80 (3H, s), 3.80–4.02 (2H, m), 3.96 (3H, s), 6.52–6.63 (2H, m), 6.81–7.04 (5H, m), 7.79 (1H, m), 8.38 (1H, d, J=7 Hz)

18) 4-[2-(Acetoxy)benzoyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.47–1.61 (2H, m), 1.64–1.93 (4H, m), 2.22–2.46 (15H, m), 3.33 (3H, s), 3.44–3.53 (2H, m), 3.58–3.68 (2H, m), 3.79 (3H, s), 3.82–4.04 (2H, m), 6.54–6.68 (2H, m), 6.80–6.95 (2H, m), 7.04 (1H, s), 7.14 (1H, d, J=8 Hz), 7.35 (1H, m), 7.51 (1H, m), 7.92 (1H, m), 8.29 (1H, br, d, J=8 Hz), 8.86 (1H, s)

19) 4-(2-Benzyloxy-4-methylbenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.48–1.61 (2H, m), 1.69–1.91 (4H, m), 2.28 (3H, s), 2.30 (3H, s), 2.32–2.44 (6H, m), 2.38 (3H, s), 3.20 (3H, s), 3.32 (3H, s), 3.50 (2H, t, J=5 Hz), 3.64 (2H, t, J=4 Hz), 3.85–4.06 (2H, m), 4.89 (2H, s), 6.60–6.68 (2H, m), 6.82–6.95 (4H, m), 7.18 (1H, dd, J=2, 7 Hz), 7.27–7.40 (5H, m), 7.98 (1H, d, J=8 Hz), 8.38 (1H, d, J=8 Hz)

20) 4-(2-Benzyloxy-4-methylbenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.47–1.86 (6H, m), 2.28 (3H, s), 2.30 (3H, s), 2.36 (3H, s), 2.32–2.48 (6H, m), 3.30 (3H, s), 3.45–3.51 (2H, m), 3.60–3.66 (2H, m), 3.63 (3H, s), 3.79–4.00 (2H, m), 5.24 (2H, d, J=9 Hz), 6.56–6.68 (2H, m), 6.80–6.93 (5H, m), 7.31–7.58 (5H, m), 8.11 (1H, d, J=8 Hz), 8.36 (1H, d, J=8 Hz)

21) 4-(2-Benzyloxy-5-methylbenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.47–1.99 (8H, m), 2.28 (3H, s), 2.31 (3H, s), 2.31–2.45 (6H, m), 3.25 (3H, s), 3.29 (2H, s), 3.48 (3H, s), 3.48–3.53 (2H, m), 3.60–3.64 (2H, m), 3.82–4.01 (2H, m), 5.27 (2H, s), 6.54–6.63 (2H, m), 6.81–6.95 (4H, m), 7.19–7.47 (7H, m), 8.02 (1H, s), 8.36 (1H, d, J=8 Hz)

22) 4-(2-Benzyloxy-4-chlorobenzoyl)amino-3-methoxy-N-methyl-N-[2-[5-(4-methylpiperazin-1-ylcarbonyl)pent-1-yl]oxy-4-methylphenyl]benzamide NMR (CDCl$_3$, δ): 1.46–1.86 (6H, m), 2.15–2.31 (2H, m), 2.29 (6H, s), 2.30–2.58 (4H, m), 3.28 (3H, s), 3.49 (2H, t, J=5 Hz), 3.60 (3H, s), 3.61 (2H, t, J=5 Hz), 3.85–4.00 (2H, m), 5.15 (2H, s), 6.54–6.67 (2H, m), 6.83–7.16 (4H, m), 7.34–7.49 (7H, m), 8.01 (1H, d, J=8 Hz), 8.19 (1H, d, J=8 Hz)

23) 4-(2-Benzyloxy-4-methoxybenzoyl)amino-3-methoxy-N-methyl-N-[2-[5-(4-methylpiperazin-1-ylcarbonyl)pent-1-yl]oxy-4-methylphenyl]benzamide NMR (CDCl$_3$, δ): 1.44–1.59 (2H, m), 1.63–1.84 (4H, m), 2.28 (3H, s), 2.30 (3H, s), 2.25–2.40 (6H, m), 3.28 (3H, s), 3.30 (3H, s), 3.48 (2H, t, J=4 Hz), 3.62 (2H, t, J=4 Hz), 3.89–4.01 (2H, m), 5.26 (2H, s), 6.52–6.67 (4H, m), 6.81–6.92 (4H, m), 7.35–7.48 (5H, m), 8.21 (1H, d, J=9 Hz), 8.38 (1H, d, J=8 Hz)

24) 4-(2-Acetoxybenzoyl)amino-3-methoxy-N-(2-benzyloxy-4-methylphenyl)-N-methylbenzamide NMR (CDCl$_3$, δ): 2.29 (3H, s), 3.39 (3H, s), 3.60 (3H, s), 4.88 (1H, d, J=12 Hz), 5.02 (1H, d, J=12 Hz), 6.68–6.73 (2H, m), 6.82 (1H, d, J=8 Hz), 7.02 (1H, s), 7.11–7.20 (2H, m), 7.31–7.42 (5H, m), 7.46–7.53 (1H, m), 7.93 (1H, d, J=8 Hz), 8.27 (1H, d, J=8 Hz), 8.86 (1H, br)

25) 4-(2-Acetoxybenzoyl)-amino-3-methoxy-N-[2-[4-(2-oxazolin-2-yl)phenylmethyl]oxy-4-methylphenyl]-N-methylbenzamide NMR (CDCl$_3$, δ): 2.27 (3H, s), 2.31 (3H, s), 3.39 (3H, s), 3.63 (3H, s), 4.07 (2H, t, J=10 Hz), 4.42 (2H, t, J=10 Hz), 4.91 (1H, d, J=12 Hz), 5.11 (1H, d, J=12 Hz), 6.61 (1H, br), 6.77 (1H, d, J=8Hz), 6.82–7.15 (5H, m), 7.24–7.50 (4H, m), 7.90 (2H, d, J=8 Hz), 8.20 (1H, J=8 Hz)

26) 4-[2-[3-(9-Fluorenylmethyl)oxycarbonylaminoprop-1-yl]thiobenzoyl]amino-3-methoxy-N-methyl-N-[2-[5-(4-dimethylaminopiperidin-1-yl)carbonylpent-1-yl]oxy-4-methylphenyl]benzamide NMR(CDCl$_3$, δ): 1.32–1.92 (12H, m), 2.29 (9H, s), 2.39 (2H, t, J=5 Hz), 2.60 (1H, t, J=10 Hz), 2.90–3.12 (3H, m), 3.29 (2H, q, J=5 Hz), 3.33 (3H, s), 3.75 (3H, s), 3.82–4.00 (4H, m), 4.38 (2H, t, J=4 Hz), 6.55–6.67 (3H, m), 6.83 (1H, d, J=8 Hz), 6.92 (1H, d, J=8 Hz), 7.02 (1H, s), 7.25–7.46 (6H, m, 7.59 (2H, d, J=7 Hz), 7.63 (1H, d, J=8 Hz), 7.77 (2H, d, J=8 Hz), 8.30 (1H, d, J=8 Hz), 8.70 (1H, s)

27) 4-[2-Acetyloxy)benzoyl]amino-3-methyl-N-methyl-N-[2-[5-(4-methylpiperazin-1-yl)carbonylpent-1-yloxy]-4-methylphenyl]benzamide NMR (CDCl$_3$, δ): 1.53 (2H, br), 1.63–1.89 (4H, m), 2.22 (3H, s), 2.30 (3H, s), 2.36 (3H, s), 2.22–2.50 (10H, m), 3.32–3.38 (3H, m), 3.52–3.57 (2H, m), 3.67 (2H, br), 3.95 (2H, br), 6.61 (2H, s), 6.83–6.93 (2H, m), 7.02–7.20 (2H, m), 7.32–7.58 (2H, m), 7.68 (1H, d, J=7 Hz), 7.85 (1H, br )

28) 4-[(2-Benzyloxy)benzoyl]amino-3-[(2-benzyloxy)-benzoyl]oxy-N-methyl-N-[2-[5-(4-methylpiperazin-1-yl)carbonylpent-1-yloxy]-4-methylphenyl]benzamine NMR (CDCl₃, δ): 1.44–1.53 (2H, m), 1.60–1.87 (4H, m), 2.28 (3H, s), 2.29 (3H, s), 2.32–2.38 (7H, m), 3.33 (3H, s), 3.43 (2H, br), 3.60 (2H, br), 3.90 (2H, br), 4.79 (2H, s), 4.93 (2H, s), 6.11–6.20 (3H, m), 6.82–7.43 (18H, m), 7.83–7.88 (1H, m), 8.12–8.15 (1H, m), 8.37–8.42 (1H, m)

29) 4-[4-(Benzyloxy)benzoyl]amino-3-methoxy-N-methyl-N-[2-[5-(4-dimethylaminopiperidin-1-yl)carbonylpent-1-yloxy]-4-methylphenyl]benzamide NMR (CDCl₃, δ): 1.30–1.45 (1H, m), 1.47–1.58 (2H, m), 1.60–1.75 (4H, m), 1.78–1.91 (2H, m), 2.27 (9H, s), 2.30–2.40 (3H, m), 2.50–2.63 (1H, m), 2.95–3.07 (1H, m), 3.30 (3H, s), 3.77 (3H, s), 3.82–3.98 (4H, m), 4.56–4.67 (1H, m), 5.11 (2H, s), 6.56–6.62 (2H, m), 6.80–6.93 (2H, m), 7.00–7.05 (3H, m), 7.34–7.45 (4H, m), 7.78–7.82 (2H, m), 8.22–8.30 (1H, m), 8.46 (1H, s)

30) 4-[4-(Benzyloxy)benzoyl]amino-3-methoxy-N-methyl-N-[2-[5-(4-methylpiperazin-1-yl)carbonylpent-1-yloxy]-4-methylphenyl]benzamide NMR (CDCl₃, δ): 1.48–1.59 (2H, m), 1.69–1.90 (4H, m), 2.28 (3H, s), 2.30 (3H, s), 2.35–2.42 (6H, m), 3.31 (3H, s), 3.48–3.50 (2H, m), 3.62–3.66 (2H, m), 3.78 (3H, s), 3.82–4.00 (2H, m), 5.13 (2H, s), 6.57–6.60 (2H, m), 6.81–6.92 (2H, m), 7.00–7.02 (2H, m), 7.30–7.43 (5H, m), 7.78–7.82 (2H, m), 8.27 (1H, d, J=7 Hz), 8.43 (1H, s)

31) 4-[2-(Benzyloxy)benzoyl]amino-2-nitro-N-methyl-N-[2-[5-(4-dimethylaminopiperidin-1-yl)carbonylpent-1-yloxy]-4-methylphenyl]benzamide NMR (CDCl₃, δ): 1.30–1.44 (2H, m), 1.50–1.94 (8H, m), 2.20 (3H, s), 2.27 (6H, s), 2.30–2.43 (3H, m), 2.52–2.63 (1H, m), 2.97–3.10 (1H, m), 3.32 (3H, s), 3.85–3.97 (4H, m), 4.57–4.68 (1H, m), 5.20 (2H, s), 6.41–6.48 (2H, m), 6.52 (1H, s), 6.90–6.93 (1H, m), 7.11–7.20 (3H, m), 7.32 (1H, s), 7.48–7.59 (6H, m), 7.69–7.73 (1H, m), 8.29 (1H, d, J=7 Hz)

32) 2-[2-(Benzyloxy)benzoyl]amino-N-methyl-N-[2-[5-(4-dimethylaminopiperidin-1-yl)carbonylpent-1-yloxy]-4-methylphenyl]-5-pyridinecarboxamide NMR (CDCl₃, δ): 1.30–1.44 (2H, m), 1.44–1.60 (2H, m), 1.60–1.95 (6H, m), 2.20 and 2.28 (total 9H, s), 2.29–2.41 (3H, m), 2.47–2.64 (1H, m), 2.93–3.09 (1H, m), 3.32 (3H, s), 3.79–3.98 (4H, m), 4.57–4.69 (1H, m), 4.97–5.17 (1H, m), 5.32 (1H, s), 6.39–6.50 (1H, m), 6.60–6.78 (2H, m), 6.85–6.90 (1H, m), 7.00–7.12 (2H, m), 7.27–7.50 (7H, m), 7.56–8.25 (2H, m)

EXAMPLE 3

To a mixture of 2-benzyloxybenzoic acid (1.55 g) and oxalyl chloride (1.18 ml) in dichloromethane (30 ml) was added 1 drop of mixture of N,N-dimethylformamide and the mixture was stirred at ambient temperature for 1 hour. After removing a solvent by evaporation, a solution of residual acid chloride in dichloromethane (30 ml) was added to a mixture of 4-amino-3-methoxy-N-methyl-N-[4-methyl-2-[5-(4-methylpiperazin-1-ylcarbonyl)pent-1-yloxy]phenyl]benzamide (3.28 g) and pyridine (1.1 ml) in dichloromethane (50 ml) and the mixture was stirred at ambient temperature for 2.5 hours. The mixture was washed with saturated sodium hydrogen carbonate solution and brine, and dried over sodium sulfate. The solvent was removed by evaporation and purified by silica gel column chromatography (SIO₂; 85 g, 2% methanol in dichloromethane) to give 4-(2-benzyloxybenzoyl)amino-3-methoxy-N-methyl-N-[2-[5-(4-methylpiperazin-1-ylcarbonyl)pent-1-yloxy]-4-methylphenyl]benzamide (4.5 g).

NMR (CDCl₃, δ): 1.44–1.59 (2H, m), 1.62–1.90 (4H, m), 2.27 (3H, s), 2.28 (3H, s), 2.30–2.43 (6H, m), 3.30 (3H, s), 3.32 (3H, s), 3.43–3.53 (2H, m), 3.57–3.67 (2H, m), 3.78–4.03 (2H, m), 5.30 (2H, s), 6.52–6.66 (2H, m), 6.78–6.96 (3H, m), 7.04 (1H, d, J=9 Hz), 7.10 (1H, dd, J=9 Hz), 7.30–7.49 (6H, m), 8.20–8.28 (1H, m), 8.37 (1H, d, J=9 Hz)

EXAMPLE 4

A solution of 4-(2-benzyloxybenzoyl)amino-N-methyl-N-[2-(5-ethoxycarbonylpent-1-yloxy)phenyl]benzamide (2.80 g) in a mixture of ethanol (50 ml) and 1N sodium hydroxide solution (10 ml) was stirred at ambient temperature for 4 hours. After removing ethanol by evaporation, the aqueous solution was adjusted to pH 2 with 1N hydrochloric acid and the mixture was extracted with chloroform (30×2). The organic phase was washed with water (40 ml) and brine (30 ml), and dried over magnesium sulfate. The solvent was evaporated to give 4-(2-benzyloxybenzoyl)amino-N-methyl-N-[2-(5-carboxylpent-1-yloxy)phenyl]benzamide (1.76 g) as a colorless oil.

NMR (CDCl₃, δ): 1.45–1.57 (2H, m), 1.66–1.83 (4H, m), 2.37 (2H, t, J=7.5 Hz), 3.32 (3H, s), 3.78–3.96 (2H, br), 5.17 (2H, s) 6.75–6.82 (2H, m), 6.93–7.02 (3H, m), 7.10–7.22 (5H, m), 7.36–7.51 (6H, m), 8.28 (1H, d, J=7 Hz)

EXAMPLE 5

The following compounds were obtained according to a similar manner to that of Example 4.

1) 4-[2-(Carboxymethoxy)benzoyl]amino-N-methyl-N-[2-[5-(4-methylpiperazin-1-yl)carbonylpent-1-yloxy]phenyl]benzamide NMR (CDCl₃, δ): 1.63 (2H, m), 1.73 (2H, m), 1.85 (2H, m), 2.28 (3H, s), 2.35–2.41 (6H, m), 3.36 (3H, s), 3.47 (2H, m), 3.61 (2H, m), 3.91 (2H, m), 4.76 (2H, s), 6.72–6.82 (2H, m), 6.86–7.01 (2H, m), 7.07–7.18 (2H, m), 7.35 (2H, d, J=8.5 Hz), 7.47 (1H, t, J=7 Hz), 7.72 (2H, d, J=8.5 Hz), 8.25 (1H, d, J=7 Hz)

2) 4-(2-Aminobenzoyl)amino-N-methyl-N-[2-(5-carboxypent-1-yloxy)-4-methylphenyl]benzamide NMR (CDCl₃, δ): 1.45–1.59 (2H, m), 1.64–1.85 (4H, m), 2.27 (3H, s), 2.38 (2H, t, J=7 Hz), 3.32 (3H, s), 3.73–4.00 (2H, m), 6.56–6.76 (4H, m), 6.93 (1H, d, J=9 Hz), 7.18–7.48 (6H, m), 7.86 (1H, br s)

3) 4-(2-Methoxybenzoyl)amino-N-methyl-N-[2-(5-carboxypent-1-yloxy)-4-methylphenyl]benzamide NMR (CDCl₃, δ): 1.46–1.62 (2H, m), 1.65–1.88 (4H, m), 2.26 (3H, s), 2.39 (2H, t, J=7 Hz), 3.33 (3H, s), 3.73–4.00 (2H, m), 4.01 (3H, s), 6.54–6.68 (2H, m), 6.91 (1H, br d, J=9 Hz), 6.99 (1H, d, J=9 Hz), 7.10 (1H, dd, J=9, 9 Hz), 7.35 (2H, br d, J=9 Hz), 7.41–7.57 (3H, m), 8.17–8.27 (1H, m), 9.84 (1H, br s)

4) 4-(2-Benzyloxybenzoyl)amino-3-methoxy-N-methyl-N-[2-(5-carboxypent-1-yloxy)phenyl]benzamide NMR (CDCl₃, δ): 1.43–1.60 (2H, m), 1.62–1.88 (4H, m), 2.38 (2H, t, J=7 Hz), 3.28 (3H, s), 3.34 (3H, s), 3.76–4.02 (2H, m), 5.28 (2H, s), 6.74–6.85 (2H, m), 6.86–6.97 (2H, m), 6.97–7.20 (4H, m), 7.28–7.50 (6H, m), 8.16–8.27 (1H, m), 8.36 (1H, d, J=8 Hz)

5) 4-[2-[(3-tert-Butoxycarbonylaminoprop-1-yl)oxy]benzoyl]amino-3-methoxy-N-methyl-N-[2-(5-carboxypent-1-yloxy)-4-methylphenyl]benzamide NMR (CDCl₃, δ): 1.31–1.96 (17H, m), 2.00–2.48 (6H, m), 3.14–3.39 (5H, m), 3.62–4.07 (5H, m), 4.10–4.30 (2H, m), 4.86 (1H, m), 6.52–6.72 (2H, m), 6.81–7.16 (5H, m), 7.37–7.53 (2H, m), 8.11–8.51 (2H, m)

6) 4-(2-Benzyloxybenzoyl)amino-2-chloro-N-methyl-N-[2-(5-carboxypent-1-yloxy)phenyl]benzamide NMR (CDCl$_3$, δ): 1.50–1.67 (2H, m), 1.68–1.98 (4H, m), 2.42 (2H, t, J=7 Hz), 3.34 (3H, s), 3.99 (2H, t, J=7 Hz), 5.16 (2H, s), 6.65–6.80 (3H, m), 6.98 (1H, d, J=8 Hz), 7.02–7.22 (5H, m), 7.40–7.61 (6H, m), 8.24 (1H, m)

7) 4-[2-[(3-tert-Butoxycarbonylaminoprop-1-yl)oxy]benzoyl]amino-3-methoxy-N-methyl-N-[4-(5-carboxypent-1-yloxy)phenyl]benzamide NMR (CDCl$_3$, δ): 1.40 (9H, s), 1.45–1.80 (8H, m), 2.18–2.27 (2H, m), 3.32–2.40 (2H, m), 3.25–3.35 (2H, m), 3.48 (3H, s), 3.80 (3H, s), 3.93 (2H, t, J=6 Hz), 4.19–4.28 (2H, m), 4.73–4.83 (1H, br), 6.73–6.80 (3H, m), 6.93–7.12 (6H, m), 7.46 (1H, t, J=8 Hz), 8.17–8.27 (1H, m)

ESI-MASS (m/z): 686 (M+Na)

8) 4-[2-(3-Aminoprop-1-yl)oxybenzoyl]amino-N-[2-(5-carboxypent-1-yl)oxy-4-methyl]phenyl-N-methylbenzamide NMR (DMSO-d$_6$, δ): 1.31–1.80 (6H, m), 1.95–2.07 (4H, m), 2.22 (3H, s), 2.86 (2H, t, J=7.5 Hz), 3.16 (3H, s), 3.70 (1H, m), 3.93 (1H, m), 4.16 (2H, t, J=7.5 Hz), 6.65 (1H, d, J=7 Hz), 6.78 (1H, s), 7.00–7.10 (2H, m), 7.20 (1H, d, J=7 Hz), 7.23 (2H, d, J=8 Hz), 7.43–7.62 (4H, m)

9) 4-[2-[3-(tert-Butoxycarbonyl)aminoprop-1-yl]oxybenzoyl]amino-N-[2-(5-carboxypent-1-yl)oxy-4-methyl]phenyl-N-methylbenzamide NMR (CDCl$_3$, δ): 1.36–1.50 (2H, m), 1.41 (9H, s), 1.50–1.62 (2H, m), 1.66–1.84 (2H, m), 2.05–2.19 (2H, m), 2.25 (3H, s), 2.36–2.44 (2H, m), 3.23–3.41 (2H, m), 3.31 (3H, s), 3.77–4.00 (2H, m), 4.16–4.29 (2H, m), 4.88 (1H, br), 6.53–6.67 (2H, m), 6.98 (2H, d, J=8 Hz), 7.08 (1H, m), 7.30–7.53 (3H, m), 8.11 (1H, m)

10) 4-[(2-Benzyloxy)benzoyl]amino-N-[2-(3-carboxyprop-1-yl)oxy]phenyl-N-methylbenzamide NMR (DMSO-d$_6$, δ): 1.90–2.01 (2H, m), 2.42 (2H, t, J=7.5 Hz), 3.20 (3H, s), 3.85–4.02 (2H, m), 5.20 (2H, s), 6.85 (1H, t, J=7 Hz), 6.98 (1H, d, J=7 Hz), 7.09 (1H, t, J=7 Hz), 7.15–7.37 (6H, m), 7.49 (2H, d, J=8 Hz), 7.62 (1H, d, J=7 Hz)

11) 4-(2-Iodobenzoyl)amino-N-[2-(5-carboxypent-1-yl)oxy]phenyl-N-methylbenzamide NMR (CDCl$_3$, δ): 1.45–1.58 (2H, m), 2.65–2.75 (2H, m), 2.75–2.84 (2H, m), 2.35 (2H, t, J=7.5 Hz), 3.32 (3H, s), 3.82–3.98 (2H, m), 6.77–6.86 (2H, m), 7.04 (1H, d, J=7 Hz), 7.09–7.21 (2H, m), 7.28–7.48 (5H, m), 7.82–7.90 (2H, m)

12) 4-(2-Dimethylamino-4-methyl)phenoxymethyl-N-[2-(5-carboxypent-1-yl)oxy]phenyl-N-methylbenzamide NMR (CDCl$_3$, δ): 1.38–1.52 (2H, m), 1.59–1.69 (2H, m), 1.72–1.85 (2H, m), 2.23 (3H, s), 2.25 (3H, s), 2.30 (2H, t, J=7.5 Hz), 2.75 (6H, s), 3.33 (3H, s), 3.11–3.25 (2H, m), 3.88–4.00 (2H, m), 5.02 (2H, s), 6.56–6.67 (3H, m), 6.71 (1H, d, J=7 Hz), 6.90–6.99 (2H, m), 7.24 (2H, d, J=8 Hz), 7.38 (2H, d, J=8 Hz)

13) 3-Methoxy-4-[2-[1-(tert-butoxycarbonyl)piperidin-4-yl]oxybenzoyl]amino-N-[2-(5-carboxypent-1-yl)oxy-4-methyl]phenyl-N-methylbenzamide NMR (CDCl$_3$, δ): 1.40–1.57 (2H, m), 1.45 (9H, s), 1.60–1.94 (6H, m), 2.01–2.22 (2H, m), 2.29 (3H, s), 2.38 (2H, t, J=7.5 Hz), 2.97–3.20 (2H, m), 3.33 (3H, s), 3.41 (2H, t, J=7.5 Hz), 3.71 (3H, s), 3.78–4.00 (2H, m), 4.67 (1H, m), 6.60–6.65 (2H, m), 6.87–7.12 (2H, m), 7.44 (1H, t, J=7 Hz), 8.20 (1H, d, J=7 Hz), 8.40 (1H, d, J=7 Hz)

14) 3-Methoxy-4-[2-[3-(tert-butoxycarbonyl)amino-1-methylprop-1-yl)oxybenzoyl]amino-N-[2-(5-carboxypent-1-yl)oxy-4-methyl]phenyl-N-methylbenzamide NMR (CDCl$_3$, δ): 1.40 (9H, s), 1.42 (3H, d, J=7.5 Hz), 1.43–1.96 (8H, m), 2.25 (3H, s), 2.33–2.42 (2H, m), 3.11–3.33 (2H, m), 3.33 (3H, s), 3.65–3.97 (5H, m), 4.70 (1H, m), 6.53–6.70 (2H, m), 6.79–7.13 (4H, m), 7.44 (1H, t, J=7 Hz), 8.23 (1H, m), 8.39 (1H, m)

15) 4-[2-[3-(tert-Butoxycarbonylamino)prop-1-yl]oxybenzoyl]amino-3-methoxy-N-[2-(3-carboxypyrid-6-yl)methoxy-4-methylphenyl]-N-methylbenzamide NMR (CDCl$_3$, δ): 1.40 (9H, s), 2.05–2.16 (2H, m), 2.27 (3H, s), 3.28 (2H, br), 3.42 (3H, br), 3.58 (3H, br), 3.86–4.00 (2H, m), 4.10–4.25 (2H, m), 4.95 (1H, br), 5.16 (1H, br), 6.62 (3H, br), 6.86–7.18 (4H, m), 7.41 (3H, br), 8.14 (1H, br), 8.33 (1H, br), 9.17 (1H, br)

16) 4-[2-(E)-(2-Carboxyethen-1-yl)benzoylamino-3-methoxy-N-methyl-N-[4-methyl-2-[5-(4-methylpiperazin-1-yl)carbonylpent-1-yl]oxy]phenylbenzamide NMR (CDCl$_3$, δ): 1.50–2.00 (6H, m), 2.27–2.52 (10H, m), 2.60–2.81 (2H, m), 3.31 (3H, s), 3.43–3.66 (2H, m), 3.83–4.22 (7H, m), 5.60 (1H, m), 6.57 (1H, m), 6.65–6.76 (4H, m), 7.01–7.12 (2H, m), 7.21 (1H, d, J=7 Hz), 7.42–7.60 (3H, m), 7.85 (1H, m)

17) 4-[2-(3-Carboxyprop-1-yl)oxybenzoyl]amino-3-methoxy-N-methyl-N-[4-methyl-2-[5-(4-methylpiperazin-1-yl)carbonylpent-1-yl]oxy]phenylbenzamide NMR (CDCl$_3$, δ): 1.44–1.57 (2H, m), 1.64–1.75 (2H, m), 1.75–1.87 (2H, m), 2.20 (3H, s), 2.34 (3H, s), 2.35–2.50 (6H, m), 2.61–2.74 (2H, m), 3.30 (3H, s), 3.33–3.46 (2H, m), 3.49–3.69 (4H, m), 3.75 (3H, s), 3.90–4.02 (2H, m), 4.17–4.27 (2H, m), 6.56–6.72 (2H, m), 6.83–6.92 (2H, m), 6.93–7.00 (2H, m), 7.07 (1H, t, J=7 Hz), 7.43 (1H, t, J=7 Hz), 7.43 (1H, t, J=7 Hz), 8.20 (1H, d, J=7 Hz), 8.40 (1H, d, J=7 Hz)

18) 4-[2-(Carboxymethoxy)benzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.51–1.92 (6H, m), 2.02 (3H, s), 2.30 (3H, s), 2.32 (2H, t, J=5 Hz), 2.43–2.68 (4H, m), 3.33 (3H, s), 3.40–3.55 (4H, m), 3.72 (3H, s), 3.75–4.07 (2H, m), 4.73 (2H, s), 6.57–6.68 (2H, m), 6.81–7.10 (6H, m), 7.35–7.45 (1H, m), 8.18 (1H, d, J=7 Hz), 8.32 (1H, d, J=8 Hz)

EXAMPLE 6

A mixture of 4-[2-[3-(phthalimido)prop-1-yl]oxy]benzoylamino-N-methyl-N-[2-[5-(4-methylpiperazin-1-yl)carbonylpent-1-yloxy]phenyl]benzamide (470 mg) and hydrazine hydrate (158 mg) in ethanol (5 ml) was stirred at ambient temperature for 6 hours and filtered through a bed of Celite. The filtrate was evaporated and the residue was subjected to silica gel column. The column was eluted with a mixture of chloroform, methanol and aqueous ammonia (10:1:0.1). The object fractions were evaporated to give 4-[2-[(3-aminoprop-1-yl)oxy]benzoyl]amino-N-methyl-N-[2-[5-(4-methylpiperazin-1-yl)carbonylpent-1-yloxy]phenyl]benzamide (256 mg) as a colorless amorphous.

NMR (CDCl$_3$, δ): 1.56 (2H, m), 1.74 (2H, m), 1.87 (2H, m), 2.09 (2H, m), 2.29 (3H, s), 2.34–2.43 (6H, m), 2.97 (2H, t, J=7.5 Hz), 3.33 (3H, s), 3.50 (2H, m), 3.65 (2H, m), 3.96 (2H, m), 4.30 (2H, t, J=7.5 Hz), 6.73–6.83 (2H, m), 6.95–7.03 (2H, m), 7.77–7.16 (2H, m), 7.34 (2H, d, J=8.5 Hz), 7.42–7.50 (3H, m), 8.22 (1H, d, J=7 Hz)

EXAMPLE 7

The following compounds were obtained according to a similar manner to that of Example 6.

1) 4-[2-(3-Aminoprop-1-yl)oxy]benzoylamino-N-methyl-N-[2-[3-(4-methylpiperazin-1-yl)carbonylaminoprop-1-yloxy]phenyl]benzamide NMR (CDCl₃, δ): 2.00 (2H, m), 2.10 (2H, m), 2.27 (3H, s), 2.34–2.39 (4H, m), 2.98 (2H, t, J=7.5 Hz), 3.35 (3H, s), 3.35–3.61 (6H, m), 3.98 (2H, m), 4.30 (2H, t, J=7.5 Hz), 6.80–6.91 (2H, m), 7.02 (2H, d, J=7 Hz), 7.07–7.21 (3H, m), 7.33–7.51 (5H, m), 8.22 (1H, d, J=7 Hz)

2) 4-[2-[(3-Aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide NMR (CDCl₃, δ): 1.53 (2H, m), 1.70 (2H, m), 1.84 (2H, m), 2.07 (2H, m), 2.26 (3H, s), 2.28 (3H, s), 2.31–2.40 (6H, m), 2.90 (2H, t, J=7.5 Hz), 3.32 (3H, s), 3.49 (2H, m), 3.60 (2H, m), 3.89 (3H, s), 3.82–3.99 (2H, m), 4.28 (2H, t, J=7.5 Hz), 6.54–6.64 (2H, m), 6.82–6.94 (2H, m), 7.00–7.11 (3H, m), 7.45 (1H, m), 8.20 (1H, m), 8.39 (1H, m)

3) (R)-4-[2-[(4-Aminobut-2-yl)oxy]benzoyl]amino-3-methoxy-N-methyl-N-[4-methyl-2-[5-(4-methylpiperazin-1-yl)carbonylpent-1-yloxy]phenyl]benzamide NMR (CDCl₃, δ): 1.42 and 1.45 (total 3H, s) 1.50–1.89 (8H, m), 2.02–2.12 (1H, m), 2.29 (3H, s), 2.31 (3H, s), 2.33–2.42 (6H, m), 2.84–2.90 (2H, m), 3.33 (3H, s), 3.46–3.52 (2H, m), 3.60–3.67 (2H, m), 3.80 (3H, s), 3.87–4.00 (2H, m), 4.78–4.87 (1H, m), 6.58 (1H, d, J=7 Hz), 6.65 (1H, s), 6.82–6.92 (2H, m), 7.03–7.10 (3H, m), 7.45 (1H, t, J=8 Hz), 8.21 (1H, dd, J=1, 8 Hz), 8.40 (1H, d, J=7 Hz)

ESI-MASS (m/z): 674 (M+H)

4) (R)-4-[2-[(4-Aminobut-2-yl)oxy]benzoyl]amino-3-methoxy-N-methyl-N-[4-methyl-2-[5-(4-dimethylaminopiperidin-1-yl)carbonylpent-1-yloxy]phenyl]benzamide NMR (CDCl₃, δ): 1.43 and 1.45 (total 3H, s) 1.46–1.91 (12H, m), 2.02–2.12 (1H, m), 2.29 (9H, s), 2.30–2.41 (4H, m), 2.52–2.63 (1H, m), 2.87 (2H, t, J=8 Hz), 2.97–3.07 (1H, m), 3.35 (3H, s), 3.80 (3H, s), 3.87 3.98 (4H, m), 4.59–4.68 (1H, m), 4.79–4.88 (1H, m), 6.59 (1H, d, J=8 Hz), 6.64 (1H, s), 6.83–6.93 (2H, m), 7.05–7.10 (3H, m), 7.45 (1H, t, J=8 Hz), 8.23 (1H, d, J=9 Hz), 8.42 (1H, d, J=8 Hz)

ESI-MASS (m/z): 702 (M+H)

5) (S)-4-[2-[(4-Aminobut-2-yl)oxy]benzoyl]amino-3-methoxy-N-methyl-N-[4-methyl-2-[5-(4-dimethylaminopiperidin-1-yl)carbonylpent-1-yloxy]phenyl]benzamide NMR (CDCl₃, δ): 1.43 and 1.45 (total 3H, s) 1.46–1.92 (12H, m), 2.02–2.13 (1H, m), 2.28 (9H, s), 2.30–2.40 (4H, m), 2.52–2.63 (1H, m), 2.86 (2H, t, J=8 Hz), 2.97–3.07 (1H, m), 3.35 (3H, s), 3.81 (3H, s), 3.87 3.98 (4H, m), 4.60–4.68 (1H, m), 4.79–4.89 (1H, m), 6.59 (1H, d, J=8 Hz), 6.54 (1H, s), 6.83–6.93 (2H, m), 7.05–7.10 (3H, m), 7.46 (1H, t, J=8 Hz), 8.23 (1H, d, J=9 Hz), 8.43 (1H, d, J=8 Hz)

ESI-MASS (m/z): 702 (M+H)

6) 4-[2-[4-Aminobut-1-yl)oxybenzoyl]amino-N-methyl-N-[2-[5-(4-methylpiperazin-1-yl)carbonylpent-1-yl]oxy]phenylbenzamide NMR (CDCl₃, δ): 1.47–1.74 (8H, m) 1.77–1.88 (2H, m, 1.95–2.06 (2H, m), 2.27 (3H, s), 2.31–2.40 (4H, m), 2.78 (2H, t, J=7.5 Hz), 3.32 (3H, s), 3.45–3.50 (2H, m), 3.58–3.65 (2H, m), 3.84–3.98 (2H, m), 4.20 (2H, t, J=7.5 Hz), 6.72–6.80 (2H, m), 6.93–7.00 (2H, m), 7.04–7.14 (2H, m), 7.30 (2H, d, J=8 Hz), 7.40–7.48 (3H, m), 8.19 (1H, d, J=7 Hz)

7) 4-[2-(3-Aminoprop-1-yl)oxybenzoyl]amino-N-[2-(5-ethoxycarbonylpent-1-yl)oxy-4-methyl]phenyl-N-methylbenzamide NMR (CDCl₃, δ): 1.24 (3H, t, J=7.5 Hz), 1.44–1.56 (2H, m), 1.63–1.87 (6H, m), 2.06–2.16 (2H, m), 2.28 (3H, s), 2.33 (2H, t, J=7.5 Hz), 2.97 (2H, t, J=7.5 Hz), 3.30 (3H, s), 3.82–3.96 (2H, m), 4.11 (2H, q, J=7.5 Hz), 4.30 (2H, t, J=7.5 Hz), 6.54–6.60 (2H, m), 6.83 (1H, d, J=7 Hz), 7.00 (1H, d, J=7 Hz), 7.09 (1H, t, J=7 Hz), 7.30 (2H, d, J=8 Hz), 7.41–7.48 (3H, m), 8.20 (1H, d, J=7 Hz)

8) 4-[2-(3-Aminoprop-1-yl)oxybenzoyl]amino-N-methyl-N-[2-[3-(4-methylpiperazin-1-yl)carbonylprop-1-yl]oxy-]phenylbenzamide NMR (CDCl₃, δ): 2.03–2.17 (2H, m), 2.29 (3H, s), 2.33–2.42 (2H, m), 2.53 (2H, t, J=7.5 Hz), 2.96 (2H, t, J=7.5 Hz), 3.38 (3H, s), 3.46–3.53 (2H, m), 3.59–3.68 (2H, m), 3.92–4.08 (2H, m), 4.28 (2H, t, J=7.5 Hz), 6.77–6.83 (2H, m), 6.98–7.18 (4H, m), 7.31 (2H, d, J=8 Hz), 7.43–7.50 (3H, m), 8.20 (1H, d, J=7 Hz)

9) 4-[2-(3-Aminoprop-1-yl)oxybenzoyl]amino-N-methyl-N-[4-methyl-2-[4-(4-methylpiperazin-1-yl)carbonyl]phenylmethoxy]phenylbenzamide NMR (CDCl₃, δ): 2.02–2.14 (2H, m), 2.37 (3H, s), 2.30 (3H, s), 2.32–2.51 (4H, m), 2.94 (2H, t, J=7.5 Hz), 3.35 (3H, s), 3.41–3.57 (2H, m), 3.67–3.86 (2H, m), 4.30 (2H, t, J=7.5 Hz), 4.96 (1H, d, J=14 Hz), 5.08 (1H, d, J=14 Hz), 6.63–6.71 (2H, m), 6.95–7.02 (2H, m), 7.11 (1H, t, J=7 Hz), 7.31 (2H, d, J=8 Hz), 7.36–7.50 (7H, m), 8.22 (1H, d, J=7 Hz)

10) 4-[2-(4-Amino-1-butyn-1-yl)benzoyl]amino-N-methyl-N-[2-[5-(4-methylpiperazin-1-yl)carbonylpent-1-yl]oxy]phenylbenzamide NMR (CDCl₃, δ): 1.42–1.90 (10H, m) 2.28 (3H, s), 2.32–2.41 (6H, m), 3.37 (3H, s), 3.46–3.51 (2H, m), 3.59–3.67 (2H, m), 3.82–4.02 (2H, m), 6.73–6.82 (2H, m), 7.00 (1H, d, J=7 Hz), 7.08–7.20 (2H, m), 7.35–7.64 (5H, m), 7.81–7.88 (2H, m)

11) 4-[2-(4-Aminobut-1-yl)benzoyl]amino-N-methyl-N-[2-[5-(4-methylpiperazin-1-yl)carbonylpent-1-yl]oxy]phenylbenzamide MASS (m/z): 614 (M+1)

12) 4-[2-(3-Aminoprop-1-yl)oxybenzoyl]amino-3-methoxy-N-methyl-N-[4-methyl-2-[4-(4-methylpiperazin-1-yl)carbonyl]phenylmethoxy]phenylbenzamide NMR (CDCl₃, δ): 2.01–2.11 (2H, m), 2.28 (3H, s), 2.31 (3H, s), 2.33–2.51 (4H, m), 2.90 (2H, t, J=7.5 Hz), 3.39 (3H, s), 3.40–3.52 (2H, m), 3.61–3.86 (2H, m), 3.67 (3H, s), 4.79 (2H, t, J=7.5 Hz), 4.90 (1H, d, J=14 Hz), 5.08 (1H, d, J=14 Hz), 6.61–6.70 (2H, m), 7.86 (1H, d, J=7 Hz), 6.94–7.10 (4H, m), 7.31–7.46 (5H, m), 8.20 (1H, d, J=7 Hz), 8.37 (1H, d, J=7 Hz)

13) 3-Methoxy-4-[2-(3-aminoprop-1-yl)oxy]phenylmethyl]amino-N-methyl-N-[4-methyl-2-[5-(4-methylpiperazin-1-yl)carbonylpent-1-yl]oxy]phenylbenzamide NMR (CDCl₃, δ): 1.45–1.54 (2H, m), 1.62–1.71 (2H, m), 1.76–1.85 (2H, m), 1.87–2.00 (2H, m), 2.27 (3H, s), 2.30 (3H, s), 2.31–2.40 (4H, m), 2.90 (2H, t, J=7.5 Hz), 3.28 (3H, s), 3.45–3.50 (2H, m), 3.57–3.64 (2H, m), 3.61 (3H, s), 3.80–3.97 (2H, m), 4.07 (2H, t, J=7.5 Hz), 4.27 (2H, s), 4.70 (1H, br), 6.37 (1H, d, J=7 Hz), 6.59 (1H, d, J=7 Hz), 6.62 (1H, s), 6.78 (1H, s), 6.82–6.90 (4H, m), 7.16–7.71 (2H, m)

14) 4-[2-(3-Aminoprop-1-yl)oxybenzoyl]amino-3-methoxy-N-methyl-N-[2-[4-(4-methylpiperazin-1-yl)carbonyl]phenyleth-1-yl]phenylbenzamide NMR (CDCl₃, δ): 2.00–2.11 (2H, m), 2.29 (3H, s), 2.32–2.50 (4H, m), 2.61–2.93 (6H, m), 3.32 (3H, s), 3.35–3.89 (2H, m), 3.59–3.81 (2H, m), 3.71 (3H, s), 4.22–4.32 (2H, m), 6.83 (1H, d, J=7 Hz), 6.94–7.33 (11H, m), 7.43 (1H, t, J=7 Hz), 8.20 (1H, d, J=7 Hz), 8.39 (1H, d, J=7 Hz)

15) 4-[2-(3-Aminoprop-1-yl)thiobenzoyl]amino-3-methoxy-N-methyl-N-[4-methyl-2-[5-(4-methylpiperazin-1-yl)carbonylpent-1-yl]oxy]phenylbenzamide MASS (m/z): 676 (M+1)

16) 4-[2-(3-Aminoprop-1-yl)sulfonylbenzoyl]amino-3-methoxy-N-methyl-N-[4-methyl-2-[5-(4-methylpiperazin-1-yl)carbonylpent-1-yl]oxy]phenylbenzamide MASS (m/z): 724 (M+1)

17) 4-[2-(3-Aminoprop-1-yl)oxybenzoyl]amino-3-methoxy-N-[2-[4-(4-dimethylaminopiperidin-1-yl)carbonyl]phenylmethoxy-4-methyl]phenyl-N-methylbenzamide MASS (m/z): 708 (M+1)

18) 4-[2-(3-Aminoprop-1-yl)oxybenzoyl]amino-3-methoxy-N-methyl-N-[2-[3-(4-methylpiperazin-1-yl)carbonylmethoxyprop-1-yl]oxy]phenylbenzamide NMR (CDCl$_3$, δ): 2.00–2.14 (4H, m), 2.23 (3H, s), 2.29–2.38 (4H, m), 2.88 (2H, t, J=7.5 Hz), 3.35 (3H, s), 3.37–3.45 (2H, m), 3.54–3.61 (2H, m), 3.66–3.76 (2H, m), 3.77 (3H, s), 3.94–4.17 (4H, m), 4.30 (2H, t, J=7.5 Hz), 6.75–7.18 (8H, m), 7.45 (1H, t, J=7 Hz), 8.20 (1H, d, J=7 Hz), 8.42 (1H, d, J=7 Hz)

19) 4-[2-(3-Aminoprop-1-yl)oxybenzoyl]amino-3-methoxy-N-[2-[(E)-5-(4-dimethylaminopiperidin-1-yl)carbonyl-4-penten-1-yl]oxy-4-methyl]phenyl-N-methylbenzamide MASS (m/z): 686 (M+1)

20) 3-Methoxy-4-[2-[3-(tert-butoxycarbonyl)aminoprop-1-yl]oxybenzoyl]amino-N-[2-(4-aminobut-1-yl)oxy-4-methyl]phenyl-N-methylbenzamide NMR (CDCl$_3$, δ): 1.41 (9H, s), 1.50–1.67 (2H, m), 1.77–1.89 (2H, m), 2.06–2.21 (2H, m), 2.27 (3H, s), 2.80 (2H, t, J=7.5 Hz), 3.23–3.36 (2H, m), 3.36 (3H, s), 3.80 (3H, s), 3.84–4.03 (2H, m), 4.26 (2H, t, J=7.5 Hz), 6.57–6.68 (2H, m), 6.83–7.15 (5H, m), 7.45 (1H, t, J=7 Hz), 8.21 (1H, d, J=7 Hz), 8.40 (1H, d, J=7 Hz)

21) 4-[2-(3-Amino-1-methylprop-1-yl)oxybenzoyl]amino-3-methoxy-N-(2-benzyloxy-4-methyl)phenyl-N-methylbenzamide NMR (CDCl$_3$, δ): 1.41 (3H, d, J=7.5 Hz), 1.70–1.83 (1H, m), 1.96–2.10 (1H, m), 2.26 (3H, s), 2.80–2.89 (2H, m), 3.37 (3H, s), 3.62 (3H, s), 4.82 (1H, m), 4.89 (1H, d, J=14 Hz), 5.07 (1H, d, J=14 Hz), 6.63–6.72 (2H, m), 7.86 (1H, d, J=7 Hz), 6.98 (1H, d, J=7 Hz), 7.02–7.11 (3H, m), 7.28–7.49 (6H, m), 8.22 (1H, d, J=7 Hz), 8.37 (1H, d, J=7 Hz)

22) 4-[2-(4-Aminobut-1-yl)oxybenzoyl]amino-3-methoxy-N-methyl-N-[4-methyl-2-[5-(4-methylpiperazin-1-yl)carbonylpent-1-yl]oxy]phenylbenzamide NMR (CDCl$_3$, δ): 1.46–2.03 (10H, m), 2.24 (3H, s), 2.28 (3H, s), 2.31–2.40 (6H, m), 2.73 (2H, t, J=7.5 Hz), 3.31 (3H, s), 3.44–3.50 (2H, m), 3.59–3.65 (2H, m), 3.77 (3H, s), 3.83–4.00 (2H, m), 4.20 (2H, t, J=7.5 Hz), 6.58 (1H, d, J=7 Hz), 7.61 (1H, s), 6.85 (1H, d, J=7 Hz), 6.90 (1H, d, J=7 Hz), 6.87–7.10 (3H, m), 7.45 (1H, t, J=7 Hz), 8.21 (1H, d, J=7 Hz), 8.40 (1H, d, J=7 Hz)

23) 4-[2-(3-Aminoprop-1-yl)oxy-3-methylbenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.49–1.91 (6H, m), 1.96–2.07 (2H, m), 2.27 (3H, s), 2.30 (3H, s), 2.35 (3H, s), 2.32–2.40 (6H, m), 2.95 (2H, t, J=5 Hz), 3.32 (3H, s), 3.46–3.53 (2H, m), 3.60–3.67 (2H, m), 3.81 (3H, s), 3.85–4.02 (4H, m), 6.56–6.66 (2H, m), 6.82–7.18 (4H, m), 7.33 (1H, d, J=8 Hz), 7.80 (1H, d, J=7 Hz), 8.36 (1H, d, J=7 Hz)

24) 4-[2-(3-Aminoprop-1-yl)oxy-4-methylbenzoyl]amino-3-methoxy-N-methyl-N-[2-[5-(4-methylpiperazin-1-ylcarbonyl)pent-1-yloxy]-4-methylphenyl]benzamide NMR (CDCl$_3$, δ): 1.46–1.90 (6 H, m), 2.13–2.25 (2 H, m), 2.26 (3 H, s), 2.28 (3 H, s), 2.30–2.58 (6 H, m), 2.37 (3 H, s), 2.99 (2 H, t, J=5 Hz), 3.30 (3 H, s), 3.49 (3 H, s), 3.49 (2 H, t, J=5 Hz), 3.61 (2 H, t, J=5 Hz), 3.79 (3 H, s), 3.83–3.92 (2 H, m), 4.28 (2 H, t, J=5 Hz), 6.56–6.65 (2 H, m), 6.80–6.93 (4 H, m), 7.00 (1 H, s), 8.02 (1 H, d, J=8 Hz), 8.39 (1 H, d, J=8 Hz)

25) 4-[2-(3-Aminoprop-1-yl)oxy-5-methylbenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.49–1.90 (6 H, m), 1.98–2.20 (4 H, m), 2.28 (3 H, s), 2.29 (3 H, s), 2.31 (3 H, s), 2.31–2.42 (4 H, m), 2.95 (2 H, t, J=5 Hz), 3.31 (3 H, s), 3.50 (2 H, t, J=4 Hz), 3.62 (2 H, t, J=4 Hz), 3.79 (3 H, s), 3.80–4.00 (2 H, m) 4.25 (2 H, t, J=5 Hz), 6.57–6.68 (2 H, m), 6.82–7.04 (4 H, m), 7.24 (1 H, d, J=8 Hz), 7.95 (1 H, s), 8.39 (1 H, d, J=8 Hz)

26) 4-[2-(3-Aminoprop-1-yl)oxy-4-chlorobenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.48–1.60 (2 H, m), 1.62–1.90 (2 H, m), 2.10 (2 H, t, J=6 Hz), 2.27 (3 H, s), 2.29 (3 H, s), 2.30–2.41 (4 H, m), 2.93 (2 H, t, J=5 Hz), 3.31 (3 H, s), 3.45–3.53 (2 H, m), 3.58–3.66 (2 H, m), 3.78 (3 H, s), 3.82–4.01 (2 H, m), 4.29 (2 H, t, J=5 Hz), 6.55–6.68 (2 H, m), 6.80–6.91 (2 H, m), 6.99–7.10 (4 H, m), 8.13 (1 H, d, J=8 Hz), 8.36 (1 H, d, J=8 Hz)

27) 4-[2-(3-Aminoprop-1-yl)oxy-4-methoxybenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.47–1.89 (6 H, m), 2.04–2.15 (2 H, m), 2.28 (3 H, s), 2.30 (3 H, s), 2.31–2.42 (6 H, m), 2.93 (2 H, t, J=5 Hz), 3.31 (3 H, s), 3.44–3.52 (2 H, m), 3.57–3.65 (1 H, m), 3.79 (3 H, s), 3.83 (3 H, s), 3.83–4.00 (2 H, m), 4.26 (2 H, t, J=5 Hz), 7.50–7.68 (4 H, m), 6.82–6.95 (2 H, m), 7.03 (3 H, s), 8.16 (1 H, d, J=8 Hz), 8.38 (1 H, d, J=8 Hz)

EXAMPLE 8

A mixture of 4-(2-benzyloxybenzoyl)amino-N-methyl-N-[2-(5-carboxypent-1-yloxy)phenyl]benzamide (1.76 g), N-ethyl-N'-(3-dimethylaminopropyl)carbodiimide hydrochloride (714 mg), N-methylpiperazine (311 mg) and 1-hydroxybenzotriazol (504 mg) in N,N-dimethylformamide (20 ml) was stirred at ambient temperature for 2 hours and the mixture was diluted with ethyl acetate (40 ml). The solution was washed successively with saturated aqueous sodium hydrogen carbonate solution (40 ml), water (40 ml) and brine (40 ml), and dried over magnesium sulfate. The solvent was evaporated to give 4-(2-benzyloxybenzoyl)amino-N-methyl-N-[2-[5-(4-methylpiperazin-1-yl)carbonylpent-1-yloxy]phenyl]benzamide (1.98 g) as a colorless oil.

NMR (CDCl$_3$, δ): 1.46–1.58 (2 H, m), 1.64–1.88 (4 H, m), 2.30 (3 H, s), 2.32–2.41 (6 H, m), 3.32 (3 H, s), 3.49 (2 H, m), 3.62 (2 H, m), 3.81–4.00 (2 H, br), 5.20 (2 H, s), 6.73–6.82 (2 H, m), 6.94–7.00 (3 H, m), 7.08–7.20 (5 H, m), 7.40–7.53 (6 H, m), 8.28 (1 H, d, J=7 Hz)

EXAMPLE 9

The following compound was obtained by using 4-[2-(carboxymethoxy)benzoyl]amino-N-methyl-N-[2-[5-(4 methylpiperazin-1-yl)carbonylpent-1-yloxy]phenyl]benzamide as a starting compound according to a similar manner to that of Example 8.

4-[2-[(4-Methylpiperazin-1-yl)carbonylmethoxy]-benzoyl]amino-N-methyl-N-[2-[5-(4-methylpiperazin-1-yl)carbonylpent-1-yloxy]phenyl]benzamide

MASS: 699 (M+1)

EXAMPLE 10

A solution of 4-(2-benzyloxybenzoyl)amino-N-methyl-N-[2-[5-(4-methylpiperazin-1-yl)carbonylpent-1-yloxy]

phenyl]benzamide (1.90 g) in methanol (30 ml) was hydrogenated under atmospheric presser in the presence of palladium hydroxide (400 mg) for 6 hours and the catalyst was removed by filtration. The filtrate was evaporated to give 4-(2-hydroxybenzoyl)amino-N-methyl-N-[2-[5-(4-methylpiperazin-1-yl)carbonylpent-1-yloxy]phenyl]benzamide (1.60 g) as a colorless amorphous.

NMR (CDCl$_3$, δ): 1.51 (2 H, m), 1.66 (2 H, m), 1.79 (2 H, m), 2.30 (2 H, m), 2.63 (3 H, s), 2.82–2.95 (4 H, m), 3.33 (3 H, s), 3.72 (2 H, m), 3.86 (2 H, m), 3.99 (2 H, m), 6.78–6.93 (3 H, m), 7.05 (2 H, m), 7.17 (1 H, t, J=7 Hz), 7.27 (2 H, d, J=8.5 Hz), 7.40 (1 H, t, J=7 Hz), 7.53 (2 H, d, J=8.5 Hz), 7.91 (1 H, m), 9.21 (1 H, br)

EXAMPLE 11

The following compounds were obtained according to a similar manner to that of Example 10.

1) 4-(2-Hydroxybenzoyl)amino-N-methyl-N-[2-[3-(4-methylpiperazin-1-yl)carbonylaminoprop-1-yloxy]phenyl]benzamide NMR (CDCl$_3$, δ): 2.00 (2 H, m), 2.71 (3 H, s), 2.90– 3.09 (4 H, m), 3.33 (3 H, s), 3.50–3.80 (6 H, m), 3.97 (2 H, m), 6.76–7.03 (5 H, m), 7.11–7.22 (2 H, m), 7.29–7.44 (3 H, m), 7.45–7.54 (2 H, m), 7.88 (1 H, m)

2) 4-(2-Hydroxybenzoyl)amino-3-methoxy-N-methyl-N-[2-[5-(4-methylpiperazin-1-ylcarbonyl)pent-1-yloxy]-4-methylphenyl]benzamide NMR (CDCl$_3$, δ): 1.46–1.62 (2 H, m), 1.65–1.90 (4 H, m), 2.29 (3 H, s), 2.30–2.43 (2 H, m), 2.82 (3 H, s), 2.88–3.30 (4 H, m), 3.31 (3 H, s), 3.48 (3 H, s), 3.79 (3 H, s), 3.77–4.07 (6 H, m), 6.58–6.69 (2 H, m), 6.84–7.08 (5 H, m), 7.43 (1 H, dd, J=9, 9 Hz), 7.52 (1 H, d, J=9 Hz), 8.20 (1 H, d, J=9 Hz), 8.82 (1 H, br s)

3) 4-(2-Hydroxybenzoyl)amino-3-methoxy-N-methyl-N-[2-[5-(4-methylpiperazin-1-yl)carbonylpent-1-yloxy]phenyl]benzamide NMR (CDCl$_3$, δ): 1.47–1.63 (2 H, m), 1.64–1.90 (4 H, m), 2.38 (2 H, t, J=7 Hz), 2.78 (3 H, s), 2.90–3.31 (4 H, m), 3.33 (3 H, s), 3.77 (3 H, s), 3.80–4.07 (6 H, m), 6.77–7.11 (7 H, m), 7.12–7.23 (1 H, m), 7.37–7.58 (2 H, m), 8.21 (1 H, d, J=9 Hz), 8.79 (1 H, s)

4) 2-Chloro-4-[2-(hydroxy)benzoyl]amino-N-methyl-N-[2-[5-(4-methylpiperazin-1-yl)carbonylpent-1-yloxy]phenyl]benzamide NMR (CDCl$_3$, δ): 1.38–1.98 (6 H, m), 2.21–2.46 (2 H, m), 2.73 (3 H, br s), 2.92–3.25 (4 H, m), 3.36 (3 H, s), 3.70–4.20 (6 H, m), 6.67–6.82 (2 H, m), 6.82–7.08 (4 H, m), 7.08–7.20 (2 H, m), 7.21–7.50 (2 H, m), 7.70 (1 H, br s), 7.92 (1 H, br d, J=8 Hz), 9.48 (1 H, s)

5) 4-(3-Hydroxybenzoyl)amino-3-methoxy-N-methyl-N-[4-methyl-2-[5-(4-dimethylaminopiperidin-1-yl)carbonylpent-1-yloxy]phenyl]benzamide NMR (CDCl$_3$, δ): 1.34–1.58 (4 H, m), 1.64–1.97 (6 H, m), 2.28 (3 H, s), 2.32 (6 H, s), 2.33–2.38 (3 H, m), 2.51–2.61 (1 H, m), 2.97–3.06 (1 H, m), 3.34 (3 H, s), 3.78–3.81 (3 H, br s), 3.85–3.97 (3 H, m), 4.60–4.69 (1 H, m), 6.58–6.65 (2 H, m), 6.84–7.06 (4 H, m), 7.38–7.60 (3 H, m), 8.17–8.23 (1 H, m)

ESI-MASS (m/z): 631 (M+H)

6) 4-(2-Hydroxybenzoyl)amino-N-[2-(5-ethoxycarbonylpent-1-yl)oxy-4-methyl]phenyl-N-methylbenzamide NMR (CDCl$_3$, δ): 1.23 (3 H, t, J=7.5 Hz), 1.41–1.53 (2 H, m), 1.62–1.84 (4 H, m), 2.27 (3 H, s), 2.32 (2 H, t, J=7.5 Hz), 3.31 (3 H, s), 3.78–3.97 (2 H, m), 4.13 (2 H, q, J=7.5 Hz), 6.56–6.61 (2 H, m), 6.84–6.91 (2 H, m), 7.02 (1 H, d, J=7 Hz), 7.28–7.45 (3 H, m), 7.62 (1 H, d, J=7 Hz), 8.47 (1 H, s)

7) 4-(2-Hydroxybenzoyl)amino-N-methyl-N-[2-[3-(4-methylpiperazin-1-yl)carbonylprop-1-yl]oxy]phenylbenzamide NMR (CDCl$_3$, δ): 2.00 (2 H, m), 2.71 (3 H, s), 2.90–3.09 (4 H, m), 3.33 (3 H, s), 3.50–3.80 (6 H, m), 3.97 (2 H, m), 6.76–7.03 (5 H, m), 7.11–7.22 (2 H, m), 7.29–7.44 (3 H, m), 7.45–7.54 (2 H, m), 7.88 (1 H, m)

8) 4-(2-Hydroxy)benzoylamino-3-methoxy-N-methyl-N-[2-[4-(4-methylpiperazin-1-yl)carbonyl]phenyleth-1-yl]phenylbenzamide MASS (m/z): 607 (M+1)

9) 4-(2-Hydroxy-3-methylbenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.50–1.90 (6 H, m), 2.27 (6 H, s), 2.28 (3 H, s), 2.33–2.40 (4 H, m), 2.70–2.78 (2 H, m), 3.30 (3 H, s), 3.80 (3 H, s), 3.85–4.10 (6 H, m), 6.59–6.65 (2 H, m), 6.77–6.97 (6 H, m), 8.19 (1 H, d, J=8 Hz), 8.70 (1 H, br s)

10) 4-(2-Hydroxy-4-methylbenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.49–1.91 (6 H, m), 2.24 (3 H, s), 2.29 (3 H, s), 2.32 (3 H, s), 2.30–2.42 (6 H, m), 3.32 (3 H, s), 3.49 (2 H, t, J=5 Hz), 3.63 (2 H, t, J=5 Hz), 3.80 (3 H, s), 3.88–4.01 (2 H, m), 6.68-6.65 (2 H, m), 6.80 (1 H, s), 6.84 (1 H, d, J=8 Hz), 6.93 (1 H, d, J=7 Hz), 7.03 (1 H, s), 7.37 (1 H, d, J=7 Hz), 8.19 (1 H, d, J=8 Hz), 8.71 (1 H, br)

11) 4-(2-Hydroxy-4-methylbenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.50–1.91 (10 H, m), 2.28 (3 H, s), 2.34 (3 H, s), 2.35 (3 H, s), 2.30–2.41 (6 H, m), 2.80 (2 H, br), 3.31 (3 H, s), 3.80 (3 H, s), 3.81–4.09 (4 H, m), 6.60–6.68 (2 H, m), 6.84–7.02 (4 H, m), 7.20–7.30 (2 H, m), 8.20 (1 H, br), 8.37 (1 H, br)

12) 4-(2-Hydroxy-4-chlorobenzoyl)amino-3-methoxy-N-methyl-N-[2-[5-(4-methylpiperazin-1-yl)carbonylpent-1-yl]oxy-4-methylphenyl]benzamide NMR (CDCl$_3$, δ): 1.46–1.89 (6 H, m), 2.23–2.45 (6 H, m), 2.27 (3 H, s), 2.32 (3 H, s), 3.30 (3 H, s), 3.44–3.68 (4 H, m), 3.80 (3 H, s), 3.80–3.99 (2 H, m), 6.53–6.65 (2 H, m), 6.72–7.03 (5 H, m), 7.41 (1 H, d, J=8 Hz), 8.12 (1 H, d, J=8 Hz), 8.74 (1 H, br)

13) 4-(2-Hydroxy-4-methoxybenzoyl)amino-3-methoxy-N-methyl-N-[2-[5-(4-methylpiperazin-1-ylcarbonyl)pent-1-yl]oxy-4-methylphenyl]benzamide NMR (CDCl$_3$, δ): 1.48–1.60 (2 H, m), 1.63–1.84 (4 H, m), 2.28 (3 H, s), 2.37 (2 H, t, J=5 Hz), 2.25–2.40 (6 H, m), 2.79 (3 H, s), 3.30 (3 H, s), 3.79 (3 H, s), 3.82 (3 H, s), 3.90–4.01 (2 H, m), 6.44–6.50 (2 H, m), 6.60–6.66 (2 H, m), 6.88–6.97 (3 H, m), 7.41 (1 H, d, J=8 Hz), 8.18 (1 H, d, J=8 Hz), 8.40 (1 H, br)

14) 4-(2-Hydroxybenzoyl)amino-3-methoxy-N-methyl-N-[2-[5-(4-dimethylaminopiperidin-1-yl)carbonylpent-1-yloxy]phenyl]benzamide NMR (CDCl$_3$, δ): 1.22–1.45 (2 H, m), 1.45–1.58 (2 H, m), 1.62–1.78 (2 H, m), 1.80–1.96 (4 H, m), 2.30 (6 H, s), 2.30–2.40 (3 H, m), 2.50–2.62 (1 H, m), 2.97-2.37 (1 H, m), 3.37 (3 H, s), 3.78 (3 H, s), 3.82–4.02 (4 H, m), 4.57–4.68 (1 H, m), 6.77–7.02 (8 H, m), 7.10–7.20 (1 H, m), 7.37–7.45 (1 H, m), 7.46–7.62 (1 H, m), 8.20 (1 H, br)

15) 4-(2-Hydroxybenzoyl)amino-3-chloro-N-methyl-N-[2-[5-(4-dimethylaminopiperidin-1-yl)carbonylpent-1-yloxy]-4-methylphenyl]benzamide NMR (CDCl$_3$, δ): 1.30–2.08 (10 H, m), 2.20–2.60 (13 H, m), 2.89–3.05 (1 H, m), 3.30 (3 H, s), 3.82–4.02 (4 H, m), 4.62–4.79 (1 H, m), 6.62 (2 H, s), 6.73–7.02 (4 H, m), 7.28–7.57 (3 H, m), 7.99 (1 H, d, J=7 Hz), 8.42 (1 H, d, J=7 Hz)

16) 3-Ethoxy-4-(2-hydroxybenzoyl)amino-N-methyl-N-[2-[5-(4-methylpiperazin-1-yl)carbonylpent-1-yloxy]-4-methylphenyl]benzamide NMR (CDCl$_3$, δ): 1.40 (3 H, t, J=6 Hz), 1.47–1.57 (2 H, m), 1.65–1.72 (2 H, m), 1.78–1.88 (2 H, m), 2.27 (3 H, s), 2.30 (3 H, s), 2.31–2.42 (7 H, m), 3.30 (3 H, s), 3.48–3.50 (2 H, m), 3.52–3.65 (2 H, m), 3.82–4.02 (4 H, m), 6.58–6.61 (2 H, m), 6.82–6.94 (3 H, m), 6.98–7.02 (2 H, m), 7.40–7.47 (2 H, m), 8.20 (1 H, d, J=7 Hz), 8.83 (1 H, s)

17) 3-Hydroxy-4-(2-hydroxybenzoyl)amino-N-methyl-N-[2-[5-(4-methylpiperazin-1-yl)carbonylpent-1-yloxy]-4-methylphenyl]benzamide NMR (CDCl$_3$, δ): 1.62 (2 H, br), 1.75 (2 H, br), 1.85 (2 H, br), 2.27 (3 H, s), 2.30 (3 H, s), 2.42 (7 H, br), 3.30 (3 H, s), 3.53 (2 H, br), 3.68 (3 H, br), 3.90 (1 H, br), 6.52 (1 H, s), 6.63–6.73 (2 H, m), 6.87 (1 H, t, J=7 Hz), 6.97 (1 H, d, J=7 Hz), 7.08 (1 H, d, J=7 Hz), 7.15 (1 H, s), 7.38 (1 H, t, J=7 Hz), 7.58 (1 H, d, J=7 Hz), 7.98 (1 H, br), 9.02 (1 H, br)

18) 2-(2-Hydroxybenzoyl)amino-N-methyl-N-[2-[5-(4-dimethylaminopiperidin-1-yl)carbonylpent-1-yloxy]-4-methylphenyl]-5-pyridinecarboxamide NMR (CDCl$_3$, δ): 1.32–2.15 (10 H, m), 2.29–2.42 (12 H, m), 2.47–2.62 (1 H, m), 2.95–3.09 (1 H, m), 3.32 (3 H, s), 3.75–4.10 (4 H, m), 4.58–4.77 (2 H, m), 6.33–8.47 (15 H, m)

19) 4-(4-Hydroxybenzoyl)amino-3-methoxy-N-methyl-N-[2-[5-(4-dimethylaminopiperidin-1-yl)carbonylpent-1-yloxy]-4-methylphenyl]benzamide NMR (CDCl$_3$, δ): 1.38–1.55 (4 H, m), 1.62–1.72 (2 H, m), 1.72–1.83 (2 H, m), 1.83–1.97 (2 H, m), 2.27 (3 H, s), 2.32–2.37 (8 H, m), 2.43–2.60 (2 H, m), 2.93–3.05 (1 H, m), 3.31 (3 H, s), 3.70 (3 H, s), 3.78–3.95 (4 H, m), 4.60–4.70 (1 H, m), 6.57–6.60 (2 H, m), 6.80–6.97 (5 H, m), 7.67 (2 H, d, J=7 Hz), 8.22 (1 H, d, J=7 Hz), 8.40 (1 H, s)

20) 4-(4-Hydroxybenzoyl)amino-3-methoxy-N-methyl-N-[2-[5-(4-methylpiperazin-1-yl)carbonylpent-1-yloxy]-4-methylphenyl]benzamide NMR (CDCl$_3$, δ): 1.47–1.58 (2 H, m), 1.67–1.75 (2 H, m), 1.75–1.87 (2 H, m), 2.27 (3 H, s), 2.32 (3 H, s), 2.38–2.48 (7 H, m), 3.35 (3 H, s), 3.48–3.53 (2 H, m), 3.60–3.70 (2 H, m), 3.70 (3 H, s), 3.80–3.90 (1 H, m), 3.90–4.00 (1 H, m), 3.58–3.60 (2 H, m), 6.82–6.97 (5 H, m), 7.68 (2 H, d, J=7 Hz), 8.24 (1 H, d, J=7 Hz), 8.40 (1 H, s)

EXAMPLE 12

A solution of 4-(2-hydroxybenzoyl)amino-N-methyl-N-[2-[5-(4-methylpiperazin-1-yl)carbonylpent-1-yloxy]phenyl]benzamide (400 mg) in N,N-dimethylformamide (15 ml) was added potassium carbonate (99 mg) and N-(3-bromopropyl)phthalimide (192 mg) and the mixture was stirred at 60° C. for 4 hours. The mixture was poured into water (30 ml) and the aqueous solution was extracted with ethyl acetate (20 ml×2). The organic phase was washed with water (20 ml) and brine (20 ml), and dried over magnesium sulfate. The solvent was evaporated to give 4-[2-[3-(phthalimido)prop-1-yl]oxy]benzoylamino-N-methyl-N-[2-[5-(4-methylpiperazin-1-yl)carbonylpent-1-yloxy]phenyl]benzamide (484 mg) as a colorless amorphous.

NMR (CDCl$_3$, δ): 1.56 (2 H, m), 1.63–1.76 (4 H, m), 1.86 (2 H, m), 2.30 (3 H, s), 2.32–2.41 (6 H, m), 3.35 (3 H, s), 3.50 (2 H, m), 3.63 (2 H, m), 3.83– 3.97 (4 H, m), 4.20 (2 H, t, J=7.5 Hz), 6.73–6.81 (2 H, m), 6.92 (1 H, d, J=7 Hz), 7.00–7.14 (3 H, m), 7.32 (2 H, d, J=8.5 Hz), 7.42 (1 H, m), 7.50 (2 H, d, J=8.5 Hz), 7.65–7.74 (4 H, m), 8.08 (1 H, d, J=7 Hz), 9.69 (1 H, s)

EXAMPLE 13

The following compounds were obtained according to a similar manner to that of Example 12.

1) 4-[2-(Ethoxycarbonylmethoxy)benzoyl]amino-N-methyl-N-[2-[5-(4-methylpiperazin-1-yl)carbonylpent-1-yloxy]phenyl]benzamide NMR (CDCl$_3$, δ): 1.31 (3 H, t, J=7.5 Hz), 1.62 (2 H, m), 1.71 (2 H, m), 1.83 (2 H, m), 2.29 (3 H, s), 2.33–2.41 (6 H, m), 3.35 (3 H, s), 3.49 (2 H, m), 3.62 (2 H, m), 3.93 (2 H, m), 4.33 (2 H, q, J=7.5 Hz), 4.76 (2 H, s), 6.72–6.82 (2 H, m), 6.87 (1 H, d, J=7 Hz), 7.00 (1 H, d, J=7 Hz), 7.07–7.18 (2 H, m), 7.33 (2 H, d, J=8.5 Hz), 7.46 (1 H, t, J=7 Hz), 7.71 (2 H, d, J=8.5 Hz), 8.26 (1 H, d, J=7 Hz)

2) 4-[2-(3-Piperidinoprop-1-yloxy)benzoyl]amino-N-methyl-N-[2-[5-(4-methylpiperazin-1-yl)carbonylpent-1-yloxy]phenyl]benzamide NMR (CDCl$_3$, δ): 1.45 (2 H, m), 1.50–1.60 (4 H, m), 1.71 (2 H, m), 1.85 (2 H, m), 2.14 (2 H, m), 2.28 (3 H, s), 2.30–2.41 (10 H, m), 2.49 (2 H, t, J=7.5 Hz), 3.34 (3 H, s), 3.49 (2 H, m), 3.63 (2 H, m), 3.94 (2 H, m), 4.23 (2 H, t, J=7.5 Hz), 6.73–6.82 (2 H, m), 6.96–7.02 (2 H, m), 7.04–7.15 (2 H, m), 7.32 (2 H, d, J=8.5 Hz), 7.43–7.50 (3 H, m), 8.22 (1 H, d, J=7 Hz)

3) 4-[2-[2-(Dimethylamino)eth-1-yloxy]benzoyl]amino-N-methyl-N-[2-[5-(4-methylpiperazin-1-yl)carbonylpent-1-yloxy]phenyl]benzamide NMR (CDCl$_3$, δ): 1.56 (2 H, m), 1.70 (2 H, m), 1.85 (2 H, m), 2.23 (6 H, s), 2.30 (3 H, s), 2.33–2.41 (6 H, m), 2.78 (2 H, t, J=7.5 Hz), 3.35 (3 H, s), 3.50 (2 H, m), 3.64 (2 H, m), 3.93 (2 H, m), 4.22 (2 H, t, J=7.5 Hz), 6.74–6.81 (2 H, m), 6.95–7.01 (2 H, m), 7.06–7.15 (2 H, m), 7.30 (2 H, d, J=8.5 Hz), 7.43 (1 H, m), 7.56 (2 H, d, J=8.5 Hz), 8.21 (1 H, d, J=7 Hz)

4) 4-[2-[3-(Phthalimido)prop-1-yl]oxy]benzoylamino-N-methyl-N-[2-[3-(4-methylpiperazin-1-yl)carbonylaminoprop-1-yloxy]phenyl]benzamide NMR (CDCl$_3$, δ): 2.01 (2 H, m), 2.25 (3 H, s), 2.25–2.38 (6 H, m), 3.33–3.45 (6 H, m), 3.35 (3 H, s), 3.87–4.00 (4 H, m), 4.21 (2 H, t, J=7.5 Hz), 6.78–7.00 (3 H, m), 7.06–7.20 (3 H, m), 7.33–7.56 (4 H, m), 7.65–7.75 (4 H, m), 7.86 (1 H, m), 8.10 (1 H, d, J=7 Hz), 9.73 (1 H, br)

5) 4-[2-[3-(Phthalimido)prop-1-yl]benzoylamino]-3-methoxy-N-methyl-N-[2-[5-(4-methylpiperazin-1-ylcarbonyl)pent-1-yloxy]-4-methylphenyl]benzamide NMR (CDCl$_3$, δ): 1.46–1.62 (2 H, m), 1.63–1.93 (4 H, m), 2.10–2.46 (14 H, m), 3.33 (3 H, s), 3.40–3.53 (2 H, m), 3.57–3.68 (2 H, m), 3.78 (3 H, s), 3.79–4.04 (4 H, m), 4.26 (2 H, t, J=7 Hz), 6.54–6.68 (2 H, m), 6.74–7.11 (5 H, m), 7.37–7.48 (1 H, m), 7.52–7.63 (3 H, m), 7.66–7.77 (1 H, m), 7.80–7.90 (1 H, m), 8.06–8.23 (2 H, m)

6) 3-Methoxy-4-[2-[3-(phthalimido)prop-1-yl]oxybenzoyl]amino-N-methyl-N-[2-[5-(4-methylpiperazin-1 -yl)carbonylpent-1-yloxy]phenyl]benzamide NMR (CDCl$_3$, δ): 1.47–1.63 (2 H, m), 1.63–1.93 (6 H, m), 2.29 (3 H, s), 2.29–2.44 (6 H, m), 3.36 (3 H, s), 3.44–3.53 (2 H, m), 3.58–3.68 (2 H, m), 3.76 (3 H, s), 3.81–4.05 (4 H, m), 4.27 (2 H, t, J=7 Hz), 6.74–6.91 (3 H, m), 6.92–7.20 (5 H, m), 7.38–7.48 (1 H, m), 7.58 (3 H, s), 7.68–7.77 (1 H, m), 7.82–7.90 (1 H, m), 8.09–8.16 (1 H, m), 8.20 (1 H, d, J=9 Hz)

7) 3-Methoxy-4-[2-[3-(phthalimido)prop-1-yl]oxybenzoyl]amino-N-methyl-N-[2-[5-(4-dimethylaminopiperidin-1-yl)carbonylpent-1-yloxy]-4-methylphenyl]benzamide NMR (CDCl$_3$, δ): 1.32–2.00 (12 H, m), 2.16–2.48 (12 H, m), 2.57 (1 H, m), 3.02 (1 H, m), 3.33 (3 H, s), 3.78 (3 H, s), 3.80–4.05 (5 H, m), 4.27 (2 H, t, J=7 Hz), 4.64 (1 H, m), 6.56–6.70 (2 H, m), 6.78–7.12 (5 H, m), 7.43 (1 H, m), 7.59 (2 H, s), 7.66–7.91 (2 H, m), 8.05–8.24 (2 H, m)

8) 4-[2-[(3-tert-Butoxycarbonylaminoprop-1-yl)oxy]benzoyl]amino-3-methoxy-N-methyl-N-[2-(5-ethoxycarbonylpent-1-yloxy)-4-methylphenyl]benzamide NMR (CDCl$_3$, δ): 1.26 (3 H, t, J=7 Hz), 1.34–1.92 (17 H, m), 2.23–2.40 (5 H, m), 3.20–3.40 (5 H, m), 3.78 (3 H, s), 3.82—4.01 (2 H, m), 4.12 (2 H, q, J=7 Hz), 4.25 (2 H, t, J=7 Hz), 4.78 (1 H, m), 6.52–6.69 (2 H, m), 6.79–7.15 (5 H, m), 7.40–7.52 (2 H, m), 8.21 (1 H, d, J=8 Hz), 8.40 (1 H, d, J=8 Hz)

9) 2-Chloro-4-[2-[3-(phthalimido)prop-1-yl]oxybenzoyl]amino-N-methyl-N-[2-[5-(4-methylpiperazin-1-yl)carbonylpent-1-yloxy]phenyl]benzamide NMR (CDCl$_3$, δ): 1.51–1.67 (2 H, m), 1.68–1.82 (2 H, m), 1.82–2.01 (2 H, m), 2.22–2.48 (11 H, m), 3.38 (3 H, s), 3.47–3.56 (2 H, m), 3.58–3.69 (2 H, m), 3.90 (2 H, t, J=7 Hz), 3.94–4.11 (2 H, m), 4.21 (2 H, t, J=7 Hz), 6.69–6.82 (2 H, m), 6.93 (1 H, d, J=8 Hz), 7.02–7.20 (4 H, m), 7.30 (1 H, m), 7.43 (1 H, m), 7.68 (4 H, s), 8.07 (1 H, m), 9.62 (1 H, s)

10) 4-[2-[(3-tert-Butoxycarbonylaminoprop-1-yl)oxy]benzoyl]amino-3-methoxy-N-methyl-N-(2-methylphenyl)benzamide NMR (CDCl$_3$, δ): 1.41 (9 H, s), 2.02–2.18 (2 H, m), 2.21 (3 H, s), 3.21–3.34 (2 H, m), 3.39 (3 H, s), 3.75 (3 H, s), 4.24 (2 H, t, J=7 Hz), 4.74 (1 H, m), 6.83–7.22 (9 H, m), 7.44 (1 H, m), 8.20 (1 H, m), 8.42 (1 H, d, J=8 Hz)

11) 4-[3-[(3-tert-Butoxycarbonylaminoprop-1-yl)oxy]benzoyl]amino-3-methoxy-N-methyl-N-[4-methyl-2-[5-(4-dimethylaminopiperidin-1-yl)carbonylpent-1-yloxy]phenyl]benzamide NMR (CDCl$_3$, δ): 1.32–1.45 (2 H, m), 1.43 (9 H, s), 1.49–1.58 (2 H, m), 1.64–1.90 (6 H, m), 1.97–2.03 (2 H, m), 2.29 (3 H, s), 2.30 (6 H, s), 2.33–2.39 (3 H, m), 2.51–2.61 (1 H, m), 2.97–3.07 (1 H, m), 3.28–3.38 (2 H, m), 3.33 (3 H, s), 3.79 (3 H, s), 3.86–3.97 (3 H, m), 4.08 (2 H, t, J=7 Hz), 4.59–4.67 (1 H, m), 4.70–4.78 (1 H, m), 6.57–6.64 (2 H, m), 6.84 (1 H, d, J=8 Hz), 6.93 (1 H, d, J=8 Hz), 7.02 (1 H, s), 7.03–7.07 (1 H, m), 7.33–7.40 (3 H, m), 8.27 (1 H, d, J=7 Hz), 8.49 (1 H, s)

ESI-MASS (m/z): 788 (M+1)

12) 4-[2-[4-(Phthalimido)but-1-yl]oxybenzoyl]amino-N-methyl-N-[2-[5-(4-methylpiperazin-1-yl)carbonylpent-1-yl]oxy]phenylbenzamide NMR (CDCl$_3$, δ): 1.48–1.60 (2 H, m), 1.65–1.77 (4 H, m), 1.80–2.06 (6 H, m), 2.29 (3 H, s), 2.33–2.41 (6 H, m), 3.38 (3 H, s), 3.45–3.51 (2 H, m), 3.60–3.67 (2 H, m), 3.78 (2 H, t, J=7.5 Hz), 3.88–4.00 (2 H, m), 4.23 (2 H, d, J=7.5 Hz), 6.73-6.42 (2 H, m), 6.99 (2 H, d, J=8 Hz), 7.08–7.17 (2 H, m), 7.36 (2 H, d, J=8 Hz), 7.44–7.50 (3 H, m), 7.68–7.77 (2 H, m), 7.81–7.91 (2 H, m), 8.22 (1 H, d, J=7 Hz)

13) 4-[2-[3-(Phthalimido)prop-1-yl]oxybenzoyl]amino-N-[2-(5-ethoxycarbonyypent-1-yl)oxy-4-methyl]phenyl]-N-methylbenzamide NMR (CDCl$_3$, δ): 1.24 (3 H, t, J=7.5 Hz), 1.45–1.57 (2 H, m), 1.64–1.88 (4 H, m), 2.25 (3 H, s), 2.28–2.37 (4 H, m), 3.31 (3 H, s), 3.84–3.95 (4 H, m), 4.10 (2 H, q, J=7.5 Hz), 4.20 (2 H, t, J=7.5 Hz), 6.52–6.62 (2 H, m), 6.88 (1 H, d, J=7 Hz), 6.92 (1 H, d, J=7 Hz), 7.07 (1 H, t, J=7 Hz), 7.31 (2 H, d, J=8 Hz), 7.39–7.50 (3 H, m), 7.62–7.64 (4 H, m), 8.10 (1 H, d, J=7 Hz), 9.68 (1 H, s)

14) 4-[2-[3-(Phthalimido)prop-1-yl]oxybenzoyl]amino-N-methyl-N-[2-[3-(4-methylpiperazin-1-yl)carbonylprop-1-yl]oxy]phenylbenzamide MASS (m/z): 718 (M+1)

15) 4-[2-[3-(Phthalimdo)prop-1-yl]oxybenzoyl]amino-N-methyl-N-[4-methyl-2-[4-(4-methylpiperazin-1-yl)carbonyl]phenylmethoxy]phenylbenzamide NMR (CDCl$_3$, δ): 2.25 (3 H, s), 2.25–2.31 (2 H, m), 2.31 (3 H, s), 2.36–2.51 (4 H, m), 3.38 (3 H, s), 3.63–3.85 (4 H, m), 3.91 (2 H, t, J=7.5 Hz), 4.20 (2 H, t, J=7.5 Hz), 4.98 (1 H, d, J=14 Hz), 5.08 (1 H, d, J=14 Hz), 6.63–6.70 (2 H, m), 6.90–7.00 (2 H, m), 7.09 (1 H, t, J=7 Hz), 7.32 (2 H, d, J=8 Hz), 7.40–7.77 (7 H, m), 8.10 (1 H, d, J=7 Hz), 9.70 (1 H, s)

16) 4-[2-(3-Hydroxyprop-1-yl)oxybenzoyl)amino-N-methyl-N-[2-[5-(4-methylpiperazin-1-yl)carbonylpent-1-yl]oxy]phenylbenzamide NMR (CDCl$_3$, δ): 1.43–1.56 (2 H, m), 1.60–1.86 (4 H, m), 2.11–2.23 (2 H, m), 2.14 (3 H, s), 2.37–2.90 (6 H, m), 3.33 (3 H, s), 3.40–3.47 (2 H, m), 3.51–3.59 (2 H, m), 3.86 (2 H, t, J=7.5 Hz), 3.86–4.00 (2 H, m), 4.32 (2 H, t, J=7.5 Hz), 6.78–6.85 (2 H, m), 6.99–7.19 (4 H, m), 7.31 (2 H, d, J=8 Hz), 7.41–7.53 (3 H, m), 8.21 (1 H, d, J=8 Hz)

17) 4-[2-(3-Aminoprop-1-yl)oxy]benzoyl]amino-3-methoxy-N-methyl-N-[4-methyl-2-[5-(4-methylpiperazin-1-yl)carbonylpent-1-yl]oxy]phenylbenzamide NMR (CDCl$_3$, δ): 1.43–1.54 (2 H, m), 1.60–1.70 (2 H, m), 1.74–1.85 (2 H, m), 2.10–2.21 (2 H, m), 2.26 (6 H, sx2), 2.30–2.41 (6 H, m), 3.32 (3 H, s), 3.40–3.48 (2 H, m), 3.55–3.61 (2 H, m), 3.77 (3 H, s), 3.77–4.00 (4 H, m), 4.31 (2 H, t, J=7.5 Hz), 6.57–6.63 (2 H, m), 6.85–6.92 (2 H, m), 7.00–7.11 (3 H, m), 7.44 (1 H, t, J=7 Hz), 8.20 (1 H, d, J=7 Hz), 8.40 (1 H, d, J=7 Hz)

18) 3-Methoxy-4-[2-[3-(phthalimido)prop-1-yl]oxybenzoyl]amino-N-methyl-N-[4-methyl-2-[4-(4-methylpiperazin-1-yl)carbonyl]phenylmethoxy]phenylbenzamide NMR (CDCl$_3$, δ): 2.19–2.32 (2 H, m), 2.25 (3 H, s), 2.33 (3 H, s), 2.36–2.52 (4 H, m), 3.33–3.50 (2 H, m), 3.39 (3 H, s), 3.67 (3 H, s), 3.71–3.91 (4 H, m), 4.28 (2 H, t, J=7.5 Hz), 4.95 (1 H, d, J=14 Hz), 5.09 (1 H, d, J=14 Hz), 6.62–6.72 (2 H, m), 6.81 (1 H, d, J=7 Hz), 6.93–7.08 (4 H, m), 7.34–7.47 (4H, m), 7.59 (1H, m), 7.68–7.75 (2H, m), 7.82–7.88 (2H, m), 8.10–8.19 (2H, m)

19) 4-[2-(3-Ethoxycarbonylprop-1-yl)oxybenzoyl]amino-3-methoxy-N-methyl-N-[4-methyl-2-[5-(4-methylpiperazin-1-yl)carbonylpent-1-yl]oxy]phenylbenzamide NMR (CDCl$_3$, δ): 1.22 (3H, t, J=7.5Hz), 1.45–1.57 (2H, m), 1.63 (3H, s), 1.63–1.73 (2H, m), 1.76–1.88 (2H, m), 2.20–2.32 (2H, m), 2.24 (3H, s), 2.27 (3H, s), 2.32–2.40 (6H, m), 2.50 (2H, t, J=7.5Hz), 3.31 (3H, s), 3.43–3.50 (2H, m), 3.58–3.67 (2H, m), 3.78 (3H, s), 3.83–4.00 (2H, m), 4.12 (2H, q, J=7.5Hz), 4.22 (2H, t, J=7.5Hz), 6.57 (1H, d, J=7Hz), 6.62 (1H, s), 6.80–6.90 (2H, m), 6.97–7.11 (3H, m), 7.45 (1H, t, J=7Hz), 8.21 (1H, d, J=7Hz), 8.40 (1H, d, J=7Hz)

20) 3-Methoxy-4-[2-[3-(phthalimido)prop-1-yl]oxy]phenylmethylamino-N-methyl-N-[4-methyl-2-[5-(4-methylpiperazin-1-yl)carbonylpent-1-yl]oxy]phenylbenzamide NMR (CDCl$_3$, δ): 1.44–1.57 (2H, m), 1.62–1.72 (2H, m), 1.72–1.95 (4H, m), 2.18 (2H, t, J=7.5Hz), 2.25 (3H, s), 2.28 (3H, s), 2.28–2.43 (4H, m), 3.28 (3H, s), 3.43–3.50 (2H, m), 3.57–3.65 (2H, m), 3.58 (3H, s), 3.80–3.96 (2H, m), 4.02 (2H, t, J=7.5Hz), 4.24 (2H, s), 4.80 (1H, s), 6.27 (1H, d, J=7Hz), 6.60 (1H, d, J=7Hz), 6.64 (1H, s), 6.80–6.95 (5H, m), 7.12–7.21 (2H, m), 7.64–7.88 (4H, m)

21) 3-Methoxy-4-[2-[3-(phthalimido)prop-1-yl]oxybenzoyl]amino-N-methyl-N-[2-[4-(4-methylpiperazin-1-yl)carbonyl]phenyleth-1-yl]phenylbenzamide NMR (CDCl$_3$, δ): 2.20–2.50 (6H, m), 2.29 (3H, s), 2.61–2.94 (6H, m), 3.30 (3H, s), 3.37–3.68 (2H, m), 3.68 (3H, s), 3.68–3.92 (2H, m), 4.20–4.30 (2H, m), 6.80 (1H, d, J=7Hz), 6.90–6.98 (2H, m), 7.05 (1H, t, J=7Hz), 7.10–7.49 (9H, m), 7.53–7.89 (4H, m), 8.12 (1H, d, J=7Hz), 8.20 (1H, d, J=7Hz)

22) 3-Methoxy-4-[2-[3-(phthalimido)prop-1-yl]oxybenzoyl]amino-N-[2-[4-(4-dimethylaminopiperidin-1-yl)carbonyl]phenylmethoxy-4-methyl]phenyl-N-methylbenzamide MASS (m/z): 824 (M+1)

23) 3-Methoxy-4-[2-[3-(phthalimido)prop-1-yl]oxybenzoyl]amino-N-methyl-N-[2-[3-(4-methylpiperazin-1-yl)carbonylmethoxyprop-1-yl]oxy]phenylbenzamide NMR (CDCl$_3$, δ): 2.04–2.17 (2H, m), 2.25 (3H, s), 2.28–2.40 (6H, m), 3.33 (3H, s), 3.38–3.46 (2H, m), 3.54–3.62 (2H, m), 3.66–3.76 (2H, m), 3.74 (3H, s), 3.80–3.90 (2H, m), 3.98–4.11 (4H, m), 4.28 (2H, t, J=7.5Hz), 6.78–7.10 (7H, m), 7.14 (1H, t, J=7Hz), 7.43 (1H, t, J=7Hz), 7.55 (2H, s), 7.68–7.75 (1H, m), 7.81–7.90 (1H, m), 8.13 (1H, d, J=7Hz), 8.20 (1H, d, J=7Hz)

24) 3-methoxy-4-[2-[3-(phthalimido)prop-1-yl]oxybenzoyl]amino-N-[2-[(E)-5-(4-dimethylaminopiperidin-1-yl)carbonyl-4-penten-1-yl]oxy-4-methyl]phenyl-N-methylbenzamide NMR (CDCl$_3$, δ): 1.27–1.47 (2H, m), 1.83–2.02 (2H, m), 2.10–2.48 (6H, m), 2.23 (3H, s), 2.26 (6H, s), 2.50–4.13 (8H, m), 3.32 (3H, s), 3.78 (3H, s), 4.26 (2H, t, J=7.5Hz), 4.62 (2H, m), 6.32 (1H, d, J=15Hz), 6.57–6.67 (2H, m), 6.80–7.16 (5H, m), 7.44 (1H, t, J=7Hz), 7.53–7.88 (5H, m), 7.57 (2H, s), 8.09–8.19 (2H, m)

25) 3-Methoxy-4-[2-(pyrid-3-yl)methoxybenzoyl]amino-N-methyl-N-[4-methyl-2-[5-(4-methylpiperazin-1-yl)carbonylpent-1-yl]oxy]phenylbenzamide NMR (CDCl$_3$, δ): 1.44–1.57 (2H, m), 1.63–1.72 (2H, m), 1.75–1.86 (2H, m), 2.27 (3H, s), 2.30 (3H, s), 2.32–2.40 (6H, m), 3.29 (3H, s), 3.31 (3H, s), 3.45–3.51 (2H, m), 3.58–3.65 (2H, m), 3.80–4.00 (2H, m), 5.30 (2H, s), 6.58 (1H, d, J=7Hz), 6.61 (1H, s), 6.83 (1H, d, J=7Hz), 6.88–6.92 (2H, m), 7.05 (1H, d, J=7Hz), 7.14 (1H, t, J=7Hz), 7.29 (1H, m), 7.46 (1H, t, J=7Hz), 7.79 (1H, d, J=7Hz), 8.22 (1H, d, J=7Hz), 8.37 (1H, d, J=7Hz), 8.62 (6H, d, J=7Hz), 8.73 (1H, s)

26) 3-Methoxy-4-[2-[4-(phthalimido)but-1-yl]oxybenzoyl]amino-N-methyl-N-[4-methyl-2-[5-(4-methylpiperazin-1-yl)carbonylpent-1-yl]oxy]phenylbenzamide NMR (CDCl$_3$, δ): 1.46–1.59 (2H, m), 1.65–1.74 (2H, m), 1.78–2.03 (6H, m), 2.26 (3H, s), 2.30 (3H, s), 2.32–2.41 (6H, m), 3.31 (3H, s), 3.43–3.50 (2H, m), 3.60–3.65 (2H, m), 3.74 (2H, t, J=7.5Hz), 3.77 (3H, s), 3.82–4.01 (2H, m), 4.22 (2H, t, J=7.5Hz), 6.58 (1H, d, J=7Hz), 6.63 (1H, s), 6.85 (1H, d, J=7Hz), 6.90 (1H, d, J=7Hz), 7.00 (1H, d, J=7Hz), 7.02 (1H, s), 7.08 (1H, t, J=7Hz), 7.45 (1H, t, J=7Hz), 7.70–7.76 (2H, m), 7.80–7.87 (2H, m), 8.21 (1H, d, J=7Hz), 8.40 (1H, d, J=7Hz)

27) 4-[2-(3-Dimethylaminoprop-1-yl)oxybenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.50–1.91 (6H, m), 2.07–2.18 (2H, m), 2.25 (6H, s), 2.28 (3H, s), 2.30 (3H, s), 2.32–2.44 (2H, m), 2.48 (2H, t, J=5Hz), 3.32 (3H, s), 3.49 (2H, t, J=5Hz), 3.63 (2H, t, J=3Hz), 3.78 (3H, s), 3.81–3.92 (2H, m), 4.25 (2H, t, J=5Hz), 6.54–6.64 (2H, m), 6.80–6.91 (2H, m), 6.99–7.11 (4H, m), 7.40–7.48 (1H, m) 8.18 (1H, d, J=7Hz), 8.38 (1H, d, J=7Hz)

28) 4-[2-(Ethoxycarbonylmethoxy)benzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.23 (3H, t, J=5Hz), 1.50–1.91 (6H, m), 2.28 (3H, s), 2.31 (3H, s), 2.35–2.47 (6H, m), 3.33 (3H, s), 3.52 (2H, t, J=5Hz), 3.67 (2H, t, J=5Hz), 3.76 (3H, s), 3.84–4.02 (2H, m), 4.24 (2H, q, J=5Hz), 4.85 (2H, s), 6.55–6.67 (2H, m), 6.81–7.19 (6H, m), 7.41–7.49 (2H, m), 8.20 (1H, d, J=8Hz), 8.34 (1H, d, J=7Hz)

29) 4-[2-[3-(Phthalimido-1-yl)prop-1-yloxy]-3-methylbenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.50–1.92 (6H, m), 2.14–2.44 (8H, m), 2.25 (3H, s), 2.28 (3H, s), 2.36 (3H, s), 3.33 (3H, s), 3.50 (2H, t, J=5Hz), 3.58 (2H, t, J=5Hz), 3.63 (2H, t, J=5Hz), 3.81 (3H, s), 3.81–4.03 (8H, m), 6.55–6.68 (2H, m), 6.82–7.38 (6H, m), 7.59–7.88 (5H, m), 8.32 (1H, d, J=8Hz)

30) 4-[2-[3-(Phthalimido-1-yl)prop-1-yl]oxy-4-methylbenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.50–1.91 (8H, m), 2.27 (3H, s), 2.30 (3H, s), 2.31–2.42 (6H, m), 2.38 (3H, s), 3.32 (3H, s), 3.50 (2H, t, J=5Hz), 3.63 (2H, t, J=5Hz), 3.78 (3H, s), 3.85–4.02 (6H, m), 4.28 (2H, t, J=5Hz), 6.58–6.67 (2H, m), 6.77 (1H, s), 6.80–6.92 (4H, m), 7.00 (1H, s), 7.58 (4H, s), 8.01 (1H, d, J=8Hz), 8.18 (1H, d, J=8Hz)

31) 4-[2-[3-(Phthalimido-1-yl)propyloxy]-5-methylbenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.52–1.91 (10H, m), 2.25 (3H, s), 2.30 (3H, s), 2.31 (3H, s), 2.31–2.45 (2H, m), 3.31 (3H, s), 3.50 (2H, t, J=4Hz), 3.59 (2H, t, J=5Hz), 3.64 (2H, t, J=4Hz), 3.78 (3H, s), 3.85–4.02 (4H, m), 4.24 (2H, t, J=5Hz), 6.58 (2H, m), 6.81–6.92 (3H, m), 7.00 (1H, s), 7.25 (1H, d, J=8Hz), 7.59 (3H, s), 7.71–7.79 (1H, m), 7.82–7.89 (1H, m), 7.92 (1H, s), 8.20 (1H, d, J=8Hz)

32) 4-[2-[3-(Phthalimido-1-yl)propyloxy]-4-chlorobenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.45–1.92 (6H, m), 2.25 (3H, s), 2.30 (3H, s), 2.29–2.44 (8H, m), 3.32 (3H, s), 3.46–3.54 (2H, m), 3.61–3.68 (2H, m), 3.78 (3H, s), 3.80–4.01 (4H, m), 4.25 (2H, t, J=5Hz), 6.56–6.77 (2H, m), 6.79–7.04 (7H, m), 7.44 (2H, s), 7.70–7.78 (1H, m), 7.81–7.88 (1H, m), 8.06 (1H, d, J=8Hz)

33) 4-[2-[3-(Phthalimido-1-yl)propyloxy]-4-methoxybenzoyl]amino-3-methoxy-N-methyl-N-[2-[5-(4-methylpiperazin-1-yl)carbonylpent-1-yl]oxy-4-methylphenyl]benzamide NMR (CDCl$_3$, δ): 1.49–1.90 (6H, m), 2.15–2.24 (2H, m), 2.28 (3H, s), 2.32 (3H, s), 2.30–2.42 (6H, m), 3.33 (3H, s), 3.50 (2H, t, J=4Hz), 3.60 (2H, t, J=5Hz), 3.63 (2H, t, J=4Hz), 3.79 (3H, s), 3.85 (3H, s), 3.82–4.02 (6H, m), 4.24 (2H, t, J=5Hz), 6.57–6.68 (2H, m), 6.82 (1H, d, J=8Hz), 6.89 (1H, d, J=8Hz), 7.00 (1H, s), 7.57 (2H, s), 7.71–7.76 (2H, m), 7.82–7.88 (2H, m), 8.11 (1H, d, J=9Hz), 8.17 (1H, d, J=8Hz)

34) 4-[2-[3-(tert-Butoxycarbonylamino)prop-1-yl]oxybenzoyl]amino-3-methoxy-N-(2-benzyloxy-4-methylphenyl)-N-methylbenzamide NMR (CDCl$_3$, δ): 1.40 (9H, s), 2.10 (2H, t, J=5Hz), 2.29 (3H, s), 3.28 (2H, q, J=5Hz), 3.39 (3H, s), 3.62 (3H, s), 4.21 (2H, t, J=5Hz), 4.90 (1H, d, J=13Hz), 5.08 (1H, d, J=13Hz), 6.63–6.71 (3H, m), 6.87 (1H, d, J=7Hz), 6.96–7.11 (6H, m), 7.31–7.48 (6H, m), 8.21 (1H, d, J=8Hz), 8.38 (1H, d, J=8Hz)

35) 4-[2-[3-(tert-Butoxycarbonylamino)prop-1-yl]oxybenzoyl]amino-3-methoxy-N-[2-[4-(2-oxazolin-2-yl)phenylmethyl]oxy-4-methylphenyl]-N-methylbenzamide NMR (CDCl$_3$, δ): 1.40 (9H, s), 2.09–2.17 (2H, m), 2.28 (3H, s), 3.27 (1H, q, J=5Hz), 3.40 (3H, s), 3.65 (3H, s), 4.05 (2H, t, J=10Hz), 4.23 (2H, t, J=5Hz), 4.40 (2H, t, J=10Hz), 4.88 (1H, d, J=12Hz), 5.08 (1H, d, J=12Hz), 6.62 (1H, s), 6.68 (1H, d), 6.97–7.11 (6H, m), 7.32 (1H, d, J=8Hz), 7.41

(1H, d, J=8Hz), 7.92 (2H, d, J=8Hz), 8.21 (1H, d, J=8Hz), 8.37 (1H, d, J=8Hz)

36) 3-Methoxy-4-[2-[3-(phthalimido)prop-1-yl]oxybenzoyl]amino-N-methyl-N-[2-[5-(4-dimethylaminopiperidin-1-yl)carbonylpent-1-yloxy]phenyl]benzamide NMR (CDCl$_3$, δ): 1.22–1.47 (2H, m), 1.47–1.80 (6H, m), 1.80–1.92 (4H, m), 2.29 (6H, s), 2.31–2.41 (3H, m), 2.50–2.63 (1H, m), 2.95–3.07 (1H, m), 3.36 (3H, s), 3.48 (1H, s), 3.49 (1H, s), 3.75 (3H, s), 3.82–4.03 (4H, m), 4.22–4.30 (2H, m), 4.60–4.70 (1H, m), 6.78–6.90 (3H, m), 6.92–7.20 (4H, m), 7.40–7.50 (1H, m), 7.55–7.63 (3H, m), 7.70–7.80 (1H, m), 7.82–7.90 (1H, m), 8.10–8.22 (2H, m)

37) 3-Methyl-4-[2-[[3-(phthalimido)prop-1-yl]oxy]benzoyl]amino-N-methyl-N-[2-[5-(4-methylpiperazin-1-yl)carbonylpent-1-yloxy]-4-methylphenyl]benzamide MASS (m/z): 774 (M+H)

38) 4-[2-[(3-tert-Butoxycarbonylaminoprop-1-yl)oxy]benzoyl]amino-3-chloro-N-methyl-N-[2-[5-(4-dimethylaminopiperidin-1-yl)carbonylpent-1-yloxy]-4-methylphenyl]benzamide NMR (CDCl$_3$, δ): 1.32–1.45 (2H, m), 1.41 (9H, s), 1.48–1.59 (2H, m), 1.62–1.91 (8H, m), 2.08–2.18 (2H, m), 2.27 (6H, s), 2.28 (3H, s), 2.30–2.40 (3H, m), 2.52–2.61 (1H, m), 2.97–3.07 (1H, m), 3.22–3.30 (2H, m), 3.30 (3H, s), 3.83–4.00 (3H, m), 4.30 (2H, t, J=6Hz), 4.57–4.68 (1H, m), 6.60–6.63 (2H, m), 6.87–6.90 (1H, m), 7.02–7.15 (3H, m), 7.46–7.57 (2H, m), 8.20–8.22 (1H, m), 8.40 (1H, d, J=7Hz)

39) 3-Ethoxy-4-[2-[[3-(phthalimido)prop-1-yl]oxy]benzoyl]amino-N-methyl-N-[2-[5-(4-methylpiperazin-1-yl)carbonylpent-1-yloxy]-4-methylphenyl]benzamide MASS (m/z): 804 (M+H)

40) 3-(3-tert-Butoxycarbonylaminoprop-1-yl)oxy-4-[2-[(3-tert-butoxycarbonylaminoprop-1-yl)oxy]benzoyl]amino-N-methyl-N-[2-[5-(4-methylpiperazin-1-yl)carbonylpent-1-yloxy]-4-methylphenyl]benzamide NMR (CDCl$_3$, δ): 1.40 and 1.43 (total 18H, s), 1.49–1.60 (2H, m), 1.62–1.98 (6H, m), 2.00–2.10 (2H, m), 2.27 (3H, s), 2.29 (3H, s), 2.31–2.41 (6H, m), 3.17–3.29 (4H, m), 3.30 (3H, s), 3.45–3.50 (2H, m), 3.59–3.69 (2H, m), 3.84–4.05 (4H, m), 4.22–4.30 (2H, m), 5.04 (2H, br), 6.55–6.63 (2H, m), 6.85 (1H, d, J=7Hz), 6.93 (1H, d, J=7Hz), 6.98–7.03 (2H, m), 7.09 (1H, t, J=7Hz), 7.43 (1H, t, J=7Hz), 8.14 (1H, d, J=7Hz), 8.36 (1H, d, J=7Hz)

41) 2-Amino-4-[2-[(3-tert-butoxycarbonylaminoprop-1-yl)oxy]benzoyl]amino-N-methyl-N-[2-[5-(4-dimethylaminopiperidin-1-yl)carbonylpent-1-yloxy]-4-methylphenyl]benzamide NMR (CDCl$_3$, δ): 1.25–1.39 (2H, m), 1.42 and 1.46 (total 9H, s), 1.48–1.60 (2H, m), 1.62–1.93 (8H, m), 2.08–2.18 (2H, m), 2.27 and 2.28 (total 9H, s), 2.33–2.39 (3H, m), 2.50–2.60 (1H, m), 2.96–3.05 (1H, m), 3.29 (3H, s), 3.31–3.40 (2H, m), 3.85–3.98 (3H, m), 4.19 (2H, t, J=6Hz), 4.57–4.67 (1H, m), 6.57–6.59 (1H, m), 6.63 (2H, s), 6.78–6.89 (2H, m), 6.96 (1H, d, J=7Hz), 7.09 (1H, t, J=6Hz), 7.15 (1H, s), 7.40–7.46 (1H, m), 8.17 (1H, d, J=6Hz)

42) 2-[2-[(3-tert-Butoxycarbonylaminoprop-1-yl)oxy]benzoyl]amino-N-methyl-N-[2-[5-(4-dimethylaminopiperidin-1-yl)carbonylpent-1-yloxy]-4-methylphenyl]-5-pyridinecarboxamide NMR (CDCl$_3$, δ): 1.30 (9H, s), 1.35–1.93 (12H, m), 2.10–2.22 (2H, m), 2.28 (9H, s), 2.30–2.40 (3H, m), 2.50–2.62 (1H, m), 2.95–3.08 (1H, m), 3.33 (3H, s), 3.38–3.49 (2H, m), 3.82–3.98 (4H, m), 4.29 (2H, t, J=6Hz), 4.57–4.67 (1H, m), 6.60–6.62 (2H, m), 6.90 (1H, d, J=6Hz), 6.99 (1H, d, J=7Hz), 7.09 (1H, d, J=7Hz), 7.44–7.55 (2H, m), 8.13–8.21 (2H, m), 8.39 (1H, s)

EXAMPLE 14

To an ice bath cooled solution of 4-[2-[(3-aminoprop-1-yl)oxy]benzoyl]amino-N-methyl-N-[2-[5-(4-methylpiperazin-1-yl)carbonylpent-1-yloxy]phenyl]benzamide (200 mg) in dichloromethane (10 ml) were added triethylamine (36.2 mg) and acetic anhydride (36.5 mg) and the mixture was stirred at ambient temperature for 4 hours. The reaction mixture was washed successively with water (10 ml), saturated aqueous sodium hydrogen carbonate solution (10 ml) and brine (10 ml), and dried over magnesium sulfate. The solvent was evaporated to give 4-[2-[(3-acetylaminoprop-1-yl)oxy]benzoyl]amino-N-methyl-N-[2-[5-(4-methylpiperazin-1-yl)carbonylpent-1-yloxy]phenyl]benzamide (201 mg) as a colorless amorphous.

NMR (CDCl$_3$, δ): 1.51 (2H, m), 1.62–1.86 (4H, m), 1.93 (3H, s), 2.11 (2H, m), 2.29 (3H, s), 2.30–2.40 (6H, m), 3.35 (3H, s), 3.40–3.50 (4H, m), 3.59 (2H, m), 3.92 (2H, m), 4.18 (2H, t, J=7.5Hz), 6.28 (1H, m), 6.75–6.83 (2H, m), 6.94–7.17 (4H, m), 7.31 (2H, d, J=8.5Hz), 7.40–7.49 (3H, m), 8.08 (1H, d, J=7Hz), 9.18 (1H, s)

EXAMPLE 15

To a mixture of 4-[2-[(3-aminoprop-1-yl)oxy]benzoyl]amino-N-methyl-N-[2-[5-(4-methylpiperazin-1-yl)carbonylpent-1-yloxy]phenyl]benzamide (220 mg) and 37% aqueous formaldehyde (290 mg) in a mixture of methanol (10 ml) and acetic acid (0.2 ml) was added sodium cyanoborohydride (44.8 mg) and the mixture was stirred at ambient temperature for 4 hours. The reaction mixture was diluted with chloroform (20 ml) and the solution was washed successively with saturated aqueous sodium hydrogen carbonate solution (20 ml), water (10 ml) and brine (10 ml). The organic phase was dried over magnesium sulfate and the solvent was evaporated to give 4-[2-[(3-dimethylaminoprop-1-yl)oxy]benzoyl]amino-N-methyl-N-[2-[5-(4-methylpiperazin-1-yl)carbonylpent-1-yloxy]phenyl]benzamide (215 mg) as a colorless amorphous.

NMR (CDCl$_3$, δ): 1.55 (2H, m), 1.73 (2H, m), 1.84 (2H, m), 2.11 (2H, m), 2.20 (6H, s), 2.30 (3H, s), 2.32–2.40 (6H, m), 2.46 (2H, t, J=7.5Hz), 3.35 (3H, s), 3.49 (2H, m), 3.62 (2H, m), 4.24 (2H, t, J=7.5Hz), 6.74–6.83 (2H, m), 6.97–7.03 (2H, m), 7.07–7.16 (2H, m), 7.32 (2H, d, J=8.5Hz), 7.42–7.50 (3H, m), 8.22 (2H, d, J=7Hz)

EXAMPLE 16

To a solution of 4-[2-[(3-aminoprop-1-yl)oxy]benzoyl]amino-N-methyl-N-[2-[5-(4-methylpiperazin-1-yl)carbonylpent-1-yloxy]phenyl]benzamide (250 mg) was added 4 N hydrogen chloride in ethyl acetate (1 ml) and the solution was stirred at ambient temperature for 10 minutes. The white solid was filtered and dried under reduced pressure to give 4-[2-[(3-aminoprop-1-yl)oxy]benzoyl]amino-N-methyl-N-[2-[5-(4-methylpiperazin-1-yl)carbonylpent-1-yloxy]phenyl]benzamide dihydrochloride (205 mg) as a white powder.

NMR (D$_2$O, δ): 1.40 (2H, m), 1.59 (2H, m), 1.70 (2H, m), 2.09 (2H, m), 2.42 (2H, t, J=7.5Hz), 2.92 (3H, s), 2.96–3.17 (6H, m), 3.24 (3H, s), 3.41–3.59 (2H, m), 3.69 (1H, m), 3.82 (1H, m), 4.04–4.20 (3H, m), 4.53 (1H, m), 6.72 (1H, d, J=7Hz), 6.81 (1H, t, J=7Hz), 6.93–7.60 (11H, m)

EXAMPLE 17

The following compounds were obtained according to a similar manner to that of Example 16.

1) 4-[2-[(3-Acetylaminoprop-1-yl)oxy]benzoyl]amino-N-methyl-N-[2-[5-(4-methylpiperazin-1-yl)carbonylpent-1-yloxy]phenyl]benzamide hydrochloride NMR (D₂O, δ): 1.38 (2H, m), 1.50–1.68 (4H, m), 1.48 (2H, m), 1.81 (3H, s), 2.42 (2H, m), 2.90 (3H, s), 2.97–3.15 (6H, m), 3.24 (3H, s), 3.40–3.61 (4H, m), 3.71–3.92 (2H, m), 4.14 (1H, m), 4.54 (1H, m), 6.62–6.77 (2H, m), 6.79–6.90 (2H, m), 7.00 (1H, m), 7.11 (1H, m), 7.19–7.33 (5H, m), 7.59 (1H, d, J=7Hz)

2) 4-[2-[(3-Dimethylaminoprop-1-yl)oxy]benzoyl]amino-N-methyl-N-[2-[5-(4-metylpiperazin-1-yl)carbonylpent-1-yloxy]phenyl]benzamide dihydrochloride NMR D₂O, δ): 1.51 (2H, m), 1.67 (2H, m), 1.81 (2H, m), 2.22 (2H, m), 2.53 (2H, t, J=7.5Hz), 2.65 (6H, s), 2.82 (3H, s), 3.00–3.17 (2H, m), 3.23 (2H, t, J=7.5Hz), 3.37 (3H, s), 3.89 (1H, m), 4.13 (1H, m), 4.07–4.20 (3H, m), 4.58 (1H, m), 6.92–7.00 (2H, m), 7.11–7.18 (2H, m), 7.26–7.48 (6H, m), 7.54–7.60 (2H, m)

3) 4-[2-[(4-Methylpiperazin-1-yl)carbonylmethoxy]benzoyl]amino-N-methyl-N-[2-[5-(4-methylpiperazin-1-yl)carbonylpent-1-yloxy]phenyl]benzamide dihydrochloride NMR (D₂O, δ): 1.36 (2H, m), 1.53 (2H, m), 1.66 (2H, m), 2.98 (6H, s), 2.91–3.25 (10H, m), 3.30 (3H, s), 3.37–3.69 (4H, m), 3.77–3.96 (2H, m), 4.35–4.56 (2H, m), 4.82 (2H, s), 6.75 (1H, d, J=7Hz), 6.84 (1H, t, J=7Hz), 6.92 (1H, d, J=7Hz), 7.03– 7.15 (2H, m), 7.22 (1H, d, J=7Hz), 7.29 (2H, d, J=8.5Hz), 7.43–7.58 (3H, m), 7.80 (1H, d, J=7Hz)

4) 4-[2-(3-Piperidinoprop-1-yloxy)benzoyl]amino-N-methyl-N-[2-[5-(4-methylpiperazin-1-yl)carbonylpent-1-yloxy]phenyl]benzamide dihydrochloride NMR (D₂O, δ): 1.42–1.67 (10H, m), 1.78 (2H, m), 2.20 (2H, m), 2.51 (2H, t, J=7.5Hz), 2.65 (2H, m), 2.94 (3H, s), 2.95–3.21 (6H, m), 3.32 (2H, m), 3.35 (3H, s), 3.57 (2H, m), 3.92–4.04 (2H, m), 4.16–4.25 (4H, m), 6.91–6.99 (2H, m), 7.08–7.17 (2H, m), 7.23–7.47 (6H, m), 7.52–7.60 (2H, m)

5) 4-[2-[2-(Dimethylamino)eth-1-yloxy]benzoyl]amino-N-methyl-N-[2-[5-(4-methylpiperazin-1-yl)carbonylpent-1-yloxy]phenyl]benzamide dihydrochloride NMR (D₂O, δ): 1.52 (2H, m), 1.68 (2H, m), 1.81 (2H, m), 2.52 (2H, t, J=7.5Hz), 2.82 (6H, s), 2.93 (3H, s), 2.97–3.21 (4H, m), 3.37 (3H, s), 3.48–3.62 (2H, m), 3.87 (1H, m), 4.01 (1H, m), 4.24 (1H, m), 4.47 (2H, m), 4.57 (1H, m), 6.92–7.00 (2H, m), 7.13–7.48 (8H, m), 7.52–7.62 (2H, m)

6) 4-[2-(3-Aminoprop-1-yl)oxy]benzoylamino-N-methyl-N-[2-[3-(4-methylpiperazin-1-yl)carbonylaminoprop-1-yloxy]phenyl]benzamide dihydrochloride NMR (D₂O, δ): 2.01 (2H, m), 2.17 (2H, m), 2.91 (3H, s), 2.95–3.46 (8H, m), 3.40 (3H, s), 3.54 (2H, m), 4.02–4.16 (4H, m), 4.27 (2H, m), 6.93–7.00 (2H, m), 7.12–7.21 (2H, m), 7.26–7.37 (2H, m), 7.39–7.48 (2H, m), 7.54–7.64 (2H, m)

7) 4-[2-[(3-Aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide dihydrochloride NMR (D₂O, δ): 1.43 (2H, m), 1.60 (2H, m), 1.72 (2H, m), 2.07 (2H, m), 2.18 (3H, s), 2.45 (2H, t, J=7.5Hz), 2.90 (3H, s), 2.92–3.13 (4H, m), 3.30 (3H, s), 3.41–3.63 (4H, m), 3.64 (3H, s), 3.82 (1H, m), 3.92 (1H, m), 4.04–4.61 (3H, m), 4.50 (1H, m), 6.66–6.74 (3H, m), 6.93–7.04 (3H, m), 7.10 (1H, d, J=7Hz), 7.41 (1H, t, J=7Hz), 7.73 (1H, d, J=7Hz), 7.95 (1H, d, J=7Hz)

8) 4-[2-(3-Aminoprop-1-yl)oxy-4-methylbenzoyl]amino-3-methoxy-N-methyl-N-[2-[5-(4-methylpiperazin-1-ylcarbonyl)pent-1-yloxy]-4-methylphenyl]benzamide dihydrochloride NMR (CDCl₃, δ): 1.48–1.96 (8H, m), 2.27 (3H, s), 2.32–2.42 (2H, m), 2.78 (3H, s), 3.11–3.22 (2H, m), 3.28 (3H, s), 3.79 (3H, s), 3.80–4.11 (2H, m), 4.22–4.32 (2H, m), 6.58–6.67 (2H, m), 6.79–6.96 (5H, m), 7.87 (1H, d, J=8Hz), 8.69–8.75 (1H, m), 9.41 (1H, br)

9) 4-[2-(3-Aminoprop-1-yl)oxy-3-methylbenzoyl]amino-3-methoxy-N-methyl-N-[2-[5-(4-methylpiperazin-1-yl)carbonylpent-1-yl]oxy-4-methylphenyl]benzamide dihydrochloride NMR (CDCl₃, δ): 1.46–1.92 (6H, m), 2.15–2.57 (4H, m), 2.24 (3H, s), 2.30 (3H, s), 2.62–2.98 (6H, m), 2.80 (3H, s), 3.02–3.29 (4H, m), 3.28 (3H, s), 3.73–4.18 (5H, m), 4.46 (1H, br), 4.62 (1H, br), 6.56–6.68 (2H, m), 6.81–6.96 (3H, m), 7.10 (1H, dd, J=2, 8Hz), 7.30 (1H, d, J=8Hz), 7.66–7.77 (1H, m), 8.28–8.52 (4H, m), 9.65 (1H, br)

10) 4-[2-(3-Acetylaminoprop-1-yl)oxybenzoyl]amino-3-methoxy-N-methyl-N-[2-[5-(4-dimethylaminopiperidin-1-yl)carbonylpent-1-yl]oxy-4-methylphenyl]benzamide hydrochloride NMR (CDCl₃, δ): 1.48–1.92 (6H, m), 1.91 (3H, s), 1.96–2.25 (2H, m), 2.30 (3H, s), 2.30–2.39 (2H, m), 2.68 (6H, s), 3.32 (3H, s), 3.35–3.47 (2H, m), 3.76 (3H, s), 4.26 (2H, br), 4.75 (1H, br), 6.56–7.12 (6H, m), 7.47 (1H, br), 8.10 (1H, br), 8.39 (1H, br)

11) 4-[2-(3-Aminoprop-1-yl)oxybenzoyl]amino-3-methoxy-N-[2-[4-(3-aminopropionyl)aminobut-1-yl]oxy-4-methylphenyl]-N-methylbenzamide dihydrochloride NMR (CDCl₃, δ): 1.59–1.90 (4H, m), 2.04–2.15 (2H, m), 2.27 (3H, s), 2.30–2.44 (2H, m), 2.87–3.08 (4H, m), 3.21–3.38 (2H, m), 3.30 (3H, s), 3.75–3.94 (2H, m), 3.76 (3H, s), 4.21–4.33 (2H, m), 6.55–6.68 (2H, m), 6.86–7.10 (5H, m), 7.29–7.48 (2H, m), 8.17 (1H, br), 8.35 (1H, br)

12) 4-[2-(3-Guanidinoprop-1-yl)oxybenzoyl]amino-3-methoxy-N-methyl-N-[2-[5-(4-dimethylaminopiperidin-1-yl)carbonylpent-1-yl]oxy-4-methylphenyl]benzamide dihydrochloride NMR (CDCl₃, δ): 1.49–1.93 (6H, m), 2.05–2.41 (8H, m), 2.27 (3H, s), 2.75 (6H, s), 3.08 (2H, br), 3.29 (3H, s), 3.47 (2), br), 3.67–4.10 (4H, m), 3.77 (3H, s), 4.27 (2H, br), 6.56–6.71 (2H, m), 6.81–7.09 (5H, m), 7.44 (1H, br), 7.98–8.19 (2H, m), 8.28–8.45 (1H, m)

13) 4-(2-Hydroxybenzoyl)amino-3-methoxy-N-methyl-N-[4-methyl-2-[5-(4-methylpiperazin-1-yl)carbonylpent-1-yloxy]phenyl]benzamide hydrochloride NMR (DMSO-d₆, δ): 1.35–1.66 (4H, m), 1.66–1.83 (2H, m), 2.22 (3H, s), 2.39 (2H, t, J=7Hz), 2.74 and 2.76 (total 3H, s), 2.80–3.10 (4H, m), 3.18 (3H, s), 3.28–3.63 (2H, m), 3.68 (3H, s), 3.77–4.18 (3H, m), 4.34–4.52 (1H, m), 6.64 (1H, d, J=9 Hz), 6.75–7.12 (6H, m), 7.40 (1H, m), 7.98 (1H, d, J=9 Hz), 8.23 (1H, d, J=9 Hz)

14) (S)-4-[2-[(3-Amino-1-methylprop-1-yl)oxy]benzoyl]amino-3-methoxy-N-methyl-N-[4-methyl-2-[5-(4-methylpiperazin-1-yl)carbonylpent-1-yloxy]phenyl]benzamide dihydrochloride NMR (DMSO-d₆, δ): 1.35 (3H, d, J=7 Hz), 1.40–1.65 (4H, m), 1.66–1.82 (2H, m), 1.92–2.20 (2H, m), 2.23 (3H, s), 2.38 (2H, t, J=7 Hz), 2.64 (3H,s), 2.78–3.43 (11H, m), 3.51–4.07 (7H, m), 4.93–5.09 (1H, m, 6.65 1(1H, d, J=8 Hz), 6.82 (1H, s), 6.89 (1H, d, J=8 Hz), 6.98 (1H, s), 7.04 (1H, d, J=8 Hz), 7.12 (1H, dd, J=8 Hz), 7.36 (1H, d, J=8 Hz), 7.57 (1H, dd, J=8, 8 Hz), 7.98–8.35 (4H, m)

15) 4-(2-Aminobenzenesulfonyl)amino-3-methoxy-N-methyl-N-[4-methyl-2-[5-(4-methylpiperazin-1-yl)carbonylpent-1-yloxy]phenyl]benzamide dihydrochloride NMR (DMSO-d₆, δ): 1.36–1.45 (2H, m), 1.50–1.59 (2H, m), 1.65–1.73 (2H, m), 2.23 and 2.29 (total 3H, s), 2.34–2.42 (4H, m), 2.77 (3H, d, J=1 Hz), 2.92–3.00 (2H, m), 3.11 and 3.13 (total 3H, s), 3.19 (3H, s), 3.36–370 (10H, m), 4.03–4.11 (1H, m), 4.40–4.48 (1H, m), 6.44–6.50 (1H, m), 6.60–6.88 (6H, m), 6.94–7.10 (2H, m), 7.27–7.32 (1H, m)

ESI-MASS (m/z): 638 (M+H)

16) (R)-4-[2-[(4-Aminobut-2-yl)oxy]benzoyl]amino-3-methoxy-N-methyl-N-[4-methyl-2-[5-(4-methylpiperazin- 1-yl)carbonylpent-1-yloxy]phenyl]benzamide dihydrochloride NMR (DMSO-d$_6$, δ): 1.37 and 1.39 (total 3H, s), 1.40–1.78 (8H, m), 1.94–2.12 (3H, m), 2.23 (3H, s), 2.30–2.40 (4H, m), 2.87–2.96 (2H, m), 3.18 (3H, s), 3.32 (3H, s), 3.46–3.58 (2H, m), 3.77 (3H, s), 3.83–3.99 (3H, m), 4.94–5.02 (1H, m), 6.65 (1H, d, J=8 Hz), 6.82 (1H, s), 6.88 (1H, d, J=8 Hz), 6.98 (1H, s), 7.03 (1H, d, J=8 Hz), 7.13 (1H, t, J=8 Hz), 7.33 (1H, d, J=9 Hz), 7.58 (1H, t, J=8 Hz), 7.88–8.02 (2H, br), 8.04 (1H, d, J=9 Hz), 8.27 (1H, d, J=8 Hz)

ESI-MASS (m/z): 674 (M+H)

17) (R)-4-[2-[(4-Aminobut-2-yl)oxy]benzoyl]amino-3-methoxy-N-methyl-N-[4-methyl-2-[5-(4-dimethylaminopiperidin-1-yl)carbonylpent-1-yloxy]phenyl]benzamide dihydrochloride NMR (DMSO-d$_6$, δ): 1.36 and 1.38 (total 3H, s), 1.40–1.80 (12H, m), 1.88–2.13 (3H, m), 2.24 (3H, s), 2.35 (2H, t, J=8 Hz), 2.51 (6H, s), 2.89–3.03 (4H, m), 3.19 (3H, s), 3.76 (3H, s), 3.83–4.00 (3H, m), 4.43–4.51 (1H, m), 4.96–5.03 (1H, m), 6.65 (1H, d, J=8 Hz), 6.83 (1H, s), 6.87–6.92 (1H, m), 6.98 (1H, s), 7.03 (1H, d, J=8 Hz), 7.14 (1H, t, J=8 Hz), 7.34 (1H, d, J=8 Hz), 7.58 (1H, t, J=8 Hz), 8.04 (1H, d, J=8 Hz), 8.24–8.30 (1H, m)

ESI-MASS (m/z): 7.02 (M+H)

18) (S)-4-[2-[(4-Aminobut-2-yl)oxy]benzoyl]amino-3-methoxy-N-methyl-N-[4-methyl-2-[5-(4-dimethylaminopiperidin-1-yl)carbonylpent-1-yloxy]phenyl]benzamide dihydrochloride NMR (DMSO-d$_6$, δ): 1.35 and 1.38 (total 3H, s), 1.42–1.79 (12H, m), 1.88–2.14 (3H, m), 2.25 (3H, s), 2.36 (2H, t, J=8 Hz), 2.51 (6H, s), 2.89–3.02 (4H, m), 3.20 (3H, s), 3.76 (3H, s), 3.84–4.00 (3H, m), 4.43–4.50 (1H, m), 4.97–5.03 (1H, m), 6.65 (1H, d, J=8 Hz), 6.82 (1H, s), 6.88–6.92 (1H, m), 6.98 (1H, s), 7.02 (1H, d, J=8 Hz), 7.15 (1H, t, J=8 Hz), 7.34 (1H, d, J=8 Hz), 7.58 (1H, t, J=8 Hz), 8.03 (1H, d, J=8 Hz), 8.24–8.30 (1H, m)

ESI-MASS (m/z): 702 (M+H)

19) 4-[2-(4-Aminobut-1-yl)oxybenzoyl]amino-N-methyl-N-[2-[5-(4-methylpiperazin-1-yl)carbonylpent-1-yl]oxy]-phenylbenzamide dihydrochloride NMR (D$_2$O, δ): 1.35–1.50 (2H, m), 1.56–1.64 (2H, m), 1.68–1.83 (4H, m), 2.47 (2H, t, J=7.5 Hz), 2.82–3.12 (5H, m), 2.92 (3H, s), 3.33 (3H, s), 3.43–3.61 (3H, m), 3.81 (1H, m), 3.95 (1H, m), 6.84 (1H, d, J=7 Hz), 6.91 (1H, t, J=7 Hz), 7.00–7.08 (3H, m), 7.19 (1H, t, J=7 Hz), 7.26–7.37 (4H, m), 7.48 (1H, t, J=7 Hz), 7.62 (1H, d, J=7 Hz)

20) 4-[2-(3-Aminoprop-1-yl)oxybenzoyl]amino-N-[2-(5-ethoxycarbonylpent-1-yl)oxy-4-methyl]phenyl-N-methylbenzamide hydrochoiride NMR (DMSO-d$_6$, δ): 1.16 (3H, t, J=7.5 Hz), 1.38–1.49 (2H, m), 1.55–1.64 (2H, m), 1.67–1.77 (2H, m), 1.98–2.08 (2H, m), 2.21 (3H, s), 2.31 (2H, t, J=7.5 Hz), 2.87–2.97 (2H, m), 3.16 (3H, s), 3.80–3.98 (2H, m), 4.03 (2H, q, J=7.5 Hz), 4.19 (2H, t, J=7.5 Hz), 6.62 (1H, d, J=7 Hz), 6.80 (1H, s), 6.98–7.07 (2H, m), 7.15 (1H, d, J=7 Hz), 7.22 (2H, d, J=8 Hz), 7.43–7.57 (4H, m), 7.86–8.00 (3H, br)

21) 4-[2-(3-Aminoprop-1yl)oxybenzoyl]amino-N-methyl-N-[4-methyl-2-[5-(4-methylpiperazin-1yl)carbonylpent-1-yl]oxy]phenylbenzamide dihydrochloride NMR (DMSO-d$_6$, δ): 1.38–1.49 (2H, m), 1.52–1.62 (2H, m), 1.68–1.78 (2H, m), 1.96–2.09 (2H, m), 2.21 (3H, s), 2.38 (2H, t, J=7.5 Hz), 2.73 (3H×½, s), 2.75 (3H×½, s), 2.81–3.07 (4H, m), 3.15 (3H, s), 3.30–3.54 (4H, m), 3.81–4.21 (5H, m), 4.45 (1H, m), 6.65 (1H, d, J=7 Hz), 6.81 (1H, s), 6.99–7.08 (2H, m), 7.15 (1H, d, J=7 Hz), 7.22 (2H, d, J=8 Hz), 7.45–7.60 (4H, m), 8.04 (2H, br)

22) 4-[2-(3-Aminoprop-1-yl)oxybenzoyl]amino-N-methyl-N-[2-[3-(4-methylpiperazin-1yl)carbonylprop-1-yl]oxy]-phenylbenzamide dihydrochloride NMR (DMSO-d$_6$, δ): 1.90–2.09 (4H, m), 2.48–2.59 (2H, m), 2.72 (3H×½, s), 2.73 (3H×½, s), 2.83–3.10 (4H, m), 3.20 (3H, s), 3.33–3.56 (3H, m), 3.88–4.09 (3H, m), 4.18 (2H, t, J=7.5 Hz), 4.47 (1H, m), 4.80 (1H, m), 6.87 (1H, t, J=7 Hz), 6.98 (1H, d, J=7 Hz), 7.04 (1H, t, J=7 Hz), 7.11–7.26 (5H, m), 7.44–7.59 (4H, m), 8.05 (2H, br)

23) 4-[2-(3-Aminoprop-1-yl)oxybenzoyl]amino-N-methyl-N-[4-methyl-2-(4-methylpiperazin-1-ylcarbonyl)phenylmethoxy]-phenylbenzamide dihydrochloride NMR (DMSO-d$_6$, δ): 1.97–2.07 (2H, m), 2.26 (3H, s), 2.75 (3H×½, s), 2.77 (3H×½, s), 2.82–2.95 (2H, m), 3.02–3.14 (2H, m), 3.21 (3H, s), 3.30–3.49 (4H, m), 3.97–4.21 (4H, m), 5.09 (1H, d, J=14 Hz), 5.20 (1H, d, J=14 Hz), 6.70 (1H, d, J=7 Hz), 6.93 (1H, s), 7.02–7.25 (5H, m), 7.43–7.57 (8H, m), 7.92–8.04 (3H, br)

24) 4-[2-(3-Hydroxyprop-1yl)oxybenzoyl]amino-N-methyl-N-[2-[5-(4-methylpiperazine-1-yl)carbonylpent-1yl]oxy]-phenylbenzamide hydrochloride NMR (DMSO-d$_6$, δ): 1.39–1.50 (2H, m), 1.52–1.62 (2H, m), 1.69–1.79 (2H, m), 1.84–1.93 (2H, m), 2.40 (2H, t, J=7.5 Hz), 2.70 (3H×½, s), 2.72 (3H×½, s), 2.82–3.07 (4H, m), 3.19 (3H, s), 3.28–3.60 (4H, m), 3.80–3.98 (2H, m), 4.10 (1H, m), 4.17 (2H, t, J=7.5 Hz), 4.45 (1H, m), 6.85 (1H, t, J=7 Hz), 6.98 (1H, d, J=7 Hz), 7.03 (1H, t, J=7 Hz), 7.13–7.24 (5H, m), 7.43–7.54 (3H, m), 7.62 (1H, d, J=7 Hz)

25) 4-[2-(4-Hydroxy-1-butyn-1-yl)benzoyl]amino-N-methyl-N-[2-[5(4-methylpiperazin-1-yl)carbonylpent-1-yl]oxy]-phenylbenzamide hydrochloride NMR (DMSO-d$_6$, δ): 1.42–1.52 (2H, m), 1.54–1.64 (2H, m), 1.70–1.82 (2H, m), 2.37–2.47 (6H, m), 2.49 (3H, s), 2.51 (3H, s), 2.84–3.05 (2H, m), 3.32–3.46 (4H, m), 3.84–3.98 (2H, m), 4.08 (1H, m), 4.47 (1H, m), 6.84 (1H, t, J=7 Hz), 6.97 (1H, d, J=7 Hz), 7.13–7.25 (4H, m), 7.41–7.53 (6H, m)

26) 4-[2-(4-Aminobut-1yl)benzoyl]amino-N-methyl-N-[2-[5(4-methylpiperazin-1-yl) carbonylpent-1yl]oxy]phenylbenzamide dihydrochloride NMR (DMSO-d$_6$, δ): 1.39–1.62 (8H, m), 1.67–1.80 (2H, m), 2.39 (3H, t, J=7.5 Hz), 2.50 (3H, s), 2.63–2.73 (4H, m), 2.81–3.08 (2H, m), 3.18 (3H, s), 3.31–3.42 (4H, m), 3.85–4.00 (2H, m), 4.04 (1H, m), 4.43 (1H, m), 6.84 (1H, t, J=7 Hz), 6.99 (1H, d, J=7 Hz), 7.11–7.42 (6H, m), 7.50–7.56 (2H, m), 7.75–7.91 (2H, m)

27) 4-[2[(3-Aminoprop-1yl)oxy]benzoyl]amion-3-methoxy-N-methyl-N-[4-methyl-2-[5-(4-methylpiperazin-1yl)carbonylpent-1-yl]oxy]phenylbenzamide hydrochloride NMR (DMSO-d$_6$, δ): 1.40–1.51 (2H, m), 1.53–1.62 (2H, m), 1.69–1.80 (2H, m), 1.98 (3H, s), 1.98–2.03 (2H, m), 2.22 (3H, s), 2.39 (2H, t, J=7.5 Hz), 2.71 (3H×½, s), 2.74 (3H×½, s), 2.83–3.05 (2H, m), 3.31–4.11 (5H, m), 4.32 (2H, t, J=7.5 Hz), 3.72 (3H, s), 3.81–3.50 (3H, m), 3.56 (2H, t, J=7.5 Hz), 4.43 (1H, m), 6.65 (1H, d, J=7 Hz), 6.81 (1H, s), 6.87–6.95 (2H, m), 7.05 (1H, d, J=7 Hz), 7.11 (1H, t, J=7 Hz), 7.26 (1H, d, J=7 Hz), 7.54 (1H, t, J=7 Hz), 8.03 (1H, d, J=7 Hz), 8.28 (1H, d, J=7 Hz)

28) 3-Methoxy-4-(2-hydroxybenzoyl)amino-N-methyl-N-[4-methyl-2-[4-(4-methylpiperazin-1yl)carbonyl]-phenylmethoxy]phenylbenzamide hydrochloride NMR (DMSO-d$_6$, δ): 2.23 (3H, s), 2.75 (3H×½, s), 2.77 (3H×½, s), 2.97–3.15 (2H, m), 3.21 (3H, s), 3.24–3.80 (6H, m), 5.06 (1H, d, J=14 Hz), 5.19 (1H, d, J=14 Hz), 6.70 (1H, d, J=7 Hz), 6.90–7.01 (3H, m), 7.10 (1H, d, J=7 Hz), 7.22 (2H, d, J=8 Hz), 7.41 (1H, d, J=7 Hz), 7.44–7.55 (7H, m), 7.87 (1H, d, J=7 Hz)

29) 4-[2-(3-Aminoprop-1yl)oxybenzoyl]amino-3methoxy-N-methyl-N-[4-methyl-2-[4-(4-methylpiperazin-1-yl)carbonyl]phenylmethoxy]phenylbenzamide dihydrochloride NMR (DMSO-d$_6$, δ): 2.06–2.19 (2H, m), 2.23 (3H, s), 2.75 (3H, s), 2.87–2.98 (2H, m), 3.02–3.15 (2H, m), 3.23 (3H, s), 3.32–3.49 (2H, m), 3.65 (3H, s), 3.71–3.96 (4H, m), 4.29–4.40 (2H, m), 5.04 (1H, d, J=14 Hz), 5.20 (1H, d, J=14 Hz), 6.76 (1H, d, J=7 Hz), 6.88 (1H, d, J=7 Hz), 6.90–6.98 (2H, m), 7.09–7.19 (2H, m), 7.28 (1H, d, J=7 Hz), 7.50–7.62 (2H, m), 7.98–8.15 (4H, m), 8.23 (1H, d, J=7 Hz)

30) 3-Methoxy-4-[2-(3-aminoprop-1-yl)oxy]phenylmethyl]-amino-N-methyl-N-[4-methyl-2-[5-(4-methylpiperazin-1-yl) carbonylpent-1-yl]oxy]phenylbenzamide trihydrochloride NMR (DMSO-d$_6$, δ): 1.35–1.47 (2H, m), 1.49–1.59 (2H, m), 1.64–1.74 (2H, m), 2.00–2.10 (2H, m), 2.22 (3H, s), 2.30–2.38 (2H, m), 2.69 (3H×½, s), 2.73 (3H×½, s), 2.82–3.03 (6H, m), 3.09 (3H, s), 3.29–3.41 (2H, m), 3.53 (3H, s), 3.83–4.12 (6H, m), 4.22 (2H, s), 4.70 (1H, br), 6.21 (1H, d, J=7 Hz), 6.58–6.66 (2H, m), 6.71–6.99 (5H, m), 7.09 (1H, d, J=7 Hz), 7.20 (1H, t, J=7 Hz), 8.02 (2H, br, d)

31) 4-(2-Dimethylamino-4-methyl)phenoxymethyl-N-methyl-N-[4-methyl-2-[5-(4-methylpiperazin-1yl)carbonylpent-1-yl]oxy]phenylbenzamide dihydrochloride NMR (DMSO-d$_6$, δ): 1.37–1.47 (2H, m), 1.50–1.61 (2H, m), 1.67–1.80 (2H, m), 2.20 (3H, s), 2.29 (3H, s), 2.39 (2H, t, J=7.5 Hz), 2.71 (3H×½, s), 2.73 (3H×½, s), 2.80–3.58 (4H, m), 3.03 (6H, s), 3.17 (3H, s), 3.72–4.48 (6H, m), 5.21 (2H, s), 6.62 (1H, d, J=7 Hz), 6.78 (1H, s), 6.91 (1H, d, J=7 Hz), 7.02 (1H, d, J=7 Hz), 7.11 (1H, d, J=7 Hz), 7.26 (2H, d, J=8 Hz), 7.37 (2H, d, J=8 Hz), 7.70 (1H, d, J=7 Hz)

32 4-[2-(3-Aminoprop-1yl)oxybenzoyl]amino-3-methoxy-N-methyl-N-[2-[4-(4-methylpiperazin-1yl)carbonyl]-phenyleth-1yl]phenylbenzamide dihydrochloride NMR (DMSO-d$_6$, δ): 2.06–2.19 (2H, m), 2.55–3.12 (10H, s), 2.71 (3H×½, s), 2.73 (3H×½, s), 3.18 (3H, s), 3.23–3.48 (2H, m), 3.66 (3H, s), 3.66–3.81 (2H, m), 4.30–4.40 (2H, m), 6.86–6.90 (2H, m), 7.11 (1H, t, J=7Hz), 7.20–7.42 (9H, m), 7.59 (1H, t, J=7 Hz), 8.01 (1H, d, J=7 Hz), 8.08 (2H, br), 8.27 (1H, d, J=7 Hz)

33) 4-[2-(3-Aminoprop-1yl)thiobenzoyl]amino-3-methoxy-N-methyl-N-[4-methyl-2-[5-(4-methylpiperazin-1yl)carbonylpent-1yl]oxy]phenylbenzamide dihydrochloride NMR (DMSO-d$_6$, δ): 1.40–1.51 (3H, m), 1.52–1.63 (2H, m), 1.70–1.88 (4H, m), 2.23 (3, s), 2.40 (3H, t, J=7.5 Hz), 2.71 (3H×½, s), 2.72 (3H×½, s), 2.80–2.91 (2H, m), 2.94–3.06 (2H, m), 3.17 (3H, s), 3.32–3.67 (8H, m), 3.60 (3H, s), 3.81–4.10 (3H, m), 4.41 (1H, m), 6.65 (1H, d, J=7 Hz), 6.82 (1H, s), 6.86–6.92 (2H, m), 7.02 (1, d, J=7 Hz), 7.27 (1H, t, J=7 Hz), 7.41–7.52 (3H, m), 7.71 (1H, d, J=7 Hz), 9.37 (1H, s)

34) 4-[2-(3-Aminoprop-1yl)oxybenzoyl]amino-3-methoxy-N-[2-[4-(4-dimethylaminopiperidin-1yl)carbonyl]phenylmethy-oxy-4-methyl]phenyl-N-methylbenzamide dihydrochloride NMR (DMSO-d$_6$, δ): 1.57–1.73 (2H, m), 2.00–2.20 (4H, m), 2.23 (3H, s) 2.70 (3H, s), 2.71 (3H, s), 2.87–3.05 (3H, m), 3.24 (3H, s), 3.33–3.50 (1H, m), 3.66 (3H, s), 3.71–4.05 (4H, m), 4.37 (2H, t, J=7.5 Hz), 5.02 (1H, d, J=14 Hz), 5.20 (1H, d, J=14 Hz), 6.73 (1H, d, J=7 Hz), 6.86 (1H, d, J=7 Hz), 6.96 (2H, s), 7.10–7.19 (2H, m), 7.29 (1H, d, J=7 Hz), 7.43–7.52 (4H, m), 7.58 (1H, t, J=7 Hz), 800 (1H, d, J=7 Hz), 8.03 (1H, d, J=7 Hz)

35) 4-[2-(3_Aminoprop-1yl)oxybenzoyl]amino-3methoxy-N-methyl-N-[2-[3-(4-methylpiperazin-1yl)carbonyl-methoxyprop-1-yl]oxy]phenylbenzamide dihydrochloride NMR (DMSO-d$_6$, δ): 1.94–2.04 (2H, m), 2.10–2.20 (2H, m), 2.71 (3H×½, s), 2.23 (3H×½, s), 2.84–3.10 (6H, m), 3.21 (3H, s), 3.31–3.50 (2H, m), 3.57–3.81 (4H, m), 3.74 (3H, s), 3.90–4.01 (2H, m), 4.20 (2H×½, s), 4.22 (2H×½, d), 4.35 (2H, t, J=7.5 Hz), 6.82–6.97 (3H, m), 7.01 (1H, d, J=7 Hz), 7.10–7.28 (4H, m), 7.58 (1H, t, J=7 Hz), 8.03 (1H, d, J=7 Hz), 8.27 (1H, d, J=7 Hz)

36) 4-[2-(3-Aminoprop-1yl)oxybenzoyl]amino-3-methoxy-N-[2-[(E)-5-(4-dimethylaminopiperidin-1yl)carbonyl-4-penten-1-yl]oxy-4-methyl]phenyl-N-methylbenzamide dihydrochloride NMR (DMSO-d$_6$, δ): 1.36–1.63 (2H, m), 1.84–1.92 (2H, m), 1.97–2.08 (2H, m), 2.10–2.22 (2H, m), 2.22 (3H, s), 2.29–2.43 (2H, m), 2.63 (3H, s), 2.65 (3H, s), 2.70–2.86 (2H, m), 2.88–3.00 (2H, m), 3.14 (3H×½, s), 3.17 (3H×½, s), 3.28–3.42 (2H, m), 3.71 (3H, s), 3.84–4.06 (2H, m), 4.37 (2H, t, J=7.5 Hz), 4.51 (1H, m), 6.52 (1H, d, J=15 Hz), 6.60 (1H, m), 6.73–7.07 (5H, m), 7.13 (1H, t, J=7 Hz), 7.27 (1H, d, J=7 Hz), 7.56 (1H, t, J=7 Hz), 8.01 (1H, d, J=7 Hz), 8.30 (1H, d, J=7 Hz)

37) 4-[2-(3-Aminoprop-1yl)oxybenzoyl]amino-3-methoxy-N-methyl-N-[4-methyl-2-[5-(4-methylpiperidin-1-yl)carbonylpent-1yl]oxy]phenylbenzamide hydrochloride NMR (CDCl$_3$, δ): 0.88 (3H, d, J=7.5 Hz), 0.90–1.10 (2H, m), 1.34–1.61 (6H, m), 1.70–1.80 (2H, m), 2.10–2.20 (2H, m), 2.23 (3H, s), 2.30 (2H, t, J=7.5 Hz), 2.45 (1H, m), 2.85–3.00 (3H, m), 3.18 (3H, s), 3.74 (3H, s), 3.75–4.02 (4H, m), 4.38 (2H, t, J=7.5 Hz), 4.78 (1H, m), 6.65 (1H, d, J=7 Hz), 6.82 (1H, s), 6.88 (1H, d, J=7 Hz), 6.98 (1H, s), 7.02 (1H, d, J=7 Hz), 7.13 (1H, t, J=7 Hz), 7.26 (1H, d, J=7 Hz), 7.59 (1H, t, J=7 Hz), 8.00 (1H, d, J=7 Hz), 8.22 (1H, d, J=7 Hz)

38) 4-(2,4-Dimethoxybenzoyl)amino-3-methoxy-N-methyl-N-[4-methyl-2-[5-(4-methylpiperazin-1-yl)carbonylpent-1yl]oxy]phenylbenzamide hydrochloride NMR (DMSO-d$_6$, δ): 1.40–1.51 (2H, m), 1.51–1.64 (2H, m), 1.69–1.82 (2H, m), 2.22 (3H, s), 2.38 (2H, t, J=7.5 Hz), 2.73 (3H, s), 2.81–3.09 (4H, m), 3.19 (3H, s), 3.25–3.50 (2H, m), 3.76 (6H, s×2), 3.77–4.15 (3H, m), 4.00 (3H, s), 4.44 (1H, m), 6.64 (1H, d, J=7 Hz), 6.81 (1H, s), 6.88–6.95 (2H, m), 7.03 (1H, d, J=7 Hz), 7.12–7.23 (2H, m), 7.57 (1H, m), 8.29 (1H, d, J=7 Hz)

39) 4-[2-(3-Aminoprop-1-yl)oxybenzoyl]amino-3-methoxy-N-[2-(3-aminoprop-1-yl)oxy-4-methyl]phenyl-N-methylbenzamide dihydrochloride NMR (DMSO-d$_6$, δ): 2.00–2.11 (2H, m), 2.13–2.20 (2H, m), 2.25 ) (3H, s), 2.87–3.00 (4H, m), 3.19 (3H, s), 3.77 (3H, s), 3.89–4.10 (2H, m), 4.36 (2H, t, J=7.5 Hz), 6.69 (1H, d, J=7 Hz), 6.82 (1H, s), 6.89 (1H, d, J=7 Hz), 7.04 (1H, s), 7.05 (1H, d, J=7 Hz), 7.15 (1H, d, J=7 Hz), 7.38 (1H, d, J=7 Hz), 7.56 (1H, t, J=7 Hz), 8.01 (1H, d, J=7 Hz), 8.28 (1H, d, J=7 Hz)

40) 4-[2-(3-Aminoprop-1-yl)oxybenzoyl]amino-3-methoxy-N-[2-(4-aminobut-1-yl)oxy-4-methyl]phenyl-N-methylbenzamide dihydrochloride NMR (DMSO-d$_6$, δ): 1.66–1.85 (4H, m), 2.10–2.20 (2H, m), 2.22 (3H, s), 2.80–3.01 (4H, m), 3.18 (3H, s), 3.75 (3H, s), 3.81–4.03 (2H, m), 4.36 (2H, t, J=7.5 Hz), 6.64 (1H, d, J=7 Hz), 6.34 (1H, s), 6.90 (1H, d, J=7 Hz), 6.96 (1H, s), 7.01 (1H, d, J=7 Hz), 7.14 (1H, t, J=7 Hz), 7.27 (1H, d, J=7 Hz), 7.57 (1H, t, J=7 Hz), 8.00 (1H, d, J=7 Hz), 8.25 (7H, d, J=7 Hz)

41) 4-[2-(3-Aminoprop-1-yl)oxybenzoyl]amino-3-methoxy-N-[2-(4-acetylaminobut-1-yl)oxy-4-methyl]phenyl-N-methylbenzamide hydrochloride NMR (DMSO-d$_6$, δ): 1.49–1.59 (2H, m), 1.67–1.77 (2H, m), 1.80 (3H, s), 2.06–2.20 (2H, m), 2.21 (3H, s), 2.86–3.00 (2H, m), 3.03–3.13 (2H, m), 3.18 (3H, s), 3.74 (3H, s), 3.80–4.02 (2H, m), 4.35 (2H, t, J=7.5 Hz), 6.64 (1H, d, J=7

Hz), 7.82 (1H, s), 7.88 (1H, d, J=7 Hz), 7.96 (1H, s), 7.02 (1H, d, J=7 Hz), 7.13 (1H, t, J=7 Hz), 7.26 (1H, d, J=7 Hz), 7.57 (1H, t, J=7 Hz), 8.00 (1H, d, J=7 Hz), 8.23 (1H, d, J=7 Hz)

42) 4-[2-(3-Aminoprop-1-yl)oxybenzoyl]amino-3-methoxy-N-[2-(4-aminoacetylaminobut-1-yl)oxy-4-methyl]phenyl-N-methylbenzamide dihydrochloride NMR (DMSO-$d_6$, δ): 1.53–1.64 (2H, m), 1.70–1.81 (2H, m), 2.09–2.21 (2H, m), 2.22 (3H, s), 2.86–2.98 (2H, m), 3.11–3.23 (2H, m), 3.17 (3H, s), 3.47–3.56 (2H, m), 3.65–4.00 (2H, m), 3.76 (3H, s), 4.38 (2H, t, J=7.5 Hz), 6.65 (1H, d, J=7 Hz), 6.82 (1H, s), 6.89 (1H, d, J=7 Hz), 6.95 (1H, s), 7.03 (1H, d, J=7 Hz), 7.12 (1H, t, J=7 Hz), 7.25 (1H, d, J=7 Hz), 7.56 (1H, t, J=7 Hz), 8.00 (1H, d, J=7 Hz), 8.22 (1H, d, J=7 Hz)

43) 3-Methoxy-4-[2-(piperidin-4-yl)oxybenzoyl]amino-N-methyl-N-[4-methyl-2-[5-(4-methylpiperazin-1-yl)carbonylpent-1-yl]oxy]phenylbenzamide dihydrochloride NMR (DMSO-$d_6$, δ): 1.38–1.49 (2H, m), 1.49–1.61 (2H, m), 1.66–1.76 (2H, m), 1.85–1.97 (2H, m), 2.20 (3H, s), 2.67 (2H, t, J=7.5 Hz), 2.73 (3H×½, s), 2.74 (3H×½, s), 2.80–3.13 (6H, m), 3.13 (3H, s), 3.22–3.51 (6H, m), 3.60–4.13 (3H, m), 3.74 (3H, s), 4.43 (1H, m), 4.91 (1H, m), 6.65 (1H, d, J=7 Hz), 6.81 (1H, s), 6.89 (1H, d, J=7 Hz), 6.96 (1H, s), 7.03 (1H, d, J=7 Hz), 7.12 (1H, t, J=7 Hz), 7.35 (1H, d, J=7 Hz), 7.56 (1H, t, J=7 Hz), 7.81 (1H, d, J=7 Hz), 8.27 (1H, d, J=7 Hz)

44) 4-[2-(3-Amino-1-methylprop-1-yl)oxybenzoyl]amino-3-methoxy-N-methyl-N-[4-methyl-2-[5-(4-methylpiperazin-1-yl) carbonylpent-1-yl]oxy]phenylbenzamide dihydrochloride NMR (DMSO-$d_6$, δ): 1.35 (3H, d, J=7.5 Hz), 1.40–1.63 (4H, m), 1.67–1.80 (2H, m), 1.90–2.18 (2H, m), 2.22 (3H, s), 2.39 (2H, t, J=7.5 Hz), 2.71 (3H×½, s), 2.74 (3H×½, s), 2.80–3.09 (4H, m), 3.18 (3H, s), 3.30–3.52 (4H, m), 3.77 (3H, s), 3.83–4.18 (3H, m), 4.42 (1H, m), 5.01 (1H, m), 6.64 (1H, d, J=7 Hz), 6.81 (1H, s), 6.89 (1H, d, J=7 Hz), 6.96 (1H, s), 7.03 (1H, d, J=7 Hz), 7.12 (1H, t, J=7 Hz), 7.34 (1H, d, J=7 Hz), 7.58 (1H, t, J=7 ), 8.03 (1H, d, J=7 Hz), 8.28 (1H, d, J=7 Hz)

45) 3-Methoxy-4-[2-(pyrid-3yl)methoxybenzoyl]amino-N-methyl-N-[4-methyl-2-[5(4-methylpiperazin-1-yl)carbonylpent-1-yl]oxy]phenylbenzamide dihydrochloride NMR (DMSO-$d_6$, δ): 1.36–1.49 (2H, m), 1.49–1.60 (2H, m), 1.66–1.79 (2H, m), 2.20 (3H, s), 2.39 (2H, t, J=7.5 Hz), 2.68 (3H×½, s), 2.70 (3H×½,s), 2.80–3.10 (4H, m), 3.16 (3H, s), 3.35 (3H, s), 3.35–3.60 (2H, m), 3.79–4.11 (3H, m), 4.41 (1, m), 5.58 (2H, s), 6.64 (1H, d, J=7 Hz), 6.80–6.90 (3H, m), 7.02 (1H, d, J=7 Hz), 7.16 (1H, t, J=7 Hz), 7.33 (1H, d, J=7 Hz), 7.57 (1H, t, J=7 Hz), 7.93–8.00 (2H, m), 8.19 (1H, d, J=7 Hz), 8.55 (1H, d, J=7 Hz), 8.88 (1H, d, J=6 Hz), 9.04 (1H, s)

46) 4-[2-(4-Aminobut-1-yl)oxybenzoyl]amino-3-methoxy-N-methyl-N-[4-methyl-2-[5-(4-methylpiperazin-1-yl)carbonylpent-1-yl]oxy]phenylbenzamide dihydrochloride NMR (DMSO-$d_6$, δ): 1.40–1.50 (2H, m), 1.50–1.61 (2H, m), 1.66–1.79 (4H, m), 1.86–1.95 (2H, m), 2.21 (3H, s), 2.39 (2H, t, J=7.5 Hz), 2.73 (3H×½,s), 2.75 (3H×½, s), 2.79–3.10 (4H, m), 3.19 (3H, s), 3.31–3.52 (4H, m), 3.74 (3H, s), 3.82–4.12 (3H, m), 4.30 (2H, t, J=7.5 Hz), 4.43 (1H, m), 6.65 (1H, d, J=7 Hz), 7.81 (1H, s), 6.89 (1H, d, J=7 Hz), 6.97 (1H, s), 7.03 (1H, d, J=7 Hz), 7.12 (1H, t, J=7 Hz), 7.30 (1H, d, J=7 Hz), 7.58 (1H, d, J=7 Hz), 8.04 (1H, d, J=7 Hz), 8.30 (1H, d, J=7 Hz)

47) 4-(2-Hydroxy-5methylbenzoyl)amino-3-methoxy-N-methyl-N-[2-[5-(4-methylpiperazin-1-yl)carbonylpent-1-yl)]oxy-4-methylphenyl]benzamide hydrochloride NMR (DMSO-$d_6$, δ): 1.53–1.96 (6H, m), 2.29 (3H, s), 2.31 (3H, s), 2.33–2.40 (2H, m), 2.79 (3H, s), 3.30 (3H, s), 3.79 (3H, s), 3.80–4.03 (2H, m), 6.63 (2H, br), 6.88–6.98 (4H, m), 7.25 (1H, d, J=8 Hz), 8.19 (1H, d, J=8 Hz), 8.71 (1H, br)

48) 4-(2-Hydroxy-4-methoxybenzoyl)amino-3-methoxy-N-methyl-N-[2-[5-(4-methylpiperazin-1yl)carbonylpent-1-yl]oxy-4-methylphenyl]benzamide hydrochloride NMR (CDCl$_3$, δ): 1.48–1.92 (6H, m), 2.28 (3H, s), 2.32–2.45 (2H, m), 2.64–3.05 (4H, m), 2.79 (3H, s), 3.29 (3H, s), 3.29–3.51 (4H, m), 3.76 (3H, s), 3.80 (3H, s), 3.81–4.05 (4H, m), 6.43–6.50 (2H, m), 6.61 (1H, br), 6.85–6.96 (3H, m), 7.36–7.43 (1H, m), 8.12–8.18 (1H, m), 8.58 (1H, br)

EXAMPLE 18

The following compounds were obtained by separating the compounds, which were prepared according to a similar manner to Example 4, by using silica gel column chromatography.

1) 4-(2-Benzyloxy)benzoylamino-3-methoxy-N-[(E)-2-(4-carboxyphenyl)ethen-1-yl]phenyl-N-methylbenzamide NMR (CDCl$_3$, δ): 3.08 (3H, s), 3.41 (3H, s), 5.19 (2H, s), 6.47 (1H, d, J=14 Hz), 6.58 (1H, d, J=14 Hz), 6.73 (2H, d, J=8 Hz), 6.84 (1H, d, J=7 Hz), 6.90–7.10 (5H, m), 7.20–7.40 (8H, m), 7.71 (2H, d, J=8 Hz), 8.26 (1H, d, J=7 Hz), 8.38 (1H, d, J=7 Hz)

2) 4-(2-Benzyloxy)benzoylamino-3-methoxy-N-[(Z)-2-(4-carboxyphenyl)ethen-1-yl]phenyl-N-methylbenzamide NMR (CDCl$_3$, δ): 3.09 (3H, s), 3.48 (3H, s), 5.25 (2H, s), 6.72–7.42 (15H, m), 7.51–7.64 (3H, m), 8.10 (2H, d, J=8 Hz), 8.22 (1H, d, J=7 Hz), 8.33 (1H, d, J=7 Hz)

EXAMPLE 19

The following compound was obtained according to a similar manner to that of Example 4 by using 4-[2-(acetoxy)benzoyl]amino-3-methoxy-N-methyl-N-[4-methyl-2-(5-ethoxycarbonylpent-1-yloxy)phenyl]benzamide as a starting compound.

4-[2-(Hydroxy)benzoyl]amino-3-methoxy-N-methyl-N-[4-methyl-2-(5-carboxypent-1-yloxy)phenyl]benzamide NMR (CDCl$_3$, δ): 1.46–1.61 (2H, m), 1.63–1.90 (4H, m), 2.28 (3H, s), 2.39 (2H, t, J=7 Hz), 3.33 (3H, s), 3.73–4.00 (5H, m), 6.61 (2H, br s), 6.82–7.11 (5H, m), 7.35–7.53 (2H, m), 8.16 (1H, d, J=8 Hz), 8.75 (1H, br s)

EXAMPLE 20

The following compounds were obtained according to a similar manner to that of Example 8.

1) 4-[2-(4-Methoxybenzyl)oxybenzoyl]amino-N-methyl-N-[4-methyl-2-[4-(4-methylpiperazin-1-yl)carbonyl]-phenylmethoxy]phenylbenzamide NMR (CDCl$_3$, δ): 2.27 (3H, s), 2.31 (3H, s), 2.35–2.53 (4H, m), 3.32 (3H, s), 3.39–3.54 (2H, m), 3.67–3.85 (3H, m), 3.82 (3H, s), 4.95 (1H, d, J=14 Hz), 5.06 (1H, d, J=14 Hz), 5.12 (2H, s), 6.59–6.67 (2H, m), 6.86–7.02 (5H, m), 7.07–7.21 (4H, m), 7.33–7.52 (7H, m), 8.28 (1H, d, J=7 Hz)

2) 4-(2-Benzyloxybenzoyl)amino-3-methoxy-N-methyl-N-[2-[5-(4-methylpiperazin-1-yl)carbonylpent-1-yloxy]phenyl]-benzamide NMR (CDCl$_3$, δ): 1.46–1.60 (2H, m), 1.63–1.92 (4H, m), 2.30 (3H, s), 2.31–2.46 (6H, m), 3.28 (3H, s), 3.35 (3H, s), 3.44–3.54 (2H, m), 3.58–3.69 (2H, m), 3.80–4.04 (2H, m), 5.30 (2H, s), 6.73–7.22 (8H, m), 7.30–7.49 (6H, m), 8.19–8.28 (1H, m), 8.38 (1H, d, J=9 Hz)

3) 4-[2-(Benzyloxy)benzoyl]amino-2-chloro-N-methyl-N-[2-[5-(4-methylpiperazin-1-yl)carbonylpent-1-yloxy]phenyl]benzamide NMR (CDCl₃, δ): 1.48–1.65 (2H, m), 1.65–1.97 (4H, m), 2.30 (3H, s), 2.32–2.48 (6H, m), 3.34 (3H, s), 3.43–3.56 (2H, m), 3.58–3.70 (2H, m), 3.97 (2H, t, J=7 Hz), 5.16 (2H, s), 6.63–6.81 (3H, m), 6.96 (1H, d, J=8 Hz), 7.02–7.20 (5H, m), 7.40–7.59 (6H, m), 8.24 (1H, m)

4) 4-[2-[(3-tert-Butoxycarbonylaminoprop-1-yl)oxy]benzoyl]amino-3-methoxy-N-methyl-N-[4-[5-(4-methylpiperazin-1-yl)carbonylpent-1-yloxy]phenyl]benzamide NMR (CDCl₃, δ): 1.42 (9H, s), 1.45–1.82 (8H, m), 2.10–2.19 (2H, m), 2.30 (3H, s), 2.31–2.41 (6H, m), 3.27–3.35 (2H, m), 3.43–3.50 (5H, m), 3.60–3.67 (2H, m), 3.82 (3H, s), 3.90 (1H, t, J=7 Hz), 4.27 (1H, t, J=7 Hz), 4.75–4.82 (1H, br), 6.76 (2H, d, J=8 Hz), 6.82 (1H, d, J=8 Hz), 6.95–7.04 (3H, m), 7.07–7.13 (1H, m), 7.47 (1H, t, J=8 Hz), 8.22 (1H, dd, J=1, 8 Hz), 8.42 (1H, d, J=8 Hz)

ESI-MASS (m/z: 746 (M+H)

5) 4-[2-[3-(tert-Butoxycarbonyl)aminoprop-1-yl]oxybenzoyl]amino-N-methyl-N-[4-methyl-2-[5-(4-methylpiperazin-1-yl)carbonylpent-1-yl]oxy]phenylbenzamide NMR (CDCl₃, δ): 1.40 (9H, s), 1.45–1.60 (2H, m), 1.65–1.74 (2H, m), 1.78–1.89 (2H, m), 2.04–2.15 (2H, m), 2.27 (3H, s), 2.30 (3H, s), 2.32–2.42 (6H, m), 3.27–3.39 (2H, m), 3.33 (3H, s), 3.44–3.50 (2H, m), 3.58–3.64 (2H, m), 3.82–4.00 (2H, m), 4.19 (2H, t, J=7.5 Hz), 4.86 (1H, br), 6.55–6.62 (2H, m), 6.86 (1H, d, J=7 Hz), 6.97 (1H, d, J=7 Hz), 7.08 (1H, t, J=7 Hz), 7.31 (2H, d, J=8 Hz), 7.40–7.53 (3H, m), 8.13 (1H, d, J=7 Hz), 9.88 (1H, s)

6) 4-(2-Iodobenzoyl)amino-N-methyl-N-[2-[5-(4-methylpiperazin-1-yl)carbonylpent-1-yl]oxy]phenylbenzamide NMR (CDCl₃, δ): 1.43–1.54 (2H, m), 1.61–1.70 (2H, m), 1.74–1.86 (2H, m), 2.28 (3H, s), 2.28–2.41 (6H, m), 3.34 (3H, s), 3.44–3.50 (2H, m), 3.52–3.59 (2H, m), 3.73–3.99 (2H, m), 6.77–6.84 (2H, m), 7.03 (1H, d, J=7 Hz), 7.10–7.19 (2H, m), 7.29–7.50 (5H, m), 7.80 (1H, s), 7.89 (1H, d, J=7 Hz)

7) 4-(2-Dimethylamino-4-methyl)phenoxymethyl-N-methyl-N-[4-methyl-2-[5-(4-methylpiperazin-1-yl)carbonylpent-1-yl]oxy]phenylbenzamide NMR (CDCl₃, δ): 1.47–1.58 (2H, m), 1.64–1.75 (2H, m), 1.77–1.88 (2H, m), 2.22 (3H, s), 2.25 (3H, s), 2.28 (3H, s), 2.31–2.41 (6H, m), 2.72 (6H, s), 3.32 (3H, s), 3.43–3.51 (2H, m), 3.58–3.67 (2H, m), 3.79–3.97 (2H, m), 5.02 (2H, s), 6.49–6.61 (3H, m), 6.71 (1H, d, J=7 Hz), 7.80–7.85 (2H, m), 7.19 (2H, d, J=8 Hz), 7.28 (2H, d, J=8 Hz)

8) 4-(2-Benzyloxy)benzoylamino-3-methoxy-N-methyl-N-[(E)-2-[4-(4-methylpiperazin-1-yl)carbonyl]phenylethen-1-yl]phenylbenzamide NMR (CDCl₃, δ): 2.11–2.40 (4H, m), 2.17 (3H, s), 3.11 (3H, s), 3.18–3.38 (2H, m), 3.44 (3H, s), 3.49–3.68 (2H, m), 5.27 (2H, s), 6.41 (1H, d, J=14 Hz), 6.56 (1H, d, J=14 Hz), 6.70 (2H, d, J=8 Hz), 6.88–7.48 (16H, m), 8.26 (1H, d, J=7 Hz), 8.38 (1H, d, J=7 Hz)

9) 3-Methoxy-4-[2-[3-(tert-butyoxycarbonylamino)prop-1-yl]oxybenzoyl]amino-N-methyl-N-[4-methyl-2-[5-(4-methylpiperidin-1-yl)carbonylpent-1-yl]oxy]phenylbenzamide NMR (CDCl₃, δ): 0.93 (3H, d, J=7.5 Hz), 0.98–1.14 (2H, m), 1.40 (9H, s), 1.42–1.87 (8H, m), 2.07–2.17 (2H, m), 2.25 (3H, s), 2.32 (2H, t, J=7.5 Hz), 2.50 (1H, m), 2.97 (1H, m), 3.21–3.32 (2H, m), 3.32 (1H, s), 3.79 (1H, m), 3.79–4.00 (4H, m), 4.26 (2H, t, J=7.5 Hz), 4.55 (1H, m), 4.84 (1H, m), 6.59 (1H, d, J=7 Hz), 6.63 (1H, s), 6.85 (1H, d, J=7 Hz), 6.92 (1H, d, J=7 Hz), 6.95–7.13 (3H, m), 7.45 (1H, t, J=7 Hz), 8.20 (1H, d, J=7 Hz), 8.40 (1H, d, J=7 Hz)

10) 3-Methoxy-4-[2-[3-(tert-butoxycarbonylamino)prop-1-yl]oxybenzoyl]amino-N-[2-[5-[(2S)-carbamoylpyrrolidin-1-yl]carbonylpent-1-yl]oxy-4methyl]phenyl-N-methylbenzamide NMR (CDCl₃, δ): 1.28–2.20 (12H, m), 1.39 (9H, s), 2.27 (3H, s), 3.19–3.25 (2H, m), 3.21 (3H, s), 3.25–3.61 (2H, m), 3.78 (3H, s), 3.81–4.03 (2H, m), 4.16–4.29 (2H, m), 4.57 (1H, m), 6.55–6.68 (2H, m), 6.80–7.13 (5H, m), 7.44 (1H, t, J=7 Hz), 8.20 (1H, d, J=7 Hz), 8.40 (1H, d, J=7 Hz)

11) 3-Methoxy-4-[2-[1-(tert-butyoxycarbonyl)piperidin-4-yl]oxybenzoyl]amino-N-methyl-N-[4-methyl-2-[5-(4-methylpiperazin-1-yl)carbonylpent-1-yl]oxy]phenylbenzamide NMR (CDCl₃, δ): 1.41–1.59 (2H, m), 1.46 (9H, s), 1.69–1.94 (6H, m), 2.00–2.13 (2H, m), 2.26 (3H, s), 2.29 (3H, s), 2.33–2.41 (8H, m), 2.96–3.17 (2H, m), 3.31 (3H, s), 3.45–3.51 (2H, m), 3.59–3.67 (2H, m), 3.74 (3H, s), 3.80–4.01 (2H, m), 4.68 (1H, m), 6.58–6.63 (2H, m), 6.85 (1H, d, J=7 Hz), 6.90 (1H, d, J=7 Hz), 6.99–7.11 (2H, m), 7.35–7.61 (2H, m), 8.19 (1H, d, J=7 Hz), 8.40 (1H, d, J=7 Hz)

12) 3-Methoxy-4-[2-[3-(tert-butoxycarbonyl)amino-1-methylprop-1-yl]oxybenzoyl]amino-N-methyl-N-[4-methyl-2-[5-(4-methylpiperazin-1-yl)carbonylpent-1-yl]oxy]phenylbenzamide NMR (CDCl₃, δ): 1.30 (9H, s), 1.31 (3H, d, J=7.5 Hz), 1.45–2.10 (8H, m), 2.27 (3H, s), 2.29 (3H, s), 2.32–2.43 (6H, m), 3.20–3.30 (2H, m), 3.32 (3H, s), 3.45–3.50 (2H, m), 3.60–3.66 (2H, m), 3.79 (3H, s), 3.82–4.00 (2H, m), 4.72 (1H, m), 6.60 (1H, d, J=7 Hz), 6.64 (1H, s), 6.81–6.93 (2H, m), 7.00–7.11 (3H, m), 7.43 (1H, t, J=7 Hz), 8.21 (1H, d, J=7 Hz), 8.42 (1H, d, J=7 Hz)

13) 4-[2-[3-(tert-Butoxycarbonylamino)prop-1-yl]oxybenzoyl]amino-3-methoxy-N-methyl-N-[2-(5-aminocarbonylpent-1-yl)oxy-4-methylphenyl]benzamide NMR (CDCl₃, δ): 1.42 (9H, s), 1.50–1.92 (6H, m), 2.12–2.26 (2H, m), 2.29 (2H, t, J=5 Hz), 2.30 (3H, s), 3.30 (2H, q, J=5 Hz), 3.35 (3H, s), 3.77 (3H, s), 3.80–4.02 (2H, m), 4.25 (2H, t, J=5 Hz), 6.61–6.70 (2H, m), 6.93–7.15 (6H, m), 7.41–7.51 (1H, m), 8.20 (1H, d, J=7 Hz), 8.42 (1H, d, J=7 Hz)

14) 4-[2-[3-(tert-Butyoxycarbonyl)aminoprop-1-yl]oxybenzoyl]amino-3-methoxy-N-methyl-N-[2-[5-[4-(tert-butoxycarbonyl)piperazin-1-yl]carbonylpent-1-yl])oxy-4-methylphenyl]benzamide NMR (CDCl₃, δ): 1.40 (9H, s), 1.49 (9H, s), 1.50–1.90 (6H, m), 2.12–2.23 (2H, m), 2.30 (3H, s), 2.39 (2H, t, J=5 Hz), 3.30 (2H, q, J=5 Hz), 3.33 (3H, s), 3.35–3.42 (4H, m), 3.44 (4H, s), 3.55–3.62 (2H, m), 3.80 (3H, s), 3.85–4.06 (2H, m), 4.24 (2H, t, J=5 Hz), 4.93 (1H, br), 6.57–6.66 (2H, m), 6.85–7.13 (6H, m), 7.44–7.52 (1H, m), 8.20 (1H, d, J=7 Hz), 8.41 (1H, d, J=7 Hz)

15) 4-[2-[3-(tert-Butoxycarbonyl)aminoprop-1-yl]oxybenzoyl]amino-3-methoxy-N-methyl-N-[2-[5-morpholin-4-yl)carbonylpent-1-yl]oxy-4-methylphenyl]benzamide NMR (CDCl₃, δ): 1.41 (9H, s), 1.50–1.88 (6H, m), 2.10–2.21 (2H, m), 2.30 (3H, s), 2.36 (2H, t, J=5 Hz), 3.30 (2H, q, J=5 Hz), 3.34 (3H, s), 3.47 (2H, t, J=4 Hz), 3.58–3.70 (6H, m), 3.79 (3H, s), 3.84–4.03 (2H, m), 4.25 (2H, t, J=5 Hz), 4.89 (1H, br), 6.56–6.68 (2H, m), 6.84–7.16 (6H, m), 7.41–7.51 (2H, m), 8.20 (1H, d, J=8 Hz), 8.41 (1H, d, J=8 Hz)

16) 4-[2-[3-(tert-Butoxycarbonyl)aminoprop-1-yl]
oxybenzoyl]amino-3-methoxy-N-methyl-N-[2-[5-(4-methylhomopiperazin-1-yl)carbonylpent-1-yl]oxy-4-methylphenyl]benzamide NMR (CDCl$_3$, δ): 1.41 (9H, s), 1.46–1.97 (8H, m), 2.09–2.21 (2H, m), 2.29 (3H, s), 2.32 (2H, t, J=5 Hz), 2.33 (3H, s), 2.52–2.66 (4H, m), 3.30 (2H, q, J=5 Hz), 3.33 (3H, s), 3.50–3.69 (4H, m), 3.79 (3H, s), 3.84–4.03 (2H, m), 4.24 (2H, t, J=5 Hz), 4.94 (1H, br), 6.56–6.67 (2H, m), 6.82–7.12 (6H, m), 7.40–7.49 (1H, m), 8.20 (1H, d, J=7 Hz), 8.41 (1H, d, J=8 Hz)

17) 4-[2-(3-tert-Butyoxycarbonylaminoprop-1-yl)
oxybenzoyl]amino-3-methoxy-N-methyl-N-[2-[5-(2-dimethylaminoeth-1-yl)aminocarbonylpent-1-yl]oxy-4-methylphenyl]benzamide NMR (CDCl$_3$, δ): 1.40 (9H, s), 1.42–1.59 (4H, m), 1.67–1.90 (4H, m), 1.97–2.32 (4H, m), 2.28 (3H, s), 2.34 (6H, s), 2.56 (2H, br), 3.25–3.42 (4H, m), 3.32 (2H, s), 3.50 (1H, s), 3.78–4.01 (2H, m), 3.80 (3H, s), 4.25 (2H, t, J=6 Hz), 4.91 (1H, br), 6.52–6.76 (3H, m), 6.87–7.13 (7H, m), 7.45 (1H, m), 8.19 (1H, d, J=8 Hz), 8.41 (1H, br)

18) 4-[2-(3-tert-Butoxycarbonylaminoprop-1-yl)
oxybenzoyl]amino-3-methoxy-N-methyl-N-[2-[5-[N-(3-dimethylaminoprop-1-yl)-N-methylcarbamoylpent-1-yl]oxy-4-methylphenyl]benzamide NMR (CDCl$_3$, δ): 1.41 (9H, s), 1.50–1.96 (6H, m), 2.11–2.25 (2H, m), 2.27 (3H, s), 2.30–2.43 (2H, m), 2.50 (6H, s), 2.91 and 3.02 (total 3H, s, rotamer), 3.08 and 3.32 (total 2H, q, rotamer, J=5 Hz), 3.33 (3H, s), 3.43 (2H, t, J=5 Hz), 3.79 (3H, s), 3.83–4.02 (2H, m), 4.25 (2H, t, J=5 Hz), 6.57–6.68 (2H, m), 6.82–7.13 (6H, m), 7.42–7.50 (1H, m), 8.21 (1H, d, J=8 Hz), 8.41 (1H, d, J=8 Hz)

19) 4-[2-(3-tert-Butoxycarbonylaminoprop-1-yl)
oxybenzoyl]amino-3-methoxy-N-methyl-N-[2-[5-[bis(2-hydroxyeth-1-yl)amino]carbonylpent-1-yl]oxy-4-methylphenyl]benzamide NMR (CDCl$_3$, δ): 1.40 (9H, s), 1.55–1.89 (6H, m), 2.11–2.20 (2H, m), 2.28 (3H, s), 2.40–2.56 (2H, m), 3.29 (2H, t, J=5 Hz), 3.40–3.57 (4H, m), 3.68–4.02 (6H, m), 4.26 (2H, t, J=5 Hz), 6.60–6.68 (2H, m), 6.90–7.15 (6H, m), 7.42–7.51 (1H, m), 8.19 (1H, d, J=8 Hz), 8.40 (1H, d, J=8 Hz)

20) 4-[2-(3-tert-Butoxycarbonylaminoprop-1-yl)
oxybenzoyl]amino-3-methoxy-N-methyl-N-[2-[5-(2,2-dimethylhydrazino)carbonylpent-1-yl]oxy-4-methylphenyl]benzamide NMR (DMSO-d$_6$, δ): 1.40 (9H, s), 1.45–1.90 (6H, m), 2.08–2.20 (2H, m), 2.28 (3H, s), 2.30–2.45 (2H, m), 2.51 (3H, s), 2.60 (3H, s), 3.29 (2H, t, J=5 Hz), 3.33 (3H, s), 3.75 (3H, s), 3.79–4.02 (2H, m), 4.25 (2H, t, J=5 Hz), 6.57–6.68 (2H, m), 6.80–7.14 (5H, m), 7.41–7.50 (1H, m), 8.21 (1H, d, J=8 Hz), 8.40–8.48 (1H, br)

21) 4-[2-(3-tert-Butoxycarbonylaminoprop-1-yl)
oxybenzoyl]amino-3-methoxy-N-methyl-N-[2-[5-(carbamoylmethylamino)carbonylpent-1-yl]oxy-4-methylphenyl]benzamide NMR (CDCl$_3$, δ): 1.41 (9H, s), 1.50–1.90 (6H, m), 2.12–2.19 (2H, m), 2.28 (3H, s), 2.53 (2H, t, J=5 Hz), 3.30 (2H, t, J=5 Hz), 3.33 (3H, s), 3.80 (3H, s), 3.84–3.99 (2H, m), 4.05 (2H, br), 4.25 (2H, t, J=5 Hz), 4.84 (1H, br), 6.58–6.67 (2H, m), 6.72–7.12 (6H, m), 7.42–7.50 (1H, m), 8.18–8.23 (1H, m), 8.41 (1H, d, J=8 Hz)

22) 4-[2-(3-tert-Butoxycarbonylaminoprop-1-yl)
oxybenzoyl]amino-3-methoxy-N-methyl-N-[2-[5-(carbamoylethylamino)carbonylpent-1-yl]oxy-4-methylphenyl]benzamide NMR (CDCl$_3$, δ): 1.41 (9H, s), 1.46–1.86 (6H, m), 2.12–2.25 (4H, m), 2.30 (3H, s), 2.41 (2H, t, J=5 Hz), 3.30 (1H, q, J=5 Hz), 3.37 (3H, s), 3.49 (1H, q, J=5 Hz), 3.79 (3H, s), 3.82–4.03 (2H, m), 4.27 (2H, t, J=5 Hz), 6.45–6.67 (4H, m), 6.88–7.15 (6H, m), 7.43–7.51 (1H, m), 8.20 (1H, d, J=8 Hz), 8.41 (1H, d, J=8 Hz)

23) 4-[2-(3-tert-Butoxycarbonylaminoprop-1-yl)
oxybenzoyl]amino-3-methoxy-N-methyl-N-[2-[5-(4-diethylaminopiperidin-1-yl)carbonylpent-1-yl]oxy-4-methylphenyl]benzamide NMR (CDCl$_3$, δ): 1.12 (6H, t, J=5 Hz), 1.41 (9H, s), 1.42–1.92 (6H, m), 2.10–2.18 (2H, m), 2.27 (3H, s), 2.27–2.69 (9H, m), 3.26 (2H, t, J=5 Hz), 3.31 (3H, s), 3.77 (3H, s), 3.87–4.02 (4H, m), 4.23 (2H, t, J=5 Hz), 6.54–6.67 (2H, m), 6.72–7.15 (6H, m), 7.42–7.51 (1H, m), 8.19 (1H, d, J=8 Hz), 8.42 (1H, d, J=8 Hz)

24) 4-[2-[3-(tert-Butyoxycarbonylamino)prop-1-yl]
oxybenzoyl]amino-3-methoxy-N-[2-[3-(4-methylpiperazin-1-yl)carbonylpyrid-6-yl]methoxy-4-methylphenol]-N-methylbenzamide NMR (CDCl$_3$, δ): 1.39 (9H, s), 2.06–2.18 (2H, m), 2.28 (3H, s), 2.31 (3H, s), 2.35–2.51 (4H, m), 3.27 (2H, q, J=5 Hz), 3.38–3.49 (2H, m), 3.41 (1H, s), 3.63 (3H, s), 3.68–3.76 (2H, m), 4.21 (2H, t, J=5 Hz), 4.97 (1H, d, J=12 Hz), 5.14 (1H, d, J=12 Hz), 6.58 (1H, s), 6.72 (1H, d, J=8 Hz), 6.91–7.11 (7H, m), 7.20–7.25 (1H, m), 7.43 (1H, dd, J=2, 8 Hz), 7.68 (1H, d, J=8 Hz), 8.19 (1H, d, J=8 Hz), 8.40 (1H, d, J=8 Hz), 8.60 (1H, s)

25) 4-[2-(Benzyloxy)benzoyl]amino-3-methoxy-N-methyl-N-[2-[5-(4-dimethylaminopiperidin-1-yl)carbonylpent-1-yloxy]phenyl]benzamide NMR (CDCl$_3$, δ): 1.30–1.42 (2H, m), 1.48–1.58 (2H, m), 1.63–1.93 (6H, m), 2.29 (6H, s), 2.30–2.40 (3H, m), 2.50–2.60 (1H, m), 2.95–3.06 (1H, m), 3.29 (3H, s), 3.38 (3H, s), 3.80–4.00 (4H, m), 4.57–4.70 (1H, m), 5.30 (2H, s), 6.74–7.20 (9H, m), 7.32–7.45 (5H, m), 8.20–8.37 (1H, m), 8.37–8.42 (1H, m)

26) 4-[(2-Benzyloxy)benzoyl]amino-N-methyl-N-[2-[3-(4-methylpiperazin-1-yl)carbonylprop-1-yl]oxy] phenybenzamide NMR (CDCl$_3$, δ): 2.05–2.16 (2H, m), 2.28 (3H, s), 2.32–2.40 (4H, m), 2.50 (2H, t, J=7.5 Hz), 3.33 (3H, s), 3.43–3.50 (2H, m), 3.59–3.65 (2H, m), 2.88–4.05 (2H, m), 5.19 (2H, s), 6.77–6.84 (2H, m), 6.95–7.02 (3H, m), 7.09–7.20 (5H, m), 7.39–7.52 (6H, m), 8.27 (1H, d, J=7 Hz)

EXAMPLE 21

The following compounds were obtained according to the similar manners to those of Examples 8 and 16.

1) 4-(6-Hydroxy-2-pyridylcarbonyl)amino-N-methyl-N-[4-methyl-2-[5-(4-methylpiperazin-1-yl)carbonylpent-1-yloxy]phenyl]benzamide dihydrochloride NMR (CDCl$_3$, δ): 1.47–1.58 (2H, m), 1.64–1.73 (2H, m), 1.78–1.87 (2H, m), 2.27 (3H, s), 2.29 (3H, s), 2.28–2.41 (8H, m), 3.33 (3H, s), 3.45–3.51 (2H, m), 3.59–3.68 (6H, m), 3.86–3.94 (1H, br), 6.55–6.61 (2H, m), 6.86 (1H, d, J=8 Hz), 7.30–7.38 (4H, m), 7.47–7.54 (2H, m), 8.06–8.10 (1H, m)

ESI-MASS (m/z): 574 (M+H)

2) 4-[2-(Methoxy)benzoyl]amino-N-methyl-N-[4-methyl-2-[5-(4-methylpiperazin-1-yl)carbonylpent-1-yloxy]phenyl]benzamide hydrochloride NMR DMSO-d$_6$, δ): 1.36–1.66 (4H, m), 1.66–1.83 (2H, m), 2.23 (3H, s), 2.39 (2H, t, J=7 Hz), 2.74 (3H, s), 2.80–3.10 (3H, m), 3.17 (3H, s), 3.23–3.53 (3H, m), 3.86 (3H, s), 3.79–3.99 (2H, m), 4.00–4.17 (1H, m), 4.37–4.52

(1H, m), 6.64 (1H, d, J=9 Hz), 6.79 (1H, s), 6.98–7.09 (2H, m), 7.11–7.28 (3H, m), 7.43–7.64 (4H, m)

EXAMPLE 22

To a solution of 4-amino-3-methoxy-N-methyl-N-[4-methyl-2-[5-(4-methylpiperazin-1-yl)carbonylpent-1-yloxy]phenyl]benzamide (327 mg) and pyridine (80.3 mg) in dichloromethane (6 ml) was added dropwise 2-nitrobenzenesulfonyl chloride (150 mg) at ambient temperature and the mixture was stirred at ambient temperature for 5 hours. The resulting mixture was diluted with dichloromethane (10 ml) and the organic layer was washed successively with saturated sodium bicarbonate aqueous solution and brine. Drying, filtering and removal of solvents afforded a crude product. The crude product was chromatographed on silica gel (eluent; 2–4% methanol in chloroform) to give 4-(2-nitrobenzenesulfonyl)amino-3-methoxy-N-methyl-N-[4-methyl-2-[5-(4-methylpiperazin-1-yl)carbonylpent-1-yloxy]phenyl]benzamide (460 mg).

NMR (CDCl$_3$, δ): 1.47–1.82 (6H, m), 2.28 (3H, s), 2.31 (3H, s), 2.35–2.42 (6H, m), 3.30 (3H, s), 3.46–3.53 (5H, m), 3.60–3.68 (4H, m), 6.56–6.96 (6H, m), 7.53–7.88 (4H, m)

EXAMPLE 23

A solution of 4-[2-[2-[3-(phthalimido)prop-1-yl]oxy]phenyl]vinyl-3-methoxybenzoic acid (370 mg) in tetrahydrofuran (20 ml) was treated at ambient temperature with triethylamine (246 mg), N-methyl-4-methyl-2-[5-(4-methylpiperazin-1-yl)carbonylpent-1-yloxy]aniline (297 mg), and diphenylphosphorochloridate (326 mg). The reaction mixture was stirred at 80° C. for 18 hours. After concentration, the residue was dissolved in chloroform and washed with brine and dried over magnesium sulfate. The crude product was purified by silica gel column chromatography (SiO$_2$ 30 g, 3% methanol in chloroform) to give 4-[2-[2-[(3-(phthalimido)prop-1-yl)oxy]phenyl]vinyl]-3-methoxy-N-methyl-N-[4-methyl-2-[5-(4-methylpiperazin-1-yl)carbonylpent-1-yloxy]phenyl]benzamide (550 mg).

NMR (CDCl$_3$, δ): 1.47–1.95 (8H, m), 2.18–2.44 (12H, m), 3.31 and 3.34 (total 3H, s), 3.42–3.52 (2H, m), 3.57–3.72 (5H, m), 3.82–4.16 (6H, m), 6.30–7.80 (16H, m)

EXAMPLE 24

The following compounds were obtained according to a similar manner to that of Example 23.

1) 4-[N-Methyl-2-[(3-tert-butoxycarbonylaminoprop-1-yl)oxy]benzoyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.40–1.75 (8H, m), 1.44 (9H, s), 1.89–1.97 (2H, m), 2.29 (6H, s), 2.32–2.42 (6H, m), 3.24 (6H, s), 3.26–3.34 (2H, m), 3.44–3.67 (6H, m), 3.77–3.88 (3H, m), 6.48–6.82 (9H, m), 6.90–6.96 (1H, m), 7.06–7.13 (1H, m)

ESI-MASS (m/z): 774 (M+H)

2) 4-[2-[(3-tert-Butoxycarbonylaminoprop-1-yl)oxy]benzoyl]amino-3-methoxy-N-methyl-N-(4-benzyloxyphenyl)benzamide NMR (CDCl$_3$, δ): 1.42 (9H, s), 2.09–2.20 (2H, m), 3.28–3.37 (2H, m), 3.48 (3H, s), 3.81 (3H, s), 4.22–4.33 (2H, m), 4.70–4.78 (1H, br), 5.00 (2H, s), 6.82–6.88 (3H, m), 6.97–7.13 (6H, m), 7.31–7.48 (6H, m), 8.23 (1H, d, J=8 Hz), 8.44 (1H, d, J=8 Hz)

ESI-MASS (m/z): 640 (M+H)

3) 4-[2-[(3-tert-Butoxycarbonylaminoprop-1-yl)oxy]benzoyl]amino-3-benzyloxy-N-methyl-N-cyclohexylbenzamide NMR (CDCl$_3$, δ): 1.01–1.12 (2H, br), 1.40 (9H, s), 1.45–1.82 (10H, m), 2.81–3.07 (5H, m), 3.80–3.89 (2H, m), 4.40–4.49 (1H, m), 5.18 (2H, s), 6.94 (1H, d, J=8 Hz), 7.02 (1H, d, J=8 Hz), 7.07–7.15 (2H, m), 7.35–7.48 (6H, m), 8.27 (1H, d, J=8 Hz) 8.68 (1H, d, J=8 Hz)

ESI-MASS (m/z: 616 (M+H)

4) 4-[(2-Benzyloxy)benzoyl]amino-3-chloro-N-methyl-N-[2-[5-(4-dimethylaminopiperidin-1-yl)carbonylpent-1-yloxy]-4-methylphenyl]benzamide NMR (CDCl$_3$, δ): 1.30–1.45 (2H, m), 1.45–1.57 (2H, m), 1.62–1.93 (6H, m), 2.22–2.40 (12H, m), 2.50–2.63 (1H, m), 2.95–3.08 (1H, m), 3.31 (3H, s), 3.80–4.00 (4H, m), 4.58–4.70 (1H, m), 5.37 (2H, s), 6.56–6.62 (2H, m), 6.83–6.88 (1H, m), 7.02–7.13 (3H, m), 7.36–7.47 (7H, m), 8.27 (1H, d, J=7 Hz), 8.42 (1H, d, J=7 Hz)

5) 4-[N-[2-[(3-tert-Butoxycarbonylaminoprop-1-yl)oxy]phenyl]-tert-butoxycarbonylamino]methyl-3-methoxy-N-methyl-N-[2-[5-(4-methylpiperazin-1-yl)carbonylpent-1-yloxy]-4-methylphenyl]benzamide NMR (CDCl$_3$, δ): 1.30 and 1.33 (total 9H, s), 1.43 (9H, s), 1.49–1.60 (2H, m), 1.62–1.98 (6H, m), 2.28 (3H, s), 2.30 (3H, s), 2.32–2.42 (6H, m), 3.20–3.29 (2H, m), 3.32 (3H, s), 3.39 (1H, s), 3.46–3.55 (4H, m), 3.62 (2H, br), 3.82 (1H, br), 3.88–4.03 (3H, m), 6.50–6.60 (2H, m), 6.65–7.00 (6H, m), 7.06–7.22 (2H, m)

6) 4-[2-[(3-tert-Butoxycarbonylaminoprop-1-yl)oxy]phenoxy]methyl-3-methoxy-N-methyl-N-[2-[5-(4-methylpiperazin-1-yl)carbonylpent-1-yloxy]-4-methylphenyl]benzamide NMR (CDCl$_3$, δ): 1.37 (9H, s), 1.47–1.57 (2H, m), 1.66–1.73 (2H, m), 1.73–1.88 (2H, m), 1.93–2.02 (2H, m), 2.28 (3H, s), 2.30 (3H, s), 2.32–2.40 (6H, m), 3.32 (3H, m), 3.25–3.38 (2H, m), 3.47–3.50 (2H, m), 3.62–3.67 (2H, m), 3.70 (3H, s), 3.80–3.88 (1H, m), 3.90–3.98 (2H, m), 4.07–4.17 (2H, m), 5.10 (2H, s), 5.50 (1H, br), 6.53–6.60 (2H, m), 6.70–6.90 (7H, m), 7.15–7.20 (1H, m)

7) 3-Benzyloxy-4-[2-[(3-tert-butoxycarbonylaminoprop-1-yl)oxy]benzoyl]amino-N-methyl-N-[2-[5-(4-methylpiperazin-1-yl)carbonylpent-1-yloxy]-4-methylphenyl]benzamide NMR (CDCl$_3$, δ): 1.40 (9H, s), 1.45–1.85 (10H, m), 2.28 (3H, s), 2.29 (3H, s), 2.32–2.39 (6H, m), 2.90–2.98 (2H, m), 3.30 (3H, s), 3.47–3.49 (2H, m), 3.60–3.63 (2H, m), 3.77–3.98 (4H, m), 4.97 (2H, s), 6.56–6.60 (2H, m), 6.80 (1H, d, J=7 Hz), 6.89–6.97 (2H, m), 7.04–7.12 (2H, m), 7.33–7.45 (6H, m), 8.19 (1H, d, J=6 Hz), 8.41 (1H, d, J=7 Hz)

8) 2-[2-[(3-tert-Butoxycarbonylaminoprop-1-yl)oxy]benzoyl]amino-N-methyl-N-[2-[5-(4-methylpiperazin-1-yl)carbonylpent-1-yloxy]-4-methylphenyl]-5-thiophenecarboxamide NMR (CDCl$_3$, δ): 1.37 (9H, s), 1.48–1.62 (2H, m), 1.62–1.76 (6H, m), 1.97–2.11 (2H, m), 2.17–2.38 (9H, m), 2.39 (3H, s), 3.31 (3H, s), 3.33–3.65 (6H, m), 3.87 (1H, br), 3.94 (1H, br), 4.02 (1H, s), 4.13–4.20 (2H, m), 6.40–6.57 (2H, m), 6.74–6.82 (2H, m), 6.92–7.14 (3H, m), 7.40–7.52 (1H, m), 8.10–8.27 (1H, m)

EXAMPLE 25

A solution of (S)-4-[2-[1-methyl-3-(phthalimido)prop-1-yl]oxybenzoyl]amino-3-methoxy-N-methyl-N-[4-methyl-2-[5-(4-methylpiperazin-1-yl)carbonylpent-1-yloxy]phenyl]benzamide (1.1 g) in methanol (30 ml) was stirred and treated with 40% methylamine in methanol (10 ml). The reaction mixture was refluxed for 30 minutes. Then the solvent was concentrated and purified by silica gel column chromatography (SiO$_2$ 40 g, chloroform/methanol/ammonia=90/10/0.5) to give (S)-4-[2-[(3-amino-1-methylprop-1-yl)oxy]benzoyl]amino-3-methoxy-N-methyl-N-[4-methyl-2-[5-(4-methylpiperazin-1-yl)carbonylpent-1-yloxy]phenyl]benzamide.

NMR (CDCl$_3$, δ): 1.42 (3H, d, J=7 Hz), 1.46–1.92 (9H, m), 1.98–2.16 (1H, m), 2.20–2.45 (12H, m), 2.86 (2H, t, J=7 Hz), 3.32 (3H, s), 3.42–3.53 (2H, m), 3.57–3.67 (2H, m), 3.79 (3H, s), 3.82–4.03 (2H, m), 4.73–4.90 (1H, m), 6.51–6.68 (2H, m), 6.79–6.95 (2H, m), 6.98–7.12 (3H, m), 7.37–7.49 (1H, m), 8.21 (1H, d, J=8 Hz), 8.41 (1H, d, J=8 Hz)

EXAMPLE 26

A solution of 4-[2-[(3-tert-butoxycarbonylaminoprop-1-yl)oxy]benzoyl]amino-3-methoxy-N-methyl-N-[2-(5-carboxypent-1-yloxy)-4-methylphenyl]benzamide (3.5 g) in ethyl acetate (30 ml) was treated at ambient temperature with triethylamine (575 mg), N-methylpiperazine (569 mg), and diphenylphosphoryl azide (1.56 g). The reaction mixture was stirred at the same temperature for 17 hours. The reaction mixture was washed with brine and dried over magnesium sulfate. The crude product was purified by silica gel column chromatography (SiO$_2$ 100 g, 3% methanol in chloroform) to give 4-[2-[(3-tert-butoxycarbonylaminoprop-1-yl)oxy]benzoyl]amino-3-methoxy-N-methyl-N-[4-methyl-2-[5-(4-methylpiperazin-1-yl)carbonylpent-1-yloxy]phenyl]benzamide (2.93 g).

NMR (CDCl$_3$, δ): 1.40 (9H, s), 1.42–1.60 (2H, m), 1.62–1.90 (4H, m), 2.06–2.20 (2H, m), 2.22–2.42 (12H, m), 3.21–3.36 (5H, m), 3.42–3.51 (2H, m), 3.56–3.67 (2H, m), 3.77 (3H, s), 3.81–4.02 (2H, m), 4.23 (2H, t, J=7 Hz), 4.86 (1H, m), 6.51–6.67 (2H, m), 6.79–6.93 (2H, m), 6.94–7.13 (3H, m), 7.44 (1H, m), 8.20 (1H, d, J=8 Hz), 8.41 (1H, d, J=8 Hz)

EXAMPLE 27

The following compound was obtained according to a similar manner to that of Example 26.

4-[2-[(3-tert-Butoxycarbonylaminoprop-1-yl)oxy]benzoyl]amino-3-methoxy-N-methyl-N-[2-[5-(4-dimethylaminopiperidin-1-yl)carbonylpent-1-yloxy]-4-methylphenyl]benzamide NMR (CDCl$_3$, δ): 1.41 (9H, s), 1.46–1.95 (8H, m), 2.06–2.42 (16H, m), 2.56 (1H, m), 3.00 (1H, m), 3.22–3.38 (5H, m), 3.79 (3H, s), 3.83–4.03 (3H, m), 4.25 (2H, t, J=7 Hz), 4.61 (1H, m), 4.87 (1H, m), 6.52–6.68 (2H, m), 6.79–6.95 (2H, m), 6.96–7.17 (3H, m), 7.46 (1H, m), 8.21 (1H, d, J=8 Hz), 8.41 (1H, d, J=8 Hz)

EXAMPLE 28

To a solution of 4-[2-(3-tert-butoxycarbonylaminoprop-1-yl)oxybenzoyl]amino-3-methoxy-N-methyl-N-[2-(5-carboxypent-1-yl)oxy-4-methylphenol]benzamide (300 mg) and N-methylmorpholine (45 mg), in N,N-dimethylformamide (5 ml) was added isobutyl chloroformate (61 mg) at −15° C. and the solution was stirred at the same temperature for 5 minutes. N,N,N'-Trimethylethylenediamine (54 mg) was added to the solution and the mixture was stirred at −15° C. for 30 minutes, and then at ambient temperature for 1 hour. The mixture was diluted with ethyl acetate (20 ml) and the solution was washed successively with aqueous sodium hydrogen carbonate solution, water (15 ml×3) and brine. The solution was dried over potassium carbonate and the solvent was removed under reduced pressure. The residue was purified on silica gel column chromatography (SiO$_2$ 40 g, 1–5% methanol in chloroform) to give 4-[2-(3-tert-butoxycarbonylaminoprop-1-yl)oxybenzoyl]amino-3-methoxy-N-methyl-N-[2-[5-[(2-dimethylaminoeth-1-yl)-N-methylaminocarbonyl]pent-1-yl]oxy-4-methylphenyl]benzamide (312 mg).

NMR (CDCl$_3$, δ): 1.40 (9H, s), 1.44–2.21 (8H, m), 2.25 (3H, s), 2.27 (6H, s), 2.29–2.50 (4H, m), 2.91 (1H, s), 3.00 (2H, s), 3.26–3.51 (4H, m), 3.31 (3H, s), 3.77 (3H, s), 3.81–4.02 (2H, m), 4.22 (2H, t, J=5 Hz), 4.88 (1H, br), 6.52–6.68 (2H, m), 6.79–7.11 (5H, m), 7.43 (1H, m), 8.20 (1H, d, J=9 Hz), 8.40 (1H, d, J=8 Hz)

EXAMPLE 29

The following compounds were obtained according to a similar manner to that of Example 28.

1) 4-[2-(3-tert-Butoxycarbonylaminoprop-1-yl)oxybenzoyl]amino-3-methoxy-N-methyl-N-[2-[5-(3-dimethylaminoprop-1-yl)aminocarbonylpent-1-yl]oxy-4-methylphenyl]benzamide NMR (CDCl$_3$, δ): 1.40 (9H, s), 1.42–1.57 (2H, m), 1.61–1.85 (6H, m), 2.04–2.35 (8H, m), 2.25 (3H, s), 2.29 (9H, s), 2.46 (2H, t, J=6 Hz), 3.20–3.38 (4H, m), 3.30 (3H, s), 3.76 (3H, s), 3.80–4.00 (2H, m), 4.24 (2H, t, J=5 Hz), 4.90 (1H, br), 6.61–6.72 (2H, m), 6.84–7.12 (6H, m), 7.43 (1H, d, J=8 Hz), 8.20 (1H, d, J=8 Hz), 8.41 (1H, d, J=8 Hz)

2) 4-[2-(3-tert-Butoxycarbonylaminoprop-1-yl)oxybenzoyl]amino-3-methoxy-N-methyl-N-[2-[5-(4-oxopiperidin-1-yl)carbonylpent-1-yl]oxy-4-methylphenyl]benzamide NMR (CDCl$_3$, δ): 1.40 (9H, s), 1.50–1.92 (8H, m), 2.15 (2H, t, J=6 Hz), 2.29 (2H, t, J=5 Hz), 2.38–2.51 (6H, m), 3.30 (2H, t, J=5 Hz), 3.32 (3H, s), 3.70–4.05 (6H, m), 3.80 (3H, s), 4.25 (2H, t, J=5 Hz), 4.85 (1H, br), 6.55–6.67 (2H, m), 6.83–7.15 (6H, m), 7.40–7.51 (1H, m), 8.20 (1H, d, J=8 Hz), 8.40 (1H, br)

3) 4-[2-(3-tert-Butoxycarbonylaminoprop-1-yl)oxybenzoyl]amino-3-methoxy-N-methyl-N-[2-[5-(4-pyridylaminocarbonyl)pent-1-yl]oxy-4-methylphenyl]benzamide NMR (CDCl$_3$, δ): 1.40 (9H, s), 1.50–1.61 (2H, m), 1.75–1.93 (4H, m), 2.09–2.20 (2H, m), 2.30 (3H, s), 2.42 (2H, br), 3.30 (1H, q, J=5 Hz), 3.36 (3H, s), 3.70 (3H, s), 3.72–4.00 (2H, m), 4.25 (2H, t, J=5 Hz), 4.90 (1H, br), 6.60 (1H, br), 6.72 (1H, d, J=8 Hz), 6.99–7.12 (6H, m), 7.43–7.51 (1H, m), 7.63 (1H, d, J=8 Hz), 8.19 (1H, d, J=8 Hz), 8.42 (1H, d, J=7 Hz), 8.46 (1H, br), 9.22 (1H, br)

EXAMPLE 30

To a solution of 4-[2-(3-tert-butoxycarbonylaminoprop-1-yl)oxybenzoyl]amino-3-methoxy-N-methyl-N-[2-(5-carboxypent-1-yl)oxy-4-methylphenyl]benzamide (250 mg) and N-methylmorpholine (37 mg) in dichloromethane (5 ml) was added pivaloyl chloride (45 mg) at −15° C. After being stirred at the same temperature for 5 minutes, to the mixture was added 1-amino-4-methylpiperazine (47 mg) and the mixture was stirred at −15° C. for 1 hour and then stirred at ambient temperature for additional 2 hours. The resulting mixture was poured into saturated aqueous sodium hydrogen carbonate solution (20 ml) and the solution was extracted with chloroform (15 ml×3). The organic layer was washed with brine and dried over magnesium sulfate. The solvent was evaporated and the residue was purified on silica gel column chromatography (SiO$_3$ 30 g, 1–15% methanol in chloroform) to give 4-[2-(3-tert-butoxycarbonylaminoprop-1-yl)oxybenzoyl]amino-3-methoxy-N-methyl-N-[2-[5-(4-methylpiperazine-1-yl)aminocarbonylpent-1-yl]oxy-4-methylphenyl]benzamide (208 mg).

NMR (CDCl₃, δ): 1.40 (9H, s), 1.45–1.90 (6H, m), 2.10–2.19 (2H, m), 2.24 (3H, s), 2.25 (3H, s), 2.51 (2H, t, J=5 Hz), 2.54–2.91 (8H, m), 3.30 (2H, t, J=5 Hz), 3.34 (3H, s), 3.75 (3H, s), 3.80–4.03 (2H, m), 4.24 (2H, t, J=5 Hz), 4.78–4.97 (1H, br), 6.53–6.67 (2H, m), 6.73–7.14 (6H, m), 7.40–7.50 (1H, m), 8.21 (1H, d, J=8 Hz), 8.45 (1H, d, J=8 Hz)

EXAMPLE 31

The following compounds were obtained according to a similar manner to that of Example 9.

1) 4-[2-(E)-[2-(4-Methylpiperazin-1-yl)carbonylethen-1-yl]benzoyl]amino-3-methoxy-N-methyl-N-[4-methyl-2-[5-(4-methylpiperazin-1-yl)carbonylpent-1-yl]oxy]phenylbenzamide NMR (CDCl₃, δ): 1.48–1.59 (2H, m), 1.67–1.76 (2H, m), 1.79–1.87 (2H, m), 2.21 (3H, s), 2.26 (3H, s), 2.31 (3H, s), 2.31–2.44 (10H, m), 3.17–3.25 (2H, m), 3.34 (3H, s), 3.47–3.52 (2H, m), 3.56–3.67 (3H, m), 3.62 (3H, s), 3.82–3.99 (3H, m), 5.71 (1H, m), 6.60–6.67 (2H, m), 6.86 (1H, d, J=7 Hz), 6.92 (1H, d, J=7 Hz), 6.98–7.03 (2H, m), 7.14 (1H, d, J=7 Hz), 7.43–7.62 (4H, m), 7.85 (1H, d, J=7 Hz)

2) 4-[2-[(4-Methylpiperazin-1-yl)carbonylmethoxy]benzoyl]amino-3-methoxy-N-[2-[5-(4-methylpiperazin-1-yl)carbonylpent-1-yl]oxy-4-methylphenyl]benzamide NMR (CDCl₃, δ): 1.30–1.90 (6H, m), 2.14 (3H, s), 2.26, (3H, s), 2.35–2.46 (3H, m), 3.34 (3H, s), 3.46–3.55 (4H, m), 3.59–3.68 (4H, m), 3.72 (3H, s), 3.80–4.01 (2H, m), 4.90 (2H, s), 6.58–6.68 (2H, m), 6.82–7.06 (4H, m), 7.13–7.20 (2H, m), 7.46–7.51 (1H, m), 8.19 (1H, d, J=8 Hz), 8.39 (1H, d, J=8 Hz)

EXAMPLE 32

A solution of 4-(2-iodobenzoyl)amino-N-[2-(4-methoxyphenyl)methoxy]phenyl-N-methylbenzamide (2.30 g) in a mixture of dichloromethane (30 ml) and trifluoroacetic acid (15 ml) was stirred at ambient temperature for 2 hours and the solvent was evaporated in vacuo. The residual oil was dissolved in chloroform (50 ml) and the solution was washed successively with water (50 ml), aqueous sodium hydrogen carbonate (50 ml) and brine (25 ml). The solution was dried over magnesium sulfate and the solvent was evaporated in vacuo to give 4-(2-iodobenzoyl)amino-N-(2-hydroxy)phenyl-N-methylbenzamide (1.20 g).

NMR (DMSO-d₆, δ): 3.20 (3H, s), 6.69 (1H, t, J=7 Hz), 6.82 (1H, d, J=7 Hz), 6.98–7.05 (3H, m), 7.40–7.54 (4H, m), 7.90 (1H, d, J=7 Hz), 9.84 (1H, s)

EXAMPLE 33

The following compounds were obtained according to a similar manner to that of Example 32.

1) 4-(2-Hydroxybenzoyl)amino-N-methyl-N-[4-methyl-2-[4-(4-methylpiperazin-1-yl)carbonyl]phenylmethoxy]phenylbenzamide NMR (CDCl₃, δ): 2.28 (3H, s), 2.32 (3H, s), 2.35–2.51 (4H, m), 3.36 (3H, s), 3.59–3.89 (2H, m), 5.02 (2H, s), 6.63–6.72 (2H, m), 6.88 (1H, t, J=7 Hz), 7.00 (2H, d, J=8 Hz), 7.20–7.46 (9H, m), 7.70 (1H, d, J=7 Hz), 8.68 (1H, s)

2) 3-Methoxy-4-(2-hydroxybenzoyl)amino-N-methyl-N-[4-methyl-2-[4-(4-methylpiperazin-1-yl)carbonyl]phenylmethoxy]phenylbenzamide NMR (CDCl₃, δ): 2.23 (3H, s), 2.30 (3H, s), 2.33–2.51 (4H, m), 3.37 (3H, s), 3.41–3.56 (2H, m), 3.69 (3H, s), 3.72–3.87 (2H, m), 4.91 (1H, d, J=14 Hz), 5.09 (1H, d, J=14 Hz), 6.63–6.71 (2H, m), 6.35–6.93 (2H, m), 7.00 (2H, d, J=8 Hz), 7.33–7.50 (7H, m), 8.14 (1H, d, J=7 Hz), 8.72 (1H, s)

3) 4[2-(3-Hydroxyprop-1-yl)thiobenzoyl]amino-3-methoxy-N-methyl-N-[4-methyl-2-[5-(4-methylpiperazin-1-yl)-carbonylpent-1-yl]oxy]phenylbenzamide NMR (CDCl₃, δ): 1.44–1.58 (2H, m), 1.61–1.73 (2H, m), 1.77–1.89 (2H, m), 2.28 (3H, s), 2.31–2.40 (6H, m), 3.02 (2H, t, J=7.5 Hz), 3.31 (3H, s), 3.42–3.50 (2H, m), 3.56–3.65 (2H, m), 3.67–3.78 (7H, m), 3.81–4.01 (2H, m), 6.58–6.67 (2H, m), 6.81–6.95 (2H, m), 7.03 (1H, s), 7.25 (1H, m), 7.36–7.50 (2H, m), 7.64 (1H, d, J=7 Hz), 8.30 (1H, d, J=7 Hz), 8.77 (1H, s)

EXAMPLE 34

The following compound was obtained by using 2-nitro-4-(2-benzyloxybenzoyl)amino-N-methyl-N-[2-[5-(4-dimethylaminopiperidin-1-yl)carbonylpent-1-yloxy]-4-methylphenyl]benzamide as a starting compound according to a similar manner to that of Example 10.

2-Amino-4-(2-hydroxybenzoyl)amino-N-methyl-N-[2-[5-(4-dimethylaminopiperidin-1-yl)carbonylpent-1-yloxy]-4-methylphenyl]benzamide NMR (CDCl₃, δ): 1.21–2.02 (10H, m,), 2.28–2.44 (12H, m), 2.48–2.69 (1H, m), 2.93–3.08 (1H, m), 3.30 (3H, s), 3.80–4.06 (4H, m), 4.68 (1H, br), 4.73 (2H, s), 5.32 (1H, s), 6.53–6.62 (3H, m), 6.78–6.96 (5H, m), 7.33–7.44 (1H, m), 7.78–7.88 (1H, m)

EXAMPLE 35

A mixture of 4-(2-hydroxybenzoyl)amino-3-methoxy-N-(2-benzyloxy-4-methyl)phenyl-N-methylbenzamide (550 mg), 1-(tert-butoxycarbonyl)-4-hydroxypiperidine (223 mg), diethyl azodicarboxylate (193 mg) and triphenylphosphine (291 mg) in tetrahydrofuran (15 ml) was stirred at ambient temperature for 8 hours and the mixture was diluted with ethyl acetate (25 ml). The solution was washed with water and brine, and organic phase was dried over magnesium sulfate. The solvent was evaporated in vacuo and the residue was purified by silica gel column (30% ethyl acetate in n-hexane) to give 3-methoxy-4-[2-[1-(tert-butoxycabony)piperidin-4-yl]oxybenzoyl]amino-N-(2-benzyloxy-4-methyl)phenyl-N-methylbenzamide (562 mg).

NMR (CDCl₃, δ): 1.44 (9H, s), 1.72–1.90 (2H, m), 1.95–2.12 (2H, m), 2.27 (3H, s), 2.95–3.16 (4H, m), 3.37 (3H, s), 3.60 (3H, s), 3.73–4.00 (2H, m), 4.6 (1H, m), 4.88 (1H, d, J=14 Hz), 5.08 (1H, d, J=14 Hz), 6.65–6.71 (2H, m), 6.86 (1H, d, J=7 Hz), 6.95–7.03 (3H, m), 7.09 (1H, t, J=7 Hz), 7.25–7.50 (6H, m), 8.18 (1H, d, J=7 Hz), 8.35 (1H, d, J=7 Hz)

EXAMPLE 36

The following compounds were obtained according to a similar manner to that of Example 35.

1) (S)-4-[2-[1-Methyl-3-(phthalimido)prop-1-yl]oxybenzoyl]amino-3-methoxy-N-methyl-N-[4-methyl-2-[5-(4-methylpiperazin-1-yl)carbonylpent-1-yloxy]phenyl]benzamide NMR (CDCl₃, δ): 1.43 (3H, d, J=7 Hz), 1.47–1.92 (7H, m), 1.98–2.13 (1H, m), 2.20–2.47 (12H, m), 3.32 (3H, s), 3.42–3.53 (2H, m), 3.57–3.67 (2H, m), 3.73–4.05 (7H, m), 4.77 (1H, m), 6.51–6.69 (2H, m), 6.78–7.12 (5H, m), 7.42 (1H, m), 7.57 (4H, s), 8.08–8.24 (2H, m)

2) (R)-4-[2-[[4-(Phthalimido-1-yl)but-2-yl]oxy]benzoyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.44 and 1.47 (total 3H, s), 1.52–1.92 (8H, m), 2.02–2.12 (1H, m), 2.28 (3H, s), 2.30 (3H, s), 2.33–2.42 (6H, m), 3.35 (3H, s), 3.47–3.53 (2H, m), 3.60–3.67 (2H, m), 3.80 (3H, s), 3.85–4.00 (2H, br), 3.88 (2H, t, J=8 Hz), 4.74–4.82 (1H, br), 6.57–6.69 (2H, m), 6.81–6.95 (2H, m), 6.98–7.09 (3H, m), 7.43 (1H, t, J=8 Hz), 7.53–7.60 (4H, br), 8.14 (1H, d, J=8 Hz), 8.20 (1H, d, J=8 Hz)

ESI-MASS (m/z): 804 (M+H)

3) (R)-4-[2-[[4-(Phthalimido-1-yl)but-2-yl]oxy]benzoyl]amino-3-methoxy-N-methyl-N-[4-methyl-2-[5-(4-dimethylaminopiperidin-1-yl)carbonylpent-1-yloxy]phenyl]benzamide NMR (CDCl$_3$, δ): 1.42 and 1.45 (total 3H, s), 1.50–1.90 (12H, m), 2.02–2.10 (1H, m), 2.28 (9H, s), 2.32–2.41 (4H, m), 2.52–2.62 (1H, m), 2.97–3.06 (1H, m), 3.35 (3H, s), 3.80 (3H, s), 3.87 (2H, t, J=8 Hz), 3.90–3.97 (2H, m), 4.58–4.68 (1H, m), 4.72–4.81 (1H, m), 6.57–6.67 (2H, m), 6.81–6.93 (2H, m), 6.98–7.08 (3H, m), 7.43 (1H, t, J=8 Hz), 7.53–7.59 (4H, br s), 8.13 (1H, d, J=8 Hz), 8.20 (1H, d, J=8 Hz)

4) (S)-4-[2-[[4-(Phthalimido-1-yl)but-2-yl]oxy]benzoyl]amino-3-methoxy-N-methyl-N-[4methyl-2-[5-(4-dimethylaminopiperidin-1-yl)carbonylpent-1-yloxy]phenyl]benzamide NMR (CDCl$_3$, δ): 1.42 and 1.44 (total 3H, s), 1.50–1.91 (12H, m), 2.02–2.10 (1H, m), 2.29 (9H, s), 2.32–2.41 (4H, m), 2.52–2.62 (1H, m), 2.95–3.05 (1H, m), 3.36 (3H, s), 3.80 (3H, s), 3.86 (2H, t, J=8 Hz), 3.90–3.97 (2H, m), 4.58–4.66 (1H, m), 4.72–4.80 (1H, m), 6.57–6.67 (2H, m), 6.81–6.92 (2H, m), 6.98–7.08 (3H, m), 7.44 (1H, t, J=8 Hz), 7.53–7.60 (4H, br s), 8.13 (1H, d, J=8Hz), 8.21 (1H, d, J=8 Hz)

ESI-MASS (m/z): 832 (M+1)

5) 3-Methoxy-4-[2-[3-(phthalimido)-1-methylprop-1-yl]oxybenzoyl]amino-N-(2-benzyloxy-4-methyl)phenyl-N-methylbenzamide NMR (CDCl$_3$, δ): 1.41 (3H, d, J=7.5 Hz), 1.96–2.12 (2H, m), 2.24 (3H, s), 2.27–2.42 (2H, m), 3.39 (3H, s), 3.60–3.69 (2H, m), 3.86 (2H, t, J=7.5 Hz), 4.77 (1H, m), 4.94 (1H, d, J=14 Hz), 5.08 (1H, d, J=14 Hz), 6.66–6.82 (3H, m), 6.95–7.08 (4H, m), 7.20–7.71 (10H, m), 8.10–8.21 (2H, m)

EXAMPLE 37

The following compounds were obtained according to a similar manner to that of Example 14.

1) 4-[2-(3-Acetylaminoprop-1-yl)oxybenzoyl]amino-3-methoxy-N-(2-acetoxy-4-methylphenyl)-N-methylbenzamide NMR (CDCl$_3$, δ): 1.86 (3H, s), 2.10–2.19 (2H, m), 2.30 (3H, s), 3.41 (2H, q, J=5 Hz), 3.72 (3H, s), 4.21 (2H, t, J=5 Hz), 5.94 (1H, br), 6.85 (1H, s), 6.90–7.11 (6H, m), 7.42–7.49 (1H, m), 8.10 (1H, d, J=8 Hz), 8.42 (1H, d, J=8 Hz)

2) 4-[2-(3-Acetylaminoprop-1-yl)oxybenzoyl]amino-3-methoxy-N-methyl-N-[2-[5-(4-dimethylaminopiperidin-1-yl)carbonylpent-1-yl]oxy-4-methylphenyl]benzamide NMR (CDCl$_3$, δ): 1.48–1.64 (2H, m), 1.58–1.85 (4H, m), 1.88 (3H, s), 2.12 (2H, t, J=5 Hz), 2.29 (6H, s), 2.34–2.42 (2H, m), 2.57 (2H, t, J=5 Hz), 3.30 (2H, q, J=5 Hz), 3.32 (3H, s), 3.39 (2H, q, J=5 Hz), 3.72–3.79 (2H, m), 3.76 (3H, s), 3.83–4.00 (2H, m), 4.20 (2H, t, J=5 Hz), 6.33 (1H, br), 6.57–6.67 (2H, m), 6.83–7.10 (6H, m), 7.43 (1H, dd, J=2, 7 Hz), 8.10 (1H, d, J=8 Hz), 8.38 (1H, d, J=8 Hz)

EXAMPLE 38

To an ice bath cooled solution of 4-[2-(3-aminoprop-1-yl)oxybenzoyl]amino-N-[2-(5-carboxypent-1-yl)oxy-4-methyl]phenyl-N-methylbenzamide (650 mg) in dichloromethane (20 ml) were added triethylamine (137 mg) and di-tert-butyldicarbonate (296 mg) and the mixture was stirred at ambient temperature overnight. The solution was washed successively with water, 10% hydrochloric acid, saturated aqueous sodium hydrogen carbonate and brine, and the organic phase was dried over magnesiua sulfate. The solvent was evaporated in vacuo to give 4-[2-[3-(tert-butoxycarbonyl)aminoprop-1-yl]oxybenzoyl]amino-N-[2-(5-ethoxycarbonylpent-1-yl)oxy-4-methyl]phenyl-N-methylbenzamide (749 mg).

NMR (CDCl$_3$, δ): 1.25 (3H, t, J=7.5 Hz), 1.40 (9H, s), 1.44–1.56 (2H, m), 1.66–1.76 (2H, m), 1.76–1.87 (2H, m), 2.06–2.15 (2H, m), 2.28 (3H, s), 2.34 (2H, t, J=7.5 Hz), 3.1 (3H, s), 3.31–3.40 (2H, m), 3.85–3.97 (2H, m), 4.13 (2H, q, J=7.5 Hz), 4.21 (2H, t, J=7.5 Hz), 4.74 (1H, br), 6.54–6.62 (2H, m), 6.86 (1H, d, J=7 Hz), 6.98 (1H, d, J=7 Hz), 7.09 (1H, d, J=7 Hz), 7.32 (2H, d, J=8 Hz), 7.41–7.52 (3H, m), 8.11 (1H, d, J=7 Hz), 9.87 (1H, s)

EXAMPLE 39

The following compound was obtained according to a similar manner to that of Example 38.

3-Methoxy-4-[2-[3-(tert-butoycarbonyl)amino-1-methylprop-1-yl]oxybenzoyl]amino-N-(2-benzyloxy-4-methyl)phenyl-N-methylbenzamide NMR (CDCl$_3$, δ): 1.37 (9H, s), 1.41 (3H, d, J=7.5 Hz), 1.84–2.11 (2H, m), 2.28 (3H, s), 3.20–3.31 (2H, m), 3.40 (3H, s), 3.64 (3H, s), 4.61 (1H, br), 4.72 (1H, m), 4.90 (1H, d, J=14 Hz), 5.09 (1H, d, J=14 Hz), 6.62–6.70 (2H, m), 6.84 (1H, d, J=7 Hz), 6.93–7.12 (4H, m), 7.28–7.72 (6H, m), 8.22 (1H, d, J=7 Hz), 8.38 (1H, d, J=7 Hz)

EXAMPLE 40

A solution of aqueous 4M sulfuric acid (0.5 ml) and 3-(phthalimid-1-yl)propanal (189 mg) in tetrahydrofuran (10 ml) was slowly added to a solution of 4-(2-aminobenzoylamino)-3-methoxy-N-methyl-N-[2-[5-(4-methylpiperazin-1-yl)carbonylpent-1-yloxy]-4-methylphenylbenzamine (560 mg) in tetrahydrofuran (10 ml) followed by the portionwise addition of sodium borohydride (59.8 mg) at 0° C. The mixture was diluted with 1,4-dioxane (5 ml) and stirred for an additional 1.5 hours at ambient temperature. The mixture was quenched with water (0.5 ml) and concentrated. The residue was partitioned with ethyl acetate and saturated aqueous sodium hydrogen carbonate. The organic extract was washed with brine and dried over sodium sulfate, concentrated, and purified by silica gel column chromatography (SiO$_2$, 30 g, 3% methanol in chloroform) to give 3-methoxy-4-[2-[3 -(phthalimido)prop-1-yl]amino]benzoylamino-N-methyl-N-[2-[5-(4-methylpiperazin-1-yl)carbonylpent-1-yloxy]phenyl]benzamide (200 mg).

NMR (CDCl$_3$, δ): 1.44–1.62 (2H, m), 1.63–1.93 (4H, m), 1.97–2.12 (2H, m), 2.21–2.46 (12H, m), 3.17–3.38 (5H, m), 3.42–3.56 (2H, m), 3.57–3.69 (2H, m), 3.70–4.04 (7H, m), 6.51–6.73 (4H, m), 6.78–6.96 (2H, m), 7.00 (1H, s), 7.20–7.35 (1H, m), 7.40 (1H, d, J=8 Hz), 7.53–7.67 (3H, m), 7.72–7.86 (2H, m), 8.13 (1H, d, J=8 Hz), 8.34 (1H, s)

EXAMPLE 41

A solution of 4-(2-nitrobenzoyl)amino-N-[2-(5-ethoxycarbonylpent-1-yloxy)-4-methylphenyl]-N-methylbenzamide (800 mg), 20% palladium hydroxide (200 mg) in ethanol (20 ml) was stirred under atmospheric pressure of hydrogen at ambient temperature. After 2 hours, the reaction mixture was filtered through a bed of Celite, and the solvent was removed by rotary evaporation and the crude product was purified by silica gel column chromatography (SiO$_2$ 30 g, ethyl acetate/hexane=3/1) to give 4-(2-aminobenzoyl)amino-N-methyl-N-[2-(5-ethoxycarbonylpent-1-yloxy)-4-methylphenyl]benzamide (700 mg).

NMR (CDCl$_3$, δ): 1.25 (3H, t, J=7 Hz), 1.41–1.57 (2H, m), 1.63–1.87 (4H, m), 2.27 (3H, s), 2.33 (2H, t, J=7 Hz), 3.32 (3H, s), 3.78–4.00 (2H, m), 4.12 (2H, q, J=7 Hz), 5.38–5.56 (2H, m), 6.55–6.64 (2H, m), 6.64–6.76 (2H, m), 6.87 (1H, d, J=9 Hz), 7.22 (1H, d, J=9 Hz), 7.28–7.50 (5H, m), 7.79 (1H, br s)

EXAMPLE 42

The following compound was obtained according to a similar manner to that of Preparation 4.

4-(2-Aminobenzenesulfonyl)amino-3-methoxy-N-methyl-N-[4 -methyl-2-[5-(4-methylpiperazin-1-yl)carbonylpent-1-yloxy]phenyl]benzamide NMR (CDCl$_3$, δ): 1.45–1.54 (2H, m), 1.65–1.82 (4H, m), 2.30 (3H, s), 2.33 (3H, s), 2.35–2.43 (6H, m), 3.29 (3H, s), 3.46–3.51 (5H, m), 3.60–3.65 (4H, m), 4.84–4.89 (2H, m), 6.56–6.89 (6H, m), 7.28–7.48 (4H, m)

ESI-MASS (m/z): 638 (M+H)

EXAMPLE 43

A solution of 4-[2-(acetyloxy)benzoyl]amino-3-methoxy-N-methyl-N-[2-[5-(4-dimethylaminopiperidin-1-yl)carbonylpent-1-yloxy]-4-methylphenyl]benzamide (400 mg) in methanol (10 ml) was treated with 1N sodium hydroxide solution (3 ml) at ambient temperature. After 6 hours, the reaction mixture was concentrated in vacuo and extracted with the mixture of dichloromethane and diluted hydrochloric acid. The organic phase was washed with brine and dried over sodium sulfate. The crude product was purified by silica gel column chromatography (SiO$_2$ 30 g, 5% methanol in chloroform) to give 4-[2-(hydroxy)benzoyl]amino-3-methoxy-N-methyl-N-[2-[5-(4-dimethylaminopiperidin-1-yl)carbonylpent-1-yloxy]-4-methylphenyl]benzamide (290 mg).

NMR (CDCl$_3$, δ): 1.27–2.00 (10H, m), 2.21–2.46 (12H, m), 2.56 (1H, m), 3.00 (1H, m), 3.33 (3H, s), 3.80 (3H, s), 3.82–4.05 (4H, m), 4.63 (1H, m), 6.55–6.68 (2H, m), 6.82–7.09 (5H, m), 7.42 (1H, m), 7.55 (1H, m), 8.20 (1H, m)

EXAMPLE 44

The following compounds were obtained according to a similar manner to that of Example 43.

1) 4-(2-Hydroxybenzoyl)amino-N-methyl-N-[2-(5-ethoxycarbonylpent-1-yloxy)-4-methylphenyl]benzamide NMR (CDCl$_3$, δ): 1.26 (3H, t, J=7 Hz), 1.42–1.58 (2H, m), 1.61–1.90 (4H, m), 2.28 (3H, s), 2.33 (2H, t, J=7 Hz), 3.32 (3H, s), 3.80 (3H, s), 3.81–4.02 (2H, m), 4.12 (2H, q, J=7 Hz), 6.53–6.67 (2H, m), 6.80–6.98 (3H, m), 7.01 (1H, d, J=8 Hz), 7.07 (1H, s), 7.42 (1H, dd, J=8, 8 Hz), 7.49 (1H, d, J=8 Hz), 8.18 (1H, d, J=8 Hz), 8.72 (1H, s)

2) 4-(2-Hydroxybenzoyl)amino-3-methoxy-N-methyl-N-(2-methylphenyl)benzamide

NMR (CDCl$_3$, δ): 2.21 (3H, s), 3.40 (3H, s), 3.78 (3H, s), 6.82–7.23 (9H, m), 7.37–7.53 (2H, m), 8.18 (1H, d, J=8 Hz), 8.69 (1H, br s)

3) 4-(2-Hydroxybenzoyl)amino-3-methoxy-N-methyl-N-[4-methyl-2-[5-(4-methylpiperazin-1-yl)carbonylpent-1-yloxy]phenyl]benzamide NMR (CDCl$_3$, δ): 1.42–1.59 (2H, m), 1.60 1.89 (4H, m), 2.20–2.46 (12H, m), 3.32 (3H, s), 3.42–3.53 (2H, m), 3.57–3.69 (2H, m), 3.71–4.02 (6H, m), 6.51–6.68 (2H, m), 6.79–7.08 (5H, m), 7.40 (1H, m), 7.51 (1H, d, J=8 Hz), 8.18 (1H, d, J=8 Hz), 8.86 (1H, br s)

4) 4-(2-Hydroxybenzoyl)amino-3-methoxy-N-(2-benzyloxy-4-methylphenyl)-N-methylbenzamide NMR (CDCl$_3$, δ): 2.30 (3H, s), 3.38 (3H, s), 3.63 (3H, s), 4.89 (1H, d, J=13 Hz), 5.08 (1H, d, J=13 Hz), 6.62–6.68 (2H, m), 6.82–7.00 (6H, m), 7.28–7.42 (5H, m), 7.47 (1H, d, J=8 Hz), 8.13 (1H, d, J=8 Hz), 8.79 (1H, s)

5) 4-(2-Hydroxybenzoyl)amino-3-methoxy-N-[2-[4-(2-oxazolin-2-yl)phenylmethyl]oxy-4-methylphenyl]-N-methylbenzamide NMR (CDCl$_3$, δ): 2.28 (3H, s), 3.40 (3H, s), 3.67 (3H, s), 4.06 (2H, t, J=10 Hz), 4.41 (2H, t, J=10 Hz), 4.92 (1H, d, J=12 Hz), 5.10 (1H, d, J=12 Hz), 6.60 (1H, s), 6.71 (1H, d, J=8 Hz), 6.87–7.08 (5H, m), 7.28 (1H, d, J=8 Hz), 7.42 (1H, dd, J=2, 8 Hz), 7.52 (1H, d, J=8 Hz), 8.16 (1H, d, J=8 Hz), 8.82 (1H, s)

6) 4-(2-Hydroxybenzoyl)amino-3-methyl-N-methyl-N-[2-[5-(4-methylpiperazin-1-yl)cabonylpent-1-yloxy]-4-methylphenyl]benzamide NMR (CDCl$_3$, δ): 1.48 (2H, br), 1.60–1.81 (4H, m), 2.19 (3H, s), 2.28 (3H, s), 2.30–2.35 (3H, m), 2.38 (3H, s), 2.50 (4H, br), 3.30 (3H, s), 3.52 (2H, br), 3.69 (2H, br), 3.83 (1H, br), 3.92 (1H, br), 6.62 (2H, s), 6.89–6.93 (2H, m), 7.02–7.10 (2H, m), 7.35 (1H, s), 7.40–7.47 (1H, m), 7.63–7.70 (2H, m), 8.52 (1H, br)

EXAMPLE 45

A solution of 4-[2-[3-(tert-butoxycarbonyl)aminoprop-1-yl]oxybenzoyl]amino-N-methyl-N-[4-methyl-2-[5-(4-methylpiperazin-1-yl)carbonylpent-1-yl]oxy]phenylbenzamide (542 mg) in 90% trifluoroacetic acid (10 ml) was stirred at ambient temperature for 3 hours and the solvent was evaporated in vacuo. The residue was stirred with chloroform (20 ml) and saturated aqueous sodium hydrogen carbonate (10 ml) and the organic phase was separated. The solution was washed with brine and dried over magnesium sulfate. The solvent was evaporated in vacuo to give 4-[2-(3-aminoprop-1-yl)oxybenzoyl]amino-N-methyl-N-[4-methyl-2-[5-(4-methylpiperazin-1-yl)carbonylpent-1-yl]oxy]phenylbenzamide (465 mg).

NMR (CDCl$_3$, δ): 1.47–1.59 (2H, m), 1.67–2.00 (6H, m), 2.06–2.66 (2H, m), 2.35 (3H, s), 2.39 (3H, s), 2.32–2.41 (4H, m), 2.95 (2H, t, J=7.5 Hz), 3.31 (3H, s), 3.45–3.50 (2H, m), 3.58–3.65 (2H, m), 3.89–3.99 (2H, m), 4.29 (2H, d, H=7.5 Hz), 6.54–6.62 (2H, m), 6.85 (1H, d, J=7 Hz), 7.01 (1H, d, J=7 Hz), 7.10 (1H, t, J=7 Hz), 7.32 (2H, d, J=8 Hz), 7.43–7.50 (3H, m), 8.20 (1H, d, J=7 Hz)

EXAMPLE 46

The following compounds were obtained according to a similar manner to that of Example 45.

1) 4-[2-[(3-Aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.40–1.92 (6H, m), 1.98–2.12 (2H, m), 2.19–2.44 (12H, m), 2.90 (2H, t, J=7 Hz), 3.32 (3H, s), 3.40–3.53 (2H, m), 3.56–3.68 (2H, m), 3.78 (3H, s), 3.80–4.02 (2H, m), 4.28 (2H, t, J=7 Hz), 6.51–6.67 (2H, m), 6.78–6.95 (2H, m), 6.97–7.16 (3H, m), 7.44 (1H, m), 8.21 (1H, d, J=8 Hz), 8.40 (1H, d, J=8 Hz)

2) 4-[2-[(3-Aminoprop-1-yl)oxy]benzoyl]amino-3-methoxy-N-methyl-N-[2-[5-(4-dimethylaminopiperidin-1-yl)carbonylpent-1-yloxy]-4-methylphenyl]benzamide NMR (CDCl$_3$, δ): 1.26–1.92 (12H, m), 1.98–2.12 (2H, m), 2.27 (9H, s), 2.29–2.42 (3H, m), 2.56 (1H, m), 2.89 (2H, t, J=7 Hz), 3.00 (1H, m), 3.32 (3H, s), 3.78 (3H, s), 3.82–4.02 (3H, m), 4.27 (2H, t, J=7 Hz), 4.61 (1H, m), 6.52–6.67 (2H, m), 6.79–6.96 (2H, m), 6.97–7.12 (3H, m), 7.43 (1H, m), 8.21 (1H, d, J=8 Hz), 8.41 (1H, d, J=8 Hz)

3) 4-[2-(3-Aminoprop-1-yl)oxybenzoyl]amino-3-methoxy-N-methyl-N-[4-methyl-2-[5-(4-methylpiperidin-1-yl)carbonylpent-1-yl]oxy]phenylbenzamide NMR (CDCl$_3$, δ): 0.95 (3H, d, J=7.5 Hz), 1.00–1.14 (2H, m), 1.46–1.90 (8H, m), 2.01–2.12 (2H, m), 2.26 (3H, s), 2.34 (2H, t, J=7.5 Hz), 2.52 (1H, m), 2.85–3.03 (3H, m), 3.31 (3H, s), 3.79 (3H, s), 3.79–4.00 (4H, m), 4.32 (2H, t, J=7.5 Hz), 4.55 (1H, m), 6.58 (1H, d, J=7 Hz), 6.62 (1H, s), 6.84 (1H, d, J=7 Hz), 6.90 (1H, d, J=7 Hz), 7.00–7.11 (3H, m), 7.42 (1H, t, J=7 Hz), 8.21 (1H, d, J=7 Hz), 8.40 (1H, d, J=7 Hz)

4) 4-[2-(3-Aminoprop-1-yl)oxybenzoyl]amino-3-methoxy-N-[2-[5-[(2S)-carbamoylpyrrolidin-1-yl]carbonylpent-1-yl]oxy-4-methyl]phenyl-N-methylbenzamide NMR (CDCl$_3$, δ): 1.48–2.20 (12H, m), 2.28 (3H, s), 2.32–2.40 (2H, m), 2.88–3.00 (2H, m), 3.31 (3H, s), 3.33–3.61 (2H, m), 3.80 (3H, s), 3.82–3.99 (2H, m), 4.29 (2H, t, J=7 Hz), 4.54 (1H, m), 6.52–6.63 (2H, m), 6.81–7.10 (5H, m), 7.43 (1H, t, J=7 Hz), 8.14 (1H, d, J=7 Hz), 8.38 (1H, d, J=7 Hz)

5) 4-[2-(3-Aminoprop-1-yl)oxybenzoyl]amino-3-methoxy-N-[2-(4-aminobut-1-yl)oxy-4-methyl]phenyl-N-methylbenzamide NMR (CDCl$_3$, δ): 1.63–1.94 (4H, m), 1.99–2.18 (2H, m), 2.23 (3H, s), 2.62–3.07 (2H, m), 3.29 (3H, s), 3.29–3.51 (2H, m), 3.75–4.00 (2H, m) 3.76 (3H, s), 4.21 (2H, t, J=7.5 Hz), 6.56–6.85 (4H, m), 7.28–7.62 (5H, m), 8.13 (1H, d, J=7 Hz), 8.40 (1H, d, J=7 Hz)

6) 4-[2-(3-Aminoprop-1-yl)oxybenzoyl]amino-3-methoxy-N-[2-(4-acetylaminobut-1-yl)oxy-4-methyl]phenyl-N-methylbenzamide NMR (CDCl$_3$, δ): 1.60–1.86 (4H, m), 2.00 (3H, s), 2.08–2.20 (2H, m), 2.27 (3H, s), 2.93–3.03 (2H, m), 3.30 (3H, s), 3.30–3.50 (2H, m), 3.77 (3H, s), 3.83–3.98 (2H, m), 4.26 (2H, t, J=7.5 Hz), 6.53–6.65 (2H, m), 6.86–7.12 (5H, m), 7.42 (1H, t, J=7 Hz), 8.12 (1H, d, J=7 Hz), 8.37 (1H, d, J=7 Hz)

7) 3-Methoxy-4-[2-(piperidin-4-yl)oxybenzoyl]amino-N-(2-hydroxy-4-methyl)phenyl-N-methylbenzamide NMR (DMSO-d$_6$, δ): 1.50–1.62 (2H, m), 1.94–2.05 (2H, m), 2.14 (3H, s), 2.57 (2H, t, J=7.5 Hz), 2.91–3.00 (2H, m), 3.16 (3H, s), 3.75 (3H, s), 4.73 (1H, m), 6.48 (1H, d, J=7 Hz), 6.64 (1H, s), 7.87 (1H, d, J=7 Hz), 7.92 (1H, d, J=7 Hz), 7.01 (1H, s), 7.09 (1H, t, J=7 Hz), 7.32 (1H, d, J=7 Hz), 7.52 (1H, t, J=7 Hz), 8.02 (1H, d, J=7 Hz), 8.27 (1H, d, J=7 Hz)

8) 3-Methoxy-4-[2-(piperidin-4-yl)oxybenzoyl]amino-N-methyl-N-[4-methyl-2-[5-(4-methylpiperazin-1-yl)carbonylpent-1-yl]oxy]phenylbenzamide NMR (CDCl$_3$, δ): 1.46–1.88 (8H, m), 2.07–2.19 (2H, m), 2.26 (3H, s), 2.29 (3H, s), 2.32–2.41 (6H, m), 2.72 (2H, t, J=7.5 Hz), 3.10–3.20 (2H, m), 3.32 (3H, s), 3.45–3.50 (2H, m), 3.60–3.66 (2H, m), 3.80 (3H, s), 3.83–4.00 (2H, m), 4.57 (1H, m), 6.58 (1H, d, J=7 Hz), 6.62 (1H, s), 6.82–6.91 (2H, m), 6.98–7.11 (3H, m), 7.43 (1H, t, J=7 Hz), 8.20 (1H, d, J=7 Hz), 8.40 (1H, d, J=7 Hz)

9) 4-[2-(3-Amino-1-methylprop-1-yl)oxybenzoyl]amino-3-methoxy-N-methyl-N-[4-methyl-2-[5-(4-methylpiperazin-1-yl)carbonylpent-1-yl]oxy]phenylbenzamide NMR (CDCl$_3$, δ): 1.42 (3H, d, J=7.5 Hz), 1.46–1.89 (6H, m), 1.99–2.11 (2H, m), 2.28 (3H, s), 2.30 (3H, s), 2.31–2.42 (6H, m), 2.85 (2H, t, J=7.5 Hz), 3.33 (3H, s), 3.45–3.50 (2H, m), 3.59–3.66 (2H, m), 3.80 (3H, s), 3.84–4.01 (2H, m), 4.80 (1H, m), 6.59 (1H, d, J=7 Hz), 6.63 (1H, s), 6.82–6.92 (2H, m), 7.01–7.10 (3H, m), 7.44 (1H, t, J=7 Hz), 8.22 (1H, d, J=7 Hz), 8.40 (1H, d, J=7 Hz)

10) 4-[2-(3-Aminoprop-1-yl)oxybenzoyl]amino-3-methoxy-N-methyl-N-[2-(5-aminocarbonylpent-1-yl)oxy-4-methylphenyl]benzamide NMR (CDCl$_3$, δ): 1.40–1.59 (2H, m), 1.61–1.90 (4H, m), 2.11–2.30 (4H, m), 2.35 (3H, s), 3.00 (2H, t, J=6 Hz), 3.11 (2H, br), 3.29 (3H, s), 3.75 (3H, s), 3.76–4.02 (2H, m), 4.23 (2H, t, J=5 Hz), 6.00 (1H, br), 6.50 (1H, br), 6.55–6.71 (2H, m), 6.87–7.12 (5H, m), 7.42 (1H, dd, J=2, 7 Hz), 8.10 (1H, d, J=9 Hz), 8.36 (1H, d, J=8 Hz)

11) 4-[2-(3-Aminoprop-1-yl)oxybenzoyl]amino-3-methoxy-N-methyl-N-[2-[5-(morpholin-4-yl)carbonylpent-1-yl]oxy-4-methylphenyl]benzamide NMR (CDCl$_3$, δ): 1.48–1.90 (6H, m), 2.11 (2H, t, J=5 Hz), 2.26 (3H, s), 2.21–2.52 (6H, m), 2.79–2.90 (3H, m), 2.96 (2H, t, J=5 Hz), 3.31 (3H, s), 3.40–3.49 (2H, m), 3.52–3.62 (2H, m), 3.80 (3H, s), 3.83–4.04 (2H, m), 4.29 (2H, t, J=5 Hz), 6.57–6.68 (2H, m), 6.81–7.12 (6H, m), 7.41–7.50 (1H, m), 8.17 (1H, d, J=8 Hz), 8.39 (1H, d, J=8 Hz)

12) 4-[2-(3-Aminoprop-1-yl)oxybenzoyl]amino-3-methoxy-N-methyl-N-[2-[5-(4-oxopiperidin-1-yl)carbonylpent-1-yl]oxy]-4-methylphenyl]benzamide NMR (CDCl$_3$, δ): 1.45–2.05 (8H, m), 2.11 (2H, t, J=5 Hz), 2.28 (3H, s), 2.41–2.52 (2H, m), 2.96 (2H, t, J=5 Hz), 3.31 (3H, s), 3.70–4.61 (8H, m), 6.52–7.55 (8H, m), 8.02–8.46 (3H, m)

13) 4-[2-(3-Aminoprop-1-yl)oxybenzoyl]amino-3-methoxy-N-(2-methoxy-4-methylphenyl)-N-methylbenzamide NMR (DMSO-d$_6$, δ): 1.90–1.98 (2H, m), 2.25 (3H, s), 2.71 (2H, t, J=6 Hz), 3.19 (3H, s), 3.73 (3H, s), 4.32 (2H, t, J=5 Hz), 6.67 (1H, d, J=8 Hz), 6.80–6.96 (2H, m), 7.26 (1H, d, J=8 Hz), 7.55 (1H, dd, J=2, 8 Hz), 8.03 (1H, d, J=8 Hz), 8.29 (1H, d, J=8 Hz)

14) 4-[2-(3-Aminoprop-1-yl)oxybenzoyl]amino-3-methoxy-N-[2-[4-(thiazol-2-yl)phenylmethyl]oxy-4-methylphenyl]-N-methylbenzamide NMR (CDCl$_3$, δ): 2.02–2.10 (2H, m), 2.29 (3H, s), 2.89 (2H, t, J=5 Hz), 3.40 (3H, s), 3.64 (3H, s), 4.25 (2H, t, J=5 Hz), 4.90 (1H, d, J=11 H), 5.09 (1H, d, J=11 Hz), 6.62–6.71 (2H, m), 6.88 (1H, d, J=8 Hz), 6.98–7.10 (5H, m), 7.24–7.48 (4H, m), 7.81 (1H, d, J=3Hz), 7.95 (1H, d, J=8 Hz), 8.20 (1H, d, J=8 Hz), 8.37 (1H, d, J=8 Hz)

15) 4-[2-(3-Aminoprop-1-yl)oxybenzoyl]amino-3-methoxy-N-[2-[4-(oxazol-2-yl)phenylmethyl]oxy-4-methylphenyl]-N-methylbenzamide NMR (CDCl$_3$, δ): 2.00–2.11 (2H, m), 2.29 (3H, s), 2.89 (2H, t, J=5 Hz), 3.40 (3H, s), 3.66 (3H, s), 4.91 (1H, d, J=12 H), 5.10 (1H, d, J=12 Hz), 6.64 (1H, s), 6.70 (1H, d, J=8 Hz), 6.87 (1H, d, J=8 Hz), 7.00–7.12 (4H, m), 7.21 (1H, s), 7.25–7.49 (4H, m), 7.65 (1H, s), 8.04 (1H, d, J=8 Hz), 8.23 (1H, d, J=8 Hz), 8.37 (1H, d, J=8 Hz)

16) 4-[2-(3-Aminoprop-1-yl)oxybenzoyl]amino-3-methoxy-N-[2-[4-(2-oxazolin-2-yl)phenylmethyl]oxymethylphenyl]-N-methylbenzamide NMR (CDCl$_3$, δ): 2.02–2.11 (2H, m), 2.28 (3H, s), 2.90 (2H, t, J=5 Hz), 3.39 (3H, s), 3.67 (3H, s), 4.05 (2H, t, J=9 Hz), 4.29 (2H, t, J=5 Hz), 4.41 (2H, t, J=5 Hz), 4.89 (1H, d, J=12 Hz), 5.09 (1H, d, J=12 Hz), 6.63 (1H, s), 6.70 (1H, d, J=8 Hz), 6.84 (1H, d, J=8 Hz), 7.00–7.12 (4H, m), 7.37 (2H, d, J=8 Hz), 7.41 (1H, d, J=8 Hz), 7.93 (2H, d, J=5 Hz), 8.20 (1H, d, J=8 Hz), 8.36 (1H, d, J=8 Hz)

17) 4-[2-(3-Aminoprop-1-yl)oxybenzoyl]amino-3-methoxy-N-[2-[4-(pyrimidin-2-yl)phenylmethyl]oxy-4-methylphenyl]-N-methylbenzamide NMR (CDCl$_3$, δ): 2.05–2.14 (2H, m), 2.27 (3H, s), 2.89 (2H, t, J=5 Hz), 3.38 (3H, s), 3.64 (3H, s), 4.24 (2H, t, J=5 Hz), 4.94 (1H, d, J=13 Hz), 5.12 (1H, d, J=13 Hz), 6.65–6.72 (2H, m), 6.85 (1H, d, J=8 Hz), 6.97–7.18 (5H, m), 7.39–7.46 (3H, m), 8.13 (1H, d, J=8 Hz), 8.35 (1H, d, J=8 Hz), 8.41 (2H, d, J=8 Hz), 8.24 (2H, d, J=3 Hz)

18) 4-[2-(3-Aminoprop-1-yl)oxybenzoyl]amino-3-methoxy-N-[2-(4-cyanophenylmethyl)oxy-4-methylphenyl]-N-methylbenzamide NMR (CDCl$_3$, δ): 2.09–2.20 (2H, m), 2.28 (3H, s), 2.97 (2H, t, J=5 Hz), 3.35 (3H, s), 3.65 (3H, s), 4.24 (2H, br), 4.88 (1H, d, J=12 Hz), 5.06 (1H, d, J=12 Hz), 6.57 (1H, s), 6.67–6.80 (2H, m), 6.95–7.08 (5H, m), 7.35–7.45 (3H, m), 7.62 (2H, d, J=8 Hz), 8.11 (1H, d, J=8 Hz), 8.30 (1H, d, J=8 Hz)

19) 4-[2-(3-Aminoprop-1-yl)oxybenzoyl]amino-3-methoxy-N-methyl-N-[2-[5-(2-dimethylaminoeth-1-yl)oxycarbonyl-pent-1-yl]oxy-4-methylphenyl]benzamide NMR (CDCl$_3$, δ): 1.47–1.60 (2H, m), 1.67–1.88 (4H, m), 2.05–2.14 (2H, m), 2.27 (9H, s), 2.38 (2H, t, J=6 Hz), 2.58 (2H, t, J=5 Hz), 2.92 (2H, t, J=5 Hz), 3.33 (3H, s), 3.80 (3H, s), 3.86–4.00 (2H, m), 4.19 (2H, t, J=5 Hz), 4.30 (2H, t, J=5 Hz), 6.57–6.67 (2H, m), 6.87 (1H, dd, J=2, 8 Hz), 7.00–7.11 (4H, m), 7.44 (1H, dd, J=2, 8 Hz), 8.20 (1H, d, J=8 Hz), 8.38 (1H, d, J=8 Hz)

20) 4-[2-(3-Aminoprop-1-yloxy)benzoyl]amino-3-methoxy-N-(2-hydroxy-4-methylphenyl)-N-methylbenzamide NMR (DMSO-d$_6$, δ): 1.92–2.03 (2H, m), 2.16 (3H, s), 2.75 (2H, t, J=5 Hz), 3.20 (3H, s), 3.75 (3H, s), 4.34 (2H, t, J=5 Hz), 6.49 (1H, d, J=8 Hz), 6.66 (1H, s), 6.87 (1H, d, J=8 Hz), 6.92 (1H, d, J=8 Hz), 7.12 (1H, dd, J=7, 8 Hz), 7.29 (1H, d, J=8 Hz), 7.58 (1H, dd, J=2, 8 Hz), 8.05 (1H, d, J=8 Hz), 8.27 (1H, d, J=8 Hz)

21) 4-[2-(3-Aminoprop-1-yl)oxybenzoyl]amino-3-methoxy-N-[2-[4-(1,5-dimethyl-3-cyanopyrrol-2-yl)phenylmethyl]oxy-4-methylphenyl]-N-methylbenzamide NMR (CDCl$_3$, δ): 2.00–2.11 (2H, m), 2.14 (3H, s), 2.21 (3H, s), 2.89 (2H, t, J=5 Hz), 3.40 (3H, s), 3.45 (3H, s), 3.62 (3H, s), 4.27 (2H, t, J=5 Hz), 4.89 (1H, d, J=13 Hz), 5.13 (1H, d, J=13 Hz), 6.22 (1H, s), 6.68–6.75 (2H, m), 6.89 (1H, d, J=8 Hz), 7.00–7.12 (5H, m), 7.38–7.47 (6H, m), 8.19 (1H, d, J=8 Hz), 8.38 (1H, d, J=8 Hz)

22) 4-[2-(3-Aminoprop-1-yloxy)benzoyl]amino-3-methoxy-N-[2-[4-(N,N-dimethylureido)but-1-yl]oxy-4-methylphenyl]-N-methylbenzamide NMR (CDCl$_3$, δ): 1.62–1.88 (4H, m), 1.90–2.15 (2H, m), 2.27 (3H, s), 2.86–2.94 (2H, m), 2.90 (6H, s), 3.22–3.35 (2H, m), 3.31 (3H, s), 3.77 (3H, s), 3.75–3.98 (2H, m), 4.27 (2H, t, J=5 Hz), 6.57–6.70 (2H, m), 6.88–7.11 (6H, m), 7.42 (1H, dd, J=2, 8 Hz), 8.19 (1H, d, J=8 Hz), 8.38 (1H, d, J=8 Hz)

23) 4-[2-(3-Aminoprop-1-yl)oxybenzoyl]amino-3-methoxy-N-[2-[3-(4-methylpiperazin-1-yl)carbonylpyrid-6-yl]methoxy-4-methylphenyl]-N-methylbenzamide NMR (CDCl$_3$, δ): 2.09–2.20 (2H, m), 2.28 (3H, s), 2.31 (3H, s), 2.34–2.52 (4H, m), 2.96 (2H, t, J=5 Hz), 3.40 (3H, s), 3.42–3.50 (2H, m), 3.69 (3H, s), 3.70–3.84 (2H, m), 4.29 (2H, t, J=5 Hz), 4.98 (1H, d, J=13 Hz), 5.18 (1H, d, J=13 Hz), 6.62 (1H, s), 6.72 (1H, d, J=8 Hz), 6.98–7.11 (5H, m), 7.26–7.34 (1H, m), 7.45 (1H, dd, J=2, 8 Hz), 7.73 (1H, d, J=8 Hz), 8.16 (1H, d, J=8 Hz), 8.36 (1H, d, J=8 Hz), 8.63 (1H, s)

24) 4-[2-(3-Aminoprop-1-yl)oxybenzoyl]amino-3-methoxy-N-[2-[4-(3-dimethylaminoprop-1-yloxycarbonyl)aminobut-1-yl]oxy-4-methylphenyl]-N-methylbenzamide NMR (CDCl$_3$, δ): 1.62–1.87 (6H, m), 2.02–2.11 (2H, m), 2.27 (6H, s), 2.41 (2H, t, J=5 Hz), 2.91 (2H, t, J=5 Hz), 3.22 (2H, q, J=5 Hz), 3.30 (3H, s), 3.78 (3H, s), 3.84–3.95 (2H, m), 4.08 (2H, t, J=5 Hz), 4.27 (2H, t, J=5 Hz), 6.60–6.66 (2H, m), 6.90 (1H, d, J=8 Hz), 6.99–7.10 (3H, m), 7.44 (1H, dd, J=2, 8 Hz), 8.18 (1H, d, J=8 Hz), 8.38 (1H, d, J=8 Hz)

25) 4-[2-(3-Aminoprop-1-yl)oxybenzoyl]amino-3-methoxy-N-methyl-N-[2-[5-(4-methylhomopiperazin-1yl)carbonylpent-1-yl]oxy-4-methylphenyl]benzamide NMR (CDCl$_3$, δ): 1.50–2.18 (8H, m), 2.30 (3H, s), 2.32 (2H, t, J=5 Hz), 2.33 (3H, s), 2.53–2.70 (4H, m), 2.93 (2H, t, J=5 Hz), 3.35 (3H, s), 3.52–3.72 (4H, m), 3.80 (3H, s), 3.82–4.09 (2H, m), 4.31 (2H, t, J=5 Hz), 6.55–6.70 (2H, m), 6.82–7.18 (6H, m), 7.42–7.53 (1H, m), 8.20 (1H, d, J=8 Hz), 8.41 (1H, d, J=8 Hz)

26) 4-[2-(3-Aminoprop-1-yl)oxybenzoyl]amino-3-methoxy-N-methyl-N-[2-[5-(2-dimethylaminoethyl)aminocarbonylpent-1-yl]oxy-4-methylphenyl]benzamide NMR (CDCl$_3$, δ): 1.45–1.60 (2H, m), 1.66–2.15 (8H, m), 2.22 (6H, s), 2.26 (3H, s), 2.41 (2H, t, J=5 Hz), 3.22–3.39 (2H, m), 3.31 (3H, s), 3.70–4.00 (2H, m), 3.78 (3H, s), 4.28 (2H, t, J=5 Hz), 6.37 (1H, br), 6.59 (2H, br), 6.81–7.13 (6H, m), 7.42 (1H, dd, J=2, 8 Hz), 8.18 (1H, d, J=8 Hz), 8.36 (1H, d, J=8 Hz)

27) 4-[2-(3-Aminoprop-1-yl)oxybenzoyl]amino-3-methoxy-N-methyl-N-[2-[5-[N-(2-dimethylaminoethyl)-N-methylaminocarbonyl]pent-1-yl]oxy-4-methylphenyl]benzamide NMR (CDCl$_3$, δ): 1.40 (9H, s), 1.44–2.21 (8H, m), 2.25 (3H, s), 2.27 (6H, s), 2.29–2.50 (4H, m), 2.91 (1H, s), 3.00 (2H, s), 3.26–3.51 (4H, m), 3.31 (3H, s), 3.77 (3H, br s), 3.81–4.02 (2H, m), 4.22 (2H, t, J=5 Hz), 4.88 (1H, br), 6.52–6.68 (2H, br), 6.79–7.11 (5H, m), 7.43–7.50 (1H, m), 8.20 (1H, d, J=8 Hz), 8.39 (1H, d, J=8 Hz)

28) 4-[2-(3-Aminoprop-1-yl)oxybenzoyl]amino-3-methoxy-N-methyl-N-[2-[5-[N-(3-dimethylaminoprop-1-yl)carbamoyl]pent-1-yl]oxy-4-methylphenyl]benzamide NMR (CDCl$_3$, δ): 1.46–1.60 (2H, m), 1.63–1.99 (8H, m), 2.03–2.14 (2H, m), 2.21 (2H, t, J=5 Hz), 2.24 (6H, s), 2.29 (3H, s), 2.39 (2H, t, J=5 Hz), 2.90 (2H, t, J=6 Hz), 3.25–3.37 (2H, m), 3.32 (3H, s), 3.79 (3H, s), 3.81–4.01 (2H, m), 4.30 (2H, t, J=5 Hz), 6.61 (2H, br), 6.85–7.14 (6H, m), 7.39–7.50 (1H, m), 8.20 (1H, d, J=8 Hz), 8.40 (1H, br)

29) 4-[2-(3-Aminoprop-1-yl)oxybenzoyl]amino-3-methoxy-N-methyl-N-[2-[5-[N-(3-dimethylaminoprop-1-yl)-N-methylcarbamoyl]pent-1-yl]oxy-4-methylphenyl]benzamide NMR (CDCl$_3$, δ): 1.52–1.94 (6H, m), 2.05–2.14 (2H, m), 2.20 (3H, s), 2.21 (3H, s), 2.26 (3H, s), 2.20–2.45 (6H, s), 2.90 (2H, t, J=5 Hz), 2.91 and 2.99 (total 3H, s, rotamer), 3.32 (3H, s), 3.40 (2H, t, J=5 Hz), 3.80 (3H, s), 4.31 (2H, t, J=5 Hz), 6.55–6.67 (2H, m), 7.41–7.49 (2H, m), 8.21 (1H, d, J=8 Hz), 8.42 (1H, d, J=8 Hz)

30) 4-[2-(3-Aminoprop-1-yl)oxybenzoyl]amino-3-methoxy-N-methyl-N-[2-[5-(4-hydroxypiperidin-1-yl)carbonylpent-1-yl]oxy-4-methylphenyl]benzamide NMR (CDCl$_3$, δ): 1.43–1.95 (6H, m), 2.03–2.51 (8H, m), 2.29 (3H, s), 2.94 (2H, t, J=5 Hz), 2.98–3.22 (4H, m), 3.32 (3H, s), 3.46–3.58 (1H, m), 3.79 (3H, s), 3.80–4.26 (6H, m), 4.28 (2H, t, J=5 Hz), 6.56–6.67 (2H, m), 6.81–7.13 (6H, m), 7.36 (1H, dd, J=8, 8 Hz), 8.10–8.20 (1H, m), 8.33–8.49 (1H, m)

31) 4-[2-(3-Aminoprop-1-yl)oxybenzoyl]amino-3-methoxy-N-methyl-N-[2-[5-(4-aminopiperidin-1-yl)carbonylpent-1-yl]oxy-4-methylphenyl]benzamide NMR (CDCl$_3$, δ): 1.51–2.03 (6H, m), 2.09–2.19 (2H, m), 2.27 (3H, s), 2.29–2.42 (4H, m), 2.59–2.71 (2H, m), 2.94 (2H, t, J=5 Hz), 2.96–3.11 (3H, m), 3.33 (3H, s), 3.78 (3H, s), 3.85–4.02 (2H, m), 4.22 (2H, t, J=5 Hz), 6.55–6.67 (2H, m), 6.81–7.12 (6H, m), 7.44 (1H, dd, J=8, 8 Hz), 8.19 (1H, d, J=8 Hz), 8.40 (1H, d, J=8 Hz)

32) 4-[2-(3-Aminoprop-1-yl)oxybenzoyl]amino-3-methoxy-N-methyl-N-[2-[5-(4-methylpiperazin-1-yl)-aminocarbonylpent-1-yl]oxy-4-methylphenyl]benzamide NMR (CDCl$_3$, δ): 1.46–1.89 (6H, m), 1.93–2.05 (4H, m), 2.25 (6H, s), 2.49 (2H, t, J=5 Hz), 2.52–2.62 (2H, m), 2.79–2.89 (2H, m), 2.92 (2H, t, J=5 Hz), 3.31 (3H, s), 3.79 (3H, s), 3.80–4.01 (2H, m), 4.28 (2H, t, J=5 Hz), 6.56–6.64 (2H, m), 6.80–7.12 (6H, m), 7.41–7.50 (1H, m), 8.18 (1H, d, J=8 Hz), 8.40 (1H, d, J=8 Hz)

33) 4-[2-(3-Aminoprop-1-yl)oxybenzoyl]amino-3-methoxy-N-methyl-N-[2-[5-[bis(2-hydroxyethy-1-yl)-aminocarbonylpent-1-yl]oxy-4-methylphenyl]benzamide NMR (CDCl$_3$, δ): 1.54–1.91 (6H, m), 2.11–2.20 (2H, m), 2.26 (3H, s), 2.38–2.59 (4H, m), 3.40–3.57 (4H, m), 3.61–3.97 (6H, m), 4.22 (2H, t, J=5 Hz), 6.60–6.68 (2H, m), 6.88–7.16 (6H, m), 7.44–7.54 (1H, m), 8.12 (1H, d, J=8 Hz), 8.41 (1H, d, J=8 Hz)

34) 4-[2-(3-Aminoprop-1-yl)oxybenzoyl]amino-3-methoxy-N-methyl-N-[2-[5-(2,2-dimethylhydrazino)carbonylpent-1-yl]oxy-4-methylphenyl]benzamide NMR (CDCl$_3$, δ): 1.47–1.91 (6H, m), 2.06–2.40 (4H, m), 2.28 (3H, s), 2.51 (3H, s), 2.57 (3H, s), 2.92 (2H, t, J=5 Hz), 3.32 (3H, s), 3.78 (3H, s), 3.80–4.02 (2H, m), 4.28 (2H, t, J=5 Hz), 6.55–6.68 (2H, m), 6.80–7.13 (5H, m), 7.46 (1H, dd, J=8 Hz), 8.19 (1H, d, J=8 Hz), 8.38 (1H, br)

35) 4-[2-(3-Aminoprop-1-yl)oxybenzoyl]amino-3-methoxy-N-methyl-N-[2-[5-(carbamoylmethylamino)carbonylpent-1-yl]oxy-4-methylphenyl]benzamide NMR (CDCl$_3$, δ): 1.47–1.58 (2H, m), 1.68–1.85 (4H, m), 2.06–2.17 (2H, m), 2.27 (3H, s), 2.94 (2H, t, J=5 Hz), 3.31 (3H, s), 3.80 (3H, s), 3.81–4.00 (2H, m), 3.89 (2H, d, J=5 Hz), 4.28 (2H, t, J=5 Hz), 5.78 (1H, br), 6.60–6.74 (3H, m), 6.90–7.13 (6H, m), 7.41–7.49 (1H, m), 8.17 (1H, d, J=8 Hz), 8.39 (1H, d, J=8 Hz)

36) 4-[2-(3-Aminoprop-1-yl)oxybenzoyl]amino-3-methoxy-N-methyl-N-[2-[5-(2-carbamoylmethylamino)carbonylpent-1-yl]oxy-4-methylphenyl]benzamide NMR (CDCl$_3$, δ): 1.45–1.58 (2H, m), 1.62–1.84 (4H, m), 2.14 (2H, t, J=5 Hz), 2.22 (2H, t, J=5 Hz), 2.29 (3H, s), 2.40 (2H, t, J=5 Hz), 2.98 (2H, br), 3.30 (3H, s), 3.40–3.55 (2H, m), 3.78 (3H, s), 3.80–4.01 (2H, m), 4.27 (2H, t, J=5 Hz), 6.58–6.79 (4H, m), 6.88– 7.12 (6H, m), 7.41–7.49 (1H, m), 8.16 (1H, d, J=8 Hz), 8.39 (1H, d, J=7 Hz)

37) 4-[2-(3-Aminoprop-1-yl)oxybenzoyl]amino-3-methoxy-N-methyl-N-[2-[5-(4-pyridylaminocarbonyl)pent-1-yl]oxy-4-methylphenyl]benzamide NMR (CDCl$_3$, δ): 1.52–1.89 (6H, m), 2.10–2.22 (2H, m), 2.26 (3H, s), 2.45 (2H, br), 2.95 (2H, t, J=5 Hz), 3.32 (3H, s), 3.72 (3H, s), 3.81–4.00 (2H, m), 4.27 (2H, t, J=5 Hz), 6.57–6.71 (2H, m), 6.90–7.15 (6H, m), 7.46 (1H, dd, J=2, 8 Hz), 7.56 (2H, br), 8.12 (1H, d, J=8 Hz), 8.35–8.50 (3H, m), 9.46 (1H, br)

38) 4-[2-(3-Aminoprop-1-yl)oxybenzoyl]amino-3-methoxy-N-methyl-N-[2-[5-[4-(diethylaminopiperidin-1-yl)carbonylpent-1-yl]oxy-4-methylphenyl]benzamide NMR (CDCl$_3$, δ): 1.05 (6H, t, J=5 Hz), 1.35–1.95 (10H, m), 2.04–2.13 (2H, m), 2.28 (3H, s), 2.36 (2H, t, J=5 Hz), 2.54 (4H, q, J=5 Hz), 2.56–2.80 (2H, m), 2.91 (2H, t, J=5 Hz), 2.93–3.07 (2H, m), 3.33 (3H, s), 3.80 (3H, s), 3.82–4.03 (2H, m), 4.30 (2H, t, J=5 Hz), 6.56–6.68 (2H, m), 6.81–7.12 (6H, m), 7.42–7.49 (1H, m), 8.22 (1H, d, J=7 Hz), 8.41 (1H, d, J=8 Hz)

39) 4-[2-(3-Aminoprop-1-yl)oxybenzoyl]amino-3-methoxy-N-methyl-N-[2-[6-(4-methylpiperazin-1yl)hex-1-yl]oxy-4-methylphenyl]benzamide NMR (CDCl$_3$, δ): 1.45–1.58 (2H, m), 1.62–1.84 (4H, m), 2.14 (2H, t, J=5 Hz), 2.29 (3H, s), 2.40 (2H, t, J=5 Hz), 2.98 (2H, br), 3.30 (3H, s), 3.40–3.55 (2H, m), 3.78 (3H, s), 3.80–4.01 (2H, m), 4.27 (2H, t, J=5 Hz), 6.58–6.79 (4H, m), 7.41–7.49 (1H, m), 8.16 (1H, d, J=8 Hz), 8.39 (1H, d, J=8 Hz)

40) 4-[2-(3-Aminoprop-1-yl)oxybenzoyl]amino-3-methoxy-N-[2-[4-(2-pyridyl)phenylmethyl]oxy-4-methylphenyl]-N-methylbenzamide NMR (CDCl$_3$, δ): 1.97–2.08 (2H, m), 2.26 (3H, s), 2.85 (2H, t, J=5 Hz), 3.40 (3H, s), 3.62 (3H, s), 4.26 (2H, t, J=5 Hz), 4.96 (1H, d, J=12 Hz), 5.14 (1H, d, J=12 Hz), 6.54–6.62 (2H, m), 6.40 (1H, d, J=7 Hz), 6.98–7.14 (5H, m), 7.39 (1H, d, J=8 Hz), 7.39–7.49 (1H, m), 7.70 (2H, s), 7.98 (1H, d, J=8 Hz), 8.22 (1H, d, J=8 Hz), 8.39 (1H d, J=8 Hz), 8.68 (1H, br)

41) 4-[2-(3-Aminoprop-1-yl)oxybenzoyl]amino-3-methoxy-N-[2-[4-[(4-methylpiperazin-1-yl)carbonylamino]but-1-yl]oxy-4-methylphenyl]-N-methylbenzamide NMR (CDCl$_3$, δ): 1.62–1.88 (4H, m), 2.30–2.15 (2H, m), 2.28 (6H, s), 2.34–2.42 (4H, m), 2.93 (2H, t, J=5 Hz), 3.25–3.48 (6H, m), 3.33 (3H, s), 3.79 (3H, s), 3.79–3.99 (2H, m), 4.30 (2H, t, J=5 Hz), 6.58–6.70 (2H, m), 6.90–7.11 (5H, m), 7.45 (1H, dd, J=2, 8 Hz), 8.20 (1H, d, J=8 Hz), 8.40 (1H, d, J=8 Hz)

42) 4-[2-(3-Aminoprop-1-yl)oxybenzoylamino]-3-methoxy-N-[2-[4-[(4-dimethylaminopiperidin-1-yl)carbonylamino]but-1-yl]oxy-4-methylphenyl]-N-methylbenzamide NMR (CDCl$_3$, δ): 1.44–1.98 (8H, m), 2.26 (3H, s), 2.49 (6H, s), 2.66–2.93 (3H, m), 3.05 (2H, t, J=5 Hz), 3.25–3.32 (2H, m), 3.29 (3H, s), 3.79 (3H, s), 3.81–3.99 (2H, m), 4.15–4.29 (4H, m), 6.57–6.64 (2H, m), 6.91–7.12 (5H, m), 7.46 (1H, dd, J=2, 8 Hz), 8.04 (1H, d, J=8 Hz), 8.35 (1H, d, J=8 Hz)

EXAMPLE 47

The following compound was obtained by using 4-[2-(3-tert-butoxycarbonylaminoprop-1-yl)oxybenzoyl]amino-3-methoxy-N-[2-(3-tert-butoxycarbonylaminoprop-1-yl)oxy-4-methyl]phenyl-N-methylbenzamide as a starting compound according to a similar manner to that of Example 45.

4-[2-(3-Aminoprop-1-yl)oxybenzoyl]amino-3-methoxy-N-[2-(3-aminoprop-1-yl)oxy-4-methyl]phenyl-N-methylbenzamide NMR (CDCl$_3$, δ): 1.87–1.98 (2H, m), 2.00–2.09 (2H, m), 2.25 (3H, s), 2.83–2.96 (4H, m), 3.30 (3H, s), 3.78 (3H, s), 3.87–4.10 (2H, m), 4.27 (2H, t, J=7.5 Hz), 6.57–6.66 (2H, m), 6.90 (1H, m), 7.00–7.10 (3H, m), 7.42 (1H, t, J=7 Hz), 8.20 (1H, d, J=7 Hz), 8.39 (1H, d, J=7 Hz)

EXAMPLE 48

The following compounds were obtained according to a similar manner to that of Example 47.

1) 4-[2-(3-Aminoprop-1-yl)oxybenzoyl]amino-3-methoxy-N-[2-(4-aminoacetylaminobut-1-yl)oxy-4-methyl]phenyl-N-methylbenzamide MASS (m/z: 592 (M+1)

2) 4-[2-(3-Aminoprop-1-yl)oxybenzoyl]amino-3-methoxy-N-methyl-N-[2-[5-(piperazin-1-yl)carbonylpent-1-yl]oxy-4-methylphenyl]benzamide NMR (CDCl$_3$, δ): 1.48–1.95 (6H, m), 2.07–2.20 (2H, m), 2.28 (3H, s), 2.32–2.63 (5H, m), 2.75–3.01 (3H, m), 3.21 (3H, s), 3.40–3.64 (4H, m), 3.78 (3H, s), 3.83–4.08 (2H, m), 4.27 (2H, t, J=5 Hz), 6.55–6.70 (2H, m), 6.82–7.17 (6H, m), 7.20–7.50 (1H, m), 8.29 (1H, d, J=7 Hz), 8.39 (1H, d, J=8 Hz)

3) 4-[2-(3-Aminoprop-1-yl)oxybenzoyl]amino-3-methoxy-N-[2-[4-(3-aminopropionyl)aminobut-1-yl]oxy-4-methylphenyl]-N-methylbenzamide NMR (CDCl$_3$, δ): 1.64–1.88 (4H, m), 2.06–2.19 (2H, m), 2.28 (3H, s), 2.32–2.46 (2H, m), 2.90–3.13 (4H, m), 3.23–3.44 (2H, m), 3.30 (3H, s), 3.77 (3H, s), 3.78–4.01 (2H, m), 4.27 (2H, br), 6.55–6.68 (2H, m), 6.88–7.11 (5H, m), 7.28–7.50 (2H, m), 8.20 (1H, d, J=8 Hz) 8.31 (1H, d, J=8 Hz)

4) 4-[2-(3-Aminoprop-1-yl)oxybenzoyl]amino-3-methoxy-N-[2-[4-(piperidin-4-yl)carbonylaminobut-1-yl]oxy-4-methylphenyl]-N-methylbenzamide NMR (CDCl$_3$, δ): 1.60–1.91 (8H, m), 2.09–2.21 (2H, m), 2.28 (3H, s), 2.70 (1H, br), 2.97 (2H, t, J=5 Hz), 3.11–3.40 (8H, m), 3.30 (3H, s), 3.72–3.96 (2H, m), 3.78 (3H, s), 4.28 (2H, t, J=5 Hz), 6.57–6.65 (2H, m), 6.90–7.08 (4H, m), 7.23–7.28 (2H, m), 7.38–7.49 (2H, m), 8.13 (1H, d, J=8 Hz), 8.38 (1H, d, J=8 Hz)

5) 4-[2-(3-Aminoprop-1-yl)oxybenzoyl]amino-3-methoxy-N-[2-(4-quanidinobut-1-yl)oxy-4-methylphenyl]-N-methylbenzamide NMR (CDCl$_3$, δ): 1.62–1.80 (4H, m), 2.05–2.14 (2H, m), 2.20 (3H, s), 2.55–2.70 (2H, m), 2.94 (2H, t, J=5 Hz), 3.31 (3H, s), 3.62–3.73 (2H, m), 3.72 (3H, s), 4.22 (1H, d, J=5 Hz), 6.48 (1H, d, J=8 Hz), 6.61 (1H, s), 6.75 (1H, d, J=8 Hz), 6.95–7.09 (5H, m), 7.43 (1H, dd, J=2, 8 Hz), 8.03 (1H, d, J=8 Hz), 8.32 (1H, d, J=8 Hz)

EXAMPLE 49

A solution of 4-hydroxy-3-methoxy-N-methyl-N-[4-methyl-2-[5-(4-methylpiperazin-1-yl)carbonylpent-1-yloxy]phenyl]-benzamide (320 mg) in N,N-dimethylformamide (8 ml) was treated with sodium hydride (29.1 mg, 60% w/w in mineral oil) at 0° C. The reaction mixture was stirred at 0° C. for 15 minutes and then at ambient temperature for 10 minutes. o-Nitrobenzyl bromide (143 mg) was added, and the reaction mixture was stirred for 2.5 hours. The reaction was quenched with water and the mixture was diluted with ethyl acetate. The organic phase was washed with saturated aqueous sodium hydrogen carbonate, and brine. The organic solution was dried over magnesium sulfate, concentrated, and purified by silica gel column chromatography (SiO$_2$ 15 g, 3% methanol in dichloromethane) to give 3-methoxy-4-(2-nitrobenzyloxy)-N-methyl-N-[4-methyl-2-[5-(4-methylpiperazin-1-yl)carbonylpent-1-yloxy]phenyl]benzamide (210 mg).

NMR (CDCl$_3$, δ): 1.43–1.59 (2H, m), 1.61–1.88 (4H, m), 2.21–2.44 (12H, m), 3.31 (3H, s), 3.42–3.52 (2H, m), 3.56–3.67 (2H, m), 3.71 (3H, s), 3.78–4.00 (2H, m), 5.46 (3H, s), 6.52–6.67 (3H, m), 6.77–6.91 (2H, m), 6.95 (1H, br s), 7.46 (1H, m), 7.64 (1H, m), 7.84 (1H, d, J=8 Hz), 8.14 (1H, d, J=8 Hz)

EXAMPLE 50

To a solution of 4-[2-(3-aminopropylthio)benzoyl]amino-3-methoxy-N-methyl-N-[4-methyl-2-[5-(4-methylpiperazin-1-yl)-carbonylpent-1-yloxy]phenyl]benzamide (160 mg) in methanol (5 ml) was added a suspension of sodium metaperiodate (50.6 mg) and 5 ml of water. The mixture was stirred for 20 hours at ice-bath temperature and diluted with chloroform. The lower chloroform layer was removed, and the water layer was extracted with chloroform. The combined organic extracts were dried over anhydrous sodium sulfate. The solvent was removed at reduced pressure, and purified by preparative thin layer chromatography (methanol/dichloromethan/ammonia=10/90/2) to give free amine (70 mg). To a solution of this amine in ethanol (3 ml) was added 1N hydrochloric acid (0.2 ml) and stirred for 5 minutes. The solution was concentrated to give 4-[2-(3-aminopropylsulfinyl)benzoyl]amino-3-methoxy-N-methyl-N-[4-methyl-2-[5-(4-methylpiperazin-1-yl)carbonylpent-1-yloxy]phenyl]benzamide dihydrochloride.

NMR (DMSO-d$_6$, δ): 1.38–1.67 (4H, m), 1.68–1.88 (2H, m), 1.94–2.13 (2H, m), 2.22 (3H, s), 2.40 (2H, t, J=7 Hz), 2.69–3.12 (9H, m), 3.12–3.58 (7H, m), 3.62 (3H, s), 3.80–4.17 (3H, m), 4.43 (1H, m), 6.64 (1H, c, J=8 Hz), 6.83 (1H, s), 6.91 (2H, br s), 7.04 (1H, d, J=8 Hz), 7.53 (1H, m), 7.68 (1H, dd, J=8, 8 Hz), 7.85 (1H, dd, J=8, 8 Hz), 7.90–8.19 (3H, s), 9.84 (1H, s)

EXAMPLE 51

To a solution of 3-methoxy-4-[2-[3-(phthalimido)prop-1-yl]thiobenzoyl]amino-N-methyl-N-[4-methyl-2-[5-(4-methylpiperazin-1-yl)carbonylpent-1-yl]oxy]phenylbenzamide (150 mg) in dichloromethane (10 ml) was added m-chloroperbenzoic acid (80.3 mg) and the mixture was stirred at ambient temperature for 2 hours. The solution was washed successively with saturated aqueous sodium hydrogen carbonate, water and brine, and the organic phase was dried over magnesium sulfate. The solvent was evaporated in vacuo and the residue was purified by silica gel column (2% methanol in chloroform) to give 3-methoxy-4-[2-[3-(phthalimido)prop-1-yl]sulfonylbenzoyl]amino-N-methyl-N-[4-methyl-2-[5-(4-methylpiperazin-1-yl)carbonylpent-1-yl]oxy]phenylbenzamide (150 mg).

MASS (m/z): 839 (M+1)

EXAMPLE 52

A solution of 4-[2-[2-[(3-aminioprop-1-yl)oxy]phenyl]-vinyl]-3-methoxy-N-methyl-N-[4-methyl-2-[5-(4-methylpiperazin-1-yl)carbonylpent-1-yloxy]phenyl]benzamide (100 mg), 20% palladium hydroxide (30 mg) in methanol (5 ml) was stirred under atmospheric pressure of hydrogen at ambient temperature. After 12 hours, the reaction mixture was filtered through a bed of Celite, and the solvent was removed by rotary evaporation and the crude product was purified by NH-silica gel (chromatorex) column chromatography (SiO₂ 10 g, 1% methanol in chloroform) to give free amine. To the solution of amine (80 mg) in ethanol (3 ml) was added 1N hydrochloric acid (0.25 ml) and stirred for 5 minutes. The solution was evaporated to give 4-[2-[2-[(3-aminoprop-1-yl)oxy]phenyl]ethyl]-3-methoxy-N-methyl-N-[4-methyl-2-[5-(4-methylpiperazin-1-yl)carbonylpent-1-yloxy]phenyl]benzamide dihydrochloride (70 mg).

NMR (DMSO-d₆, δ): 1.36–1.65 (4H, m), 1.65–1.82 (2H, m), 1.97–2.13 (2H, m), 2.22 (3H, s), 2.39 (2H, t, J=7 Hz), 2.58–3.11 (13H, m), 3.17 (3H, s), 3.26–3.68 (5H, m), 3.72–4.21 (5H, m), 4.42 (1H, m), 6.63 (1H, d, J=8 Hz), 6.70–7.05 (8H, m), 7.13 (1H, dd, J=8, 8 Hz), 8.00–8.24 (2H, m)

EXAMPLE 53

The following compounds were obtained according to a similar manner to that of Example 10.

1) 4-[2-[(3-tert-Butoxycarbonylaminoprop-1-yl)oxy]benzoyl]-amino-3-methoxy-N-methyl-N-(4-hydroxyphenyl)benzamide NMR (CDCl₃, δ): 1.43 (9H, s), 1.60–1.68 (2H, m), 3.16–3.25 (2H, m), 3.49 (3H, s), 3.63 (3H, s), 4.16–4.23 (2H, m), 4.73–4.80 (1H, br), 6.67–6.74 (3H, m), 6.84–7.01 (5H, m), 7.07–7.14 (2H, m), 7.47 (1H, t, J=8 Hz), 8.16 (1H, d, J=8 Hz), 8.52 (1H, d, J=8 Hz)

ESI-MASS (m/z): 550 (M+H)

2) 3-Methoxy-4-[2-[1-(tert-butoxycarbonyl)piperidin-4-yl]oxybenzoyl]amino-N-(2-hydroxy-4-methyl)phenyl-N-methylbenzamide NMR (CDCl₃, δ): 1.43 (9H, s), 1.68–2.10 (4H, m), 2.23 (3H, s), 2.96–3.17 (2H, m), 3.36 (3H, s), 3.64–3.98 (5H, m), 4.60 (1H, m), 6.36–7.03 (7H, m), 7.10 (1H, t, J=7 Hz), 7.43 (1H, t, J=7 Hz), 8.19 (1H, d, J=7 Hz)

3) 4-[2-(3-Amino-1-methylprop-1-yl)oxybenzoyl]amino-3-methoxy-N-(2-hydroxy-4-methyl)phenyl-N-methylbenzamide NMR (DMSO-d₆, δ): 1.33 (3H, d, J=7.5 Hz), 1.63–1.76 (1H, m), 1.87–1.98 (1H, m), 2.14 (3H, s), 2.65 (2H, t, J=7.5 Hz), 3.18 (3H, s), 3.74 (3H, s), 4.96 (1H, m), 6.47 (1H, d, J=7 Hz), 6.63 (1H, s), 6.86 (1H, d, J=7 Hz), 7.91 (1H, d, J=7 Hz), 7.01 (1H, s), 7.09 (1H, t, J=7 Hz), 7.32 (1H, d, J=7 Hz), 7.52 (1H, t, J=7 Hz), 8.04 (1H, d, J=7 Hz), 8.30 (1H, d, J=7 Hz)

4) 3-Methoxy-4-[2-[3-(tert-butoxycarbonyl)amino-1-methylprop-1-yl]oxybenzoyl]amino-N-(2-hydroxy-4-methyl)phenyl-N-methylbenzamide NMR (CDCl₃, δ): 1.36 (3H, d, J=7.5 Hz), 1.40 (9H, s), 1.80–2.10 (2H, m), 2.22(3H, s), 3.16–3.28 (2H, m), 3.35 (3H, s), 3.69 (3H, s), 4.64 (1H, m), 4.79 (1H, br), 6.52 (1H, m), 6.70–6.82 (2H, m), 6.91–7.11 (4H, m), 7.41 (1H, t, J=7 Hz), 8.21 (1H, d, J=7 Hz), 8.47 (1H, m)

5) 4-(2-Hydroxybenzoylamino-3-methoxy-N-(2-hydroxy-4-methylphenyl)-N-methylbenzamide NMR (CDCl₃, δ): 2.26 (3H, s), 3.36 (3H, s), 6.56 (1H, m), 6.65–6.86 (4H, m), 6.96–7.08 (2H, m), 7.35–7.44 (2H, m), 8.20 (1H, br), 8.61 (1H, br)

6) 4-[2-[3-(tert-Butoxycarbonylamino)prop-1-yl]oxybenzoyl]-amino-3-methoxy-N-(2-hydroxy-4-methylphenyl)-N-methylbenzamide NMR (CDCl₃, δ): 1.42 (9H, s), 1.68 (2H, br), 1.99 (2H, br), 2.22 (3H, s), 3.19 (2H, br), 3.39 (3H, s), 3.49 (2H, br), 5.03 (1H, br), 6.43–6.72 (6H, m), 7.08 (2H, br), 7.39 (1H, br), 8.21 (1H, d, J=8 Hz), 8.45 (1H, br)

EXAMPLE 54

The following compounds were obtained according to a similar manner to that of Example 12.

1) 4-[2-[(3-tert-Butoxycarbonylaminoprop-1-yl)oxy]benzoyl]-amino-3-methoxy-N-methyl-N-[4-(5-ethoxycarbonylpent-1-yloxy)phenyl]benzamide NMR (CDCl₃, δ): 1.21–1.29 (3H, m), 1.40 (9H, s), 1.42–1.90 (8H, m), 2.09–2.19 (2H, m), 3.27–3.34 (2H, m), 3.47 (3H, s), 3.82 (3H, s), 3.89 (2H, t, J=8 Hz), 4.08–4.17 (2H, m), 4.26 (2H, t, J=8 Hz), 4.70–4.77 (1H, br), 6.75 (2H, d, J=8 Hz), 6.83 (1H, d, J=8 Hz), 6.94–7.02 (3H, m), 7.07–7.13 (2H, m), 7.46 (1H, t, J=8 Hz), 8.21 (1H, d, J=8 Hz), 8.42 (1H, d, J=8 Hz)

ESI-MASS (m/z): 692 (M+H)

2) 4-[2-Benzyloxy)benzoyl]amino-N-[2-(3-ethoxycarbonylprop-1-yl)oxy]phenyl-N-methylbenzamide NMR (CDCl₃, δ): 1.26 (3H, t, J=7.5 Hz), 2.03–2.17 (2H, m), 2.50 (2H, t, J=7.5 Hz), 3.32 (3H, s), 3.87–4.04 (2H, m), 4.16 (2H, q, J=7.5 Hz), 5.19 (2H, s), 6.78 (2H, d, J=8 Hz), 6.92–7.00 (3H, m), 7.07–7.21 (5H, m), 7.38–7.53 (6H, m), 8.26 (1H, d, J=7 Hz)

3) 4-(2-Iodobenzoyl)amino-N-[2-(5-ethoxycarbonylpent-1-yl)oxy]phenyl-N-methylbenzamide NMR (CDCl₃, δ): 1.24 (3H, t, J=7.5 Hz), 1.42–1.55 (2H, m), 1.63–1.72 (2H, m), 1.76–1.88 (2H, m), 2.31 (2H, t, J=7.5 Hz), 3.31 (3H, s), 3.81–3.99 (2H, m), 4.11 (2H, q, J=7.5 Hz), 6.76–6.83 (2H, m), 7.00 (1H, d, J=7 Hz), 8.08–7.17 (2H, m), 7.29–7.49 (5H, m), 7.66 (1H, s), 7.88 (1H, d, J=7 Hz)

4) 3-Methoxy-4-[2-[3-(tert-butoxycarbonyl)aminoprop-1-yl]-oxybenzoyl]amino-N-[2-[3-(tert-butoxycarbonyl)aminoprop-1-yl]oxy-4-methyl]phenyl-N-methylbenzamide NMR (CDCl₃, δ): 1.39 (9H, s), 1.41 (9H, s), 1.93–1.97 (2H, m), 2.07–2.17 (2H, m), 2.26 (3H, s), 3.22–3.32 (4H, m), 3.30 (3H, s), 3.78 (3H, s), 3.82–4.05 (2H, m), 6.60–6.66 (2H, m), 6.86–6.91 (2H, m), 7.00 (1H, d, J=7 Hz), 7.03–7.10 (2H, m), 7.43 (1H, t, J=7 Hz), 8.20 (1H, d, J=7 Hz), 8.39 (1H, d, J=7 Hz)

5) 3-Methoxy-4-[2-[3-(tert-butoxycarbonyl)aminoprop-1-yl]oxybenzoyl]amino-N-methyl-N-[4-methyl-2-[4-(phthalimido)but-1-yl]oxy]phenylbenzamide NMR (CDCl₃, δ): 1.40 (9H, s), 1.85–1.92 (2H, m), 2.10–2.17 (2H, m), 2.27 (3H, s), 3.22–3.32 (2H, m), 3.28 (3H, s), 3.74–3.81 (2H, m), 3.81 (3H, s), 3.92–4.15 (2H, m), 4.24 (2H, t, J=7.5 Hz), 6.57–6.65 (2H, m), 6.83–6.90 (2H, m), 6.97–7.14 (3H, m), 7.24 (1H, t, J=7 Hz), 7.69–7.77 (2H, m), 7.82–7.91 (2H, m), 8.21 (1H, d, J=7 Hz), 8.40 (1H, d, J=7 Hz)

6) 3-Methoxy-4-[2-[1-(tert-butoxycarboyl)piperidin-4-yl]oxybenzoyl]amino-N-[2-(5-ethoxycarbonylpent-1-yl)oxy-4-methyl]phenyl-N-methylbenzamide NMR (CDCl₃, δ): 1.25 (3H, t, J=7.5 Hz), 1.42–1.91 (6H, m), 1.45 (9H, s), 2.02–2.12 (2H, m), 2.27 (3H, s), 2.27–2.88 (2H, m), 2.97–3.18 (2H, m), 3.32 (3H, s), 3.40 (3H, t, J=7 Hz), 3.74 (3H, s), 3.89–4.00 (2H, m), 4.13 (2H, q, J=7.5 Hz), 4.66 (1H, m), 6.59 (1H, d, J=7 Hz), 6.61 (1H, s, J=7 Hz), 6.80–6.92 (2H, m), 6.98–7.12 (3H, m), 7.43 (1H, t, J=7 Hz), 8.19 (1H, d, J=7 Hz), 8.39 (1H, d, J=7 Hz)

7) 3-Methoxy-4-[2-[3-(tert-butoxycarbonyl)amino-1-methyl-prop-1-yl]oxybenzoyl]amino-N-[2-(5-ethoxycarbonylpent-1-yl)oxy-4-methyl]phenyl-N-methylbenzamide NMR (CDCl₃, δ): 1.24 (3H, t, J=7.5 Hz), 1.38 (9H, s), 1.40 (2H, d, J=7.5 Hz), 1.41–2.10 (8H, m), 2.26 (3H, s), 2.27–2.33 (2H, m), 3.23–3.30 (2H, m), 3.30 (3H, s), 3.79 (3H, s), 3.83–3.99 (2H, m), 4.12 (2H, q, J=7.5 Hz), 4.62–4.77 (2H, m), 6.58–6.63 (2H, m), 6.82 (1H, t, J=7 Hz), 7.01 (1H, d, J=7 Hz), 7.05–7.12 (2H, m), 7.43 (1H, t, J=7 Hz), 8.21 (1H, d, J=7 Hz), 8.39 (1H, d, J=7 Hz)

8) 4-[2-[3-(tert-Butoxycarbonylamino)prop-1-yl]oxybenzoyl]-amino-3-methoxy-N-(2-methoxy-4-methylphenyl)-N-methylbenzamide NMR (CDCl$_3$, δ): 1.40 (9H, s), 2.08–2.20 (2H, m), 2.29 (3H, s), 3.28 (2H, q, J=5 Hz), 3.31 (3H, s), 3.75 (3H, s), 3.80 (3H, s), 4.25 (2H, t, J=5 Hz), 4.74 (1H, br), 6.59–6.65 (2H, m), 6.89 (1H, d, J=8 Hz), 7.00 (1H, d, J=8 Hz), 7.06–7.13 (2H, m), 7.46 (1H, dd, J=2, 8 Hz), 8.21 (1H, d, J=8 Hz), 8.40 (1H, d, J=8 Hz)

9) 4-[2-[3-(tert-Butoxycarbonylamino)prop-1-yl]oxybenzoyl]-amino-3-methoxy-N-[2-[4-(2-pyridyl)phenylmethyl]oxy-4-methylphenyl]-N-methylbenzamide NMR (CDCl$_3$, δ): 1.39 (9H, s), 2.09 (2H, t, J=5 Hz), 2.29 (3H, s), 3.27 (2H, q, J=5 Hz), 3.40 (3H, s), 3.61 (3H, s), 4.21 (2H, t, J=5 Hz), 4.82 (1H, br), 4.97 (1H, d, J=12 Hz), 5.14 (1H, d, J=12 Hz), 6.55–6.74 (2H, m), 6.89–7.12 (7H, m), 7.19–7.24 (1H, m), 7.39 (1H, d, J=8 Hz), 7.41–7.49 (1H, m), 7.70 (2H, s), 7.99 (1H, d, J=8 Hz), 8.21 (1H, d, J=8 Hz), 8.40 (1H, d, J=8 Hz), 8.67 (1H, d, J=5 Hz)

10) 4-[2-[3-(tert-Butoxycarbonylamino)prop-1-yl]oxybenzoyl]-amino-3-methoxy-N-[2-[4-(1,5-dimethyl-3-cyanopyrrol-2-yl)phenylmethyl]oxy-4-methylphenyl)-N-methylbenzamide NMR (CDCl$_3$, δ): 1.40 (9H, s), 2.03–2.15 (2H, m), 2.13 (3H, s), 2.30 (3H, s), 3.26 (2H, q, J=5 Hz), 3.40 (3H, s), 3.46 (3H, s), 3.58 (3H, s), 4.19 (2H, t, J=5 Hz), 4.86 (1H, d, J=12 Hz), 5.10 (1H, d, J=12 Hz), 6.65–6.73 (2H, m), 6.82 (1H, d, J=8 Hz), 6.95–7.10 (4H, m), 7.34–7.44 (6H, m), 8.00 (1H, s), 8.19 (1H, d, J=8 Hz), 8.36 (1H, d, J=8 Hz)

11) 4-[2-[3-(tert-Butoxycarbonylamino)prop-1-yl]oxybenzoyl]amino-3-methoxy-N-[2-[4-(thiazol-2-yl)phenylmethyl]oxy-4-methylphenyl]-N-methylbenzamide NMR (CDCl$_3$, δ): 1.40 (9H, s), 2.05–2.16 (2H, m), 3.27 (2H, q, J=5 Hz), 3.40 (3H, s), 3.62 (3H, s), 4.20 (2H, t, J=5 Hz), 4.76 (1H, br), 4.89 (1H, d, J=12 Hz), 5.07 (1H, d, J=12 Hz), 6.62–6.72 (2H, m), 6.89 (1H, d, J=8 Hz), 6.96–7.11 (4H, m), 7.28 (1H, d, J=3 Hz), 7.31 (2H, d, J=8 Hz), 7.42 (1H, dd, J=2, 8 Hz), 7.81 (1H, d, J=8 Hz), 7.93 (2H, d, J=8 Hz), 8.00 (1H, s), 8.20 (1H, d, J=8 Hz), 8.38 (1H, d, J=8 Hz)

12) 4-[2-[3-(tert-Butoxycarbonylamio)prop-1-yl]oxybenzoyl]amino-3-methoxy-N-[2-[4-(oxazol-2-yl)phenylmethyl]oxy-4-methylphenyl]-N-methylbenzamide
p1 NMR (CDCl$_3$, δ): 1.40 (9H, s), 2.05–2.16 (2H, m), 2.29 (3H, s), 3.27 (2H, q, J=5 Hz), 3.40 (3H, s), 3.65 (3H, s), 4.21 (2H, t, J=5 Hz), 4.78 (1H, br), 4.90 (1H, d, J=13 Hz), 5.10 (1H, d, J=13 Hz), 6.64 (1H, s), 6.70 (1H, d, J=8 Hz), 6.85 (1H, d, J=8 Hz), 6.98–7.17 (5H, m), 7.20 (1H, s), 7.30–7.49 (3H, m), 7.63 (1H, s), 8.03 (1H, d, J=8 Hz), 8.22 (1H, d, J=8 Hz), 8.40 (1H, d, J=8 Hz)

13) 4-[2-[3-(tert-Butoxycarbonylamino)prop-1-yl]oxybenzoyl]amino-3-methoxy-N-[2-[4-(pyrimidin-2-yl)phenylmethyl]oxy-4-methylphenyl]-N-methylbenzamide NMR (CDCl$_3$, δ): 1.40 (9H, s), 2.05–2.16 (2H, m), 2.28 (3H, s), 3.28 (2H, q, J=5 Hz), 3.40 (3H, s), 3.65 (3H, s), 4.22 (2H, t, J=5 Hz), 4.78 (1H, br), 4.95 (1H, d, J=12 Hz), 5.14 (1H, d, J=12 Hz), 6.65–6.70 (2H, m), 6.88 (1H, d, J=8 Hz), 6.96–7.19 (5H, m), 7.38–7.46 (3H, m), 8.21 (1H, d, J=8 Hz), 8.35–8.44 (3H, m), 8.74 (1H, d, J=3 Hz)

14) 4-[2-[3-(tert-Butoxycarbonylamino)prop-1-yl]oxybenzoyl]-amino-3-methoxy-N-[2-(4-cyanophenylmethyl)oxy-4-methylphenyl]-N-methylbenzamide NMR (CDCl$_3$, δ): 1.41 (9H, s), 2.08–2.20 (2H, m), 2.30 (3H, s), 3.30 (2H, q, J=5 Hz), 3.40 (3H, s), 3.68 (3H, s), 4.26 (2H, t, J=5 Hz), 4.89 (1H, d, J=13 Hz), 5.09 (1H, d, J=13 Hz), 6.60 (1H, s), 6.73 (1H, d, J=8 Hz), 6.98–7.12 (5H, m), 7.39–7.52 (3H, m), 7.68 (1H, d, J=8 Hz), 8.20 (1H, d, J=8 Hz), 8.34 (1H, d, J=8 Hz)

15) 4-[2-[3-(tert-Butoxycarbonylamino)prop-1-yl]oxybenzoyl]amino-3-methoxy-N-[2-(4-phthalimidobut-1-yl)oxy-4-methylphenyl]-N-methylbenzamide NMR (CDCl$_3$, δ): 1.40 (9H, s), 1.72–1.95 (4H, m), 2.08–2.19 (2H, m), 2.29 (3H, s), 3.31 (2H, q, J=5 Hz), 3.33 (3H, s), 3.79 (2H, t, J=5 Hz), 3.81 (3H, s), 3.84–4.06 (2H, m), 4.25 (2H, t, J=5 Hz), 4.82 (1H, br), 6.57 (1H, d, J=8 Hz), 6.62 (1H, s), 6.81–6.89 (2H, m), 6.97 (1H, d, J=8 Hz), 7.04–7.10 (2H, m), 7.40–7.48 (1H, m), 7.68–7.74 (2H, m), 7.81–7.89 (2H, m), 8.20 (1H, d, J=8 Hz), 8.39 (1H, d, J=8 Hz)

16) 4-[2-[3-(tert-Butoxycarbonylamino)prop-1-yl]oxybenzoyl]-amino-3-methoxy-N-[2-(3-methoxycarbonylpyrid-6-yl)methoxy-4-methylphenyl]-N-methylbenzamide NMR (CDCl$_3$, δ): 1.39 (9H, s), 2.07–2.16 (2H, m), 2.27 (3H, s), 3.29 (2H, q, J=5 Hz), 3.42 (3H, s), 3.63 (3H, s), 3.89 (3H, s), 4.24 (2H, t, J=5 Hz), 4.95 (1H, d, J=12 Hz), 5.08 (1H, d, J=12 Hz), 6.58 (1H, s), 6.73 (1H, d, J=8 Hz), 6.89 (1H, d, J=8 Hz), 6.98 (2H, d, J=8 Hz), 7.05–7.12 (3H, m), 7.34 (1H, d, J=8 Hz), 7.44 (1H, dd, J=2, 8 Hz), 8.20 (1H, d, J=8 Hz), 8.28 (1H, d, J=8 Hz), 8.37 (1H, d, J=8 Hz), 9.14 (1H, s)

EXAMPLE 55

The following compound was obtained according to a similar manner to that of Example 35.

4-[2-[3-(tert-Butoxycarbonylamino)prop-1-yl]oxybenzoylamino-3-methoxy-N-[2-[4-(tert-butoxycarbonylguanidino)but-1-yl]oxy-4-methylphenyl]-N-methylbenzamide NMR (CDCl$_3$, δ): 1.43 (9H, s), 1.44 (9H, s), 1.52–1.60 (2H, m), 1.65–1.74 (2H, m), 1.92–2.07 (2H, m), 2.21 (3H, s), 3.10–3.25 (4H, m), 3.38 (3H, s), 3.50 (2H, br), 3.66 (3H, br), 3.78–4.05 (2H, m), 6.49 (2H, br), 6.63–6.82 (3H, m), 7.01–7.10 (2H, m), 7.38 (1H, dd, J=2, 8 Hz), 8.20 (1H, d, J=8 Hz), 8.44 (1H, br)

EXAMPLE 56

The following compounds were obtained according to a similar manner to that of Example 10.

1) 4-[2-[(3-tert-Butoxycarbonylaminoprop-1-yl)oxy]benzoyl]-amino-3-hydroxy-N-methyl-N-cyclohexylbenzamide NMR (CDCl$_3$, δ): 1.07–1.17 (2H, m), 1.41 (9H, s), 1.47–1.76 (8H, m), 2.10–2.20 (2H, m), 2.92–3.00 (2H, m), 3.36–3.44 (2H, m), 3.49 (3H, s), 4.19–4.27 (2H, m), 4.98–5.06 (1H, br), 6.87–6.92 (1H, br), 6.98–7.03 (2H, m), 7.12 (1H, t, J=8 Hz), 7.47 (1H, t, J=8 Hz), 8.12–8.22 (1H, br), 8.28 (1H, d, J=8 Hz), 9.72–9.80 (1H, br)

ESI-MASS (m/z): 526 (M+H)

2) 4-[2-[(3-tert-Butoxycarbonylaminoprop-1-yl)oxy]benzoyl]-amino-3-hydroxy-N-methyl-N-[2-[5-(4-methylpiperazin-1-yl)carbonylpent-1-yloxy]-4-methylphenyl]benzamide NMR (CDCl₃, δ): 1.42 (9H, s), 1.50–1.90 (8H, m), 2.20–2.22 (2H, m), 2.27 (3H, s), 2.32 (3H, s), 2.35–2.53 (6H, m), 3.29 (3H, s), 3.32–3.42 (2H, m), 3.50–3.66 (3H, m), 3.72 (2H, br), 3.89 (1H, br), 4.20 (2H, t, J=6 Hz), 5.29 (1H, br), 6.54 (1H, s), 6.67 (1H, d, J=7 Hz), 6.72 (1H, br), 6.96–7.10 (4H, m), 7.40–7.47 (1H, m), 8.10 (1H, br), 8.27 (1H, d, J=6 Hz)

EXAMPLE 57

To a solution of 4-[(2-benzyloxy)benzoyl]amino-3-[(2-benzyloxy)benzoyl]oxy-N-methyl-N-[2-[5-(4-methylpiperazin-1-yl)carbonylpent-1-yloxy]-4-methylphenyl]benzamide (1.2 g) in ethanol (20 ml) was added 1N sodium hydroxide solution (10 ml) and the mixture was stirred at ambient temperature for 2 hours. The mixture was concentrated in vacuo and the solution was adjusted to pH 7 with 1N hydrochloric acid. The solution was extracted with ethyl acetate (20 ml) and the organic layer was washed with brine (20 ml). The organic layer was dried over magnesium sulfate and the solution was concentrated in vacuo to give 4-[(2-benzyloxy)benzoyl]amino-3-hydroxy-N-methyl-N-[2-[5-(4-methylpiperazin-1-yl)carbonylpent-1-yloxy]-4-methylphenyl]benzamide (930 mg)

NMR (CDCl₃, δ): 1.48–1.59 (2H, m), 1.70 (4H, br), 2.29–2.42 (13H, m), 3.29 (3H, s), 3.48 (2H, br), 3.53 (2H, br), 3.80 (1H, br), 3.90 (1H, br), 5.28 (2H, s), 6.53–6.65 (3H, m), 6.72 (1H, br), 6.90–7.12 (4H, m), 7.34–7.37 (3H, m), 7.40–7.49 (4H, m), 8.20–8.27 (1H, m)

EXAMPLE 58

The following compounds were obtained according to a similar manner to that of Example 12.

1) 4-[2-[(3-tert-Butoxycarbonylaminoprop-1-yl)oxy]benzoyl]-amino-3-ethoxycarbonylmethoxy-N-methyl-N-cyclohexylbenzamide NMR (CDCl₃, δ): 1.29 (3H, t, J=8 Hz), 1.41 (9H, s), 1.45–1.85 (10H, m), 2.07–2.12 (2H, m), 2.86–3.06 (3H, br), 3.25–3.32 (2H, m), 4.22–4.33 (4H, m), 4.76 (2H, s), 4.98–5.07 (1H, br), 6.91 (1H, s), 7.01–7.15 (3H, m), 7.48 (1H, t, J=8 Hz), 8.23 (1H, d, J=8 Hz), 8.69 (1H, d, J=8 Hz)

ESI-MASS (m/z): 634 (M+Na)

2) 4-[2-[(3-tert-Butoxycarbonylaminoprop-1-yl)oxy]benzoyl]-amino-3-isopropoxy-N-methyl-N-[2-[5-(4-methylpiperazin-1-yl)carbonylpent-1-yloxy]-4-methylphenyl]benzamide NMR (CDCl₃, δ): 1.19–1.28 (6H, m), 1.38 (9H, s), 1.46–1.58 (2H, m), 1.65–1.88 (6H, m), 1.99–2.10 (2H, m), 2.25 (3H, s), 2.29 (3H, s), 2.32–2.42 (6H, m), 3.15–3.23 (2H, m), 3.31 (3H, s), 3.45–3.50 (2H, m), 3.60–3.64 (2H, m), 3.84–3.97 (2H, m), 4.24–4.36 (3H, m), 6.56–6.65 (2H, m), 6.85 (1H, d, J=7 Hz), 6.94–7.02 (3H, m), 7.10 (1H, t, J=6 Hz), 7.47 (1H, t, J=7 Hz), 8.15 (1H, d, J=7 Hz), 8.41 (1H, d, J=7 Hz)

3) 4-[2-[(3-tert-Butoxycarbonylaminoprop-1-yl)oxy]benzoyl]-amino-N-methyl-N-[2-[5-(4-methylpiperazin-1-yl)carbonylpent-1-yloxy]-4-methylphenyl]-3-propoxybenzamide NMR (CDCl₃, δ): 0.97 (3H, t, J=7 Hz), 1.42 (9H, s), 1.47–1.58 (2H, m), 1.67–1.88 (8H, m), 1.98–2.10 (2H, m), 2.27 (3H, s), 2.28 (3H, s), 2.31–2.41 (6H, m), 3.16–3.26 (2H, m), 3.31 (3H, s), 3.45–3.50 (2H, m), 3.58–3.65 (2H, m), 3.84–3.97 (4H, m), 4.26 (2H, t, J=7 Hz), 6.58 (1H, d, J=7 Hz), 6.64 (1H, s), 6.84 (1H, d, J=6 Hz), 6.95 (1H, d, J=7 Hz), 6.99–7.03 (2H, m), 7.09 (1H, t, J=7 Hz), 7.45 (1H, t, J=7 Hz), 8.16 (1H, d, J=7 Hz), 8.38 (1H, d, J=7 Hz)

4) 4-[2-[(3-tert-Butoxycarbonylaminoprop-1-yl)oxy]benzoyl]-amino-3-(3-ethoxycarbonylprop-1-yl)oxy-N-methyl-N-[2-[5-(4-methylpiperazin-1-yl)carbonylpent-1-yloxy]-4-methylphenyl]benzamide NMR (CDCl₃, δ): 1.11 and 1.23 (total 3H, t, J=6 Hz), 1.40 (9H, s), 1.48–1.60 (2H, m), 1.60–1.75 (4H, m), 1.75–1.88 (2H, m), 1.98–2.10 (4H, m), 2.26 (3H, s), 2.29 (3H, s), 2.32–2.42 (8H, m), 3.18–3.28 (2H, m), 3.30 (3H, s), 3.45–3.50 (2H, m), 3.62 (2H, br), 3.88–4.10 (5H, m), 4.27 (2H, t, J=6 Hz), 6.57 (1H, d, J=7 Hz), 6.63 (1H, s), 6.82 (1H, d, J=7 Hz), 6.87–6.92 (1H, m), 6.98–7.10 (3H, m), 7.42 (1H, t, J=6 Hz), 8.10–8.13 (1H, m), 8.37 (1H, d, J=7 Hz)

5) 4-[2-[(3-tert-Butoxycarbonylaminoprop-1-yl)oxy]-benzoyl]amino-3-ethoxycarbonylmethoxy-N-methyl-N-[2-[5-(4-methylpiperazin-1-yl)carbonylpent-1-yloxy]-4-methylphenyl]benzamide NMR (CDCl₃, δ): 1.29 (3H, t, J=7 Hz), 1.39 (9H, s), 1.46–1.90 (8H, m), 2.00–2.10 (2H, m), 2.28 (3H, s), 2.29 (3H, s), 2.30–2.42 (6H, m), 3.18–3.29 (2H, m), 3.30 (3H, s), 3.42–3.50 (2H, m), 3.58–3.65 (2H, m), 3.85–3.97 (2H, m), 4.18–4.29 (4H, m), 4.52 (2H, s), 6.52–6.13 (2H, m), 6.80 (1H, d, J=7 Hz), 6.89–6.99 (3H, m), 7.38–7.48 (1H, m), 8.15 (1H, d, J=7 Hz), 8.41 (1H, d, J=7 Hz)

6) 4-[(2-Benzyloxy)benzoyl]amino-3-ethoxyl-N-methyl-N-[2-[5-(4-methylpiperazin-1-yl)carbonylpent-1-yloxy]-4-methylphenyl]benzamide NMR (CDCl₃, δ): 1.08 (3H, t, J=6 Hz), 1.45–1.57 (2H, m), 1.60–1.75 (2H, m), 1.77–1.87 (2H, m), 2.25 (3H, s), 2.29 (3H, s), 2.31–2.39 (7H, m), 3.30 (3H, s), 3.46–3.49 (2H, m), 3.60–3.63 (2H, m), 3.70–3.80 (2H, m), 3.82–3.98 (2H, m), 5.34 (2H, s), 6.52–6.60 (2H, m), 6.80–7.10 (5H, m), 7.27–7.38 (6H, m), 8.20–8.22 (1H, m), 8.38–8.43 (1H, m)

EXAMPLE 59

The following compounds were obtained according to a similar manner to that of Example 4.

1) 4-[2-[(3-tert-Butoxycarbonylaminoprop-1-yl)oxy]benzoyl]-amino-3-carboxymethoxy-N-methyl-N-cyclohexylbenzamide NMR (CDCl₃, δ): 1.03–1.17 (2H, m), 1.39 (9H, s), 1.45–1.85 (8H, m), 2.03–2.12 (2H, m), 2.85–2.98 (3H, m), 3.21–3.33 (2H, m), 4.23–4.31 (2H, m), 4.73 (3H, s), 5.08–5.13 (1H, br), 6.98–7.07 (3H, m), 7.10 (1H, t, J=8 Hz), 7.48 (1H, t, J=8 Hz), 8.18–8.24 (1H, m), 8.56–8.61 (1H, m)

ESI-MASS (m/z): 606 (M+Na)

2) 4-[2-[(3-Aminoprop-1-yl)oxy]benzoyl]amino-3-carboxymethoxy-N-methyl-N-[2-[5-(4-methylpiperazin-1-yl)carbonylpent-1-yloxy]-4-methylphenyl]benzamide dihydrochloride NMR (DMSO-d₆, δ): 1.38–1.49 (2H, m), 1.49–1.62 (2H, m), 1.67–1.78 (2H, m), 2.02–2.34 (13H, m), 2.78–2.89 (2H, m), 3.38–3.43 (4H, m), 3.58 (3H, s), 3.89–3.96 (2H, m), 4.00–4.18 (2H, m), 4.30 (2H, br), 6.62 (1H, d, J=6 Hz), 6.72–6.87 (3H, m), 6.89–6.97 (1H, m), 7.11 (1H, t, J=7 Hz), 7.19 (1H, d, J=7 Hz) 7.54 (1H, t, J=6 Hz), 7.94 (1H, d, J=6 Hz), 8.22 (1H, d, J=7 Hz)

3) 4-[2-[(3-tert-Butoxycarbonylaminoprop-1-yl)oxy]benzoyl]-amino-3-carboxymethoxy-N-methyl-N-[2-[5-(4-methylpiperazin-1-yl)carbonylpent-1-yloxy]-4-methylphenyl]benzamide MASS (m/z): 804 (M+H)

EXAMPLE 60

To a mixture of 4-(2-iodobenzoyl)amino-N-methyl-N-[2-[5-(4-methylpiperazin-1-yl)carbonylpent-1-yl]oxy]phenylbenzamide (1.12 g) and 3-butyn-1-ol (153 mg) in a mixture of tetrahydrofuran (15 ml) and ethylamine (15 ml) were added bis(triphenylphosphine)palladium(II) chloride (23.5 mg) and copper (I) iodide (3.19 mg) and the mixture was refluxed for 8 hours. The solution was diluted with chloroform (50 ml) and the solution was washed with water and brine. The solution was dried over magnesium sulfate and the solvent was evaporated in vacuo to give an oil. The oil was purified by silica gel column (2% methanol in chloroform) to give 4-[2-(4-hydroxy-1-butyn-1-yl)benzoyl]amino-N-methyl-N-[2-[5-(4-methylpiperazin-1-yl)carbonylpent-1-yl]oxy]phenylbenzamide (755 mg).

NMR (CDCl$_3$, δ): 1.44–1.57 (2H, m), 1.61–1.86 (4H, m), 2.27 (3H, s), 2.29–2.40 (6H, m), 2.70 (2H, t, J=7.5 Hz), 3.33 (3H, s), 3.44–3.49 (2H, m), 3.53–3.60 (2H, m), 3.74 (2H, t, J=7.5 Hz), 3.79–3.99 (2H, m), 6.76–6.84 (2H, m), 7.06 (1H, d, J=7 Hz), 7.13 (1H, t, J=7 Hz), 7.34 (2H, d, J=8 Hz), 7.40–7.47 (2H, m), 7.48–7.56 (3H, m), 7.99 (1H, m), 9.19 (1H, s)

EXAMPLE 61

To an ice cooled solution of 4-[2-(4-hydroxy-1-butyn-1-yl)benzoyl]amino-N-methyl-N-[2-[5-(4-methylpiperazin-1-yl)carbonylpent-1-yl]oxy]phenylbenzamide (755 mg) in dichloromethane (20 ml) were added triethylamine (150 mg) and methanesulfonyl chloride (156 mg), and the mixture was stirred in an ice bath for 2 hours. The solution was washed successively with water, 10% hydrochloric acid, saturated aqueous sodium hydrogen carbonate and brine, and the organic phase was dried over magnesium sulfate. The solvent was evaporated in vacuo to give 4-[2-(4-methanesulfonyloxy-1-butyn-1-yl)benzoyl]amino-N-methyl-N-[2-[5-(4-methylpiperazin-1-yl)carbonylpent-1-yl]oxy]phenylbenzamide (789 mg).

NMR (CDCl$_3$, δ): 1.49–1.60 (2H, m), 1.67–1.86 (2H, m), 1.87–1.90 (2H, m), 2.37 (2H, t, J=7.5 Hz), 2.68 (3H, s), 2.86–3.06 (6H, m), 2.92 (3H, s), 3.31 (3H, s), 3.77–4.02 (6H, m), 4.32 (2H, t, J=7.5 Hz), 6.77–6.87 (2H, m), 7.04 (1H, d, J=7 Hz), 7.17 (1H, t, J=7 Hz), 7.32 (2H, d, J=8 Hz), 7.41–7.53 (5H, m), 7.90 (1H, m), 8.86 (1H, s)

EXAMPLE 62

The following compounds were obtained according to a similar manner to that of Example 61.

1) 4-[2-(4-Methanesulfonyloxybut-1-yl)benzoyl]amino-N-methyl-N-[2-[5-(4-methylpiperazin-1-yl)carbonylpent-1-yl]oxy]phenylbenzamide MASS (m/z): 693 (M+1)

2) 4-[2-(3-Methanesulfonyloxyprop-1-yl)thiobenzoyl]amino-3-methoxy-N-methyl-N-[4-methyl-2-[5-(4-methylpiperazin-1-yl)carbonylpent-1-yl]oxy]phenylbenzamide NMR (CDCl$_3$, δ): 1.48–1.60 (2H, m), 1.65–1.74 (2H, m), 1.75–1.86 (2H, m), 1.98–2.07 (2H, m), 2.26 (3H, s), 2.30–2.39 (2H, m), 2.70–2.78 (4H, m), 2.79–3.42 (2H, m), 2.90 (3H, s), 2.95–3.07 (2H, m), 3.26 (3H, s), 3.71 (3H, s), 3.80–4.01 (4H, m), 4.29 (2H, t, J=7.5 Hz), 6.56–6.66 (2H, m), 6.82–7.00 (3H, m), 7.30 (1H, m), 7.39–7.47 (2H, m), 7.60 (1H, d, J=7 Hz), 8.27 (1H, d, J=7 Hz), 8.58 (1H, s)

EXAMPLE 63

A mixture of 4-[2-(4-methanesulfonyloxy-1-butyn-1-yl)benzoyl]amino-N-methyl-N-[2-[5-(4-methylpiperazin-1-yl)carbonylpent-1-yl]oxy]phenylbenzamide (800 mg) and potassium phthalimide (430 mg) in dimethyl sulfoxide (20 ml) was stirred at 60° C. for 5 hours, and the solution was diluted with ethyl acetate (60 ml). The solution was washed with water and brine, and dried over magnesium sulfate. The solvent was evaporated in vacuo to give 4-[2-[4-(phthalimido)-1-butyn-1-yl]benzoyl]amino-N-methyl-N-[2-[5-(4-methylpiperazin-1-yl)carbonylpent-1-yl]oxy]phenylbenzamide (620 mg).

NMR (CDCl$_3$, δ): 1.50–1.61 (2H, m), 1.67–1.92 (6H, m), 2.30 (3H, s), 2.33–2.44 (6H, m), 3.38 (3H, s), 3.48–3.52 (2H, m), 3.60–3.67 (2H, m), 3.84–4.01 (4H, m), 6.78–6.85 (2H, m), 7.02 (1H, d, J=7 Hz), 7.09–7.19 (2H, m), 7.30–7.70 (6H, m), 7.70–7.77 (2H, m), 7.81–7.90 (2H, m), 8.18 (1H, m)

EXAMPLE 64

The following compounds were obtained according to a similar manner to that of Example 63.

1) 4-[2-[4-(Phthalimido)but-1-yl]benzoyl]amino-N-[2-[5-(4-methylpiperazin-1-yl)carbonylpent-1-yl]oxy]phenyl-N-methylbenzamide MASS (m/z): 693 (M+1)

2) 3-Methoxy-4-[2-[3-(phthalimido)prop-1-yl]thiobenzoyl]-amino-N-methyl-N-[4-methyl-2-[5-(4-methylpiperazin-1-yl)carbonylpent-1-yl]oxy]phenylbenzamide NMR (CDCl$_3$, δ): 1.47–1.59 (2H, m), 1.61–1.74 (2H, m), 1.78–1.87 (2H, m), 1.92–2.03 (2H, m), 2.26 (3H, s), 2.29 (3H, s), 2.31–2.42 (6H, m), 2.94 (2H, t, J=7.5 Hz), 3.31 (3H, s), 3.45–3.53 (2H, m), 3.58–3.67 (2H, m), 3.69–3.81 (2H, m), 3.73 (3H, s), 3.84–4.00 (2H, m), 6.55–6.66 (2H, m), 6.80–6.92 (2H, m), 7.02 (1H, s), 7.27 (1H, m), 7.34–7.44 (2H, m), 7.60–7.90 (5H, m), 8.25 (1H, d, J=7 Hz), 8.82 (1H, s)

EXAMPLE 65

To an ice cooled mixture of 4-[2-(4-amino-1-butyn-1-yl)benzoyl]amino-N-methyl-N-[2-[5-(4-methylpiperazin-1-yl)carbonylpent-1-yl]oxy]phenylbenzamide (310 mg), nickel chloride hexahydrate (181 mg) in a mixture of tetrahydrofuran (5 ml) and methanol (5 ml) was added sodium borohydride (96.2 mg) in small portions and the mixture was stirred at the same temperature for 2 hours. The mixture was filtered through bed of Celite and the filtrate was evaporated in vacuo. The residue was dissolved in chloroform (20 ml) and washed with water and brine. The organic solution was dried over magnesium sulfate and the solvent was evaporated in vacuo to give a syrup. The residue was purified by silica gel column (chloroform:methanol:ammonia= 100:10:1) to give 4-[2-(4-aminobut-1-yl)benzoyl]amino-N-methyl-N-[2-[5-(4-methylpiperazin-1-yl)carbonylpent-1-yl]oxy]phenylbenzamide (295 mg).

MASS (m/z): 597 (M+1)

EXAMPLE 66

The following compound was obtained according to a similar manner to that of Example 65.

4-[2-(4-hydroxybut-1-yl)benzoyl]amino-N-methyl-N-[2-[5-(4-methylpiperazin-1-yl)carbonylpent-1-yl]oxy]phenylbenzamide MASS (m/z): 615 (M+1)

EXAMPLE 67

A mixture of 4-amino-3-methoxy-N-methyl-N-[4-methyl-2-[4-(4-methylpiperazin-1-yl)carbonyl]phenylmethoxy]phenylbenzamide (200 mg) and salicyl aldehyde (48.6 mg) in methanol (10 ml) was refluxed overnight in the presence of 3 Å molecular sieves (100 mg). The solution was filtered and the filtrate was treated with sodium borohydride (15.1 mg) at 5° C. for 2 hours. The reaction mixture was diluted with chloroform (20 ml) and the solution was washed with water and brine. The organic solution was dried over magnesium sulfate and the solvent was evaporated in vacuo to give a crude oil. The product was purified by silica gel column (2% methanol in chloroform) to give 3-methoxy-4-(2-hydroxyphenyl)methylamino-N-methyl-N-[4-methyl-2-[4-(4-methylpiperazin-1-yl)carbonyl]phenylmethoxy]phenylbenzamide (152 mg).

NMR (CDCl$_3$, δ): 2.27 (3H, s), 2.32 (3H, s), 2.32–2.59 (4H, m), 3.34 (3H, s), 3.40–3.55 (2H, m), 3.52 (3H, s), 3.75–3.88 (2H, m), 4.25–4.34 (2H, m), 4.63 (1H, br), 4.42 (1H, d, J=14 Hz), 5.08 (1H, d, J=14 Hz), 6.43 (1H, d, J=7 Hz), 6.62 (1H, s), 6.70 (1H, d, J=7 Hz), 6.80–6.88 (4H, m), 7.00 (1H, d, J=7 Hz), 7.09–7.18 (2H, m), 7.28 (2H, d, J=8 Hz), 7.38 (2H, d, J=8 Hz)

EXAMPLE 68

The following compound was obtained according to a similar manner to that of Example 67.

3-Methoxy-4-(2-hydroxyphenyl)methylamino-N-methyl-N-[4-methyl-2-[5-(4-methylpiperazin-1-yl)carbonylpent-1-yl]oxy]phenylbenzamide NMR (CDCl$_3$, δ): 1.41–1.52 (2H, m), 1.60–1.69 (2H, m), 1.70–1.80 (2H, m), 2.25 (3H, s), 2.29 (3H, s), 2.30–2.43 (6H, m), 3.28 (3H, s), 3.34–3.48 (2H, m), 3.55 (3H, s), 3.65–4.00 (2H, m), 4.30 (2H, d, J=7 Hz), 4.62 (1H, br t, J=7 Hz), 6.51 (1H, d, J=7 Hz), 6.57–6.64 (2H, m), 6.76–6.95 (5H, m), 7.61–7.68 (2H, m)

EXAMPLE 69

To an ice bath cooled solution of 4-(2-dimethylamino-4-methyl)phenoxymethyl-N-[2-(5-ethoxycarbonylpent-1-yl)oxy]phenylbenzamide (860 mg) in N,N-dimethylformamide (15 ml) was added sodium hydride (60% in oil, 71 mg) and the solution was stirred at the same temperature for 30 minutes. Iodomethane (0.121 ml) was added to the solution and the mixture was stirred at ambient temperature for 3 hours. The mixture was diluted with ethyl acetate (50 ml) and the solution was washed with water and brine. The organic phase was dried over magnesium sulfate and the solvent was evaporated in vacuo to give a crude oil. The crude product was purified by silica gel column chromatography (1% methanol in chloroform) to give 4-(2-dimethylamino-4-methyl)phenoxymethyl-N-[2-(5-ethoxycarbonylpent-1-yl)oxy]phenyl-N-methylbenzamide (632 mg).

NMR (CDCl$_3$, δ): 1.26 (3H, t, J=7.5 Hz), 1.42–1.55 (2H, m), 1.63–1.74 (2H, m), 1.76–1.87 (2H, m), 2.20 (3H, s), 2.23 (3H, s), 2.33 (2H, t, J=7.5 Hz), 2.72 (6H, s), 3.30 (3H, s), 3.76–3.97 (2H, m), 4.12 (2H, q, J=7.5 Hz), 5.02 (2H, s), 6.52–6.60 (3H, m), 6.70 (1H, d, J=7 Hz), 6.80–6.88 (2H, m), 7.20 (2H, d, J=8 Hz), 7.31 (2H, d, J=8 Hz)

EXAMPLE 70

The following compound was obtained by using 3-methoxy-4-[2-[3-(tert-butoxycarbonyl)aminoprop-1-yl]oxybenzoyl]amino-N-[2-(4-aminobut-1-yl)oxy-4-methyl]phenyl-N-methylbenzamide as a starting compound according to a similar manner to that of Example 14.

3-Methoxy-4-[2-[3-(tert-butoxycarbonyl)aminoprop-1-yl]oxybenzoyl]amino-N-[2-(4-acetylaminobut-1-yl)oxy-4-methyl]phenyl-N-methylbenzamide NMR (CDCl$_3$, δ): 1.40 (9H, s), 1.65–1.82 (4H, m), 1.76 (3H, s), 2.05 (3H, s), 2.07–2.21 (2H, m), 2.26 (3H, s), 3.22–3.38 (2H, m), 3.38 (3H, s), 3.77 (3H, s), 3.77–3.96 (2H, m), 4.24 (2H, t, J=7.5 Hz), 6.53–6.71 (2H, m), 6.93–7.14 (5H, m), 7.25 (1H, t, J=7 Hz), 8.20 (1H, d, J=7 Hz), 8.43 (7H, d, J=7 Hz)

EXAMPLE 71

To a mixture of 3-methoxy-4-[2-[3-(tert-butoxycarbonyl)aminoprop-1-yl]oxybenzoyl]amino-N-[2-(4-aminobut-1-yl)oxy-4-methyl]phenyl-N-methylbenzamide (365 mg) and N-(tert-butoxycarbonyl)glycine (111 mg) in N,N-dimethylformamide (15 ml) were added N-ethyl-N'-(3-dimethylaminopropyl)carbodiimide hydrochloride (132 mg) and hydroxybenzotriazole (93.2 mg) and the mixture was stirred at ambient temperature overnight. The solution was diluted with ethyl acetate (30 ml) and the solution was washed successively with saturated aqueous sodium hydrogen carbonate, water and brine. The organic phase was dried over magnesium sulfate and the solvent was evaporated in vacuo to give an amorphous. The crude product was purified by silica gel column chromatography (1% methanol in chloroform) to give 3-methoxy-4-[2-[3-tert-butoxycarbonyl)aminoprop-1-yl]oxybenzoyl]amino-N-[2-4-(tert-butoxycarbonylamino)acetylaminobut-1-yl)oxy-4-methyl]phenyl-N-methylbenzamide (320 mg).

NMR (CDCl$_3$, δ): 1.39 (9H, s), 1.42 (9H, s), 1.58–1.70 (2H, m), 1.70–1.80 (2H, m), 2.05–2.17 (2H, m), 2.27 (3H, s), 3.20–3.34 (4H, m), 3.30 (3H, s), 3.70–3.95 (4H, m), 3.74 (3H, s), 4.22 (2H, t, J=7.5 Hz), 6.56–6.68 (2H, m), 6.88–7.11 (5H, m), 7.45 (1H, t, J=7 Hz), 8.20 (1H, d, J=7 Hz), 8.28 (1H, d, J=7 Hz)

EXAMPLE 72

The following compounds were obtained according to a similar manner to that of Example 71.

1) 4-[2-[3-(tert-Butoxycarbonylamino)prop-1-yl]oxybenzoyl]amino-3-methoxy-N-[2-[4-[3-(tert-butoxycarbonyl)aminopropionylamino]but-1-yl]oxy-4-methylphenyl]-N-methylbenzamide NMR (CDCl$_3$, δ): 1.40 (9H, s), 1.41 (9H, s), 1.60–1.82 (4H, m), 2.10–2.19 (2H, m), 2.29 (3H, s), 2.48 (2H, br), 3.25–3.42 (6H, m), 3.32 (3H, s), 3.79 (3H, s), 3.80–3.97 (2H, m), 4.25 (2H, t, J=5 Hz), 6.59 (1H, s), 6.67 (1H, d, J=8 Hz), 6.94–7.11 (5H, m), 7.45 (1H, dd, J=2, 8 Hz), 8.20 (1H, d, J=8 Hz), 8.39 (1H, d, J=8 Hz)

2) 4-[2-[3-(tert-Butoxycarbonylamino)prop-1-yl]oxybenzoyl]amino-3-methoxy-N-[2-[4-[[1-(tert-butoxycarbonyl)piperidin-4-yl]carbonylamino]but-1-yl]oxy-4-methylphenyl]-4-methylbenzamide NMR (CDCl$_3$, δ): 1.40 (9H, s), 1.44 (9H, s), 1.60–1.81 (8H, m), 2.08–2.18 (2H, m), 2.29 (3H, s), 2.70 (1H, br), 3.30

(2H, q, J=5 Hz), 3.32 (3H, s), 3.76 (3H, s), 3.76–4.15 (6H, m), 4.22 (2H, t, J=5 Hz), 6.59 (1H, s), 6.65 (1H, d, J=8 Hz), 6.94–7.10 (6H, m), 7.44 (1H, dd, J=2, 8 Hz), 8.20 (1H, d, J=8 Hz), 8.39 (1H, d, J=8 Hz)

EXAMPLE 73

To an ice-cooled mixture of 4-[2-[3-(tert-butoxycarbonylamino)prop-1-yl]oxybenzoyl]amino-3-methoxy-N-[2-(4-aminobut-1-yl)oxy-4-methylphenyl]-N-methylbenzamide (430 mg) and triethylamine (68 mg) in dichloromethane (10 ml) was added phenyl chlorocarbonate (106 mg) dropwise and the solution was stirred at the same temperature for 30 minutes. The resulting mixture was diluted with dichloromethane (10 ml) and the solution was washed successively with 1N hydrochloric acid saturated aqueous sodium hydrogen carbonate and brine. The solvent was dried over magnesium sulfate and removed under reduced pressure to give 4-[2-[3-(tert-butoxycarbonylamino)prop-1-yl]oxybenzoyl]amino-3-methoxy-N-[(2-(4-phenoxycarbonylaminobut-1-yl)oxy-4-methylphenyl]-N-methylbenzamide (471 mg).

NMR (CDCl$_3$, δ): 1.40 (9H, s), 1.60–1.90 (4H, m), 2.08–2.17 (2H, m), 2.29 (3H, s), 3.27 (2H, q, J=5 Hz), 3.31 (2H, t, J=5 Hz), 3.36 (3H, s), 3.78 (3H, s), 3.82–4.00 (2H, m), 4.21 (2H, t, J=5 Hz), 4.73 (1H, br), 5.38 (1H, br), 6.61–6.68 (2H, m), 6.91–6.99 (4H, m), 7.06–7.20 (5H, m), 7.30–7.38 (2H, m), 7.42 (1H, dd, J=2, 8 Hz), 8.20 (1H, d, J=8 Hz), 8.40 (1H, d, J=8 Hz)

EXAMPLE 74

A mixture of 4-[2-[3-(tert-butoxycarbonylamino)prop-1-yl]oxybenzoyl]amino-3-methoxy-N-[2-(4-aminobut-1-yl)oxy-4-methylphenyl]-N-methylbenzamide (120 mg) and 3-(dimethylamino)prop-1-yl phenyl carbonate (127 mg) in N,N-dimethylformamide (5 ml) was stirred at 50° C. for 8 hours. The reaction mixture was diluted with ethyl acetate (15 ml) and the solution was washed successively with saturated aqueous sodium bicarbonate solution and brine. The solution was dried over potassium carbonate. The solvent was evaporated and the residue was purified on silica gel column chromatography (SiO$_2$ 20 g, 3–15% methanol in chloroform) to give 4-[2-[3-(tert-butoxycarbonylamino)prop-1-yl]oxybenzoyl]amino-3-methoxy-N-[2-(3-dimethylaminoprop-1-yl)oxycarbonylamino]but-1-yl]oxy-4-methylphenyl]-N-methylbenzamide (64 mg).

NMR (CDCl$_3$, δ): 1.40 (9H, s), 1.62–1.87 (6H, m), 2.05–2.18 (2H, m), 2.28 (3H, s), 2.30 (6H, s), 2.44 (2H, t, J=5 Hz), 3.20–3.32 (4H, m), 3.32 (3H, s), 3.78 (3H, s), 3.80–4.00 (2H, m), 4.12 (2H, t, J=5 Hz), 4.24 (2H, t, J=5 Hz), 6.59–6.64 (2H, m), 6.88–7.12 (5H, m), 7.44 (1H, dd, J=2, 8 Hz), 8.21 (1H, d, J=8 Hz), 8.40 (1H, br)

EXAMPLE 75

To a solution of 4-[2-[(3-tert-butoxycarbonylaminoprop-1-yl)oxy]benzoyl]amino-3-methoxy-N-methyl-N-[2-[5-(4-oxopiperidin-1-yl)carbonylpent-1-yl]oxy-4-methylphenyl] benzamide (192 mg) in methanol (5 ml) was added sodium borohydride (19 mg) at ambient temperature and the mixture was stirred at the same temperate for 1 hour. The reaction was quenched with 0.5N hydrochloric acid (10 ml) and the mixture was extracted with chloroform (15 ml×3). The organic layer was washed with aqueous sodium hydrogen carbonate and brine, and the solution was dried over magnesium sulfate. The solvent was evaporated in vacuo to give 4-[2-[(3-tert-butoxycarbonylaminoprop-1-yl)oxy]benzoyl]amino-3-methoxy-N-methyl-N-[2-[5-(4-hydroxypiperidin-1-yl)carbonylpent-1-yl]oxy-4-methylphenyl]benzamide (199 mg).

NMR (CDCl$_3$, δ): 1.39 (9H, s), 1.41–1.99 (10H, m), 2.05–2.20 (2H, m), 2.27 (3H, s), 2.30–2.51 (2H, m), 3.01–3.22 (2H, m), 3.30 (3H, s), 3.65–4.14 (7H, m), 3.76 (3H, s), 4.22 (2H, t, J=5 Hz), 6.52–6.67 (2H, m), 6.78–7.10 (5H, m), 7.38–7.47 (1H, m), 8.19 (1H, d, J=7 Hz), 8.39 (1H, d, J=7 Hz)

EXAMPLE 76

To a mixture of 4-[2-[(3-tert-butoxycarbonylaminoprop-1-yl)oxy]benzoyl]amino-3-methoxy-N-methyl-N-[2-[5-(4-oxopiperidin-1-yl)carbonylpent-1-yl]oxy-4-methylphenyl] benzamide (250 mg), ammonium acetate (51 mg) and acetic acid (0.5 ml) in methanol (10 ml) was added sodium cyanoborohydride (21 mg) at 0° C. and the mixture was stirred at ambient temperature for 12 hours. The mixture was poured into ice-cooled 1N aqueous sodium hydroxide solution (15 ml) and the solution was extracted with chloroform (15 ml×3). The organic layer was washed with brine and dried over potassium carbonate. The solvent was evaporated in vacuo and the residue was purified by silica gel column chromatography (SiO$_2$ 40 g, 5–15% methanol in chloroform) to give 4-[2-[(3-tert-butoxycarbonylaminoprop-1-yl)oxy]benzoyl]amino-3-methoxy-N-methyl-N-[2-[5-(4-aminopiperidin-1-yl)carbonylpent-1-yl]oxy-4-methylphenyl]benzamide (91 mg).

NMR (CDCl$_3$, δ): 1.41 (9H, s), 1.45–2.01 (12H, m), 2.09–2.20 (2H, m), 2.28 (3H, s), 2.23–2.45 (4H, m), 2.56–2.71 (1H, br), 2.93–3.12 (2H, m), 3.25–3.36 (2H, m), 3.32 (3H, s), 3.79 (3H, s), 3.81–4.02 (2H, m), 4.23 (2H, t, J=5 Hz), 4.91–4.08 (1H, br), 6.56–6.68 (2H, m), 6.82–7.13 (5H, m), 7.45 (2H, d, J=8 Hz), 8.20 (1H, d, J=8 Hz), 8.40 (1H, d, J=8 Hz)

EXAMPLE 77

The following compound was obtained according to a similar manner to that of Example 76.

4-[2-(3-tert-Butoxycarbonylaminoprop-1-yl)oxybenzoyl]amino-3-methoxy-N-methyl-N-[2-[6-(4-methylpiperazin-1-yl)hex-1-yl]oxy-4-methylphenyl]benzamide NMR (CDCl$_3$, δ): 1.39 (9H, s), 1.45–1.84 (8H, m), 2.09–2.22 (2H, m), 2.27 (3H, s), 2.28 (3H, s), 2.32–2.59 (8H, m), 3.32 (1H, q, J=5 Hz), 3.34 (3H, s), 3.80 (3H, s), 3.82–4.01 (2H, m), 4.28 (2H, t, J=5 Hz), 6.56–6.65 (2H, m), 6.28–7.12 (6H, m), 7.43–7.50 (1H, m), 8.20 (1H, d, J=8 Hz), 8.38 (1H, d, J=8 Hz)

EXAMPLE 78

To a mixture of 4-[2-(3-tert-butoxycarbonylaminoprop-1-yl)oxybenzoyl]amino-3-methoxy-N-methyl-N-[2-[5-carboxypent-1 -yl]oxy-4-methylphenyl]benzamide (250 mg), 2-dimethylaminoethyl (99 mg) and 4-dimethylaminopyridine (36 mg) in dichloromethane (10 ml) was added N-ethyl-N'-(3-dimethylaminoprop-1-yl) carbodiimide hydrochloride (71 mg) at 0° C. and stirred at the same temperature for 7 hours. The mixture was diluted with chloroform (20 ml) and the solution was washed with water (20 ml×2) and brine. The solution was dried over magnesium sulfate and the solvent was removed under reduced pressure. This residue was purified by silica gel column chromatography (SiO$_2$ 30 g, 1–10% methanol in chloroform) to give 4-[2-(3-tert-butoxycarbonylaminoprop-1-yl)oxybenzoyl]amino-3-methoxy-N-methyl-N-[2-[5-(2-dimethylaminoeth-1-yl)oxycarbonylpent-1-yl]oxy-4-methylphenyl]benzamide (238 mg).

NMR (CDCl$_3$, δ): 1.40 (9H, s), 1.45–1.57 (2H, m), 1.65–1.90 (4H, m), 2.10–2.21 (2H, m), 2.28 (9H, s), 2.39

(2H, t, J=5 Hz), 2.55 (2H, t, J=5 Hz), 3.30 (2H, t, J=5 Hz), 3.32 (3H, s), 3.79 (3H, s), 3.82–4.00 (2H, m), 4.18 (2H, t, J=5 Hz), 4.24 (2H, t, J=5 Hz), 4.75–4.86 (1H, br), 6.54–6.67 (2H, m), 6.81–7.11 (5H, m), 7.41–7.49 (1H, m), 8.20 (1H, d, J=8 Hz), 8.49 (1H, d, J=8 Hz)

EXAMPLE 79

To a solution of 4-[2-(3-tert-butoxycarbonylaminoprop-1-yl)oxybenzoyl]amino-3-methoxy-N-methyl-N-[2-(5-ethoxycarbonylpent-1-yl)oxy-4-methylphenyl]benzamide (400 mg) in tetrahydrofuran (5 ml) was added lithium aluminum hydride (12 mg) at −23° C. and the mixture was stirred at 0° C. for 3 hours. The reaction was quenched with slow addition of 0.5N hydrochloric acid (15 ml) and the solution was stirred at ambient temperature for 20 minutes. The solution was extracted with chloroform (15 ml×3) and the organic layer was washed with aqueous saturated sodium bicarbonate solution and brine. The solution was dried over magnesium sulfate and the solvent was removed under reduced pressure to give 4-[2-(3-tert-butoxycarbonylaminoprop-1-yl)oxybenzoyl]amino-3-methoxy-N-methyl-N-[2-(6-hydroxyhex-1-yl)oxy-4-methylphenyl]benzamide (456 mg).

NMR (CDCl$_3$, δ): 1.40 (9H, s), 1.45–2.20 (10H, m), 2.27 (3H, s), 3.30 (2H, q, J=5 Hz), 3.32 (3H, s), 3.64 (2H, t, J=5 Hz), 3.78 (3H, s), 3.81–4.02 (2H, m), 4.23 (2H, t, J=5 Hz), 6.57–6.63 (2H, m), 6.84–7.13 (6H, m), 7.41–7.49 (1H, m), 8.20 (1H, d, J=7 Hz) 8.41 (1H, d, J=7 Hz)

EXAMPLE 80

To a solution of oxalyl chloride (95 mg) in dichloromethane (10 ml) was added dimethyl sulfoxide (117 mg) dropwise at −78° C. The mixture was warmed to −15° C. and a solution of 4-[2-(3-tert-butoxycarbonylaminoprop-1-yl)oxybenzoyl]amino-3-methoxy-N-methyl-N-[2-(6-hydroxyhex-1-yl)oxy-4-methylphenyl]benzamide (450 mg) in dichloromethane (10 ml) was added thereto. After being stirred at the same temperature for 10 minutes, to the reaction mixture was added triethylamine (343 mg) and stirred at the same temperature for 5 minutes. The resulting solution was warmed to ambient temperature and poured into water. The mixture was extracted with chloroform (15 ml×3) and the organic layer was washed with brine. The solution was dried over magnesium sulfate and the solvent was evaporated to give 4-[2-(3-tert-butoxycarbonylaminoprop-1-yl)oxybenzoyl]amino-3-methoxy-N-methyl-N-[2-(5-formylpent-1-yl)oxy-4-methylphenyl]benzamide (546 mg)

NMR (CDCl$_3$, δ): 1.40 (9H, s), 1.50–1.91 (6H, m), 2.11–2.23 (2H, m), 2.27 (3H, s), 2.50 (2H, t, J=5 Hz), 3.31 (1H, q, J=5 Hz), 3.34 (3H, s), 3.79 (3H, s), 3.85–4.00 (2H, m), 4.27 (2H, t, J=5 Hz), 6.60–6.68 (2H, m), 6.81–7.12 (6H, m), 7.42–7.51 (1H, m), 8.21 (1H, d, J=7 Hz), 8.41 (1H, d, J=7 Hz), 9.89 (1H, s)

EXAMPLE 81

To a solution of 4-[2-[3-(tert-butoxycarbonyl)aminoprop-1-yl]oxybenzoyl]amino-3-methoxy-N-[2-(4-cyanophenylmethyl)oxy-4-methylphenyl]-N-methylbenzamide (360 mg) in xylene (8 ml) was added trimethyltin azide (218 mg) and the solution was stirred at 120° C. for 3 days. The solution was cooled to ambient temperature and 12N hydrochloric acid (10 ml) was added to the solution to decompose tin salt of the tetrazole compound and the excess reagent. Then the solution was adjusted to pH 7 with saturated aqueous sodium hydroxide at 0° C., and the solution was extracted with ethyl acetate (50 ml×3). The organic layer was washed with brine, and dried over magnesium sulfate. The solvent was evaporated to give a crude product. The crude product was purified by silica gel column chromatography (SiO$_2$ 30 g, 2–25% methanol in chloroform) to give 4-[2-(3-aminoprop-1-yl)oxybenzoyl]amino-3-methoxy-N-[2-[4-(tetrazol-5-yl)phenylmethyl]oxy-4-methylphenyl]-N-methylbenzamide (227 mg).

NMR CDCl$_3$, δ): 2.15 (3H, br s), 2.14–2.26 (2H, m), 3.17 (2H, q, J=5 Hz), 3.40 (3H, s), 3.57 (3H, s), 4.20 (2H, t, J=5 Hz), 4.95 (1H, d, J=12 Hz), 5.22 (1H, d, J=12 Hz), 6.55–6.64 (2H, m), 6.80 (1H, s), 6.92–7.08 (6H, m), 7.23 (1H, br), 7.43 (1H, dd, J=2, 8 Hz), 7.78 (2H, d, J=8 Hz), 8.20 (1H, d, J=8 Hz)

EXAMPLE 82

A mixture of 4-[2-(3-aminoprop-1-yl)oxybenzoyl]amino-3-methoxy-N-methyl-N-[2-[5-(4-dimethylaminopiperidin-1-yl)carbonylpent-1-yl]oxy-4-methylphenyl]benzamide (275 mg) and O-methylisourea (44 mg) in ethanol (5 ml) was refluxed for 3 days. The solvent was evaporated in vacuo and the residue was purified on basic silica gel column chromatography (SiO$_2$ 17 g, 1–80% methanol in chloroform) to give 4-[2-(3-guanidinoprop-1-yl)oxybenzoyl]amino-3-methoxy-N-methyl-N-[2-[5-(4-dimethylaminopiperidin-1-yl)carbonylpent-1-yl]oxy-4-methylphenyl]benzamide (53 mg).

NMR (CDCl$_3$, δ): 1.40–1.97 (6H, m), 2.06–2.20 (2H, m), 2.27 (6H, s), 2.28 (3H, s), 2.29–2.41 (4H, m), 2.50 (1H, br), 3.04 (2H, br), 3.30 (3H, s), 3.42 (2H, br), 3.76 (3H, s), 3.78 (2H, br), 3.82–4.01 (2H, m), 4.25 (2H, br), 6.55–6.68 (2H, m), 6.81–7.09 (5H, m), 7.28 (1H, s), 7.42 (1H, dd, J=2, 8 Hz), 7.99 (1H, d, J=8 Hz), 8.29 (1H, br)

EXAMPLE 83

The following compound was obtained according to a similar manner to that of Example 6.

4-[2-[3-(tert-Butoxycarbonylamino)prop-1-yl]oxybenzoyl]amino-3-methoxy-N-[2-(4-aminobut-1-yl)oxy-4-methylphenyl]-N-methylbenzamide NMR (CDCl$_3$, δ): 1.40 (9H, s), 1.81–1.99 (4H, m), 2.05–2.14 (2H, m), 2.24 (3H, s), 3.08 (2H, br), 3.29 (2H, br), 3.30 (3H, s), 3.70 (3H, s), 3.76–3.96 (2H, m), 4.14 (2H, t, J=5 Hz), 5.07 (1H, br), 6.54–6.61 (2H, m), 6.85–7.04 (4H, m), 7.25 (1H, s), 7.37 (1H, dd, J=2, 8 Hz), 8.14 (1H, d, J=8 Hz), 8.38 (1H, d, J=8 Hz)

EXAMPLE 84

To a solution of 4-[2-[3-(tert-butoxycarbonylamino)prop-1-yloxy]benzoylamino]-3-methoxy-N-[2-[4-(phenoxycarbonylamino)but-1-yl]-4-methylphenyl]-N-methylbenzamide (200 mg) in N,N-dimethylformamide (5 ml) was added 1-methylpiperazine (88 μl) and the solution was stirred at 80° C. for 7 hours. The solution was diluted with ethyl acetate (15 ml) and washed successively with water (20 ml×4) and brine. The solvent was dried over magnesium sulfate and removed under reduced pressure. The crude product was purified on silica gel column chromatography (SiO$_2$ 25 g, chloroform-methanol 2–10%) to give pure 4-[2-[3-(tert-butoxycarbonylamino)prop-1-yl]oxybenzoyl]amino-3-methoxy-N-[2-[4-[(4-methylpiperazin-1-yl)carbonylamino]but-1-yl]oxy-4-methylphenyl]-N-methylbenzamide (124 mg).

NMR (CDCl$_3$, δ): 1.40 (9H, s), 1.60–1.81 (4H, m), 2.13–2.22 (2H, m), 2.29 (6H, s), 2.39 (4H, br), 3.79 (3H, s), 3.25–3.51 (8H, m), 3.32 (3H, s), 3.75–3.99 (2H, m), 4.26 (2H, t, J=5 Hz), 6.57–6.71 (2H, m), 6.92–7.18 (6H, m), 7.48 (1H, dd, J=2, 8 Hz), 8.20 (1H, d, J=8 Hz), 8.41 (1H, d, J=8 Hz)

EXAMPLE 85

The following compounds were obtained according to a similar manner to that of Example 84.

1) 4-[2-[3-(tert-Butoxycarbonylamino)prop-1-yl]oxybenzoyl]amino-3-methoxy-N-[2-[4-[(4-dimethylaminopiperidin-1-yl)carbonylamino]but-1-yl]oxy-4-methylphenyl]-N-methylbenzamide NMR (CDCl$_3$, δ): 1.40 (9H, s), 1.65–1.90 (4H, m), 2.29 (3H, s), 2.30 (6H, s), 2.77 (1H, t, J=11 Hz), 3.29 (2H, q, J=5 Hz), 3.32 (3H, s), 3.78 (3H, s), 3.85–4.11 (6H, m), 4.25 (2H, t, J=5 Hz), 6.55–6.70 (2H, m), 6.92–7.13 (5H, m), 7.45 (1H, dd, J=2, 8 Hz), 8.20 (1H, d, J=8 Hz), 8.40 (1H, d, J=8 Hz)

2) 4-[2-[3-(tert-Butoxycarbonylamino)prop-1-yl]oxybenzoyl]amino-3-methoxy-N-[2-(4-ureidobut-1-yl)oxy-4-methylphenyl]-N-methylbenzamide NMR (CDCl$_3$, δ): 1.40 (9H, s), 1.45–1.80 (4H, m), 2.01–2.11 (2H, m), 2.27 (3H, s), 3.22–3.31 (2H, m), 3.30 (3H, s), 3.65–3.77 (2H, m), 3.71 (3H, s), 4.22 (2H, t, J=5 Hz), 5.16 (2H, br), 6.48 (1H, s), 6.71 (1H, d, J=8 Hz), 6.90–7.15 (5H, m), 7.41 (1H, dd, J=2, 8 Hz), 8.11 (1H, d, J=8 Hz), 8.35 (1H, d, J=8 Hz)

EXAMPLE 86

To a solution of 4-[2-[3-(tert-butoxycarbonylamino)prop-1-yloxy]benzoylamino]-3-methoxy-N-[2-[4-(phenoxycarbonylamino)but-1-yl]-4-methylphenyl]-N-methylbenzamide (150 mg) in N,N-dimethylformamide (5 ml) was added dimethylamine hydrochloride (40 mg) and the mixture was stirred at 80° C. for 7 hours. The mixture was cooled to ambient temperature and diluted with ethyl acetate (15 ml). The solution was washed with water (15 ml×5) and brine, and dried over magnesium sulfate. The solvent was removed in vacuo and the residue was purified on silica gel column chromatography (SiO$_2$ 20 g, chloroform-methanol 1–5%) to give 4-[2-[3-(tert-butoxycarbonylamino)prop-1-yloxy]benzoylamino]-3-methoxy-N-[2-[4-(N,N-dimethylureido)but-1-yloxy]-4-methylphenyl]-N-methylbenzamide (115 mg).

NMR (CDCl$_3$, δ): 1.40 (9H, s), 1.60–1.87 (4H, m), 2.06–2.18 (2H, m), 2.28 (3H, s), 2.90 (6H, s), 3.30 (2H, q, J=5 Hz), 3.34 (3H, s), 3.79 (3H, s), 3.85–4.02 (2H, m), 4.23 (2H, t, J=5 Hz), 6.57–6.64 (2H, m), 6.90–7.10 (5H, m), 7.44 (1H, dd, J=2, 8 Hz), 8.20 (1H, d, J=8 Hz), 8.41 (1H, d, J=8 Hz)

EXAMPLE 87

To a solution of 4-[2-[(3-tert-butoxycarbonylaminoprop-1-yl)oxy]benzoyl]amino-3-carboxymethoxy-N-methyl-N-[2-[5-(4-methylpiperazin-1-yl)carbonylpent-1-yloxy]-4-methylphenyl]benzamide (128 mg) in methanol (5 ml) was added dropwise trimethylsilyldiazomethane (5 ml, 2.0M n-hexane solution) and stirred at ambient temperature for 30 minutes. The solution was concentrated in vacuo and the residue was purified by preparative thin layer silica gel chromatography (chloroform:methanol:28% aqueous ammonia solution, 50:5:1) to give 4-[2-[(3-tert-butoxycarbonylaminoprop-1-yl)oxy]benzoyl]amino-3-methoxycarbonylmethoxy-N-methyl-N-[2-[5-(4-methylpiperazin-1-yl)carbonylpent-1-yloxy]-4-methylphenyl]benzamide (85 mg).

NMR (CDCl$_3$, δ): 1.39 (9H, s), 1.45–1.37 (8H, m), 2.00–2.10 (2H, m), 2.26 (3H, s), 2.29 (3H, s), 2.30–2.42 (6H, m), 3.18–3.27 (2H, m), 3.30 (3H, s), 3.45–3.51 (2H, m), 3.63 (2H, br), 3.79 (3H, s), 3.87–3.96 (2H, m), 4.22–4.29 (2H, m), 4.54 (2H, s), 6.53–6.13 (2H, m), 6.77–6.85 (1H, m), 6.89 (1H, br), 6.92–7.02 (2H, m), 7.02–7.10 (1H, m), 7.43–7.47 (1H, m), 8.14–8.19 (1H, m), 8.40–8.45 (1H, m)

EXAMPLE 88

The following compound was obtained according to a similar manner to that of Example 8.

4-[2-[(3-tert-Butoxycarbonylaminoprop-1-yl)oxy]benzoyl]amino-3-dimethylaminocarbonylmethoxy-N-methyl-N-[2-[5-(4-methylpiperazin-1-yl)carbonylpent-1-yloxy]-4-methylphenyl]benzamide NMR (CDCl$_3$, δ): 1.39 (9H, s), 1.48–1.58 (2H, m), 1.63–1.88 (6H, m), 1.97–2.09 (2H, m), 2.28 (3H, s), 2.30 (3H, s), 2.31–2.42 (6H, m), 2.99 (3H, s), 3.02 (3H, s), 3.17–3.27 (2H, m), 3.32 (3H, s), 3.50 (2H, br), 3.63 (2H, br), 3.83–3.97 (2H, m), 4.22–4.29 (2H, m), 4.67 (2H, s), 6.53–6.63 (2H, m), 6.80–6.90 (2H, m), 6.96–7.09 (3H, m), 7.93 (1H, t, J=6 Hz), 8.14 (1H, d, J=6 Hz), 8.38 (1H, d, J=7 Hz)

EXAMPLE 89

To a solution of 4-[2-[(3-tert-butoxycarbonylaminoprop-1-yl)oxy]benzoyl]amino-3-ethoxycarbonylmethoxy-N-methyl-N-[2-[5-(4-methylpiperazin-1-yl)carbonylpent-1-yloxy]-4-methylphenyl]benzamide (102 mg) in 7.5N ammonia in methanol (5 ml) was stirred at ambient temperature for 24 hours. The solution was concentrated in vacuo to give 4-[2-[(3-tert-butoxycarbonylaminoprop-1-yl)oxy]benzoyl]amino-3-aminocarbonylmethoxy-N-methyl-N-[2-[5-(4-methylpiperazin-1-yl)carbonylpent-1-yloxy]-4-methylphenyl]benzamide (92 mg).

NMR (CDCl$_3$, δ): 1.37 (9H, s), 1.48–1.60 (2H, m), 1.60–1.75 (4H, m), 1.75–1.88 (2H, m), 1.97–2.08 (2H, m), 2.27 (3H, s), 2.28 (3H, s), 2.30—2.41 (6H, m), 3.17–3.27 (2H, m), 3.30 (3H, s), 3.47 (3H, s), 3.52–3.62 (2H, m), 3.90–3.97 (2H, m), 4.16–4.29 (4H, m), 5.85 (1H, br), 6.57 (1H, d, J=7 Hz), 6.67 (1H, s), 6.75–6.90 (2H, m), 7.00 (1H, d, J=7 Hz), 7.07–7.17 (2H, m), 8.00 (1H, s), 8.18–8.21 (1H, m), 8.25 (1H, d, J=7 Hz)

EXAMPLE 90

The following compound was obtained according to a similar manner to that of Example 89.

4-[2-[(3-tert-Butoxycarbonylaminoprop-1-yl)oxy]benzoyl]amino-3-methylaminocarbonylmethoxy-N-methyl-N-[2-[5-(4-methylpiperazin-1-yl)carbonylpent-1-yloxy]-4-methylphenyl]benzamide NMR (CDCl$_3$, δ): 3.37 (9H, s), 1.45–1.77 (6H, m), 1.77–1.88 (2H, m), 1.96–2.08 (2H, m), 2.28 (3H, s), 2.29 (3H, s), 2.29–2.40 (6H, m), 2.82–2.83 (3H, s), 3.18–3.27 (2H, m), 3.30 (3H, s), 3.43–3.50 (3H, m), 3.57 (2H, br), 3.90–3.97 (2H, m), 4.18–4.30 (3H, m), 6.57 (1H, d, J=6 Hz), 6.65 (1H, s), 6.76–6.83 (2H, m), 7.00 (1H, d, J=7 Hz), 7.06–7.15 (2H, m), 7.45 (1H, t, J=7 Hz), 8.16–8.22 (2H, m)

EXAMPLE 91

The following compound was obtained according to similar manners to those of Examples 8 and 16.

4-(2-Aminobenzoyl)amino-N-methyl-N-[4-methyl-2-[5-(4-methylpiperazin-1-yl)carbonylpent-1-yloxy]phenyl]benzamide dihydrochloride NMR (DMSO-d$_6$, δ): 1.35–1.66 (4H, m), 1.66–1.82 (2H, m), 2.22 (3H, s), 2.40 (2H, t, J=7 Hz), 2.73 (3H, s), 2.77–3.11 (3H, m), 3.17 (3H, s), 3.28–3.56 (3H, m), 3.76–4.17 (3H, m), 4.35–4.52 (1H, m), 6.63 (1H, d, J=9 Hz), 6.79 (1H, s), 6.91 (1H, dd, J=9, 9 Hz), 6.98–7.11 (2H, m), 7.22 (2H, d, J=9 Hz), 7.36 (1H, dd, J=9, 9 Hz), 7.54 (2H, d, J=9 Hz), 7.69 (1H, d, J=9 Hz)

EXAMPLE 92

The following compounds were obtained according to similar manners to those of Examples 6 and 16.

1) 4-[2-[(3-Aminoprop-1-yl)amino]benzoyl]amino-3-methoxy-N-methyl-N-[4-methyl-2-[5-(4-methylpiperazin-1-yl)carbonylpent-1-yloxy]phenyl]benzamide trihydrochloride NMR (DMSO-d$_6$, δ): 1.36–1.65 (4H, m), 1.66–1.92 (4H, m), 2.23 (3H, s), 2.38 (2H, t, J=7 Hz), 2.68–2.77 (3H, m), 2.77–3.12 (4H, m), 3.18 (3H, s), 3.22 (2H, t, J=7 Hz), 3.28–3.56 (3H, m), 3.63 (3H, s), 3.75–4.32 (4H, m), 4.42 (1H, m), 6.58–6.69 (2H, m), 6.78 (1H, d, J=8 Hz), 6.83 (1H, s), 6.86–6.96 (2H, m), 7.03 (1H, d, J=8 Hz), 7.34 (1H, dd, J=8, 8 Hz), 7.61 (1H, d, J=8 Hz), 7.67 (1H, d, J=8 Hz), 7.91–8.17 (3H, m), 9.23 (1H, s)

2) 4-[2-(3-Aminoprop-1-yl)oxybenzoyl]amino-3-methoxy-N-methyl-N-[2-[5-(4-methylpiperazin-1-yl)carbonylpent-1-yloxy]phenyl]benzamide dihydrochloride NMR (DMSO-d$_6$, δ): 1.34–1.66 (4H, m), 1.66–1.83 (2H, m), 2.04–2.24 (2H, m), 2.32–2.46 (2H, m), 2.74 (3H, s), 2.79–3.12 (4H, m), 3.22 (3H, s), 3.29–3.58 (3H, m), 3.63–4.19 (7H, m), 4.28–4.52 (3H, m), 6.80–7.08 (4H, m), 7.08–7.36 (4H, m), 7.58 (1H, dd, J=9, 9 Hz), 8.02 (1H, d, J=9 Hz), 8.13 (2H, br s), 8.28 (1H, d, J=9 Hz)

3) 4-[2-(3-Aminoprop-1-yl)oxybenzoyl]amino-3-methoxy-N-methyl-N-[2-[5-(4-dimethylaminopiperidin-1-yl)carbonylpent-1-yloxy]-4-methylphenyl]benzamide dihydrochloride NMR (DMSO-d$_6$, δ): 1.28–1.82 (8H, m), 1.90–2.51 (11H, m), 2.64 (6H, s), 2.74–3.06 (3H, m), 3.18 (3H, s), 3.22–4.08 (6H, m), 4.29–4.41 (2H, m), 4.51 (1H, m), 6.64 (1H, d, J=8 Hz), 6.75–7.20 (5H, m), 7.27 (1H, d, J=8 Hz), 7.58 (1H, m), 7.94–8.32 (5H, m)

4) 4-[2-(3-Aminoprop-1-yl)oxybenzoyl]amino-2-chloro-N-methyl-N-[2-[5-(4-methylpiperazin-1-ylcarbonyl)pent-1-yloxy]phenyl]benzamide dihydrochloride NMR (DMSO-d$_6$, δ): 1.39–1.68 (4H, m), 1.69–1.90 (2H, m), 1.92–2.12 (2H, m), 2.31–2.50 (2H, m), 2.73 (3H, br s), 2.79–3.10 (4H, m), 3.17–3.61 (7H, m), 3.92–4.26 (5H, m), 4.42 (1H, m), 6.77 (1H, m), 6.92–7.23 (6H, m), 7.34–7.58 (3H, m), 7.81 (1H, s), 7.90–8.14 (3H, m)

5) 4-[2-(3-Aminoprop-1-yl)oxy-5-methylbenzoyl]amino-3-methoxy-N-methyl-N-[2-[5-(4-methylpiperazin-1-yl)carbonylpent-1-yl]oxy-4-methylphenyl]benzamide dihydrochloride NMR (CDCl$_3$, δ): 1.50–1.93 (8H, m), 2.28 (3H, s), 2.28–2.36 (2H, m), 2.31 (3H, s), 2.79 (3H, s), 3.09–3.20 (2H, m), 3.29 (3H, s), 3.80 (3H, s), 3.85–4.04 (2H, m), 4.18–4.28 (2H, m), 6.57–6.66 (2H, m), 6.80–6.95 (4H, m), 7.20–7.25 (1H, m), 7.72 (1H, br), 8.51 (1H, br)

6) 4-[2-(3-Aminoprop-1-yl)oxy-4-chlorobenzoyl]amino-3-methoxy-N-methyl-N-[2-[5-(4-methylpiperazin-1-yl)carbonylpent-1-yl]oxy-4-methylphenyl]benzamide dihydrochloride NMR (CDCl$_3$, δ): 1.45–1.86 (8H, m), 2.23 (3H, s), 2.29–2.43 (2H, m), 2.78 (3H, s), 3.05–3.16 (2H, m), 3.23 (3H, s), 3.78 (3H, s), 3.82–4.03 (2H, m), 4.18–4.32 (2H, m), 6.54–6.64 (2H, m), 6.78–7.08 (4H, m), 7.94 (1H, d, J=8 Hz), 8.58 (1H, br)

7) 4-[2-(3-Aminoprop-1-yl)oxy-4-methoxybenzoyl]amino-3-methoxy-N-methyl-N-[2-[5-(4-methylpiperazin-1-yl)carbonylpent-1-yl]oxy-4-methylphenyl]benzamide dihydrochloride NMR (CDCl$_3$, δ): 1.40–1.89 (6H, m), 2.28 (3H, s), 2.30–2.61 (6H, m), 2.70–3.04 (4H, m), 3.08–3.25 (2H, m), 3.28 (3H, s), 3.80 (6H, s), 3.82–4.08 (2H, m), 4.26 (2H, br), 6.49–6.66 (4H, m), 6.78–7.00 (3H, m), 7.93–8.02 (1H, m), 8.30 (1H, br), 8.52 (2H, br)

8) 4-[2-[(3-Aminoprop-1-yl)oxy]benzoyl]amino-3-methoxy-N-methyl-N-methyl-N-[2-[5-(4-dimethylaminopiperidin-1-yl)carbonylpent-1-yloxy]phenyl]benzamide dihydrochloride NMR (DMSO-d$_6$, δ): 1.42 (2H, br), 1.53 (2H, br), 1.74 (2H, br), 2.03 (2H, br), 2.13–2.20 (2H, m), 2.30–2.38 (2H, m), 2.66 (3H, s), 2.67 (3H, s), 2.94 (4H, br), 3.20 (3H, s), 3.28–3.40 (2H, m), 3.73 (3H, s), 3.82–4.08 (4H, m), 4.33–4.40 (2H, m), 4.47–4.57 (1H, m), 6.82–7.00 (4H, m), 7.10–7.29 (4H, m), 7.53–7.60 (1H, m), 8.00 (1H, d, J=7 Hz), 8.22–8.30 (1H, m)

9) 4-[2-[(3-Aminoprop-1-yl)oxy]benzoyl]amino-3-methyl-N-methyl-N-[2-[5-(4-methylpiperazin-1-yl)carbonylpent-1-yloxy]-4-methylphenyl]benzamide dihydrochloride NMR (DMSO-d$_6$, δ): 1.40–1.53 (2H, m), 1.53–1.65 (2H, m), 1.66–1.82 (2H, m), 2.01–2.13 (2H, m), 2.18 (3H, s), 2.23 (3H, s), 2.36–2.46 (2H, m), 2.73–2.74 (3H, s), 2.78–3.08 (6H, m), 3.18 (3H, s), 4.27 (2H, br), 4.40–4.50 (1H, m), 6.65 (1H, d, J=6 Hz), 6.82 (1H, s), 6.98–7.13 (3H, m), 7.17–7.30 (2H, m), 7.45–7.57 (2H, m), 7.22 (1H, d, J=6 Hz), 9.67 (1H, s)

10) 4-[2-[(3-Aminoprop-1-yl)oxy]benzoyl]amino-3-ethoxy-N-methyl-N-[2-[5-(4-methylpiperazin-1-yl)carbonylpent-1-yloxy]-4-methylphenyl]benzamide dihydrochloride NMR (DMSO-d$_6$, δ): 1.23 (3H, t, J=6 Hz), 1.38–1.50 (2H, m), 1.50–1.65 (2H, m), 1.65–1.82 (2H, m), 2.05–2.17 (2H, m), 2.21 (3H, s), 2.32–2.43 (2H, m), 2.70–2.73 (3H, m), 2.80–3.08 (7H, m), 3.18 (3H, s), 3.22–3.55 (6H, m), 3.92–4.15 (2H, m), 4.32–4.48 (4H, m), 6.63 (1H, d, J=7 Hz), 6.83 (1H, s), 6.89–6.92 (2H, m), 7.02 (1H, d, J=7 Hz), 7.13 (1H, t, J=6 Hz), 7.29 (1H, d, J=7 Hz), 7.58 (1H, t, J=7 Hz), 7.99 (1H, d, J=7 Hz), 8.18–8.27 (1H, m)

EXAMPLE 93

The following compounds were obtained according to similar manners to those of Examples 1 and 16.

1) 4-[2-(Dimethylamino)benzoyl]amino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.36–1.65 (4H, m), 1.67–1.82 (2H, m), 2.22 (3H, s), 2.38 (2H, t, J=7 Hz), 2.64–3.14 (12H, m), 3.18 (3H, s), 3.28–3.42 (2H, m), 3.50 (1H, m), 3.73 (3H, s), 3.79–4.14 (3H, m), 4.42 (1H, m), 6.64 (1H, d, J=8 Hz), 6.82 (1H, s), 6.83–6.97 (2H, m), 7.02 (1H, d, J=8 Hz), 7.35 (1H, m), 7.52–7.67 (2H, m), 8.07 (1H, d, J=8 Hz), 8.14 (1H, m)

2) 4-[2-(Dimethylaminosulfonyl)benzoyl]amino-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.38–1.64 (4H, m), 1.67–1.82 (2H, m), 2.23 (3H, s), 2.38 (2H, t, J=7 Hz), 2.69 (6H, s), 2.74 (3H, s), 2.80–3.12 (4H, m), 3.18 (3H, s), 3.23–3.52 (2H, m), 3.59 (3H, s), 3.81–4.16 (3H, m), 4.44 (1H, m), 6.66 (1H, d, J=9 Hz), 6.77–6.96 (3H, m), 7.02 (1H, d, J=9 Hz), 7.51 (1H, m), 7.60–7.92 (4H, m)

3) 3-Methoxy-4-[2-(morpholinosulfonyl)benzoyl]amino-N-methyl-N-[4-methyl-2-[5-(4-methylpiperazin-1yl)carbonylpent-1-yloxy]phenyl]benzamide hydrochloride NMR (DMSO-$d_6$, δ): 1.37–1.65 (4H, m), 1.66–1.83 (2H, m), 2.23 (3H, s), 2.32–2.44 (2H, m), 2.73 (3H, s), 2.81–3.10 (6H, m), 3.18 (3H, s), 3.25–3.71 (11H, m), 3.80–4.20 (3H, m), 4.42 (1H, m), 6.66 (1H, d, J=8 Hz), 6.76–6.96 (3H, m), 7.02 (1H, d, J=8 Hz), 7.53 (1H, d, J=8 Hz), 7.62–7.93 (4H, m), 8.31 (1H, s)

4) 4-[2-(Isoprop-1-yl)oxybenzoyl]amino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.39 (6H, d, J=7 Hz), 1.38–1.66 (4H, m), 1.67–1.83 (2H, m), 2.22 (3H, s), 2.39 (2H, t, J=7 Hz), 2.76 (3H, s), 2.82–3.11 (4H, m), 3.18 (3H, s), 3.74 (3H, s), 3.79–4.18 (5H, m), 4.36–4.52 (1H, m), 4.98 (1H, m), 6.65 (1H, d, J=8 Hz), 6.73–7.17 (5H, m), 7.30 (1H, d, J=8 Hz), 7.54 (1H, dd, J=8, 8 Hz), 8.04 (1H, d, J=8 Hz), 8.31 (1H, d, J=8 Hz)

EXAMPLE 94

The following compound was obtained according to similar manners to those of Examples 16 and 30.

4-[2-[2-[(3-Aminoprop-1-yl)oxy]phenyl]vinyl]-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.33–1.64 (4H, m), 1.64–1.83 (2H, m), 1.95–2.17 (2H, m), 2.22 (3H, s), 2.39 (2H, t, J=7 Hz), 2.72 (3H, s), 2.78–3.10 (6H, m), 3.15 and 3.16 (total 3H, s), 3.28–3.60 (2H, m), 3.64 (3H, s), 3.80–4.20 (5H, m), 4.42 (1H, m), 6.44–7.60 (12H, m), 8.00–8.26 (2H, m)

EXAMPLE 95

The following compounds were obtained according to similar manners to those of Examples 1 and 43.

1) 4-(2-Hydroxybenzoyl)amino-3-methoxy-N-[2-[4-(4-dimethylaminopiperidin-1-yl)carbonyl-4-methyl]phenylmethoxy]phenyl-N-methylbenzamide MASS (m/z): 637 (M+1)

2) 4-(2-Hydroxy)benzoylamino-3-methoxy-N-methyl-N-[2-[3-(4-methylpiperazin-1-yl)carbonylmethoxyprop-1-yl]oxy]phenylbenzamide NMR (CDCl$_3$, δ): 2.05–2.16 (2H, m), 2.28 (3H, s), 2.33–2.40 (4H, m), 3.35 (3H, s), 3.40–3.45 (2H, m), 3.57–3.63 (2H, m), 3.69 (2H, t, J=7.5 Hz), 3.78 (3H, s), 3.94–4.11 (2H, m), 4.12 (2H, s), 6.79–7.04 (7H, m), 7.18 (1H, t, J=7 Hz), 7.42 (1H, t, J=7 Hz), 7.50 (1H, d, J=7 Hz), 8.20 (1H, d, J=7 Hz), 8.81 (1H, s)

3) 4-(2-Hydroxy)benzoyl-3-methoxy-N-[2-[(E)-5-(4-dimethylaminopiperidin-1-yl)carbonyl-4-penten-1-yl]oxy-4-methyl]phenyl-N-methylbenzamide NMR (CDCl$_3$, δ): 1.33–1.53 (2H, m), 1.84–2.05 (4H, m), 2.27 (3H, s), 2.33 (3H, s), 2.40 (3H, s), 2.30–4.13 (11H, m), 3.32 (3H, s), 4.67 (1H, m), 6.30 (1H, d, J=15 Hz), 6.55–6.66 (2H, m), 6.78–7.56 (8H, m), 8.18 (1H, m)

EXAMPLE 96

The following compound was obtained according to similar manners to those of Examples 4, 16 and 45.

4-[2-[(3-Aminoprop-1-yl)oxy]benzoyl]amino-3-(3-carboxyprop-1-yl)oxy-N-methyl-N-[2-[5-(4-methylpiperazin-1-yl)carbonylpent-1-yloxy]-4-methylphenyl]benzamide dihydrochloride NMR (DMSO-$d_6$, δ): 1.38–1.52 (2H, m), 1.52–1.65 (2H, m), 1.67–1.93 (4H, m), 2.05–2.16 (2H, m), 2.01 (3H, s), 2.29–2.43 (5H, m), 2.73 (3H, s), 3.22–3.56 (4H, m), 3.82–4.14 (5H, m), 4.30–4.47 (3H, m), 8.63 (1H, d, J=7 Hz), 8.81 (1H, s), 8.88–8.92 (2H, m), 7.03 (1H, d, J=7 Hz), 7.13 (1H, t, J=7 Hz), 7.27 (1H, d, J=7 Hz), 7.56 (1H, t, J=6 Hz), 7.96 (1H, d, J=6 Hz), 8.22 (1H, d, J=7 Hz)

EXAMPLE 97

The following compound was obtained according to similar manners to those of Preparation 4 and Example 16.

4-(2-Aminobenzyloxy)-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.35–1.64 (4H, m), 1.64–1.81 (2H, m), 2.23 (3H, s), 2.39 (2H, t, J=7 Hz), 2.75 (3H, s), 2.80–3.09 (2H, m), 3.16 (3H, s), 3.27–3.50 (2H, m), 3.57 (3H, s), 3.73–4.15 (5H, m), 4.43 (1H, m), 5.08 (2H, s), 6.64 (1H, d, J=8 Hz), 6.76–7.42 (9H, m)

EXAMPLE 98

The following compound was obtained according to similar manners to those of Examples 14 and 16.

4-[2-(3-Acetylaminoprop-1-yl)oxybenzoyl]amino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.36–1.50 (2H, m), 1.50–1.64 (2H, m), 1.67–1.84 (2H, m), 1.92–2.06 (2H, m), 2.22 (3H, s), 2.32–2.44 (2H, m), 2.50 (3H, s), 2.74 (3H, s), 2.74 and 2.75 (total 3H, s), 2.81–3.08 (3H, m), 3.19 (3H, s), 3.30–3.54 (3H, m), 3.70 (3H, s), 3.79–4.16 (3H, m), 4.20–4.30 (2H, m), 6.64 (1H, d, J=8 Hz), 6.81 (1H, s), 6.83–6.97 (2H, m), 7.03 (1H, d, J=8 Hz), 7.12 (1H, dd, J=8, 8 Hz), 7.25 (1H, d, J=8 Hz), 7.51–7.61 (1H, m), 7.92–8.08 (2H, m), 8.28 (1H, d, J=8 Hz)

EXAMPLE 99

The following compound was obtained according to similar manners to those of Examples 15 and 26.

4-[2-(3-Dimethylaminoprop-1-yl)oxybenzoyl]amino-3-methoxy-N-methyl-N-[2-[5-(4-dimethylaminopiperidin-1-yl)carbonylpent-1-yl]oxy-4-methylphenyl)benzamide dihydrochloride NMR (CDCl$_3$, δ): 1.46–1.87 (6H, m), 2.26 (3H, s), 2.37 (2H, t, J=5 Hz), 2.50 (2H, br), 2.76 (6H, s), 2.77 (6H, s), 3.02–3.30 (3H, m), 3.29 (3H, s), 3.79 (3H, s), 3.80–4.04 (2H, m), 4.33 (2H, br), 6.54–6.62 (2H, m), 6.72–7.13 (5H, m), 8.05 (1H, d, J=8 Hz), 8.37 (1H, d, J=8 Hz), 9.85 (1H, br)

EXAMPLE 100

The following compound was obtained according to similar manners to those of Examples 8 and 45.

4-[2-(3-Aminoprop-1-yl)oxybenzoyl]amino-3-methoxy-N-methyl-N-[2-(5-dimethylaminocarbonyl)pent-1-yloxy-4-methylphenyl]benzamide NMR (CDCl$_3$, δ): 1.51–2.19 (10H, m), 2.27 (3H, s), 2.35 (2H, t, J=6 Hz), 2.92 (3H, s), 3.00 (3H, s), 3.32 (3H, s), 3.77 (3H, s), 3.80–4.08 (2H, m), 4.29 (2H, t, J=4 Hz), 6.55–6.76 (2H, m), 6.83–7.20 (5H, m), 7.46 (1H, br), 8.21 (1H, d, J=8 Hz), 8.40 (1H, d, J=8 Hz)

EXAMPLE 101

The following compound was obtained according to similar manners to those of Examples 16 and 41.

4-(2-Aminobenzoyl)amino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.38–1.66 (4H, m), 1.68–1.83 (2H, m), 2.24 (3H, s), 2.34–2.44 (2H, m), 2.76 (3H, s), 2.80–3.09 (3H, m), 3.19 (3H, s), 3.30–3.53 (3H, m), 3.64 (3H, s), 3.80–4.51 (4H, m), 6.60–6.76 (2H, m), 6.79–6.97 (4H, m), 7.05 (1H, d, J=9 Hz), 7.26 (1H, dd, J=9, 9 Hz), 7.58–7.72 (2H, m), 9.19 (1H, br s)

EXAMPLE 102

To a solution of 4-[2-[(3-aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide (7.35 g) in ethanol (230 ml) was added 0.5M sulfuric acid in ethanol (22.3 ml) at 80° C. The mixture was stirred for 24 hours at ambient temperature. The precipitate was filtered through a glass funnel followed by rinsing with ethanol. The resulting white, crystalline solid was dried over air for 7 days to give 4-[2-[(3-aminoprop-1-yl)oxy]benzoyl]amino-3-methoxy-N-methyl-N-[4- methyl-2-[5-(4-methylpiperazin-1-yl)carbonylpent-1-yloxy]phenyl]benzamide sulfate (5.2 g).

NMR (DMSO-d$_6$, δ): 1.35–1.63 (4H, m), 1.65–1.81 (2H, m), 2.04–2.40 (14H, m), 2.96 (2H, t, J=7 Hz), 3.03–4.06 (12H, m), 4.35 (2H, t, J=7 Hz), 6.64 (1H, d, J=8 Hz), 6.83 (1H, s), 6.89 (1H, d, J=8 Hz), 6.98 (1H, s), 7.02 (1H, d, J=8 Hz), 7.13 (1H, dd, J=8, 8 Hz), 7.26 (1H, d, J=8 Hz), 7.59 (1H, dd, J=8, 8 Hz), 8.01 (1H, d, J=8 Hz), 8.23 (1H, d, J=8 Hz)

EXAMPLE 103

To a solution of 4-[2-[(3-aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide (10.7 g) in ethanol (155 ml) was added a solution of L-(+) tartaric acid (2.43 g) in ethanol (60 ml) at 80° C. The solution was stirred at ambient temperature for 1 hour. The solvent was removed at reduced pressure and resulting solid was dissolved in distilled water (1 l) and the solution was filtered through micro filter and the filtrate was lyophilized to give 4-[2-[(3-aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide tartrate (5.2 g).

NMR (DMSO-d$_6$, δ): 1.34–1.62 (4H, m), 1.66–1.81 (2H, m), 2.03–2.38 (14H, m), 2.96 (2H, t, J=7 Hz), 3.18 (3H, s), 3.37–3.48 (4H, m), 3.74 (3H, s), 3.80–4.04 (4H, m), 4.33 (2H, t, J=7 Hz), 6.64 (1H, d, J=8 Hz), 6.83 (1H, s), 6.89 (1H, d, J=8 Hz), 6.97 (1H, s), 7.02 (1H, d, J=8 Hz), 7.13 (1H, dd, J=8, 8 Hz), 7.26 (1H, d, J=8 Hz), 7.58 (1H, dd, J=8, 8 Hz), 8.02 (1H, d, J=8 Hz), 8.25 (1H, d, J=8 Hz)

EXAMPLE 104

The following compounds were obtained according to similar manners to those of Examples 16 and 45.

1) 4-[2-[(3-Aminoprop-1-yl)oxy]benzoyl]amino-3-methoxy-N-methyl-N-(2-methylphenyl)benzamide hydrochloride NMR (DMSO-d$_6$, δ): 2.06–2.32 (5H, m), 2.87–3.05 (2H, m), 3.26 (3H, s), 3.72 (3H, s), 4.35 (2H, t, J=7 Hz), 6.84–6.98 (2H, m), 7.08–7.36 (6H, m), 7.58 (1H, dd, J=8, 8 Hz), 7.89–8.16 (4H, m), 8.26 (1H, d, J=8 Hz)

2) 4-[3-[(3-Aminoprop-1-yl)oxy]benzoyl]amino-3-methoxy-N-methyl-N-[4-methyl-2-[5-(4-dimethylaminopiperidin-1-yl)carbonylpent-1-yloxy]phenyl]benzamide dihydrochloride NMR (DMSO-d$_6$, δ): 1.38–1.78 (12H, m), 1.98–2.07 (4H, m), 2.24 (3H, s), 2.36 (2H, t, J=8 Hz), 2.43–2.54 (1H, m), 2.67 (3H, s), 2.69 (3H, s), 2.92–3.01 (2H, m), 3.19 (3H, s), 3.64 (3H, s), 3.88–4.03 (1H, m), 4.13 (2H, t, J=8 Hz), 4.48–4.57 (1H, m), 6.65 (1H, d, J=8 Hz), 6.82 (1H, s), 6.88–6.93 (2H, m), 7.03 (1H, d, J=8 Hz), 7.17 (1H, d, J=8 Hz), 7.38–7.52 (3H, m), 7.62 (1H, d, J=8 Hz), 7.92–8.01 (2H, br), 9.33 (1H, s) ESI-MASS (m/z): 688 (M+H)

3) 4-[N-Methyl-2-[(3-aminoprop-1-yl)oxy]benzoyl]amino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.32–1.65 (8H, m), 2.27 (3H, s), 2.33–2.40 (2H, m), 2.77 (3H, s), 2.86–3.02 (5H, m), 3.12 (3H, s), 3.33–3.70 (13H, m), 4.00–4.10 (1H, m), 4.40–4.50 (1H, m), 6.58–6.78 (6H, m), 6.84–7.00 (3H, m), 7.20 (1H, t, J=8 Hz), 7.89–7.97 (2H, br s) ESI-MASS (m/z): 674

4) 4-[2-[3-Aminoprop-1-yl)oxy]benzoyl]amino-3-methoxy-N-methyl-N-[4-[5-(4-methylpiperazin-1-yl)carbonylpent-1-yloxy]phenyl]benzamide dihydrochloride NMR (DMSO-d$_6$, δ): 1.37–1.73 (8H, m), 2.12–2.20 (2H, m), 2.37 (2H, t, J=8 Hz), 2.72–2.79 (4H, m), 2.89–3.01 (4H, m), 3.29–3.40 (4H, m), 3.80 (3H, s), 3.89 (2H, t, J=8 Hz), 3.98–4.04 (1H, m), 4.34–4.41 (3H, m), 6.80–6.86 (3H, m), 7.04–7.19 (4H, m), 7.29 (1H, t, J=8 Hz), 7.59 (1H, t, J=8 Hz), 7.95–8.06 (4H, m), 8.27 (1H, d, J=8 Hz) ESI-MASS (m/z): 646 (M+H)

5) 4-[2-(3-Aminoprop-1-yl)oxybenzoyl]amino-3-methoxy-N-methyl-N-[2-[5-(4-methylhomopiperazin-1-yl)carbonylpent-1-yl]oxy-4-methylphenyl]benzamide dihydrochloride NMR (CDCl$_3$, δ): 1.47–1.89 (8H, m), 2.27 (3H, s), 2.30–2.46 (4H, m), 2.77–2.96 (2H, m), 3.15–3.63 (11H, m), 3.30 (3H, s), 3.76–4.04 (5H, m), 4.15–4.40 (2H, m), 6.60 (2H, br), 6.78–7.11 (5H, m), 7.43 (1H, br), 7.98–8.05 (1H, m), 8.29–8.37 (1H, m), 8.52 (2H, br)

6) 4-[2-(3-Aminoprop-1-yl)oxybenzoyl]amino-3-methoxy-N-methyl-N-[2-[5-(2-dimethylaminoethyl)aminocarbonyl]pent-1-yl]oxy-4-methylphenyl]benzamide dihydrochloride NMR (CDCl$_3$, δ): 1.38–1.87 (6H, m), 2.06–2.45 (4H, m), 2.22 (3H, s), 2.25–2.44 (2H, m), 2.76 (3H, s), 2.80 (3H, s), 3.07–3.22 (2H, m), 3.24 (3H, s), 3.54 (2H, br), 3.77–3.95 (2H, m), 3.80 (3H, s), 4.24 (2H, br), 6.57–6.62 (2H, m), 6.80–7.08 (4H, m), 7.39–7.47 (1H, m), 7.97 (1H, d, J=8 Hz), 8.20–8.38 (2H, m)

7) 4-[2-(3-Aminoprop-1-yl)oxybenzoyl]amino-3-methoxy-N-methyl-N-[2-[5-[N-(2-dimethylaminoethyl)-N-methylaminocarbonyl]pent-1-yl]oxy-4-methylphenyl]benzamide dihydrochloride NMR (CDCl$_3$, δ): 1.37–1.82 (6H, m), 2.22 (3H, s), 2.29–2.47 (4H, m), 2.85 (6H, s), 3.02 (3H, s), 3.08–3.33 (6H, m), 3.26 (3H, s), 3.58–3.95 (4H, m), 3.83 (3H, s), 4.28 (3H, br), 6.55–6.65 (2H, m), 6.82–7.06 (5H, m), 7.39–7.47 (1H, m), 8.03 (1H, d, J=8 Hz), 8.33 (1H, br)

8) 4-[2-(3-Aminoprop-1-yl)oxybenzoyl]amino-3-methoxy-N-methyl-N-[2-[5-[N-(3-dimethylaminoprop-1-yl)carbamoyl]pent-1-yl]oxy-4-methylphenyl]benzamide dihydrochloride NMR (CDCl$_3$, δ): 1.37–1.99 (8H, m), 2.23 (3H, s), 2.25–2.44 (4H, m), 2.76 (6H, s), 3.05–3.41 (6H, m), 3.22 (3H, s), 3.78–3.94 (2H, m), 4.22 (2H, br), 6.56 (2H, br), 6.81–7.04 (5H, m), 7.39 (1H, br), 8.00 (1H, br), 8.29 (1H, br), 8.56 (3H, br)

9) 4-[2-(3-Aminoprop-1-yl)oxybenzoyl]amino-3-methoxy-N-methyl-N-[2-[5-[N-(3-dimethylaminoprop-1-yl)-N-methylcarbamoyl]pent-1-yl]oxy-4-methylphenyl]benzamide dihydrochloride NMR (CDCl$_3$, δ): 1.33–1.99 (8H, m), 2.26 (3H, s), 2.26–2.47 (4H, m), 2.78 (6H, s), 2.96 (3H, s), 3.05–3.39

(6H, m), 3.26 (3H, s), 3.79–3.99 (2H, m), 3.78 (3H, s), 4.30 (2H, br), 6.62 (2H, m), 6.83–7.08 (5H, m), 7.45 (1H, br), 8.01 (1H, br), 8.35 (1H, br), 8.64 (2H, br)

10) 4-[2-(3-Aminoprop-1-yl)oxybenzoyl]amino-3-methoxy-N-methyl-N-[2-[5-(4-hydroxypiperidin-1-yl)carbonylpent-1-yl]oxy-4-methylphenyl]benzamide hydrochloride NMR (CDCl$_3$, δ): 1.32–2.06 (10H, m), 2.23 (3H, s), 2.25–2.40 (4H, m), 2.99–3.07 (2H, m), 3.23 (3H, s), 3.43–4.00 (7H, m), 4.23 (2H, br), 6.52–6.63 (2H, m), 6.81–7.12 (4H, m), 7.38–7.49 (1H, m), 7.97 (1H, br), 8.30 (1H, br)

11) 4-[2-(3-Aminoprop-1-yl)oxybenzoyl]amino-3-methoxy-N-methyl-N-[2-[5-(4-aminopiperidin-1-yl)carbonylpent-1-yl]oxy-4-methylphenyl]benzamide dihydrochloride NMR (CDCl$_3$, δ): 1.40–1.85 (12H, m), 2.24 (3H, s), 2.28–2.45 (2H), 2.87–3.11 (7H, m), 3.25 (3H, s), 3.84–4.00 (2H, m), 3.79 (3H, s), 4.25 (2H, br), 6.54–6.63 (2H, m), 6.95–7.09 (4H, m), 7.43 (1H, br), 8.04 (1H, br), 8.41 (1H, br)

12) 4-[2-(3-Aminoprop-1-yl)oxybenzoyl]amino-3-methoxy-N-methyl-N-[2-[5-(4-methylpiperazin-1-yl)aminocarbonylpent-1-yl]oxy-4-methylphenyl]benzamide trihydrochloride NMR (CDCl$_3$, δ): 1.32–1.80 (6H, m), 2.04–2.15 (2H, m), 2.26 (3H, s), 2.90–3.36 (10H, m), 3.24 (3H, s), 3.76 (3H, s), 3.85–4.02 (2H, m), 4.26 (2H, br), 6.54–6.63 (2H, m), 6.75–7.09 (4H, m), 7.40–7.49 (1H, m), 8.00 (1H, d, J=8 Hz), 8.39 (1H, br), 8.62 (1H, br)

13) 4-[2-(3-Aminoprop-1-yl)oxybenzoyl]amino-3-methoxy-N-methyl-N-[2-[5-[bis(2-hydroxyeth-1-yl)amino]carbonylpent-1-yl]oxy-4-methylphenyl]benzamide hydrochloride NMR (CDCl$_3$, δ): 1.50–1.88 (6H, m), 2.05–2.54 (4H, m), 2.28 (3H, s), 3.03 (2H, br), 3.30 (3H, s), 3.41–3.69 (8H, m), 3.78 (3H, s), 3.82–4.00 (2H, m), 4.23 (2H, br), 6.59–6.69 (2H, m), 6.81–7.22 (4H, m), 7.46 (1H, br), 8.09 (1H, br), 8.38 (1H, br)

14) 4-[2-(3-Aminoprop-1-yl)oxybenzoyl]amino-3-methoxy-N-methyl-N-[2-[5-(2,2-dimethylhydrazino)carbonylpent-1-yl]oxy-4-methylphenyl]benzamide dihydrochloride NMR (CDCl$_3$, δ): 1.36–1.82 (6H, m), 2.22 (3H, s), 2.26–2.39 (4H, m), 2.88–3.11 (2H, m), 3.11 (6H, s), 3.32 (3H, s), 3.70–3.94 (2H, m), 3.77 (3H, s), 4.21 (2H, br), 6.52–6.61 (2H, m), 6.80–7.14 (5H, m), 7.42 (1H, br), 7.97 (1H, br), 8.25 (3H, br)

15) 4-[2-(3-Aminoprop-1-yl)oxybenzoyl]amino-3-methoxy-N-methyl-N-[2-[5-(carbamoylmethylamino)carbonylpent-1-yl]oxy-4-methylphenyl]benzamide hydrochloride NMR (CDCl$_3$, δ): 1.20–1.68 (6H, m), 2.08–2.41 (7H, m), 2.97–3.35 (5H, m), 3.29–4.27 (9H, m), 6.38–7.04 (6H, m), 7.90–8.29 (6H, m)

16) 4-[2-(3-Aminoprop-1-yl)oxybenzoyl]amino-3-methoxy-N-methyl-N-[2-[5-(2-carbamoylethylamino)carbonylpent-1-yl]oxy-4-methylphenyl]benzamide hydrochloride NMR (CDCl$_3$, δ): 1.36–1.81 (6H, m), 2.06–2.40 (6H, m), 2.23 (3H, s), 3.13 (2H, br), 3.22 (3H, s), 3.32 (2H, br), 3.55–3.93 (2H, m), 3.78 (3H, s), 4.22 (2H, br), 6.53–6.63 (2H, m), 6.81–7.04 (5H, m), 7.39 (1H, br), 7.77 (1H, br), 7.99 (1H, br), 8.28–8.47 (3H, m)

17) 4-[2-(3-Aminoprop-1-yl)oxybenzoyl]amino-3-methoxy-N-methyl-N-[2-[5-(4-pyridylaminocarbonyl)pent-1-yl]oxy-4-methylphenyl]benzamide dihydrochloride NMR (CDCl$_3$, δ): 1.25–1.83 (6H, m), 2.10–2.49 (4H, m), 2.22 (3H, s), 2.90–3.37 (2H, m), 3.23 (3H, s), 3.68–3.95 (2H, m), 3.76 (3H, s), 4.21 (2H, br), 6.51–6.63 (2H, m), 6.66–7.04 (6H, m), 7.88–8.51 (7H, m)

18) 4-[2-(3-Aminoprop-1-yl)oxybenzoyl]amino-3-methoxy-N-methyl-N-[2-[5-[4-(diethylaminopiperidin-1-yl)carbonylpent-1-yl]oxy-4-methylphenyl]benzamide dihydrochloride NMR (CDCl$_3$, δ): 1.38 (6H, t, J=8 Hz), 1.45–1.90 (10H, m), 1.93–2.08 (2H, m), 2.28 (3H, s), 2.30–2.48 (2H, m), 2.92–3.23 (5H, m), 3.25–3.36 (4H, m), 3.29 (3H, s), 3.69 (3H, s), 3.75–4.08 (3H, m), 4.28 (2H, br), 6.54–6.65 (2H, m), 6.81–7.08 (5H, m), 7.45 (1H, br), 7.93 (1H, br), 8.36 (1H, br)

19) 4-[2-(3-Aminoprop-1-yl)oxybenzoyl]amino-3-methoxy-N-methyl-N-[2-[6-(4-methylpiperazin-1-yl)hex-1-yl]oxy-4-methylphenyl]benzamide trihydrochloride NMR (CDCl$_3$, δ): 1.36–1.94 (8H, m), 2.21 (3H, s), 2.25–2.42 (2H, m), 2.90–3.39 (6H, m), 3.10 (3H, s), 3.19 (3H, s), 3.58–4.04 (6H, m), 3.82 (3H, s), 4.18 (1H, br), 6.46–6.63 (2H, m), 6.74–6.98 (4H, m), 7.38 (1H, br), 7.97 (1H, br), 8.28 (1H, br), 8.45 (2H, br)

20) 4-[2-(3-Aminoprop-1-yl)oxybenzoyl]amino-3-methoxy-N-[2-[4-(2-pyridyl)phenylmethyl]oxy-4-methylphenyl]-N-methylbenzamide dihydrochloride NMR (CDCl$_3$, δ): 2.29 (3H, s), 2.39 (2H, br), 3.17 (2H, br), 3.37 (3H, s), 3.44 (3H, br), 4.12–4.30 (2H, m), 4.73 (1H, br), 5.07 (1H, br), 6.61 (1H, br), 6.70–6.79 (2H, m), 6.94–7.03 (2H, m), 7.12 (1H, d, J=8 Hz), 7.38–7.47 (3H, m), 7.89–8.23 (5H, m), 8.73 (3H, br), 8.90 (1H, br)

21) 4-[2-(3-Aminoprop-1-yl)oxybenzoyl]amino-3-methoxy-N-[2-[4-[(4-methylpiperazin-1-yl)carbonylamino]but-1-yl]oxy-4-methylphenyl]-N-methylbenzamide dihydrochloride NMR (CDCl$_3$, δ): 1.62–2.04 (4H, m), 2.23 (3H, s), 2.27–2.40 (2H, m), 2.74 (3H, s), 3.03–3.14 (2H, m), 3.22 (3H, s), 3.35–3.51 (4H, m), 3.78 (3H, s), 3.85–3.96 (2H, m), 4.26 (2H, br), 6.57–6.64 (2H, m), 6.67–7.09 (5H, m), 7.42 (1H, m), 7.96 (1H, d, J=8 Hz), 8.30 (1H, d, J=8 Hz), 8.60 (3H, m)

22) 4-[2-(3-Aminoprop-1-yl)oxybenzoylamino]-3-methoxy-N-[2-[4-[(4-dimethylaminopiperidin-1-yl)carbonylamino]but-1-yl]oxy-4-methylphenyl]-N-methylbenzamide dihydrochloride NMR (CDCl$_3$, δ): 1.58–2.12 (10H, m), 2.27 (3H, s), 2.30–2.48 (2H, m), 2.57–2.81 (8H, m), 3.05–3.31 (7H, m), 3.27 (3H, s), 3.75–3.99 (5H, m), 4.27 (1H, br), 6.57–6.63 (2H, m), 6.85–7.09 (5H, m), 7.44 (2H, br), 7.96 (1H, br), 8.34 (1H, br), 8.75 (1H, br)

23) 4-[2-(3-Aminoprop-1-yl)oxybenzoyl]amino-3-methoxy-N-[2-(4-ureidobut-1-yl)oxy-4-methylphenyl]-N-methylbenzamide hydrochloride NMR (CDCl$_3$, δ): 1.42–1.81 (4H, m), 2.00–2.15 (2H, m), 2.25 (3H, s), 2.88 (2H, t, J=5 Hz), 2.92 (2H, br), 3.30 (3H, s), 3.63–3.80 (2H, m), 3.71 (3H, s), 4.21 (2H, t, J=5 Hz), 6.51 (1H, s), 6.71 (1H, d, J=8 Hz), 6.85–7.12 (5H, m), 7.44 (1H, dd, J=2, 8 Hz), 8.12 (1H, d, J=8 Hz), 8.36 (1H, d, J=8 Hz)

24) 4-[2-[3-Aminoprop-1-yl)oxy]benzoyl]amino-3-chloro-N-methyl-N-[2-[5-(4-dimethylaminopiperidin-1-yl)carbonylpent-1-yloxy]-4-methylphenyl]benzamide dihydrochloride NMR (DMSO-d$_6$, δ): 1.34–1.50 (2H, m), 1.50–1.62 (2H, m), 1.65–1.80 (2H, m), 1.98–2.17 (4H, m), 2.22 (3H, s), 2.30–2.40 (2H, m), 2.66 (3H, s), 2.67 (3H, s), 2.85–3.05 (3H, m), 3.17 (3H, s), 3.33 (1H, br), 3.80–4.07 (3H, m), 4.33–4.42 (2H, m), 4.47–4.57 (1H, m), 6.68 (1H, d, J=7 Hz), 25) 3-(3-Aminoprop-1-yl)oxy-4-[2-[3-aminoprop-1-yl) oxy]benzoyl]amino-N-methyl-N-[2-[5-(4-methylpiperazin-1-yl)carbonylpent-1-yloxy]-4-methylphenyl]benzamide trihydrochloride NMR (DMSO-$d_6$, δ): 1.37–1.50 (2H, m), 1.50–1.62 (2H, m), 1.67–1.80 (2H, m), 1.97–2.19 (4H, m), 2.22 (3H, s), 2.30–2.41 (2H, m), 2.57 (1H, s), 2.92 (6H, br), 3.17 (3H, s), 3.68 (1H, br), 3.93 (2H, br), 4.10 (2H, br), 4.40 (2H, br), 6.66 (1H, d, J=6 Hz), 6.78–6.87 (2H, m), 6.95–7.04 (2H, m), 7.12 (1H, t, J=6 Hz), 7.29 (1H, d, J=7 Hz), 7.57 (1H, t, J=6 Hz), 7.93 (1H, d, J=6 Hz), 8.14 (1H, d, J=7 Hz)

26) 2-Amino-4-[2-[(3-aminoprop-1-yl)oxy]benzoyl] amino-N-methyl-N-[2-[5-(4-dimethylaminopiperidin-1-yl) carbonylpent-1-yloxy]-4-methylphenyl]benzamide trihydrochloride NMR (DMSO-$d_6$, δ): 1.41–1.51 (2H, m), 1.51–1.66 (1H, m), 1.74–1.84 (1H, m), 1.98–2.12 (4H, m), 2.30–2.40 (2H, m), 2.67 (3H, s), 2.68 (3H, s), 2.89–3.06 (4H, m), 3.16 (3H, s), 3.33 (2H, br), 3.96–4.10 (4H, m), 4.13–4.20 (2H, m), 4.47–4.58 (1H, m), 6.60 (1H, d, J=7 Hz), 6.78 (2H, s), 6.85 (1H, s), 6.97–7.07 (2H, m), 7.13 (1H, d, J=7 Hz), 7.27 (1H, s), 7.43–7.56 (2H, m)

27) 2-[2-[(3-Aminoprop-1-yl)oxy]benzoyl]amino-N-methyl-N-[2-[5-(4-dimethylaminopiperidin-1-yl) carbonyl-pent-1-yloxy]-4-methylphenyl]-5-pyridinecarboxamide trihydrochloride NMR (DMSO-$d_6$, δ): 1.32–1.80 (8H, m), 1.97–2.20 (4H, m), 2.22 (3H, s), 2.27–2.40 (3H, m), 2.65 (3H, s), 2.67 (3H, s), 2.92–3.10 (4H, m), 3.19 (3H, s), 3.33 (1H, br), 3.80–4.07 (3H, m), 4.22–4.29 (2H, m), 6.69 (1H, d, J=7 Hz), 6.82 (1H, s), 7.07–7.14 (2H, m), 7.20 (1H, d, J=7 Hz), 7.56 (1H, t, J=6 Hz), 7.66 (1H, d, J=6 Hz), 7.78 (1H, d, J=7 Hz), 8.00–8.04 (1H, m), 8.23 (1H, s)

28) 4-[N-[2-[(3-Aminoprop-1-yl)oxy]phenyl]amino] methyl-3-methoxy-N-methyl-N-[2-[5-(4-methylpiperazin-1-yl)carbonylpent-1-yloxy]-4-methylphenyl]benzamide trihydrochloride NMR (DMSO-$d_6$, δ): 1.35–1.49 (2H, m), 1.49–1.62 (2H, m), 1.62–1.79 (2H, m), 2.01–2.16 (2H, m), 2.23 (3H, s), 2.34–2.40 (2H, m), 2.71 and 2.72 (total 3H, s), 2.76–3.12 (8H, m), 3.17 (3H, s), 3.27–3.41 (2H, m), 3.41–3.54 (4H, m), 3.70–3.81 (1H, m), 3.89–3.98 (1H, m), 4.02–4.08 (3H, m), 4.25 (2H, s), 4.39–4.45 (1H, m), 6.60–6.80 (6H, m), 6.93 (2H, s), 6.98 (1H, d, J=7 Hz), 7.10 (1H, d, J=7 Hz)

29) 4-[2-[(3-Aminoprop-1-yl)oxy]phenyl]oxymethyl-3-methoxy-N-methyl-N-[2-[5-(4-methylpiperazin-1-yl) carbonylpent-1-yloxy]-4-methylphenyl]benzamide dihydrochloride NMR (DMSO-$d_6$, δ): 1.39–1.50 (2H, m), 1.50–1.63 (2H, m), 1.65–1.82 (2H, m), 1.97–2.10 (2H, m), 2.21 (3H, s), 2.35–2.41 (2H, m), 2.71 and 2.72 (total 3H, s), 2.78–3.10 (7H, m), 3.18 (3H, s), 3.29–3.41 (2H, m), 3.41–3.67 (4H, m), 3.82 (1H, br), 3.89–4.00 (1H, m), 4.00–4.12 (3H, m), 4.38–4.48 (1H, m), 4.57 and 4.93 (total 2H, s), 6.61 (1H, d, J=7 Hz), 6.69–6.97 (6H, m), 6.97–7.07 (2H, m), 7.20–7.25 (1H, m)

30) 4-[2-[(3-Aminoprop-1yl)oxy]benzoyl]amino-3-benzyloxy-N-methyl-N-[2-[5-(4-methylpiperazin-1-yl) carbonylpent-1-yloxy]-4-methylphenyl]benzamide dihydrochloride NMR (DMSO-$d_6$, δ): 1.37–1.50 (2H, m), 1.50–1.63 (2H, m), 1.63–1.79 (2H, m), 1.79–1.91 (2H, m), 2.22 (3H, s), 2.39 (2H, t, J=6 Hz), 2.60–2.77 (5H, m), 2.79–3.10 (4H, m), 3.15 (3H, s), 3.30–3.67 (3H, m), 3.77–4.12 (5H, m), 4.37–4.49 (1H, m), 5.06 (2H, s), 6.62 (1H, d, J=6 Hz), 6.82 (1H, s), 6.90 (1H, d, J=7 Hz), 6.97 (1H, d, J=7 Hz), 7.03 (1H, s), 7.12 (1H, t, J=7 Hz), 7.22 (1H, d, J=7 Hz), 7.30–7.46 (5H, m), 7.54 (1H, t, J=6 Hz), 7.97 (1H, d, J=7 Hz), 8.23 (1H, d, J=7 Hz)

31) 4-[2-[(3-Aminoprop-1yl)oxy]benzoyl]amino-3-hydroxy-N-methyl-N-[2-[5-(4-methylpiperazin-1-yl) carbonylpent-1-yloxy]-4-methylphenyl]benzamide dihydrochloride NMR (DMSO-$d_6$, δ): 1.43 (2H, br), 1.49–1.62 (2H, m), 1.63–1.82 (2H, m), 2.00–2.40 (16H, m), 2.90–2.97 (2H, m), 3.14 (3H, s), 3.30–3.50 (5H, m), 3.89 (2H, br), 4.20–4.38 (2H, m), 6.50–6.68 (2H, m), 6.80 (1H, s), 6.87–6.99 (2H, m), 7.12 (1H, t, J=6 Hz), 7.22 (1H, d, J=6 Hz), 7.49–7.60 (1H, m), 7.97–8.18 (2H, m)

32) 4-[2-[(3-Aminoprop-1-yl)oxy]benzoyl]amino-3-ethoxycarbonylmethoxy-N-methyl-N-[2-[5-(4-methylpiperazin-1-yl)carbonylpent-1-yloxy]-4-methylphenyl]benzamide dihydrochloride NMR (DMSO-$d_6$, δ): 1.09 and 1.22 (total 3H, t, J=6 Hz), 1.37–1.51 (2H, m), 1.51–1.66 (2H, m), 1.67–1.80 (2H, m), 2.05–2.18 (2H, m), 2.23 (3H, s), 2.38 (2H, t, J=6 Hz), 2.73–2.74 (3H, m), 2.90–3.10 (5H, m), 3.17 (3H, s), 3.30–3.58 (2H, m), 3.80–4.00 (2H, m), 4.00–4.20 (3H, m), 4.32–4.50 (3H, m), 4.80 (2H, s), 6.62 (1H, d, J=6 Hz), 6.82 (1H, s), 6.89–6.92 (2H, m), 7.01 (1H, d, J=7 Hz), 7.15 (1H, t, J=6 Hz), 7.27 (1H, d, J=7 Hz), 7.58 (1H, t, J=6 Hz), 8.00 (1H, d, J=6 Hz), 8.27 (1H, d, J=7 Hz)

33) 4-[2-[(3-Aminoprop-1-yl)oxy]benzoyl]amino-3-methoxycarbonylmethoxy-N-methyl-N-[2-[5-(4-methylpiperazin-1-yl)carbonylpent-1-yloxy]-4-methylphenyl]benzamide dihydrochloride NMR (DMSO-$d_6$, δ): 1.35–1.50 (2H, m), 1.50–1.63 (2H, m), 1.63–1.90 (2H, m), 2.00–2.14 (2H, m), 2.21 (3H, s), 2.25–2.43 (2H, m), 2.71 (3H, s), 2.77–3.05 (5H, m), 3.15 (3H, s), 3.18–3.57 (6H, m), 3.70 (3H, s), 3.73–4.12 (3H, m), 4.12–4.49 (3H, m), 4.80 (2H, s), 6.63 (1H, d, J=7 Hz), 6.70–7.20 (5H, m), 7.27 (1H, d, J=7 Hz), 7.57 (1H, t, J=7 Hz), 7.93–8.10 (1H, m), 8.23 (1H, d, J=6 Hz)

34) 4-[2-[(3-Aminoprop-1-yl)oxy]benzoyl]amino-3-dimethylaminocarbonylmethoxy-N-methyl-N-[2-[5-(4-methylpiperazin-1-yl)carbonylpent-1-yloxy]-4-methylphenyl]benzamide dihydrochloride NMR (DMSO-$d_6$, δ): 1.37–1.49 (2H, m), 1.50–1.62 (2H, m), 1.63–1.79 (2H, m), 1.98–2.10 (2H, m), 2.21 (3H, s), 2.32–2.43 (2H, m), 2.71 (3H, s), 2.86 (3H, s), 2.98 (3H, s), 2.82–3.05 (5H, m), 3.15 (3H, s), 3.90 (2H, br), 4.02–4.12 (2H, m), 4.28–4.38 (2H, m), 4.38–4.48 (1H, m), 4.83 (2H, s), 6.62 (1H, d, J=7 Hz), 6.80 (1H, s), 6.82–6.92 (2H, m), 7.00 (1H, d, J=7 Hz), 7.12 (1H, t, J=7 Hz), 7.23 (1H, d, J=7 Hz), 7.55 (1H, t, J=7 Hz), 8.20 (1H, d, J=7 Hz)

35) 4-[2-[(3-Aminoprop-1-yl)oxy]benzoyl]amino-3-methylaminocarbonylmethoxy-N-methyl-N-[2-[5-(4-methylpiperazin-1-yl)carbonylpent-1-yloxy]-4-methylphenyl]benzamide dihydrochloride NMR (DMSO$_6$, δ): 1.38–1.51 (1H, m), 1.51–1.65 (2H, m), 1.68–1.80 (2H, m), 2.00–2.23 (2H, m), 2.22 (3H, s), 2.34–2.40 (3H, m), 2.50 (3H, s), 2.58 (2H, br), 2.62 (3H, s), 2.63 (3H, s), 2.90 (4H, br), 3.15 (3H, s), 3.88–3.97 (2H, m), 4.26–4.33 (2H, m), 4.37–4.54 (2H, m), 6.62 (1H, d, J=7 Hz), 6.82 (2H, s), 6.88 (1H, d, J=7 Hz), 6.97 (1H, d, J=7 Hz), 7.12 (1H, t, J=7 Hz), 7.22 (1H, d, J=7 Hz), 7.57 (1H, t, J=7 Hz), 7.90 (1H, d, J=7 Hz), 8.12–8.25 (2H, m)

36) 4-[2-[(3-Aminoprop-1-yl)oxy]benzoyl]amino-3-aminocarbonylmethoxy-N-methyl-N-[2-[5-(4-methylpiperazin-1-yl)carbonylpent-1-yloxy]-4-methylphenyl]benzamide dihydrochloride NMR (DMSO-$d_6$, δ): 1.38–1.52 (2H, m), 1.52–1.67 (2H, m), 1.68–1.83 (2H, m), 2.00–2.15 (2H, m), 2.23 (3H, s), 2.39 (2H, t, J=6 Hz), 2.62 and 2.63 (total 3H, s), 2.72 and 2.73 (total 3H, s), 2.80–3.10 (6H, m), 3.15 (3H, s), 3.87–3.98 (2H, m), 4.03–4.13 (1H, m), 6.27–6.37 (1H, m), 6.37–6.56 (2H, m), 6.62 (1H, d, J=7 Hz), 6.82 (2H, s), 6.90 (1H, d, J=7 Hz), 6.98 (1H, d, J=6 Hz), 7.12 (1H, t, J=7 Hz), 7.26 (1H, d, J=7 Hz), 7.57 (1H, t, J=6 Hz), 7.92 (1H, d, J=7 Hz), 8.13–8.30 (2H, m)

37) 4-[2-[(3-Aminoprop-1-yl)oxy]benzoyl]amino-N-methyl-N-[2-[5-(4-methylpiperazin-1-yl)carbonylpent-1-yloxy]-4-methylphenyl]-3-propoxybenzamide dihydrochloride NMR (DMSO-$d_6$, δ): 0.89 (3H, t, J=6 Hz), 1.37–1.50 (2H, m), 1.50–1.68 (4H, m), 1.68–1.80 (2H, m), 2.02–2.18 (2H, m), 2.20 (3H, s), 2.38 (2H, t, J=6 Hz), 2.47 (3H, s), 2.75–3.12 (5H, m), 3.17 (3H, s), 3.30–3.42 (2H, m), 3.42–3.56 (1H, m), 3.80–4.00 (4H, m), 4.00–4.13 (1H, m), 4.32–4.50 (4H, m), 6.61 (1H, d, J=7 Hz), 6.82 (1H, s), 6.88 (1H, s), 6.94 (1H, d, J=7 Hz), 7.02 (1H, d, J=7 Hz), 7.13 (1H, t, J=7 Hz), 7.29 (1H, d, J=7 Hz), 7.56 (1H, t, J=7 Hz), 7.97 (1H, d, J=7 Hz), 8.22 (1H, d, J=7 Hz)

38) 4-[2-[(3-Aminoprop-1-yl)oxy]benzoyl]amino-3-isopropoxy-N-methyl-N-[2-[5-(4-methylpiperazin-1-yl)carbonylpent-1-yloxy]-4-methylphenyl]benzamide dihydrochloride NMR (DMSO-$d_6$, δ): 1.10–1.27 (6H, m), 1.37–1.50 (2H, m), 1.50–1.64 (2H, m), 1.67–1.82 (2H, m), 2.03–2.07 (2H, m), 2.22 (3H, s), 2.39 (2H, t, J=6 Hz), 2.72 and 2.73 (total 3H, s), 2.78–3.12 (6H, m), 3.17 (3H, s), 3.30–3.43 (2H, m), 3.43–3.60 (1H, m), 3.80–4.02 (2H, m), 4.02–4.13 (1H, m), 4.23–4.50 (4H, m), 6.64 (1H, d, J=7 Hz), 6.81–6.90 (2H, m), 6.98 (1H, d, J=7 Hz), 7.03 (1H, d, J=7 Hz), 7.13 (1H, t, J=6 Hz), 7.32 (1H, d, J=7 Hz) 7.56 (1H, t, J=6 Hz), 7.94 (1H, d, J=6 Hz), 8.22 (1H, d, J=7 Hz)

39) 2-[2-[(3-Aminoprop-1-yl)oxy]benzoyl]amino-N-methyl-N-[2-[5-(4-methylpiperazin-1-yl)carbonylpent-1-yloxy]-4-methylphenyl]-5-thiophenecarboxamide dihydrochloride NMR (DMSO-$d_6$, δ): 1.20–1.38 (2H, m), 1.38–1.52 (2H, m), 1.53–1.70 (2H, m), 1.98–2.10 (2H, m), 2.22–2.32 (2H, m), 2.33 (3H, s), 2.69–2.72 (3H, m), 2.76–3.07 (5H, m), 3.16 (3H, s), 3.27–3.54 (3H, m), 3.78–4.09 (3H, m), 4.10–4.20 (2H, m), 4.33–4.47 (2H, m), 6.15 (1H, br), 6.55 (1H, d, J=5 Hz), 6.81 (1H, d, J=7 Hz), 6.97 (1H, s), 7.07 (1H, t, J=6 Hz), 7.13–7.20 (2H, m), 7.44–7.60 (2H, m)

EXAMPLE 105

To a solution of 4-[2-[(3-tert-butoxycarbonylaminoprop-1-yl)oxy]benzoyl]amino-3-methoxy-N-methyl-N-(4-hydroxyphenyl)benzamide (50 mg) in chloroform (3.0 ml) was added a solution of 4N hydrogen chloride in ethyl acetate (1.0 ml) and the mixture was stirred at ambient temperature for 2 hours. The resulting mixture was evaporated in vacuo and the residue was solidified with diethyl ether. Diethyl ether was removed in vacuo to give 4-[2-[(3-aminoprop-1-yl)oxy]benzoyl]amino-3-methoxy-N-methyl-N-(4-hydroxyphenyl)benzamide hydrochloride (40 mg).

NMR (DMSO-$d_6$, δ): 2.11–2.21 (2H, m), 2.96 (2H, q, J=8 Hz), 3.30 (3H, s), 3.78 (3H, s), 4.37 (2H, t, J=8 Hz), 6.66 (2H, d, J=8 Hz), 6.88 (1H, d, J=8 Hz), 6.97 (1H, s), 6.99 (2H, d, J=8 Hz), 7.15 (1H, t, J=8 Hz), 7.27 (1H, d, J=8 Hz), 7.55–7.62 (1H, m), 7.97–8.05 (3H, m), 8.28 (1H, d, J=8 Hz), 9.54–9.59 (1H, br s)

ESI-MASS (m/z): 450 (M+H)

EXAMPLE 106

The following compound was obtained according to a similar manner to that of Example 105.

4-[2-[(3-Aminoprop-1-yl)oxy]benzoyl]amino-3-carboxymethoxy-N-methyl-N-cyclohexylbenzamide hydrochloride NMR (DMSO-$d_6$, δ): 1.02–1.10 (2H, m), 1.46–1.80 (8H, m), 2.08–2.12 (2H, m), 2.80 (3H, s), 2.92–2.99 (2H, m), 3.30–3.47 (2H, br), 4.39 (2H, t, J=7 Hz), 4.96 (2H, s), 6.98–7.04 (2H, br s), 7.18 (1H, t, J=8 Hz), 7.30 (1H, d, J=8 Hz), 7.60 (1H, t, J=8 Hz), 7.95–8.05 (3H, br), 8.07 (1H, d, J=8 Hz), 8.51 (1H, d, J=8 Hz)

ESI-MASS (m/z): 4.84 (M+H)

EXAMPLE 107

1) A solution of 4-[2-[3-(9-fluorenylmethyl)oxycarbonylamininoprop-1-yl]thiobenzoyl]amino-3-methoxy-N-methyl-N-[2-[5-(4-dimethylaminopiperidin-1-yl)carbonylpent-1-yl]oxy-4-methylphenyl]benzamide (110 mg) in a mixture of N,N-dimethylformamide and piperidine (4:1, 5 ml) was stirred at ambient temperature for 30 minutes and the resulting solution was diluted with ethyl acetate (20 ml). The solution was washed with water (10 ml×3) and brine, and the solution was dried over potassium carbonate. The solvent was evaporated and the residue was purified on basic silica gel column chromatography (SiO$_2$ 30 g, 1–15% methanol in chloroform) to give 4-[2-(3-aminoprop-1-yl)thiobenzoyl]amino-3-methoxy-N-methyl-N-[2-[5-(4-dimethylaminopiperidin-1-yl]carbonylpent-1-yl]oxy-4-methylphenyl]benzamide.

NMR (CDCl$_3$, δ): 1.36–1.92 (12H, m), 2.29 (6H, s), 2.30 (3H, s), 2.36 (2H, t, J=5 Hz), 2.59 (1H, t, J=11 Hz), 2.77 (2H, t, J=5 Hz), 2.99 (2H, t, J=5 Hz), 3.32 (3H, s), 3.75 (3H, s), 3.85–4.03 (4H, m), 6.57–6.66 (2H, m), 6.84–6.90 (1H, d, J=8 Hz), 7.02 (1H, s), 7.39–7.48 (3H, m), 7.65 (1H, d, J=8 Hz), 8.30 (1H, d, J=8 Hz), 8.80 (1H, s)

2) To a solution of the obtained compound in ethanol (5 ml) was added 1N hydrochloric acid (0.15 ml). The volatile solvent was removed by evaporation and the residue was lyophilized to give 4-[2-(3-aminoprop-1-yl)thiobenzoyl]amino-3-methoxy-N-methyl-N-[2-[5-(4-dimethylaminopiperidin-1-yl]carbonylpent-1-yl]oxy-4-methylphenyl]benzamide dihydrochloride (45 mg).

NMR (CDCl$_3$, δ): 1.44–1.92 (6H, m), 2.02–2.16 (2H, m), 2.28 (3H, s), 2.30–2.41 (2H, m), 2.73 (6H, br), 2.99–3.14 (2H, m), 3.27–3.33 (1H, m), 3.31 (3H, s), 3.62–3.79 (4H, m), 3.71 (3H, s), 3.82–4.10 (2H, m), 6.55–6.67 (2H, m), 6.83–7.02 (5H, m), 7.35–7.52 (2H, m), 8.23 (1H, br), 8.54 (2H, br)

EXAMPLE 108

The following compound was obtained according to a similar manner to that of Example 15.

4-2-(3-Dimethylaminoprop-1-yl)oxybenzoyl]amino-3-methoxy-N-methyl-N-[2-[5-(4-dimethylaminopiperidin-1-yl)carbonylpent-1-yl]oxy-4-methylphenyl]benzamide NMR (CDCl$_3$, δ): 1.49–1.60 (2H, m), 1.66–1.95 (4H, m), 2.21 (6H, s), 2.27 (6H, s), 2.35–2.48 (4H, m), 2.58 (2H, t, J=11 Hz), 3.32 (2H, t, J=11 Hz), 3.33 (3H, s), 3.80 (3H, s), 3.82–4.00 (2H, m), 4.25 (2H, t, J=5 Hz), 4.64 (1H, br), 6.55–6.64 (2H, m), 6.85 (1H, d, J=8 Hz), 6.89 (1H, d, J=8 Hz), 7.00–7.11 (3H, m), 7.26 (1H, s), 7.40–7.48 (1H, m), 8.21 (1H, d, J=8 Hz), 8.40 (1H, d, J=8 Hz)

We claim:
1. A compound of the formula:

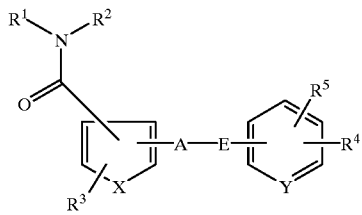
(I)

wherein
R¹ is aryl which is substituted with alkoxy optionally substituted with acyl, substituted acyl, acylamino or substituted acylamino;
R² is hydrogen; lower alkyl optionally substituted with hydroxy, aryl or acyl; or cyclo(lower)alkyl;
R³ is hydrogen; halogen; hydroxy; acyloxy; substituted acyloxy; lower alkyl optionally substituted with hydroxy or lower alkoxy; lower alkoxy optionally substituted with aryl, amino, protected amino, acyl, hydroxy, cyano or lower alkylthio; nitro; amino; acyl; substituted acyl; or cyclo(lower)alkyloxy;
R⁴ is lower alkoxy optionally substituted with hydroxy, aryl, substituted aryl, acyl, substituted acyl, amino, lower alkylamino, acylamino, substituted acylamino, protected amino, a heterocyclic group or guanidino;
R⁵ is hydrogen, lower alkyl, lower alkoxy or halogen;
A is NH;
E is

X is —CH=CH—; and
Y is CH;
and pharmaceutically acceptable salts thereof.
2. A compound according to claim 1, wherein
R¹ is aryl which is substituted with lower alkoxy optionally substituted with acylamino or acyl;
R² is lower alkyl;
R³ is hydrogen, lower alkyl or lower alkoxy;
R⁴ is lower alkoxy, which may be substituted with hydroxy, acyl, amino, lower alkylamino, acylamino, protected amino or a heterocyclic group;
R⁵ is hydrogen, lower alkyl, lower alkoxy or halogen;
A is NH;

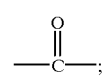

X is —CH=CH—; and
Y is CH.
3. A compound according to claim 2, wherein
R¹ is phenyl or tolyl, each of which is substituted with lower alkoxy substituted with acyl;
R³ is lower alkoxy or lower alkyl; and
R⁴ is lower alkoxy, which is substituted with amino or hydroxy.
4. A compound according to claim 3, wherein
R¹ is phenyl or tolyl, each of which is substituted with lower alkoxy substituted with N-(lower alkyl) piperazinylcarbonyl;
R³ is lower alkoxy;
R⁴ is lower alkoxy substituted with amino; and
R⁵ is hydrogen.
5. A pharmaceutical composition comprising a compound of claim 1, as an active ingredient, in association with a pharmaceutically acceptable, substantially non-toxic carrier or excipient.
6. A method of therapeutic treatment of hypertension, heart failure, renal insufficiency, edema, ascites, vasopressin parasecretion syndrome, hepatocirrhosis, hyponatremia, hypokalemia, diabetic, circulation disorder, cerebrovascular disease, Meniere's syndrome or motion sickness which comprises administering an effective amount of a compound of claim 1 to human beings or animals.

* * * * *